(12) United States Patent
Vazales et al.

(10) Patent No.: US 9,579,012 B2
(45) Date of Patent: Feb. 28, 2017

(54) VISUALIZED ENDOTRACHEAL TUBE PLACEMENT SYSTEMS

(71) Applicant: ENDOCLEAR LLC, Petoskey, MI (US)

(72) Inventors: Brad E. Vazales, Petoskey, MI (US); Arthur Bertolero, Danville, CA (US); Alan Davidner, Claremont, CA (US); Ken Watson, Milwaukee, WI (US); James M Gracy, Harbor Springs, MI (US); Clifton P Colwell, Peoria, AZ (US); Craig B. Berky, Milford, OH (US); Dwight Morejohn, Davis, CA (US); Dwayne Griffin, Petoskey, MI (US); Richard Tefo, Petoskey, MI (US)

(73) Assignee: ENDOCLEAR LLC, San Ramon, CA (US)

( * ) Notice: Subject to any disclaimer, the term of this patent is extended or adjusted under 35 U.S.C. 154(b) by 38 days.

(21) Appl. No.: 13/645,984

(22) Filed: Oct. 5, 2012

(65) Prior Publication Data
US 2013/0030249 A1    Jan. 31, 2013

Related U.S. Application Data

(63) Continuation of application No. 13/638,567, filed as application No. PCT/US2011/030229 on Mar. 28, (Continued)

(51) Int. Cl.
*A61M 16/04* (2006.01)
*A61B 1/00* (2006.01)
(Continued)

(52) U.S. Cl.
CPC ........ *A61B 1/00045* (2013.01); *A61B 1/0669* (2013.01); *A61B 1/267* (2013.01);
(Continued)

(58) Field of Classification Search
CPC ...... A61B 1/267; A61B 1/00052; A61B 1/042
(Continued)

(56) References Cited

U.S. PATENT DOCUMENTS

| 62,816 A | 3/1867 | Christoffel |
|---|---|---|
| 139,633 A | 6/1873 | Turner |

(Continued)

FOREIGN PATENT DOCUMENTS

| DE | 3107392 | 9/1982 |
|---|---|---|
| EP | 0343094 | 11/1989 |

(Continued)

OTHER PUBLICATIONS

U.S. Appl. No. 12/701,421, filed Feb. 5, 2010, Methods for Cleaning Enotracheal Tubes.
(Continued)

*Primary Examiner* — John P Leubecker
*Assistant Examiner* — Rajaa El Alami
(74) *Attorney, Agent, or Firm* — Knobbe Martens Olson & Bear LLP

(57) ABSTRACT

Systems, methods, and devices for facilitating insertion of an endotracheal tube and/or for verifying the position of the endotracheal tube within an airway of a patient with respect to an anatomical landmark of a patient are disclosed. Systems, methods, and devices for facilitating removal of debris from the distal airways of a patient under direct visualization are also disclosed.

23 Claims, 56 Drawing Sheets

Related U.S. Application Data 2011, now Pat. No. 9,398,837, which is a continuation-in-part of application No. 12/849,672, filed on Aug. 3, 2010, now Pat. No. 8,468,637.

(60) Provisional application No. 61/318,761, filed on Mar. 29, 2010, provisional application No. 61/370,425, filed on Aug. 3, 2010.

(51) Int. Cl.
*A61B 1/06* (2006.01)
*A61B 1/267* (2006.01)
*A61B 1/05* (2006.01)
*A61B 17/3207* (2006.01)

(52) U.S. Cl.
CPC ............ *A61B 90/70* (2016.02); *A61M 16/04* (2013.01); *A61M 16/0463* (2013.01); *A61M 16/0472* (2013.01); *A61B 1/00135* (2013.01); *A61B 1/00142* (2013.01); *A61B 1/00165* (2013.01); *A61B 1/05* (2013.01); *A61B 1/2676* (2013.01); *A61B 17/320725* (2013.01); *A61B 2090/701* (2016.02); *A61M 16/0434* (2013.01); *A61M 2202/203* (2013.01)

(58) Field of Classification Search
USPC ................ 600/120–121, 109, 173, 179
See application file for complete search history.

(56) References Cited

U.S. PATENT DOCUMENTS

| | | |
|---|---|---|
| 491,791 A | 2/1893 | Wilson |
| 655,313 A | 8/1900 | Tucker |
| 707,913 A | 8/1902 | Garrison |
| 1,040,088 A | 10/1912 | Wright et al. |
| 1,166,901 A | 1/1916 | Grobl |
| 1,588,557 A | 6/1926 | Thompson et al. |
| 1,608,347 A | 11/1926 | Thompson et al. |
| 1,612,842 A | 1/1927 | Thompson et al. |
| 1,656,465 A | 1/1928 | Baker |
| 1,738,601 A | 12/1929 | Metzger |
| 2,018,124 A | 10/1935 | Forster |
| 2,038,170 A | 4/1936 | Flavin |
| 2,073,811 A | 3/1937 | Shultz |
| 2,125,864 A | 8/1938 | Auckland |
| 2,157,421 A | 5/1939 | McFarland |
| 2,173,606 A | 9/1939 | Forster |
| 2,175,726 A | 10/1939 | Gebauer |
| 2,552,339 A | 5/1951 | Moon |
| 2,599,077 A | 6/1952 | Sturgis |
| 2,653,334 A | 9/1953 | Bay |
| 2,930,059 A | 3/1960 | Frank |
| 2,932,837 A | 4/1960 | Nooy |
| 2,957,189 A | 10/1960 | Nelson et al. |
| 2,958,884 A | 11/1960 | Hill et al. |
| 3,096,756 A | 7/1963 | Rosenfeld et al. |
| 3,105,555 A | 10/1963 | Villalon, Jr. |
| 3,130,431 A | 4/1964 | Reinhart |
| 3,257,698 A | 6/1966 | Ruegsegger |
| 3,445,879 A | 5/1969 | Taylor |
| 3,525,111 A | 8/1970 | Von Arx |
| 3,610,242 A | 10/1971 | Sheridan et al. |
| 3,667,475 A | 6/1972 | Venturelli et al. |
| 3,669,098 A | 6/1972 | Takahashi |
| 3,776,222 A | 12/1973 | Smiddy |
| 3,946,459 A | 3/1976 | Armstrong |
| 3,948,273 A | 4/1976 | Sanders |
| 3,977,331 A | 8/1976 | Clavin |
| 3,991,762 A | 11/1976 | Radford |
| 3,996,938 A | 12/1976 | Clark |
| 4,031,590 A | 6/1977 | Clavin |
| 4,041,936 A | 8/1977 | Carden |
| 4,185,639 A | 1/1980 | Linder |
| 4,222,142 A | 9/1980 | DiProspero |
| 4,319,378 A | 3/1982 | Bowman et al. |
| 4,327,720 A | 5/1982 | Bronson et al. |
| 4,342,315 A | 8/1982 | Jackson |
| 4,351,328 A | 9/1982 | Bodai |
| 4,365,381 A | 12/1982 | Neuman |
| 4,502,482 A | 3/1985 | DeLuccia et al. |
| 4,527,553 A | 7/1985 | Upsher |
| 4,538,316 A | 9/1985 | Reinhart et al. |
| 4,565,187 A | 1/1986 | Soloway |
| 4,567,882 A | 2/1986 | Heller |
| 4,584,998 A | 4/1986 | McGrail |
| 4,585,000 A | 4/1986 | Hershenson |
| 4,586,491 A | 5/1986 | Carpenter |
| 4,622,709 A | 11/1986 | Matsuda |
| 4,637,389 A | 1/1987 | Heyden |
| 4,646,722 A | 3/1987 | Silverstein et al. |
| 4,662,871 A | 5/1987 | Rafelson |
| 4,698,932 A | 10/1987 | Schneider |
| 4,805,611 A | 2/1989 | Hodgkins |
| 4,815,459 A | 3/1989 | Beran |
| 4,825,859 A | 5/1989 | Lambert |
| 4,827,553 A | 5/1989 | Turpin, Sr. et al. |
| 4,846,153 A | 7/1989 | Berci |
| 4,850,348 A | 7/1989 | Pell et al. |
| 4,877,016 A | 10/1989 | Kantor et al. |
| 4,889,106 A | 12/1989 | Watanabe |
| 4,892,095 A | 1/1990 | Nakhgevany |
| 4,976,261 A | 12/1990 | Gluck et al. |
| 5,000,260 A | 3/1991 | Fontenot |
| 5,003,657 A | 4/1991 | Boiteau et al. |
| 5,029,580 A | 7/1991 | Radford et al. |
| 5,030,201 A | 7/1991 | Palestrant |
| 5,065,754 A | 11/1991 | Jensen |
| 5,083,561 A | 1/1992 | Russo |
| 5,168,593 A | 12/1992 | Poje et al. |
| 5,176,638 A * | 1/1993 | Don Michael ........... 604/101.03 |
| 5,193,525 A | 3/1993 | Silverstein et al. |
| 5,193,544 A | 3/1993 | Jaffe |
| 5,203,320 A | 4/1993 | Augustine |
| 5,240,675 A | 8/1993 | Wilk et al. |
| 5,251,356 A | 10/1993 | Oaki et al. |
| 5,257,620 A | 11/1993 | Schermerhorn |
| 5,271,381 A | 12/1993 | Ailinger et al. |
| 5,279,549 A | 1/1994 | Ranford |
| 5,285,778 A | 2/1994 | Mackin |
| 5,287,848 A | 2/1994 | Cubb et al. |
| 5,297,310 A | 3/1994 | Coz et al. |
| 5,329,940 A * | 7/1994 | Adair ....................... 128/200.26 |
| 5,337,730 A | 8/1994 | Maguire |
| 5,364,358 A | 11/1994 | Hewitt et al. |
| 5,375,589 A | 12/1994 | Bhatta |
| 5,383,243 A | 1/1995 | Thacker et al. |
| 5,400,771 A | 3/1995 | Pirak et al. |
| 5,405,755 A | 4/1995 | Markus et al. |
| 5,407,807 A | 4/1995 | Markus |
| 5,419,310 A | 5/1995 | Frassica et al. |
| 5,431,150 A | 7/1995 | Yabe et al. |
| 5,431,152 A | 7/1995 | Flam et al. |
| 5,431,637 A | 7/1995 | Okada et al. |
| 5,447,418 A | 9/1995 | Takeda et al. |
| 5,483,951 A | 1/1996 | Frassica et al. |
| 5,513,628 A | 5/1996 | Coles et al. |
| 5,520,607 A | 5/1996 | Frassica et al. |
| 5,540,225 A | 7/1996 | Schutt |
| 5,578,006 A | 11/1996 | Schon |
| 5,603,688 A | 2/1997 | Upsher |
| 5,615,439 A | 4/1997 | Bourrelly |
| 5,630,795 A | 5/1997 | Kuramoto et al. |
| 5,636,625 A * | 6/1997 | Miyagi et al. ........... 128/200.26 |
| 5,643,221 A | 7/1997 | Bullard |
| 5,647,358 A | 7/1997 | Vilasi |
| 5,653,231 A | 8/1997 | Bell |
| 5,667,476 A | 9/1997 | Frassica et al. |
| 5,676,635 A | 10/1997 | Levin |
| 5,687,714 A | 11/1997 | Kolobow et al. |
| 5,692,729 A | 12/1997 | Harhen |
| 5,695,448 A | 12/1997 | Kimura et al. |
| 5,702,348 A | 12/1997 | Harhen |

(56) References Cited

U.S. PATENT DOCUMENTS

| | | |
|---|---|---|
| 5,709,691 A | 1/1998 | Morejon |
| 5,713,849 A | 2/1998 | Bosma et al. |
| 5,725,478 A | 3/1998 | Saad |
| 5,733,242 A | 3/1998 | Rayburn et al. |
| 5,768,741 A | 6/1998 | Leiman et al. |
| 5,791,337 A | 8/1998 | Coles et al. |
| 5,795,404 A | 8/1998 | Murphy et al. |
| 5,797,993 A | 8/1998 | Woehleke |
| 5,819,727 A | 10/1998 | Linder |
| 5,827,177 A | 10/1998 | Oneda et al. |
| 5,830,127 A | 11/1998 | DeCastro |
| 5,832,920 A | 11/1998 | Field |
| 5,836,918 A | 11/1998 | Dondlinger |
| 5,840,251 A | 11/1998 | Iwaki |
| 5,842,973 A | 12/1998 | Bullard |
| 5,845,634 A | 12/1998 | Parker |
| 5,846,183 A | 12/1998 | Chilcoat |
| 5,876,329 A | 3/1999 | Harhen |
| 5,897,567 A | 4/1999 | Ressemann |
| 5,902,413 A | 5/1999 | Puszko et al. |
| 5,904,648 A | 5/1999 | Arndt et al. |
| 5,913,816 A | 6/1999 | Sanders et al. |
| 5,921,917 A | 7/1999 | Barthel et al. |
| 5,931,831 A | 8/1999 | Linder |
| 5,941,816 A | 8/1999 | Barthel et al. |
| 5,964,004 A | 10/1999 | Bean |
| 5,964,223 A | 10/1999 | Baran |
| 5,966,768 A | 10/1999 | Hahn |
| 5,987,683 A | 11/1999 | Leiman et al. |
| 6,045,623 A | 4/2000 | Cannon |
| 6,047,431 A | 4/2000 | Canonica |
| 6,082,361 A | 7/2000 | Morejon |
| 6,086,529 A | 7/2000 | Arndt et al. |
| 6,115,523 A | 9/2000 | Choi et al. |
| 6,120,434 A | 9/2000 | Kimura et al. |
| 6,123,666 A | 9/2000 | Wrenn et al. |
| 6,168,579 B1 | 1/2001 | Tsugita |
| 6,174,280 B1 * | 1/2001 | Oneda et al. ............... 600/121 |
| 6,189,533 B1 | 2/2001 | Simon et al. |
| 6,190,330 B1 | 2/2001 | Harhen |
| 6,227,200 B1 | 5/2001 | Crump et al. |
| 6,276,017 B1 | 8/2001 | Lino et al. |
| 6,276,018 B1 | 8/2001 | Leiman et al. |
| 6,286,172 B1 | 9/2001 | Castagnoli |
| 6,299,576 B1 | 10/2001 | Ouchi |
| 6,318,368 B1 | 11/2001 | Morejon |
| 6,319,195 B1 | 11/2001 | Nakaichi et al. |
| 6,322,498 B1 | 11/2001 | Gravenstein et al. |
| 6,350,231 B1 | 2/2002 | Ailinger et al. |
| 6,353,774 B1 | 3/2002 | Goldenberg et al. |
| 6,354,993 B1 | 3/2002 | Kaplan et al. |
| 6,379,296 B1 | 4/2002 | Baggett |
| 6,398,775 B1 | 6/2002 | Perkins et al. |
| 6,461,294 B1 | 10/2002 | Oneda et al. |
| 6,484,345 B2 | 11/2002 | Seder et al. |
| 6,494,208 B1 | 12/2002 | Morejon |
| 6,500,271 B1 | 12/2002 | Moore et al. |
| 6,517,477 B1 | 2/2003 | Wendlandt |
| 6,520,907 B1 | 2/2003 | Foley et al. |
| 6,526,976 B1 | 3/2003 | Baran |
| 6,527,761 B1 | 3/2003 | Buch et al. |
| 6,530,881 B1 | 3/2003 | Ailinger et al. |
| 6,538,431 B2 | 3/2003 | Couchman et al. |
| 6,543,447 B2 | 4/2003 | Pacey |
| 6,554,765 B1 | 4/2003 | Yarush et al. |
| 6,569,089 B1 | 5/2003 | Covington et al. |
| 6,629,924 B2 | 10/2003 | Aydelotte |
| 6,655,377 B2 | 12/2003 | Pacey |
| 6,679,262 B1 | 1/2004 | Morejon |
| 6,681,783 B2 | 1/2004 | Kawazoe |
| 6,699,182 B2 | 3/2004 | Pilvisto |
| 6,699,331 B1 | 3/2004 | Kritzler |
| 6,725,492 B2 | 4/2004 | Moore et al. |
| 6,729,334 B1 | 5/2004 | Baran |
| 6,775,872 B1 | 8/2004 | Appleton et al. |
| 6,775,874 B2 | 8/2004 | Horton |
| 6,793,661 B2 | 9/2004 | Hamilton et al. |
| 6,832,986 B2 | 12/2004 | Chhibber et al. |
| 6,843,769 B1 | 1/2005 | Gandarias |
| 6,889,400 B2 | 5/2005 | Kawazoe et al. |
| 6,889,402 B2 | 5/2005 | Galantai |
| 6,890,298 B2 | 5/2005 | Berci et al. |
| 6,920,662 B2 | 7/2005 | Moore |
| 6,928,686 B2 | 8/2005 | Tomooka et al. |
| 6,929,600 B2 | 8/2005 | Hill |
| 7,036,510 B2 | 5/2006 | Zgoda et al. |
| 7,051,737 B2 | 5/2006 | Kolobow et al. |
| 7,052,456 B2 | 5/2006 | Simon |
| 7,056,284 B2 | 6/2006 | Martone et al. |
| 7,060,135 B2 | 6/2006 | Morejon |
| 7,081,097 B2 | 7/2006 | Martone et al. |
| 7,107,997 B1 | 9/2006 | Moses et al. |
| 7,121,336 B2 | 10/2006 | Hatley |
| 7,128,071 B2 | 10/2006 | Brain |
| 7,159,590 B2 | 1/2007 | Rife |
| 7,182,728 B2 | 2/2007 | Cubb et al. |
| 7,243,653 B2 | 7/2007 | Nelson |
| 7,297,105 B2 | 11/2007 | Mackin |
| 7,322,357 B2 | 1/2008 | Nelson |
| 7,458,375 B2 | 12/2008 | Schwartz et al. |
| 7,458,955 B2 | 12/2008 | Owens et al. |
| 7,469,700 B2 | 12/2008 | Baran |
| 7,472,705 B2 | 1/2009 | Baran |
| 7,473,219 B1 | 1/2009 | Glenn |
| 7,478,636 B2 | 1/2009 | Madsen et al. |
| 7,503,328 B2 | 3/2009 | Kolobow et al. |
| 7,527,058 B2 | 5/2009 | Wright et al. |
| 7,552,729 B2 | 6/2009 | O'Mara |
| 7,607,436 B2 | 10/2009 | Smaldone et al. |
| 7,658,708 B2 | 2/2010 | Schwarts et al. |
| 7,658,711 B2 | 2/2010 | Klemm |
| 7,669,600 B2 | 3/2010 | Morejon |
| 8,142,422 B2 | 3/2012 | Makower et al. |
| 8,157,919 B2 | 4/2012 | Vazales et al. |
| 8,381,345 B2 | 2/2013 | Vazales et al. |
| 8,382,908 B2 | 2/2013 | Vazales et al. |
| 8,458,844 B2 | 6/2013 | Vazales et al. |
| 8,468,637 B2 | 6/2013 | Vazales et al. |
| 8,534,287 B2 | 9/2013 | Vazales et al. |
| 8,601,633 B2 | 12/2013 | Vazales et al. |
| 9,095,286 B2 | 8/2015 | Vazales et al. |
| 9,332,891 B2 | 5/2016 | Vazales et al. |
| 2001/0014768 A1 | 8/2001 | Kaplan et al. |
| 2002/0068851 A1 | 6/2002 | Gravenstein et al. |
| 2002/0108614 A1 | 8/2002 | Schultz |
| 2002/0162557 A1 | 11/2002 | Simon et al. |
| 2003/0109837 A1 | 6/2003 | McBride-Sakal |
| 2003/0188749 A1 | 10/2003 | Nichols et al. |
| 2003/0209258 A1 | 11/2003 | Morejon |
| 2003/0213501 A1 | 11/2003 | Thomson et al. |
| 2004/0039252 A1 | 2/2004 | Koch, III |
| 2004/0084050 A1 * | 5/2004 | Baran .................. 128/207.14 |
| 2004/0154115 A1 | 8/2004 | Schultz |
| 2004/0176731 A1 | 9/2004 | Cheng et al. |
| 2004/0181194 A1 | 9/2004 | Perkins |
| 2004/0187892 A1 | 9/2004 | Maguire, Jr. et al. |
| 2004/0187893 A1 | 9/2004 | Maguire, Jr. et al. |
| 2004/0215061 A1 | 10/2004 | Kimmel et al. |
| 2004/0220451 A1 | 11/2004 | Gravenstein et al. |
| 2004/0221852 A1 | 11/2004 | Madsen et al. |
| 2005/0039754 A1 | 2/2005 | Simon |
| 2005/0090712 A1 | 4/2005 | Cubb |
| 2005/0172971 A1 * | 8/2005 | Kolobow et al. ......... 128/207.14 |
| 2005/0182297 A1 | 8/2005 | Gravenstein et al. |
| 2005/0235995 A1 | 10/2005 | Tresnak et al. |
| 2006/0004260 A1 | 1/2006 | Boedeker et al. |
| 2006/0069312 A1 | 3/2006 | O-Connor |
| 2006/0090761 A1 | 5/2006 | Kurrus |
| 2006/0100483 A1 | 5/2006 | Sundet et al. |
| 2006/0102200 A1 | 5/2006 | Esquenet et al. |
| 2006/0130847 A1 * | 6/2006 | Morejon .................. 128/207.15 |
| 2006/0135947 A1 | 6/2006 | Soltesz et al. |
| 2006/0157059 A1 | 7/2006 | Johnson et al. |
| 2006/0191087 A1 | 8/2006 | Maguire, Jr. et al. |

(56) References Cited

U.S. PATENT DOCUMENTS

| | | |
|---|---|---|
| 2006/0202387 A1 | 9/2006 | Durand et al. |
| 2006/0207602 A1 | 9/2006 | Kolobow et al. |
| 2006/0264988 A1* | 11/2006 | Boyle .................... 606/159 |
| 2006/0287667 A1 | 12/2006 | Abela |
| 2007/0049794 A1 | 3/2007 | Glassenberg et al. |
| 2007/0106117 A1 | 5/2007 | Yokota |
| 2007/0106121 A1 | 5/2007 | Yokota et al. |
| 2007/0106122 A1 | 5/2007 | Yokota et al. |
| 2007/0106302 A1 | 5/2007 | Ortiz |
| 2007/0129603 A1 | 6/2007 | Hirsh |
| 2007/0137651 A1 | 6/2007 | Glassenberg et al. |
| 2007/0142709 A1* | 6/2007 | Martone et al. .......... 600/121 |
| 2007/0167686 A1 | 7/2007 | McGrath |
| 2007/0175482 A1 | 8/2007 | Kimmel et al. |
| 2007/0185383 A1 | 8/2007 | Mulhern et al. |
| 2007/0215162 A1 | 9/2007 | Glassenberg et al. |
| 2007/0226927 A1 | 10/2007 | Suzuki et al. |
| 2007/0234494 A1 | 10/2007 | Suzuki et al. |
| 2008/0011304 A1 | 1/2008 | Stewart et al. |
| 2008/0021273 A1 | 1/2008 | MacKin |
| 2008/0045801 A1 | 2/2008 | Shalman et al. |
| 2008/0098543 A1 | 5/2008 | Esquenet et al. |
| 2008/0105199 A1 | 5/2008 | Martin et al. |
| 2008/0141473 A1 | 6/2008 | Arai et al. |
| 2008/0142049 A1 | 6/2008 | Onishi et al. |
| 2008/0172033 A1 | 7/2008 | Keith et al. |
| 2008/0200761 A1 | 8/2008 | Schwartz et al. |
| 2008/0208000 A1 | 8/2008 | Schwarts et al. |
| 2008/0257355 A1 | 10/2008 | Rao et al. |
| 2008/0267688 A1 | 10/2008 | Busted |
| 2008/0281293 A1 | 11/2008 | Peh |
| 2009/0032016 A1 | 2/2009 | Law et al. |
| 2009/0044353 A1 | 2/2009 | Galantai et al. |
| 2009/0049627 A1 | 2/2009 | Kritzler |
| 2009/0062871 A1 | 3/2009 | Chin et al. |
| 2009/0099421 A1 | 4/2009 | Shalman et al. |
| 2009/0107503 A1 | 4/2009 | Baran |
| 2009/0118580 A1 | 5/2009 | Sun et al. |
| 2009/0119856 A1 | 5/2009 | Onishi |
| 2009/0143645 A1 | 6/2009 | Matthes |
| 2009/0149716 A1 | 6/2009 | Diao |
| 2009/0155770 A1 | 6/2009 | Brown et al. |
| 2009/0178681 A1 | 7/2009 | Bracken |
| 2009/0192355 A1 | 7/2009 | Mejia |
| 2009/0318757 A1 | 12/2009 | Singh |
| 2009/0320834 A1 | 12/2009 | Cuevas et al. |
| 2010/0010307 A1 | 1/2010 | Schramm |
| 2010/0036410 A1 | 2/2010 | Krolik |
| 2010/0069722 A1 | 3/2010 | Shalman et al. |
| 2010/0094090 A1 | 4/2010 | Mejia |
| 2010/0106102 A1 | 4/2010 | Ziebol et al. |
| 2010/0113916 A1 | 5/2010 | Kumar |
| 2010/0186748 A1 | 7/2010 | Morejon |
| 2010/0199448 A1 | 8/2010 | Vazales et al. |
| 2010/0199999 A1 | 8/2010 | Vazales et al. |
| 2011/0023885 A1 | 2/2011 | Vazales et al. |
| 2011/0023886 A1 | 2/2011 | Vazales et al. |
| 2011/0023887 A1 | 2/2011 | Vazales et al. |
| 2011/0023888 A1 | 2/2011 | Vazales et al. |
| 2011/0048427 A1 | 3/2011 | Zachar |
| 2011/0197894 A1 | 8/2011 | Morejon |
| 2011/0290246 A1 | 12/2011 | Zachar |
| 2012/0180791 A1 | 7/2012 | Ciccone |
| 2013/0023729 A1 | 1/2013 | Vazales et al. |
| 2013/0104884 A1 | 5/2013 | Vazales et al. |
| 2014/0012074 A1 | 1/2014 | Vazales et al. |
| 2014/0033455 A1 | 2/2014 | Vazales et al. |
| 2014/0090194 A1 | 4/2014 | Stadelman et al. |
| 2014/0090195 A1 | 4/2014 | Stadelman et al. |
| 2014/0090642 A1 | 4/2014 | Bagwell et al. |
| 2014/0150782 A1 | 6/2014 | Vazales et al. |
| 2014/0200554 A1 | 7/2014 | Vitullo et al. |
| 2014/0246015 A1 | 9/2014 | Einav et al. |
| 2015/0133864 A1 | 5/2015 | Zachar et al. |
| 2015/0343182 A1 | 12/2015 | Vazales et al. |

FOREIGN PATENT DOCUMENTS

| | | | |
|---|---|---|---|
| EP | 10739200.3 | 2/2010 | |
| EP | 11766438.3 | 10/2012 | |
| IN | 6745/DELNP/2011 | 2/2013 | |
| JP | 08-029699 | 2/1996 | |
| JP | 2006-026344 | 2/2006 | |
| WO | WO 94/03226 | 2/1994 | |
| WO | WO 9403226 A1 * | 2/1994 | ............ A61M 16/00 |
| WO | WO2012/131626 | 10/2012 | |
| WO | WO2012/176112 | 12/2012 | |
| WO | WO2013/030821 | 3/2013 | |

OTHER PUBLICATIONS

PCT/US2010/023400, Feb. 5, 2010, Methods for Cleaning Endotracheal Tubes.
U.S. Appl. No. 12/748,326, filed Mar. 26, 2010, Devices for Cleaning Endotracheal Tubes.
U.S. Appl. No. 13/775,024, filed Feb. 22, 2013, Cleaning of Body-Inserted Medical Tubes.
U.S. Appl. No. 12/849,672, filed Aug. 3, 2010, Mechanically-Actuated Endotracheal Tube Cleaning Device.
U.S. Appl. No. 12/850,476, filed Aug. 4, 2010, Medical Tube Cleaning Apparatus.
U.S. Appl. No. 12/850,563, filed Aug. 4, 2010, Methods for Removing Debris From Medical Tubes.
U.S. Appl. No. 12/850,549, filed Aug. 4, 2010, Methods for Tracheostomy Visualization.
U.S. Appl. No. 13/924,835, filed Jun. 24, 2013, Visualization Systems and Methods.
PCT/US2011/030229, Mar. 28, 2011, Airway Cleaning and Visualization.
U.S. 13/638,567, filed Sep. 28, 2012, Methods for Confirming Placement of Endotracheal Tubes.
U.S. Appl. No. 13/662,313, filed Oct. 26, 2012, Endotracheal Tube Coupling Adapters.
PCT/US2012/062296, Oct. 26, 2012, Endotracheal Tube Coupling Adapters.
Product/Catalog of EndoSheath® Technology in 2 pages. Vision Sciences [retrieved in Mar. 2010; Publication Date Unavailable]; retrieved at www.visionsciences.com/Swappid/96/SubPageID/32590.
Product/Catalog of Endoscopy Systems and EndoSheath® Technologies—BRS-5000 Flexible Digital Video Bronchoscope in 2 pages. Vision Sciences [retrieved in Mar. 2010; Publication Date Unavailable]; retrieved at www.visionsciences.com/SWAPPID/96/SubPageID/38845.
Healthcare Professionals Distribution Pulmonology, Global in 3 pages. Vision Sciences [retrieved in Mar. 2010; Publication Date Unavailable]; retrieved at www.visionsciences.com/Swappid/96/SubPageID/39771.
Conti, G., et al., A new device to remove obstruction from endotracheal tubes during mechanical ventilation in critically ill patients, Intensive Care Medicine, Sep. 1994, pp. 573-576; vol. 20.
Wilson et al., Increases in Endotracheal Tube Resistance Are Unpredictable Relative to Duration of Intubation. Manuscript received Aug. 7, 2008. Chest, vol. 136, p. 1006-1013, Oct. 2009 Issue.
Product brochure in 2 pages for GlideScope® Cobalt of Verathon Medical, Inc., dated 2010.
Product brochure in 2 pages For Rescue Cath™ Complete Airway Management (CAM) Catheters of Omneotech, dated 2010.
Product information for CAM Endotrach Cath™ and CAM Rescue Cath™ catheter systems and other general information in 35 pages retrieved on Apr. 6, 2010 from the Omneotech website at www.omneotech.com.
Glass, Connie et al., Endotracheal Tube Narrowing After Closed-System Suctioning: Prevalence and Risk Factors, American Journal of Critical Care, vol. 8, No. 2, pp. 93-100 (Mar. 1999).
Inglis, Timothy J.J. et al, Tracheal Tube Biofilm as a Source of Bacterial Colonization of the Lung, Journal of Clinical Microbiology, vol. 27, No. 9, pp. 2014-2018 (Sep. 1989).

(56) References Cited

OTHER PUBLICATIONS

Kawati, Rafael MD et al, Peak Airway Pressure Increase Is a Late Warning Sign of Partial Endotracheal Tube Obstruction Whereas Change in Expiratory Flow Is an Early Warning Sign, Anesth Analg., vol. 100, pp. 889-893 (2005).
El-Khatib, M.F. et al., Changes in resistances of endotracheal tubes with reductions in the cross-sectional area, European Journal of Anaesthesiology, vol. 25, pp. 275-279 (2008).
Shah, Chirag MD et al., Endotracheal tube intraluminal vol. loss among mechanically ventilated patients. Crit. Care Med, vol. 32, No. 1, pp. 120-125 (2004).
Van Surell, Catherine et al., Acoustic Method to Estimate the Longitudinal Area Profile of Endotracheal Tubes, Am J Respir Crit Care Med, vol. 149, pp. 28-33 (1994).
Boque, MC et al. Endotracheal tube intraluminal diameter narrowing after mechanical ventilation: use of acoustic reflectometry, Intensive Care Med vol. 30, pp. 2204-2209 (2004).
Apostolopoulou, Eleni Ph.D. et al., Incidence and Risk Factors for Ventilator-Associated Pneumonia in 4 Multidisciplinary Intensive Care Units in Athens, Greece, Respiratory Care, vol. 48, No. 7, pp. 681-688 (Jul. 2003).
Seckel, Maureen, Implementing Evidence-Based Practice Guidelines to Minimize Ventilator-Associated Pneumonia (2005).
Berra, Lorenzo et al.; A clinical assessment of the Mucus Shaver; Crit Care Med 2012 vol. 40, No. 1; pp. 119-124.

\* cited by examiner

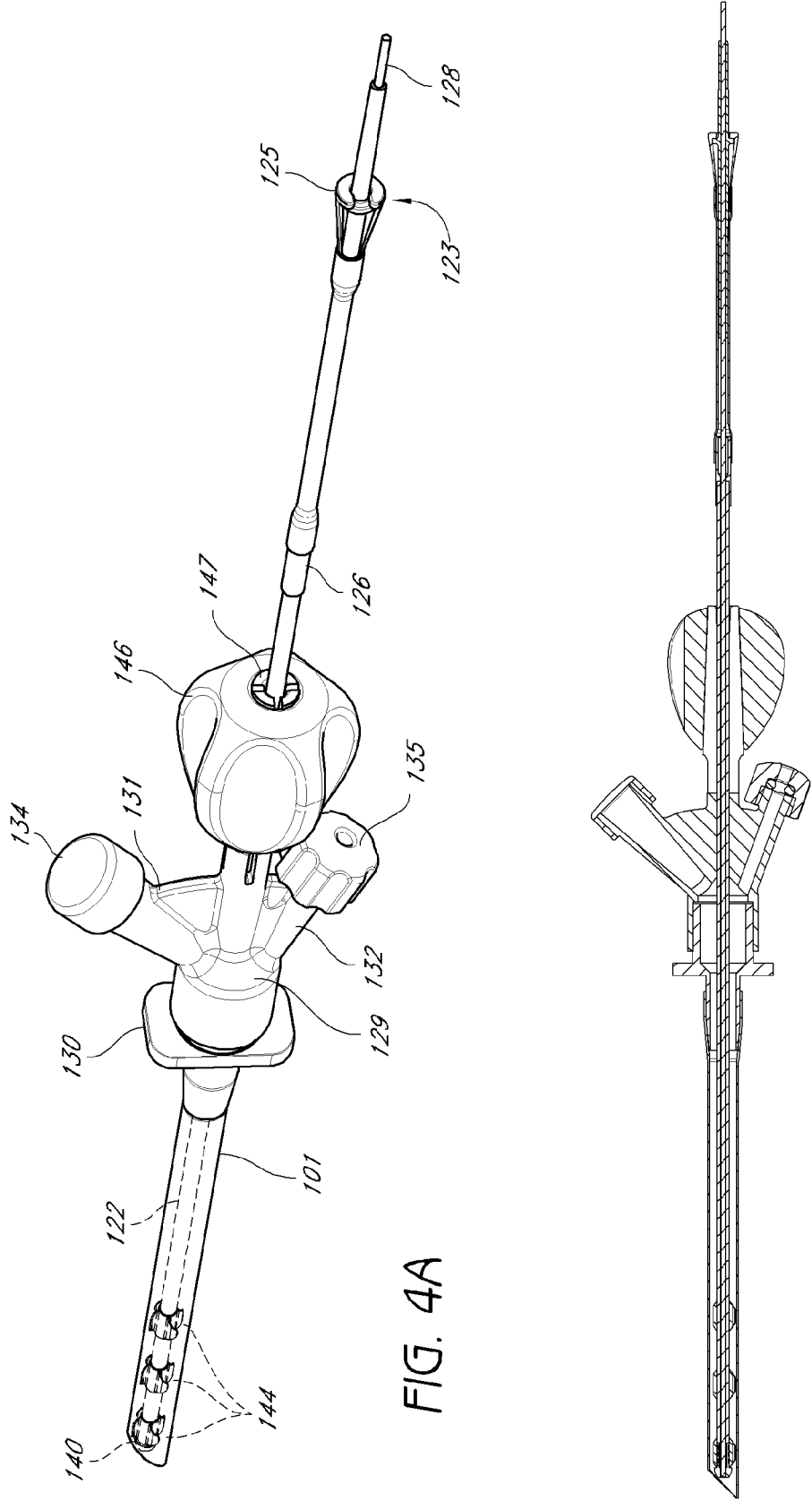

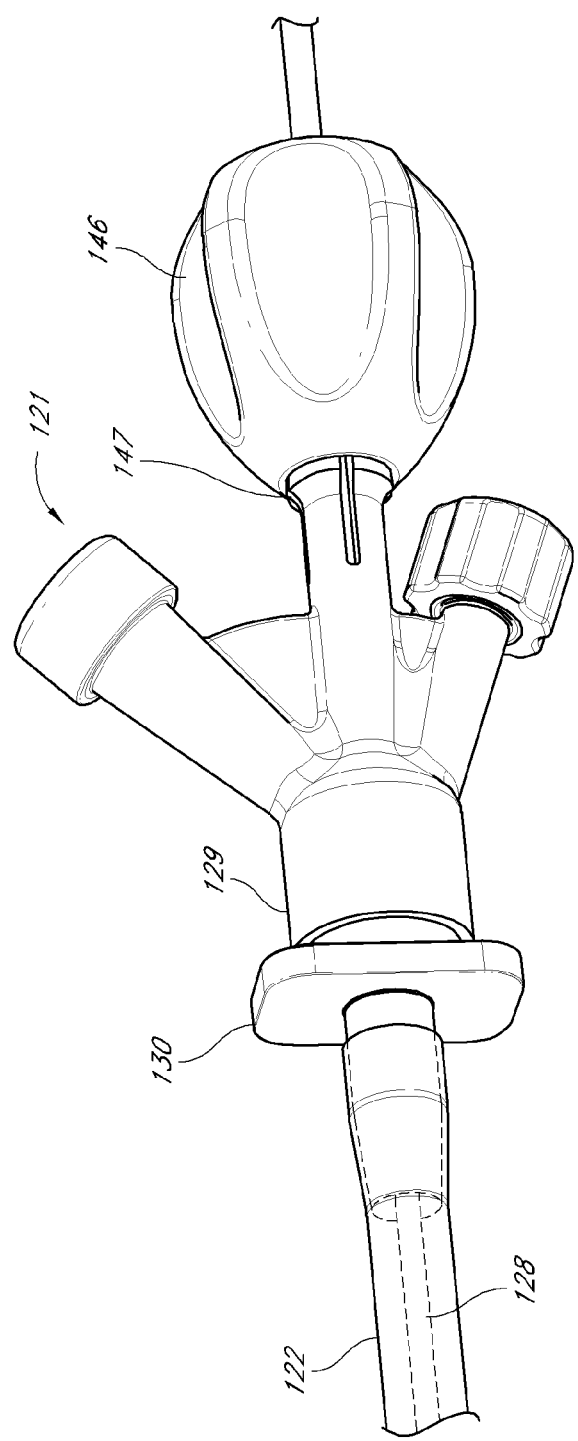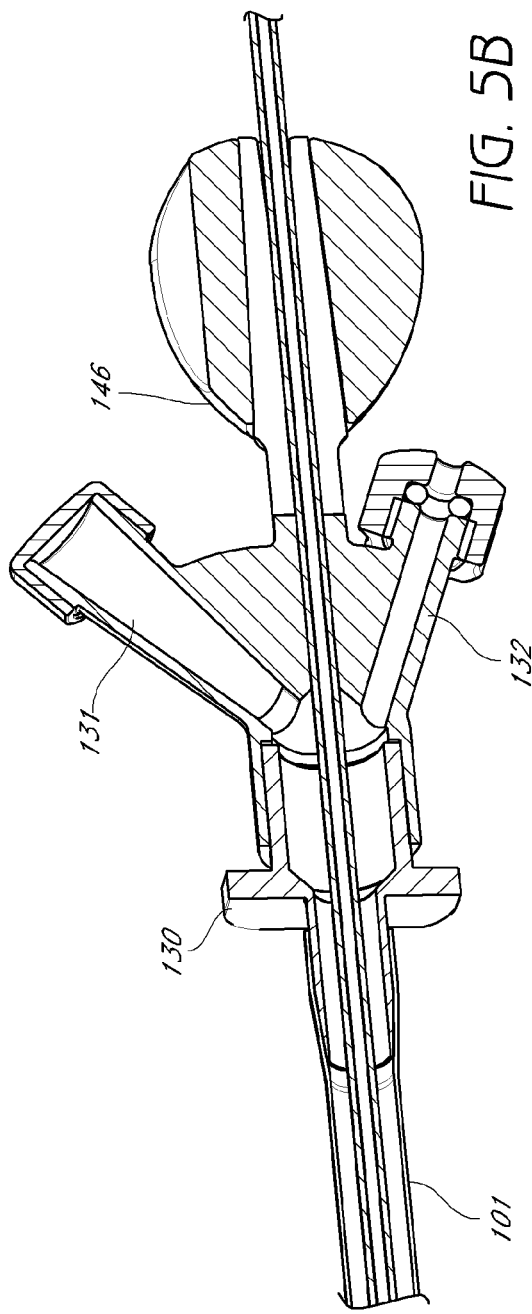
FIG. 5A
FIG. 5B

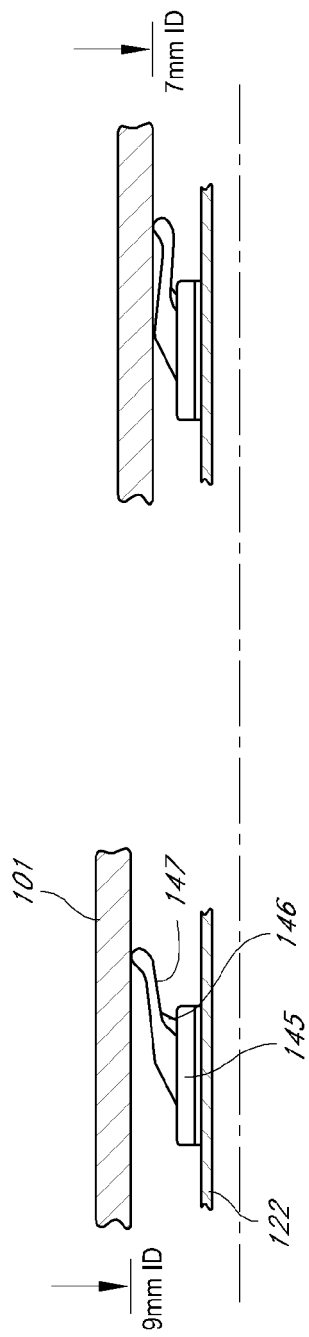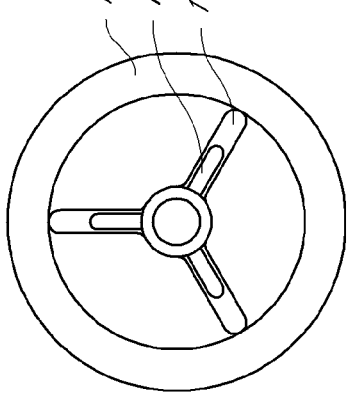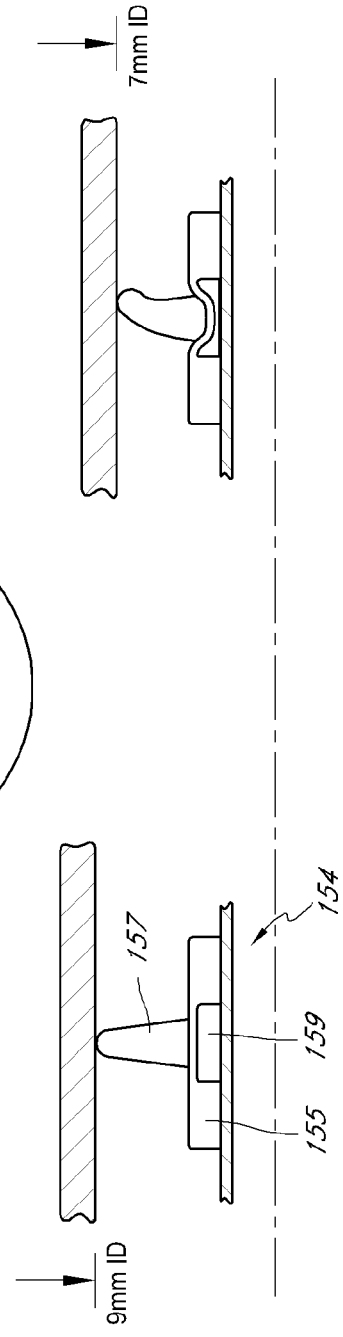

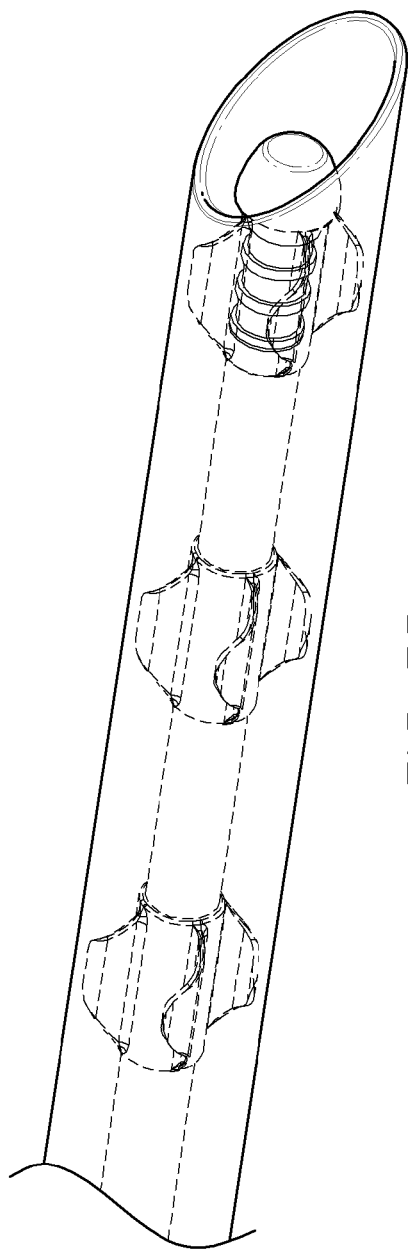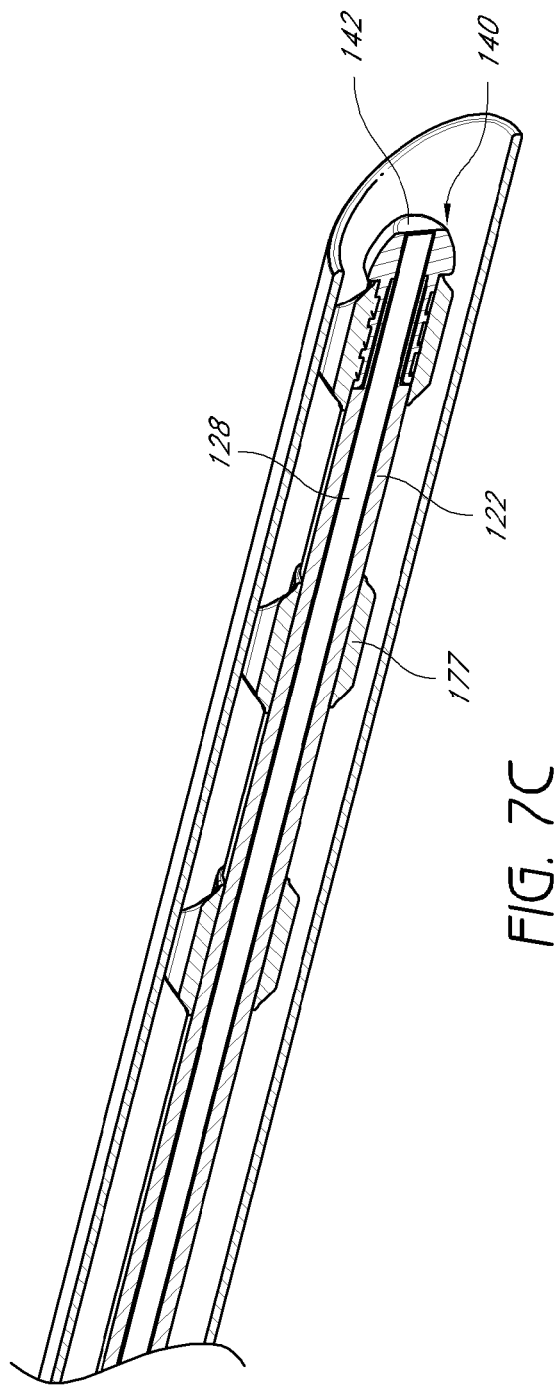
FIG. 7B
FIG. 7C

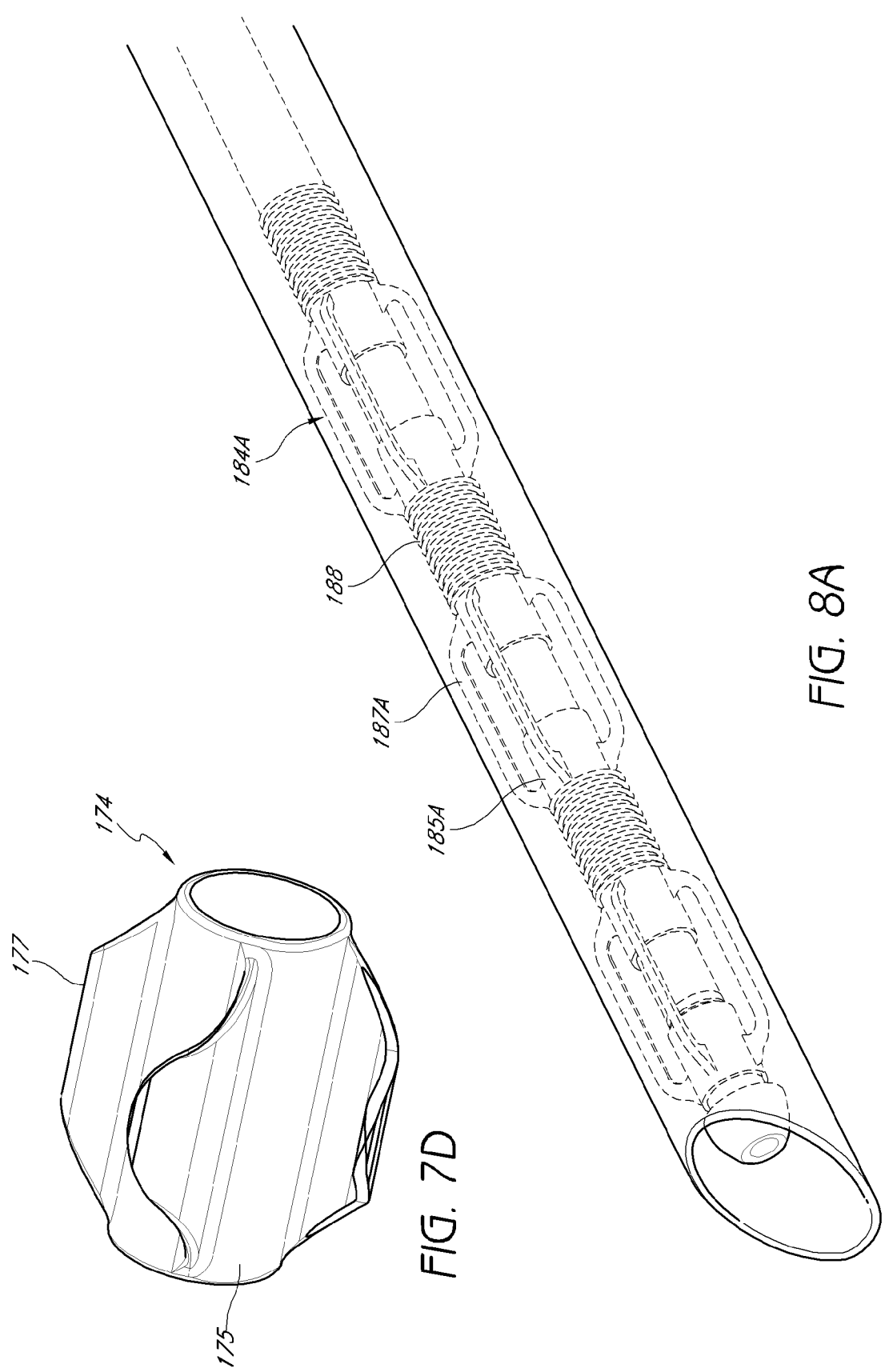

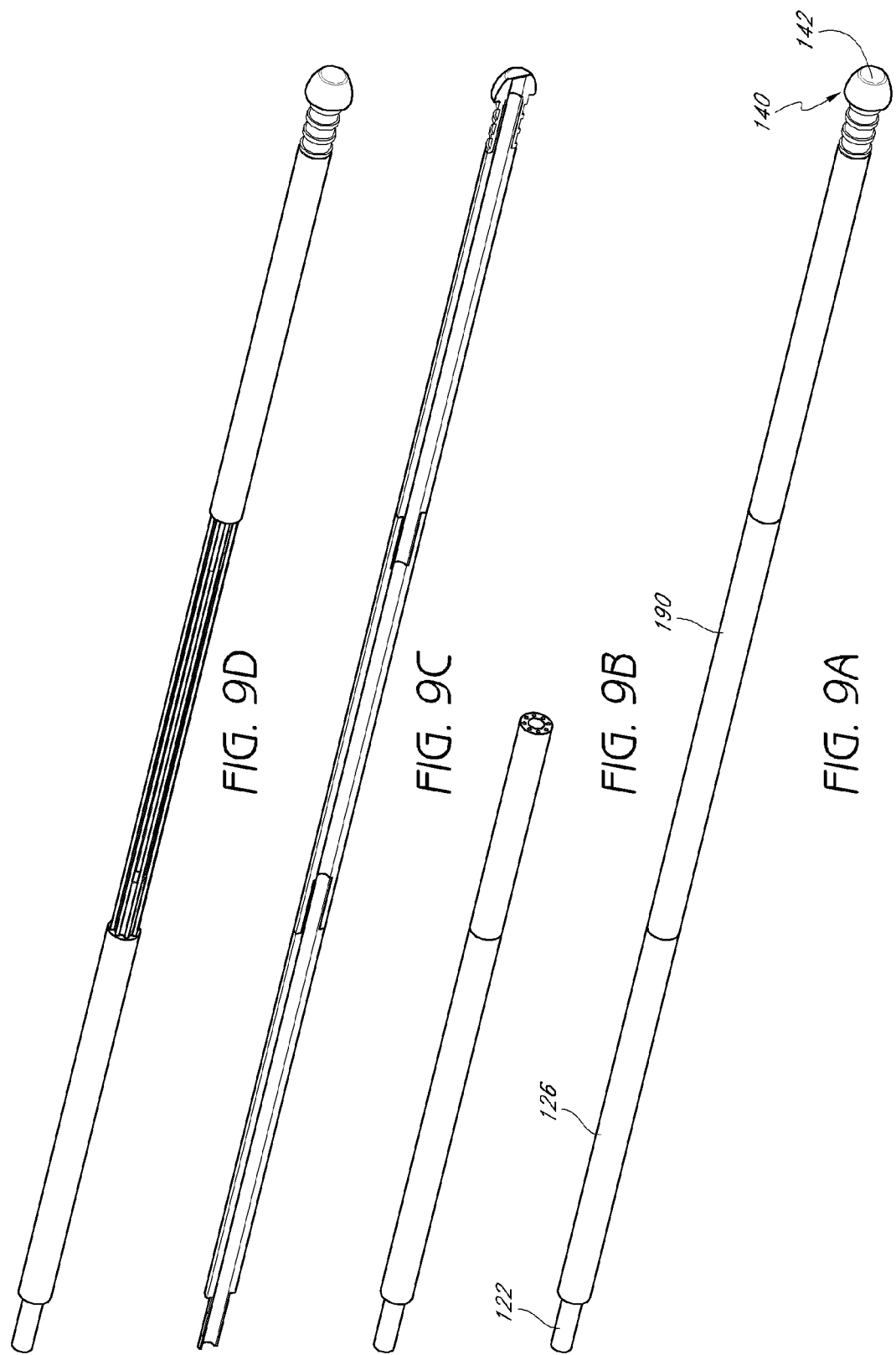

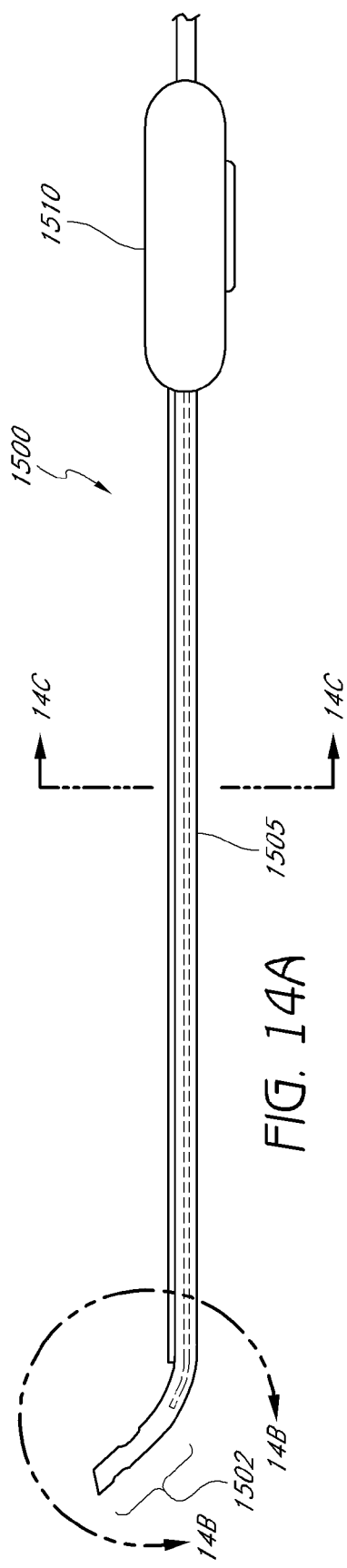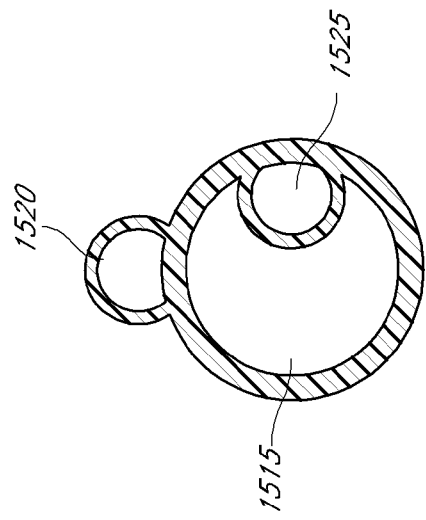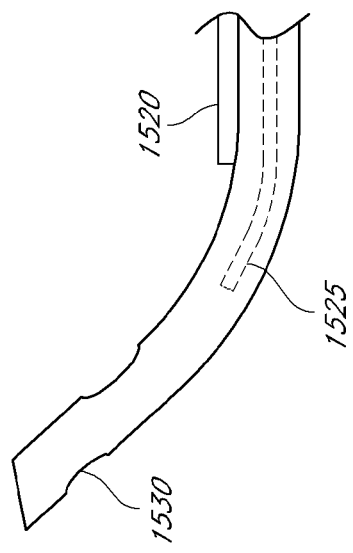
FIG. 14A
FIG. 14B
FIG. 14C

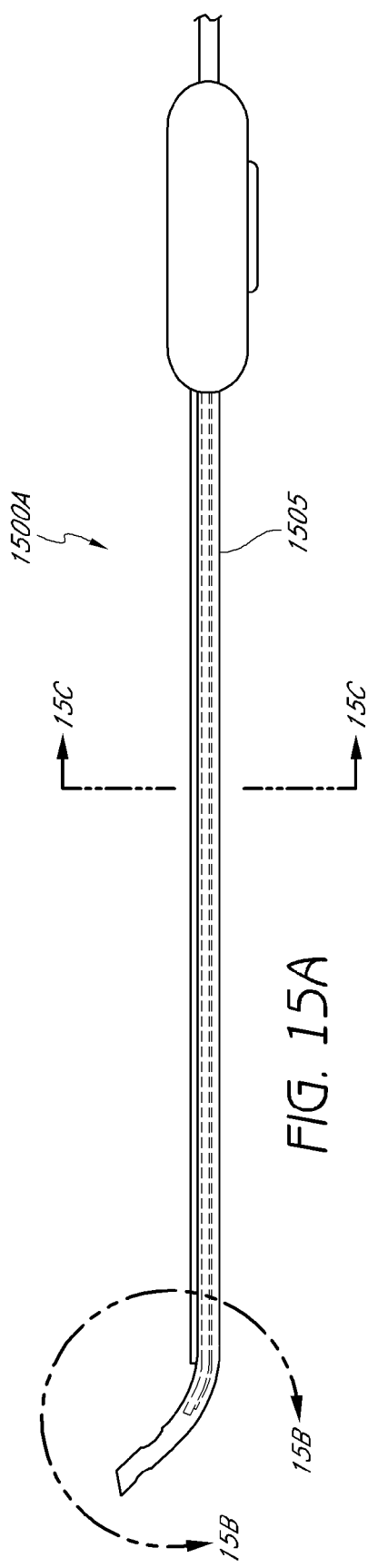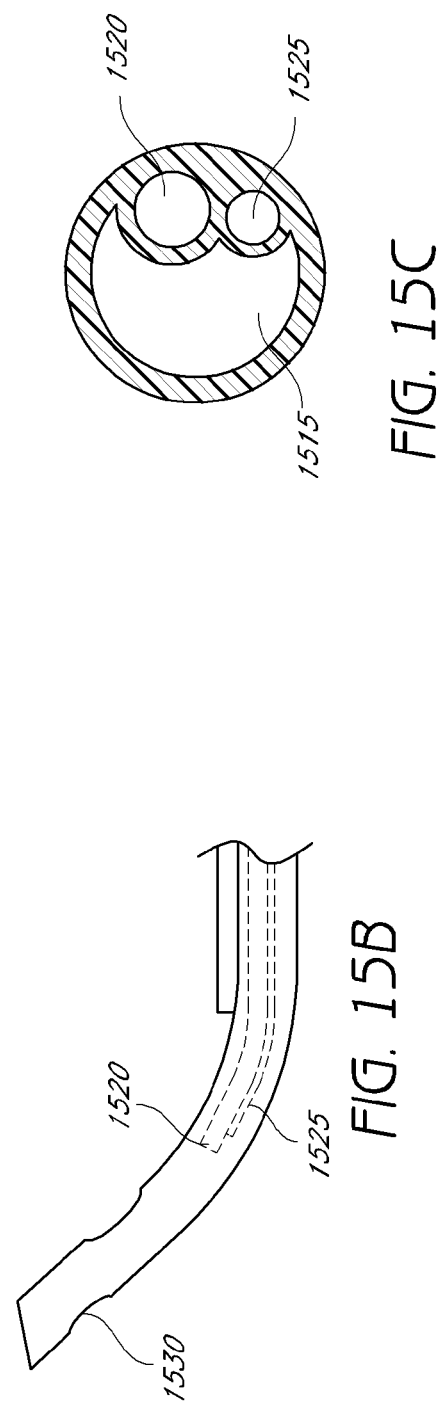
FIG. 15A
FIG. 15B
FIG. 15C

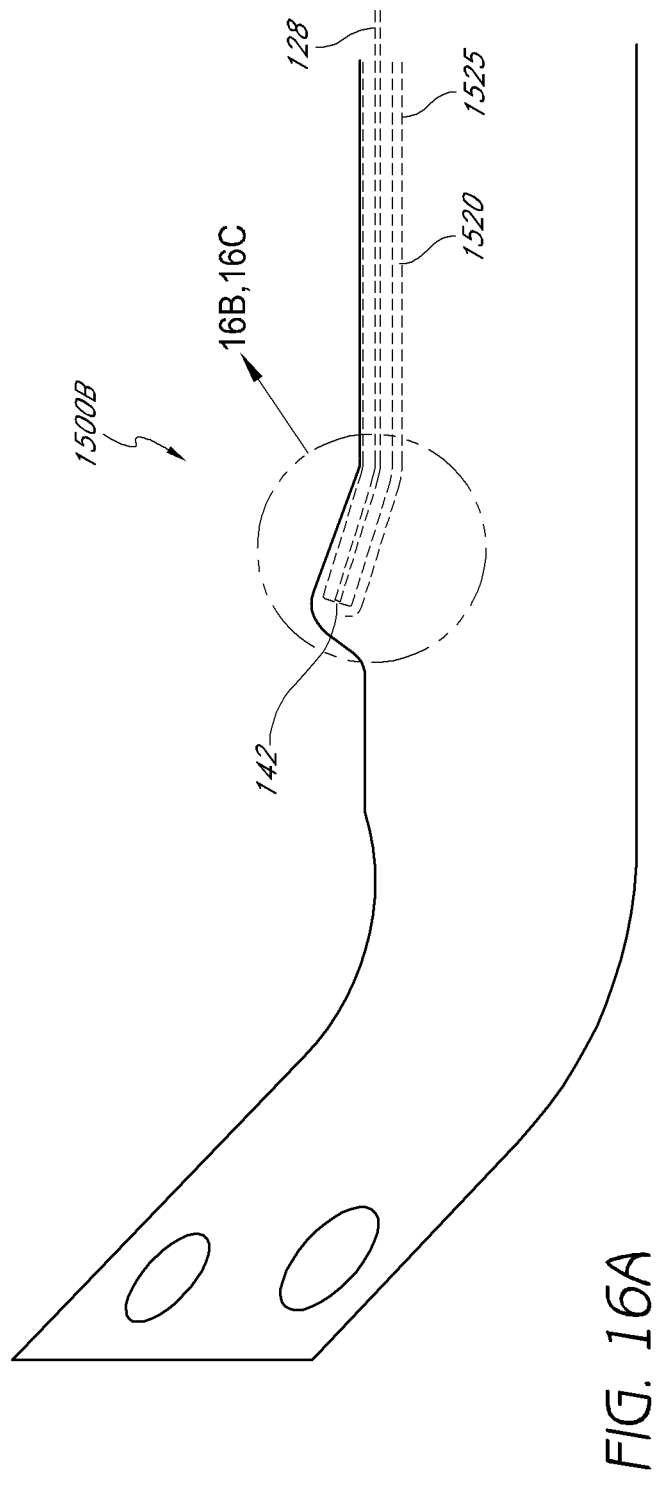
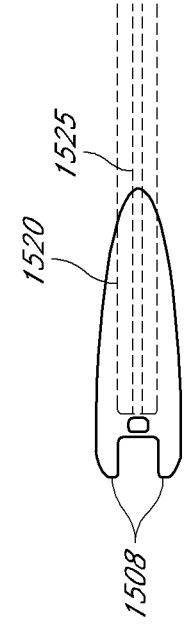
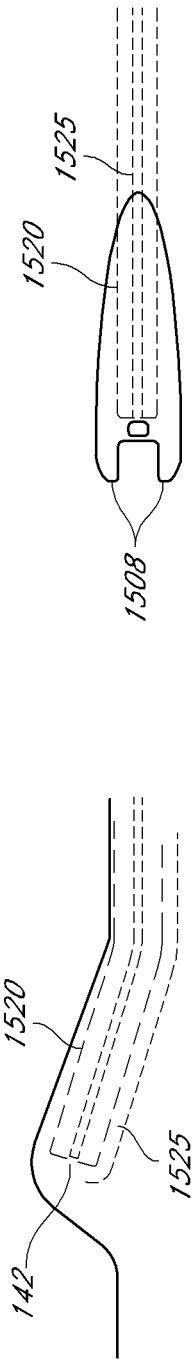
FIG. 16A
FIG. 16B
FIG. 16C

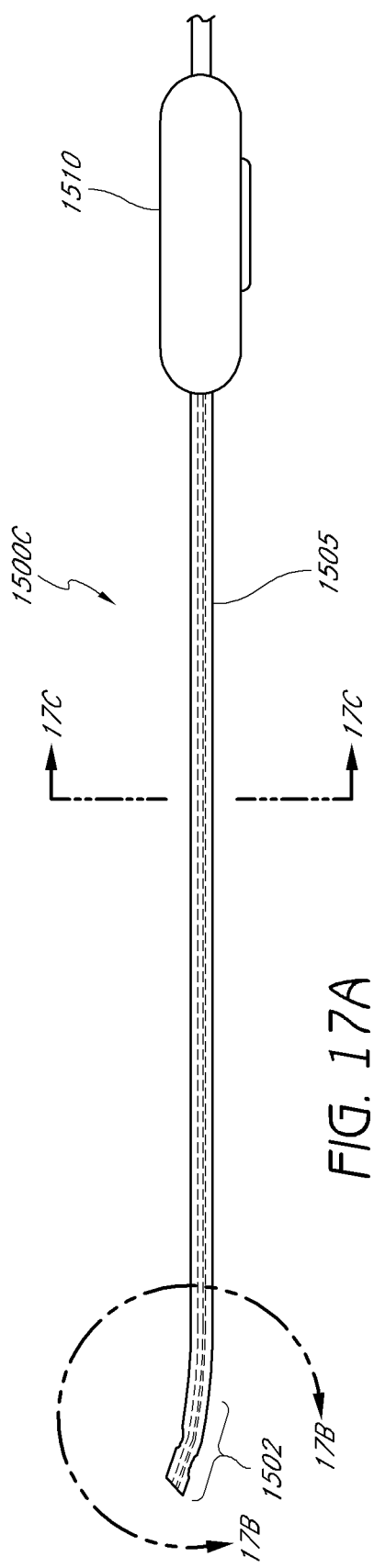
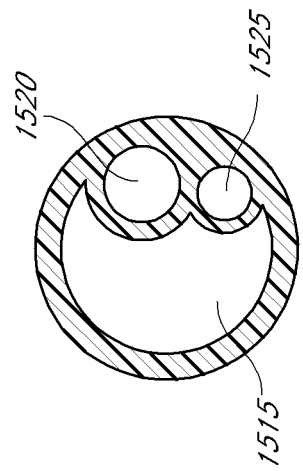
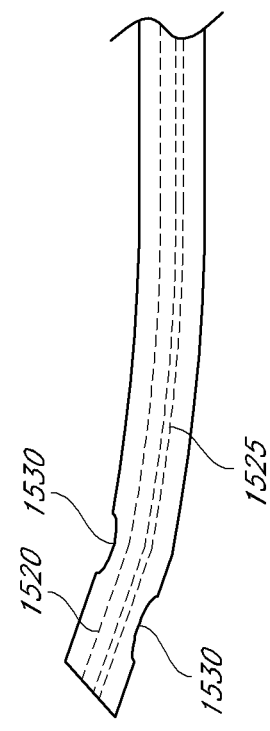
FIG. 17A
FIG. 17B
FIG. 17C

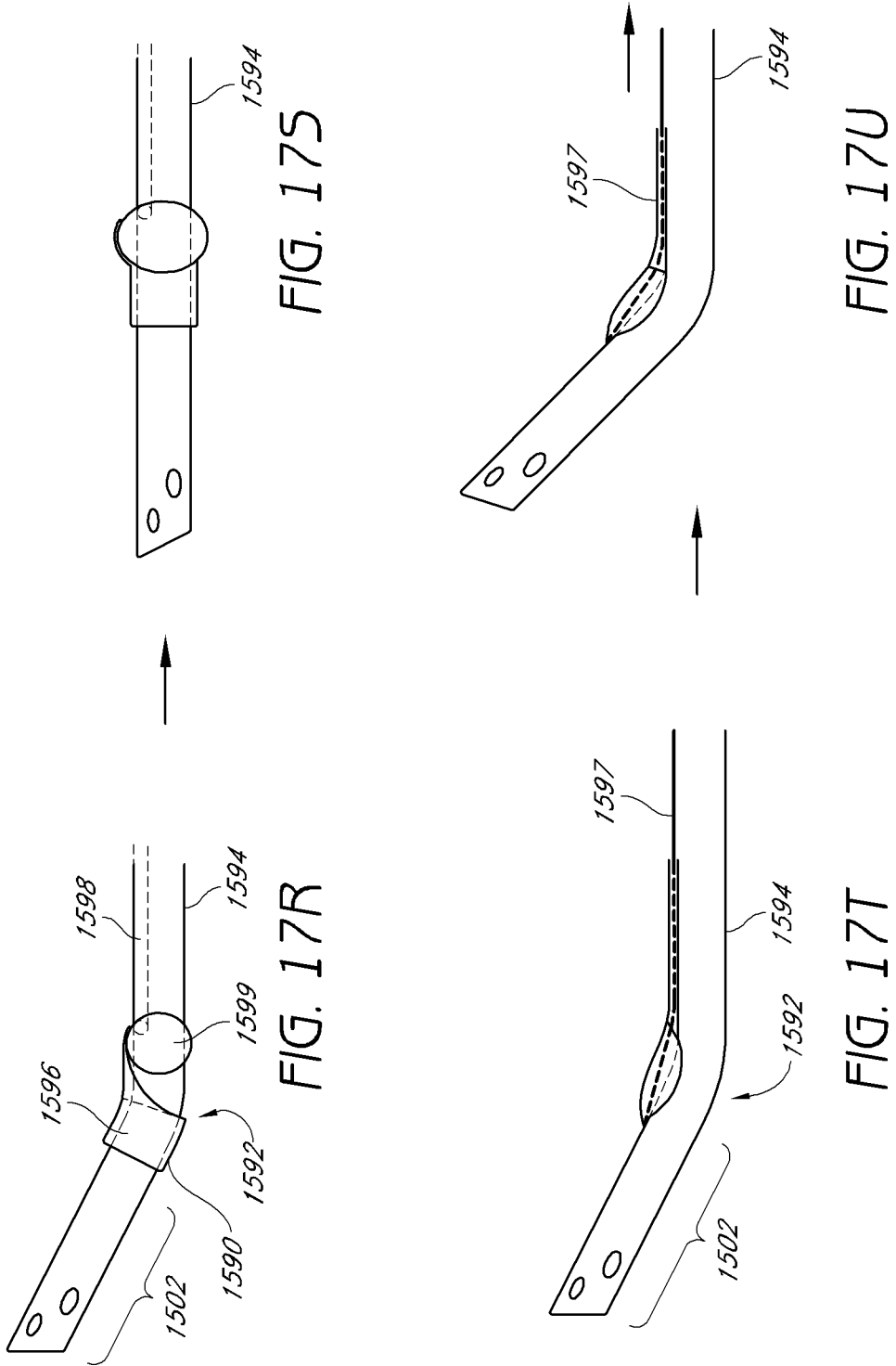

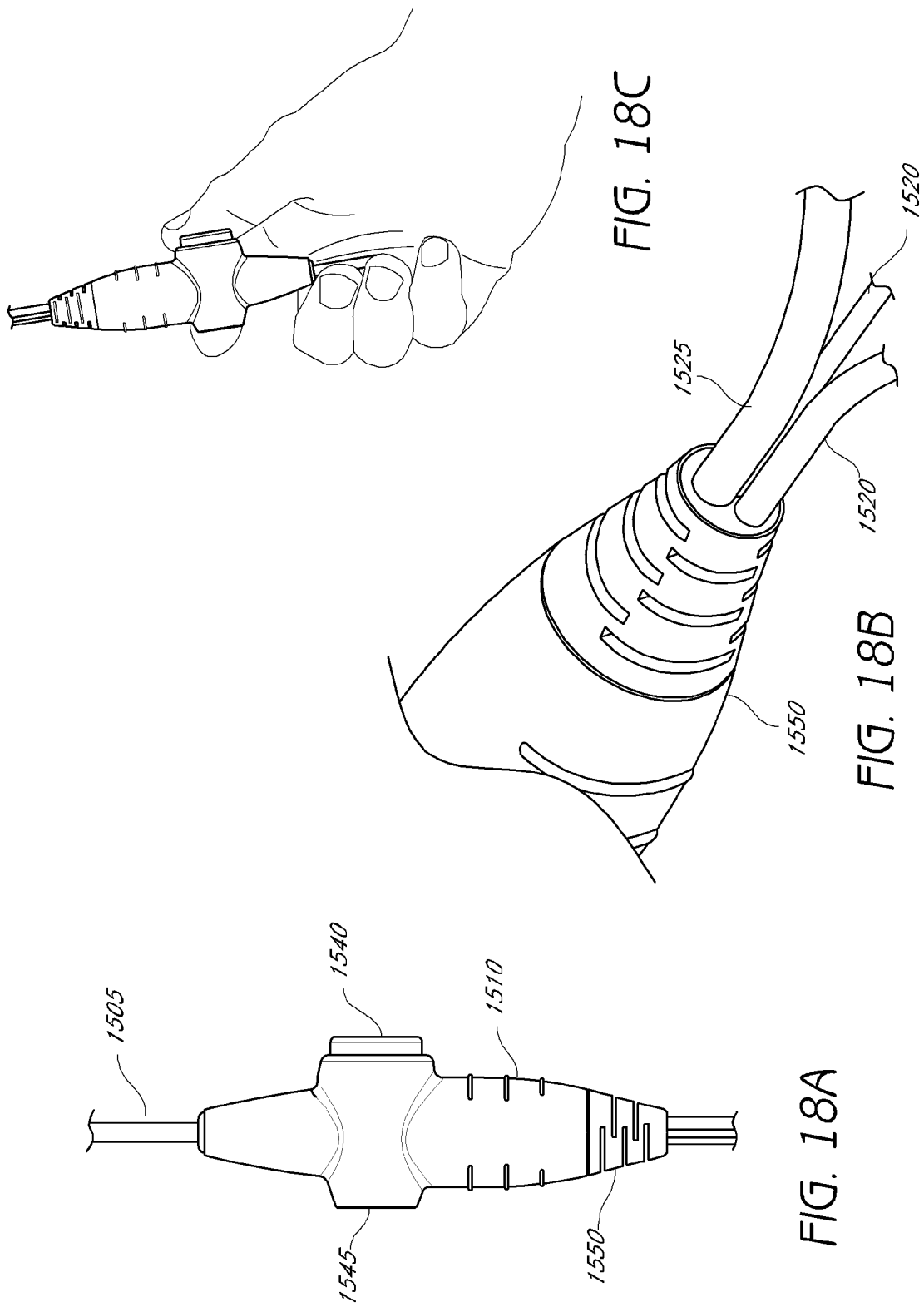

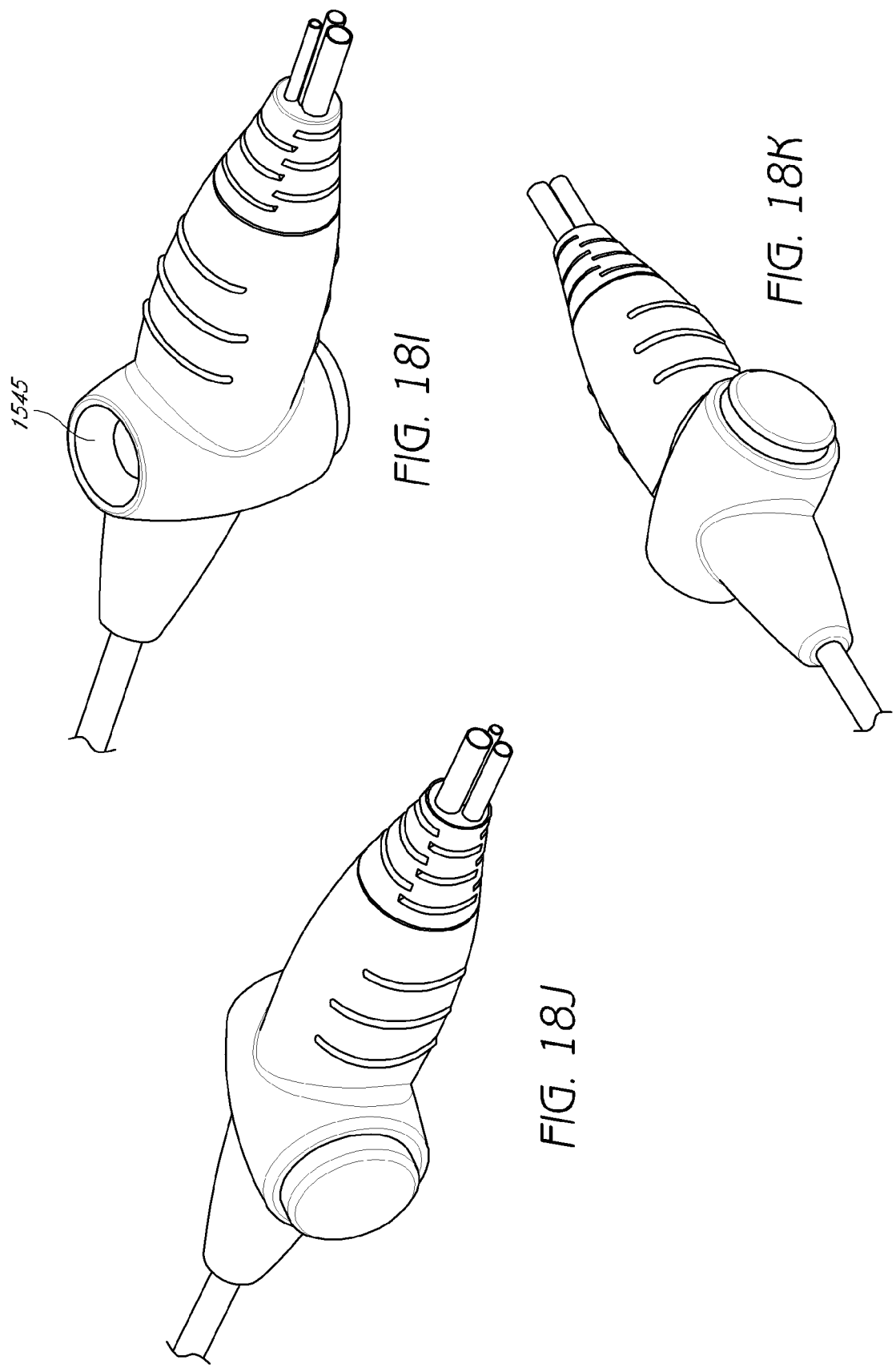

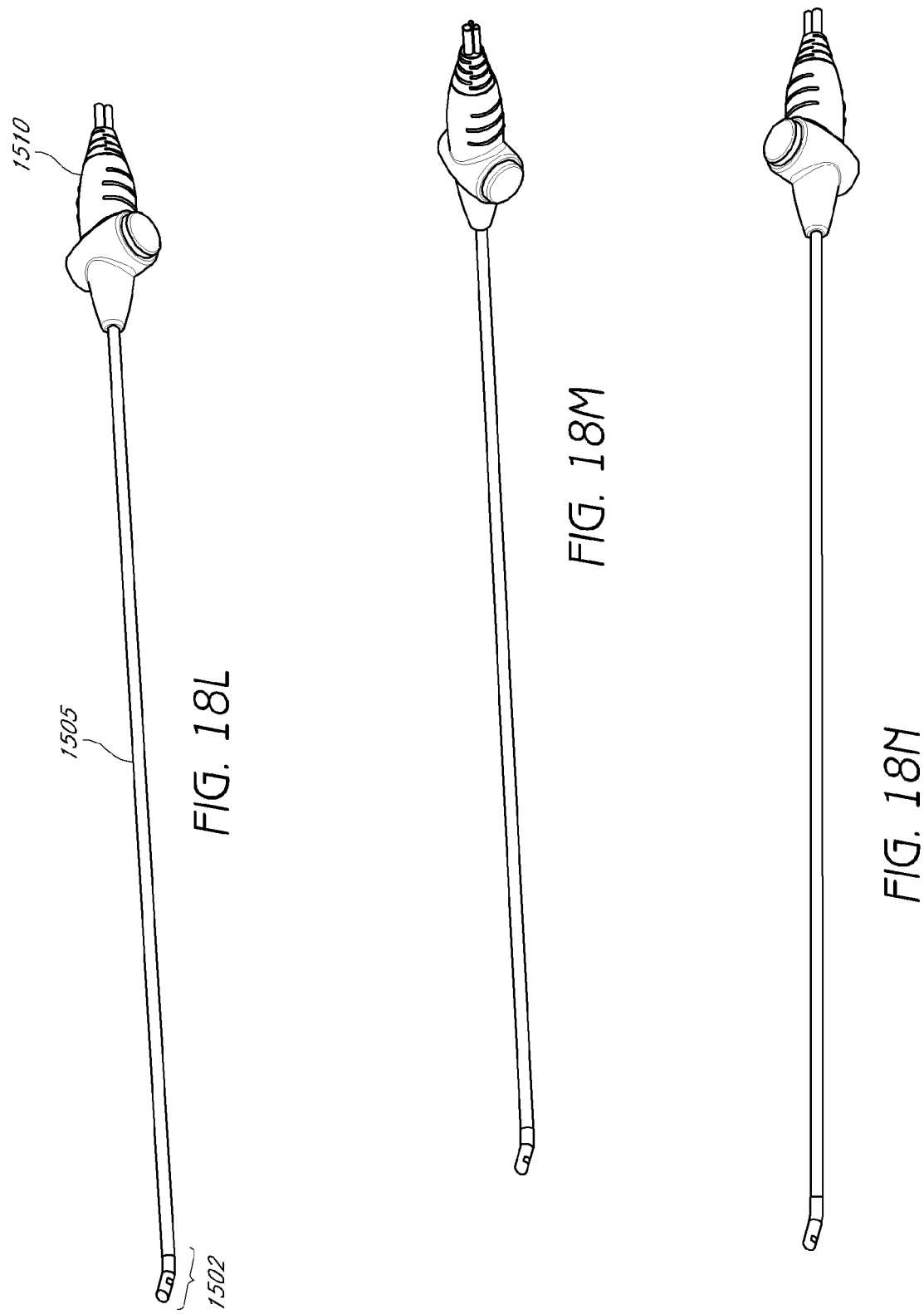

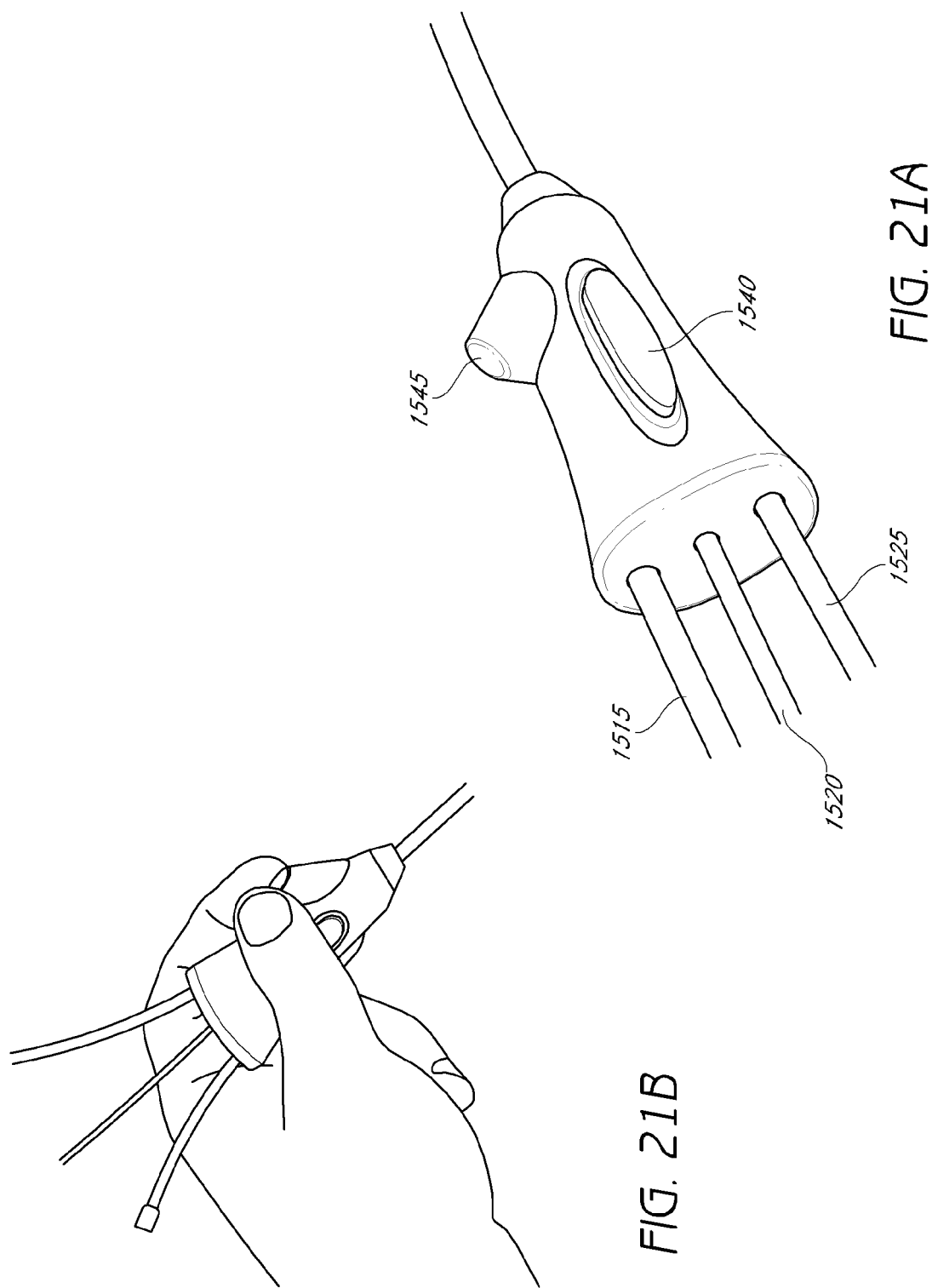

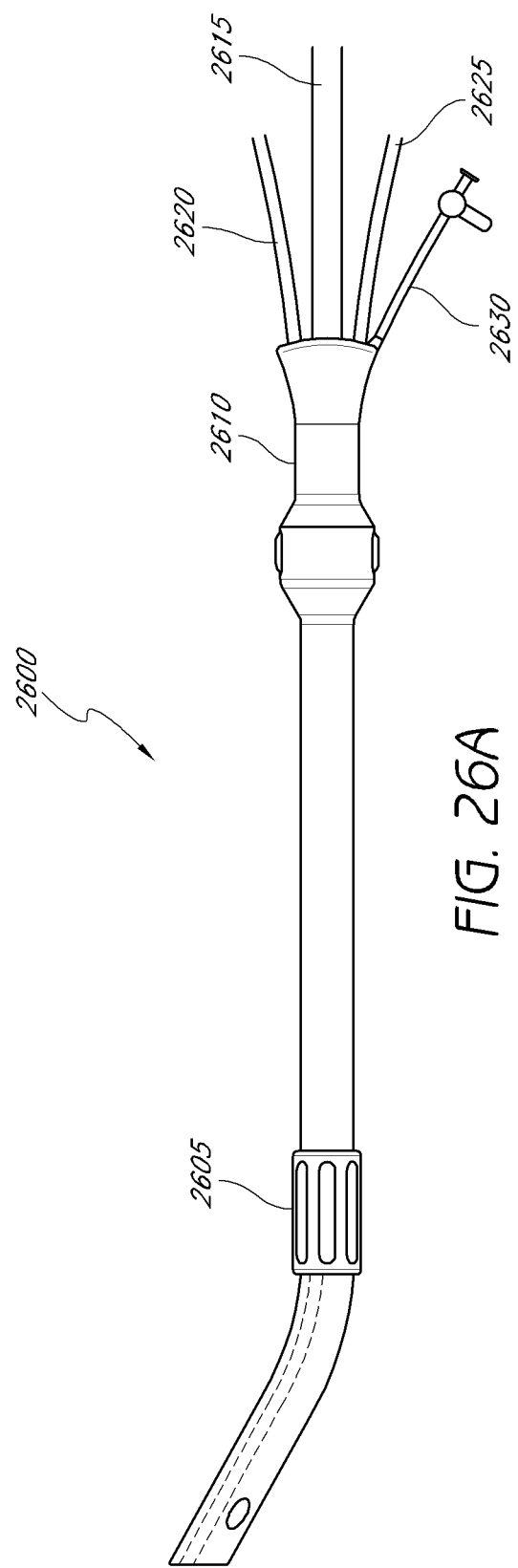

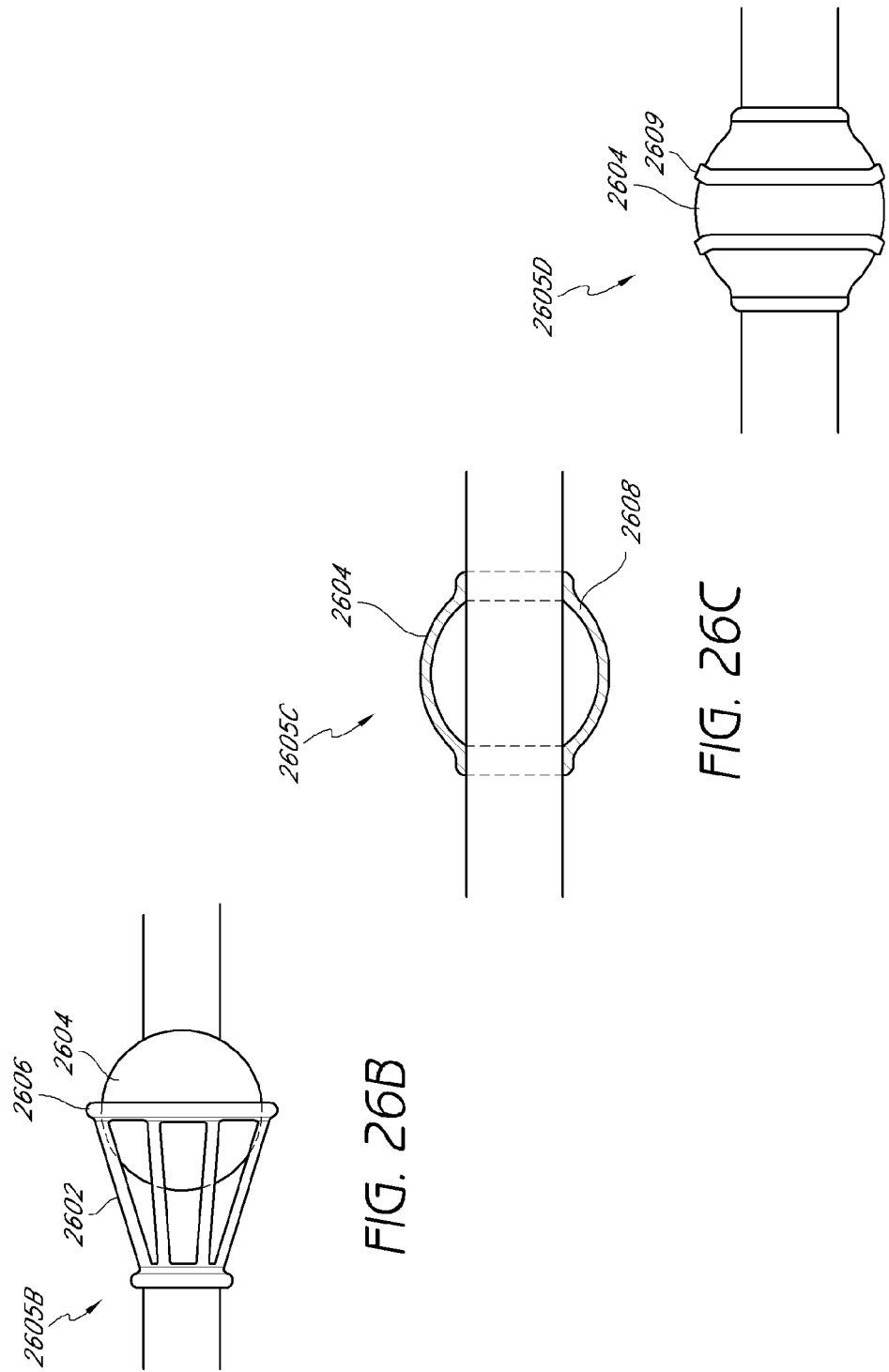

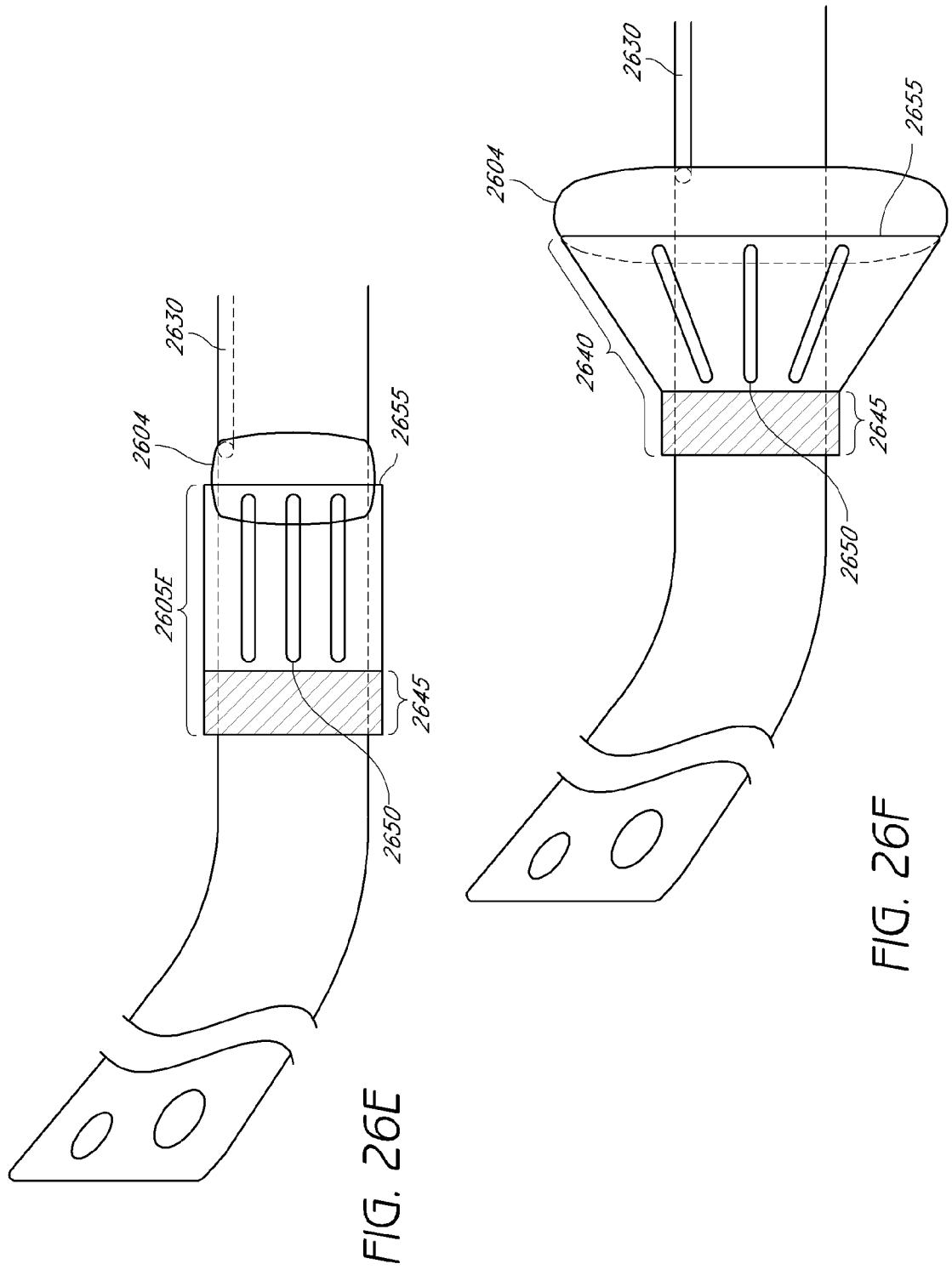

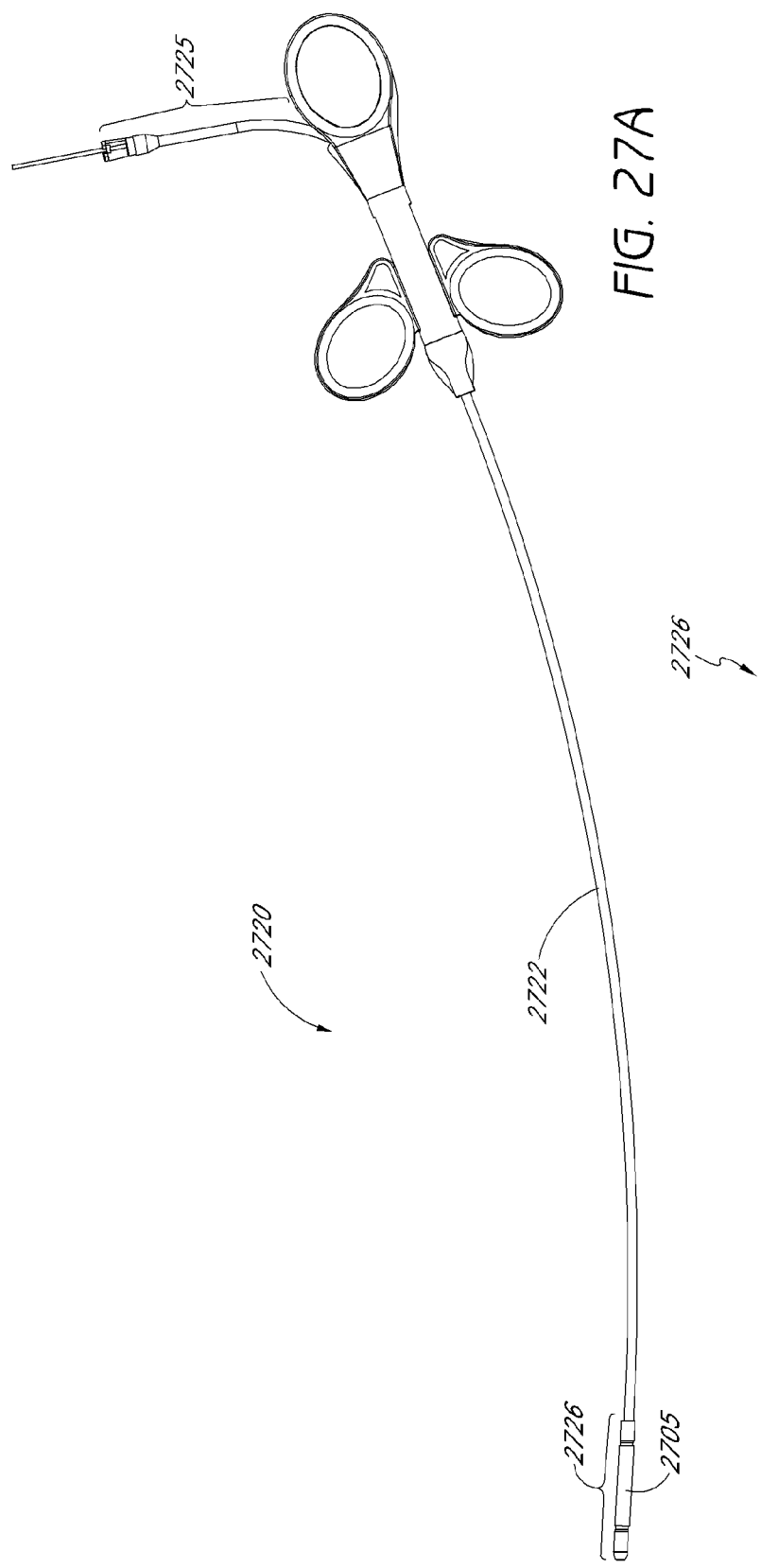
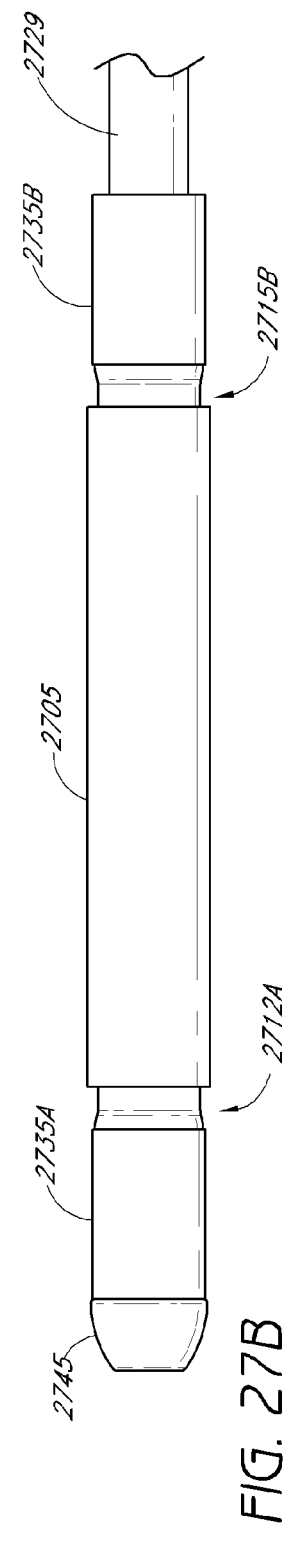

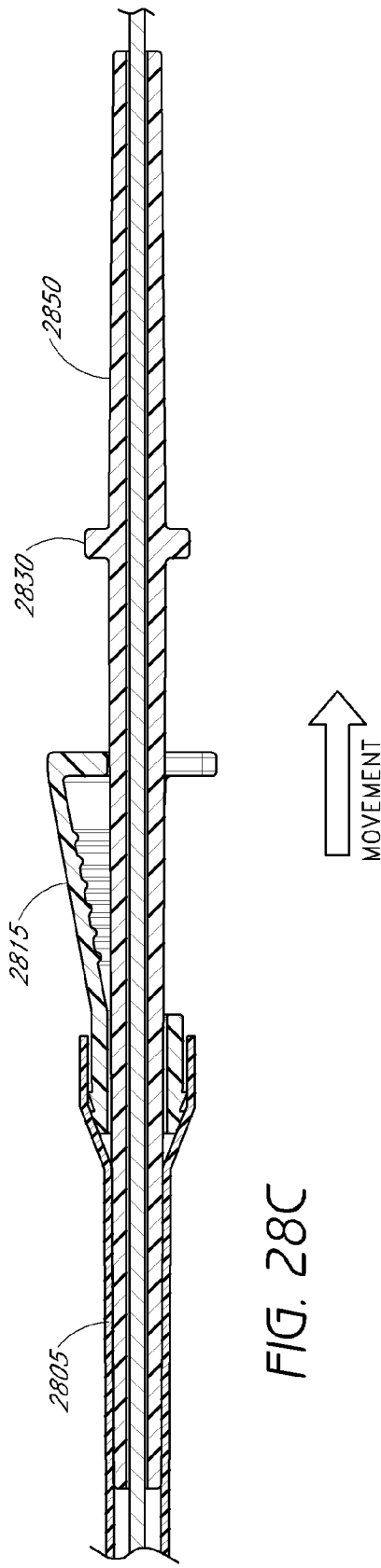
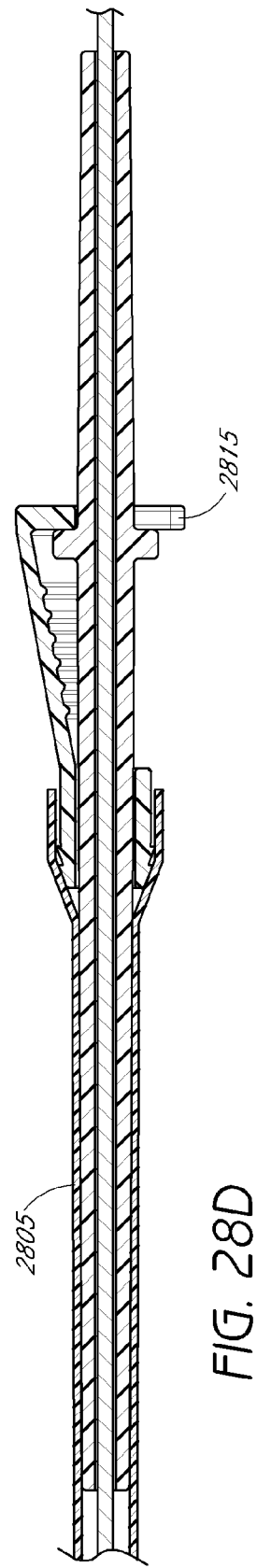
FIG. 28C
FIG. 28D

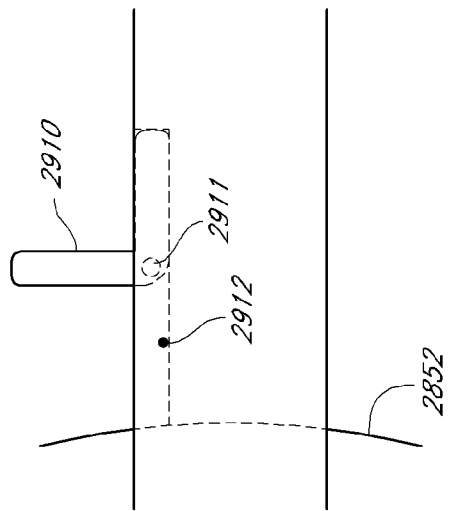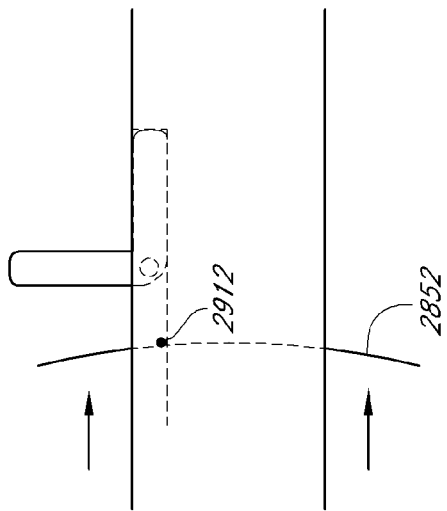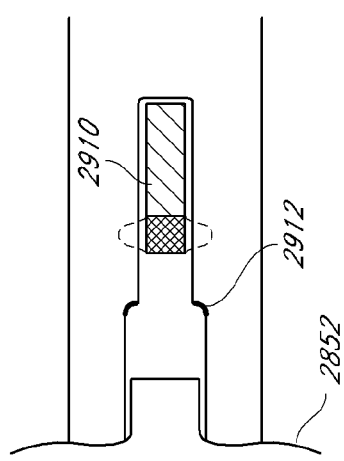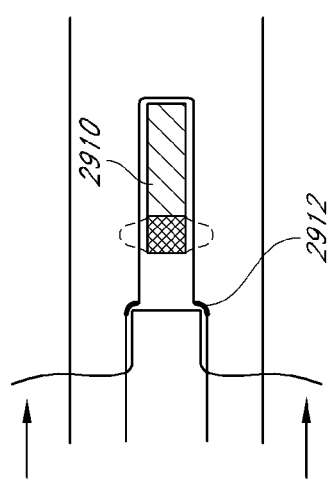

VISUALIZED ENDOTRACHEAL TUBE PLACEMENT SYSTEMS

CROSS-REFERENCE TO RELATED APPLICATIONS

This application is a continuation of U.S. patent application Ser. No. 13/638,567, which is a United States National Phase application filed under 35 U.S.C. §371 of International Application No. PCT/US2011/030229, filed Mar. 28, 2011, which (1) claims priority to U.S. Provisional Application No. 61/318,761, filed Mar. 29, 2010, and U.S. Provisional Application No. 61/370,425, filed Aug. 3, 2010; and (2) is a continuation-in-part of U.S. application Ser. No. 12/849,672, filed Aug. 3, 2010, the disclosures of each of which are hereby incorporated by reference herein.

FIELD

Embodiments disclosed herein relate generally to cleaning and/or visualization of native airways and other anatomical passages, and more specifically, to removal of pooled secretions or debris from and/or verification of positioning and placement of body-inserted tubes within one or more native airways of a patient.

BACKGROUND

During an intubation procedure, endotracheal tubes can be placed in patients who are unable to effectively maintain life-sustaining ventilation and respiration on their own. Use of an endotracheal tube is appropriate when the integrity of the airway is, or may become, challenged due to trauma or pathology, or if a patient cannot otherwise breathe unaided. Often the endotracheal tube is coupled to a mechanical ventilator to aid the patient's respiration, and can be expected to remain in situ for an extended time until the patient is once again able to breathe on his or her own. The endotracheal tubes can be inserted within a patient's native airway for short periods of time (e.g., for a matter of hours during anesthesia for surgery) or the endotracheal tubes can remain in place to provide ventilator-assisted breathing for days or weeks.

The institution of mechanical ventilation can result in increased production of secretions within the patient's native airway. The insertion of an endotracheal tube within the patient's airway removes the normal cough mechanism for clearing of secretions. The secretions, therefore, can pool in dependent portions of the lung over time due to gravity and, if not removed in a timely manner, can result in ventilator-acquired pneumonia (VAP) or other undesired conditions or ailments. Because the cough mechanism is not intact, invasive removal is required to remove the pooled secretions with a suction catheter.

The insertion of endotracheal tubes is often performed in emergency situations, which can result in inappropriate placement of the endotracheal tube. Inappropriate placement of the endotracheal tube within the patient can result in severe clinical compromise of the intubated patient and, in some instances, can lead to severe injury or death if not corrected. The most commonly reported errors in positioning include positioning the tube in the esophagus, introducing the endotracheal tube beyond the carina with the tip in the right main stem bronchus, and not introducing the tube far enough such that the endotracheal tube balloon is inflated at the level of the vocal cords or just proximal thereto.

SUMMARY

According to some embodiments, the devices and/or systems disclosed herein are advantageously disposable and relatively inexpensive to manufacture. Thus, such embodiments do not require subsequent cleaning, sterilization, and repackaging. Some embodiments are advantageous because they can be performed via the natural airway of a patient while a patient undergoes assisted ventilation utilizing an endotracheal or tracheostomy tube. Several embodiments provide high quality optics and imaging while being easy to use without extensive, specialized training. Some embodiments of the inventions include low-cost visualization members, elements, or scopes that can be reused many times (e.g., 20-200 times) to provide high quality optics and visualization at a very low cost per use, thereby enabling hospitals or other patient care facilities to provide better, more cost effective, health care.

In some embodiments, the devices, methods and systems described herein facilitate intubation by direct visualization of the patient's native airway as the endotracheal tube is inserted and/or provide for confirmation of the position of the endotracheal tube within the native airway (e.g., trachea) after insertion of the endotracheal tube. In some embodiments, an image of the position is obtained to document the position for the patient's medical record and is stored in a memory device. The embodiments described herein advantageously obviate the need to perform a chest x-ray of the patient to confirm the position of the endotracheal tube. Depending on how busy the x-ray department is at the time and other unpredictable factors, such as time of day and number of personnel available, a confirmatory chest x-ray can take a relatively long time to be obtained and interpreted, which can seriously threaten the survival of an acutely ill patient. In addition, chest x-rays are relatively expensive and expose the patient to unnecessary or undesirable radiation.

In some embodiments, a visualization tube, or sheath, is provided that comprises one or more stabilizing assemblies for guiding the introduction of the visualization tube into an endotracheal tube or other body-inserted tube and for stabilizing (e.g., centering) the visualization tube within the endotracheal tube. One or more viewing fibers and one or more illumination fibers of a fiber optic scope can be inserted within a central lumen of the visualization tube to view the trachea and portions of the lungs beyond the distal end of the endotracheal tube for confirming and documenting the proper placement of the endotracheal tube. In some embodiments, the visualization tube, or sheath, has a closed distal end and an open proximal end, with the distal end having a window less than 0.012 inches in thickness. The visualization tube can be preformed to match the general shape of an endotracheal tube and can have wings, tines, or stabilizers protruding from its outer surface to effectively center the visualization tube in the middle of the endotracheal tube. In some embodiments, the visualization tube can be used with any endotracheal tube (e.g., endotracheal tubes from 7.0-9.0 mm in diameter) and is shaped in such a way to permit the use of stylets and the unimpeded delivery of oxygen to the patient.

According to several embodiments, a visualization system is provided for confirming proper positioning or placement of an endotracheal tube within a patient that comprises a visualization scope (e.g., fiber optic scope) sized and shaped to be removably received within a disposable visualization tube, or sheath, having a sealed distal end that can be inserted within the endotracheal tube. The sealed distal end of the visualization tube can comprise a clear or transparent viewing window to accommodate visualization of the patient's airway distal to the endotracheal tube, thereby providing confirmation of the proper positioning of the endotracheal tube within the patient's airway. Because the visualization scope never comes in contact with the patient or with any fluid due to the sealed nature of the visualization tube, the visualization scope can advantageously be reused on multiple patients without requiring resterilization.

In accordance with several embodiments of the invention, a visualization system for confirming proper positioning or facilitating proper placement of an endotracheal tube within a patient is provided. In some embodiments, the visualization system comprises a visualization scope, a visualization tube and a coupling assembly. In some embodiments, the visualization tube has a closed distal end and an open proximal end. The closed distal end of the visualization tube can comprise a window. In some embodiments, the window comprises a clear or transparent window to provide visualization of a patient's airway distal to an endotracheal tube into which the visualization tube is inserted (e.g., to confirm positioning of the endotracheal tube with respect to the carina). In some embodiments, the visualization tube, or sheath, is sized and shaped to removably receive the visualization scope.

In some embodiments, the visualization tube comprises at least one centering assembly. The centering assembly can be configured to center or otherwise stabilize the visualization tube (and the visualization scope inserted therein) within the endotracheal tube. In some embodiments, the centering assembly comprises two or more centering tines (e.g., wings, flexible arms, protrusions) that protrude from the outer surface of the visualization tube to center the visualization tube upon insertion within an endotracheal tube.

In some embodiments, the visualization system comprises a locking or retention member, such as a locking ring, configured to couple to the visualization scope. The locking or retention member can be formed integral with the visualization scope or can be formed on a retaining sleeve permanently or detachably coupled to the visualization scope. In some embodiments, the visualization system comprises a scope retention assembly coupled to the coupling assembly. In some embodiments, the locking ring of the visualization scope is configured to engage, mate or otherwise couple with a receiving structure of the scope retention assembly to exert a force on the visualization scope in the direction of the closed distal end of the visualization tube.

In accordance with several embodiments, a visualization device for accommodating a visualization scope for confirming proper positioning of an endotracheal tube comprises a visualization tube having a closed or sealed distal end and an open proximal end and a coupling assembly configured to couple the enclosed visualization tube to any endotracheal tube (e.g., endotracheal tubes having a diameter between 6 and 10 mm). In some embodiments, the visualization device comprises a scope retention assembly configured to retain a visualization scope or other visualization member within the visualization tube. For example, the scope retention assembly can exert a backwardly-directed static force on a visualization scope inserted within the visualization tube such that a distal end of the visualization scope is pressed against the distal end of the visualization tube, thereby forming an intimate and uniform contact between the visualization scope and a window of the visualization tube. In some embodiments, the backwardly-directed force in the direction of the distal end of the visualization tube advantageously provides protection of the scope and reduces glare and otherwise improves the quality of the images captured by the visualization scope.

The locking or retention member can be formed integral with the visualization scope or can be formed on a retaining sleeve permanently or detachably coupled to the visualization scope. The locking or retention member can be positioned at a predetermined position on the visualization scope determined by the distance to the distal end of the visualization scope. In one embodiment, the scope retention assembly comprises an outer sleeve (e.g., elastomeric sleeve) that is coupled to the visualization tube, or sheath, at its distal end and is coupled to a scope retention member at its proximal end. The scope retention member can be configured to mate with the locking or retention member that is coupled to the visualization scope (with or without a separate sleeve). For example, the scope retention member can comprise a slot, groove, recess, notch, or other coupling structure configured to receive the locking member of the visualization scope. In other embodiments, the locking member can comprise a slot, groove, recess, notch, or other coupling structure and a corresponding coupling structure of the scope retention member can be received by the locking member. The sleeve can comprise an elastomeric material that can be stretched a sufficient amount to allow the scope retention member at the proximal end of the sleeve to engage with, or otherwise, temporarily couple to, the locking or retention member of the visualization scope. After coupling of the scope retention member with the locking member, the scope retention assembly is released, thereby exerting a force on the visualization scope in the direction of the distal end of the visualization tube due to the elastomeric nature of the sleeve. The visualization scope can be inserted through the sleeve of the scope retention assembly during insertion of the visualization scope within the visualization tube. In various embodiments, the scope retention assembly can be reused several times (e.g., 100-1000) times while still maintaining its effectiveness.

In some embodiments, the visualization tube has an inner diameter of less than 2 mm such that the visualization tube can receive a visualization scope having an outer diameter of less than 2 mm (e.g., about 1.1 mm, 1.2 mm, 1.3 mm, 1.4 mm, 1.5 mm, 1.6 mm, 1.7 mm, 1.8 mm. 1.9 mm, or less than 1.1 mm). In some embodiments, the thickness of the window of the visualization tube is less than 0.012 inches or less than 0.009 inches. In one embodiment, the visualization scope comprises a fiber optic scope having both imaging fibers and light fibers. In some embodiments, the visualization tube is advantageously inserted within a central lumen of the endotracheal tube and not within a channel or lumen defined within a wall of the endotracheal tube. In some embodiments, the coupling assembly is sized and shaped to couple with a universal connector of any endotracheal tube.

In some embodiments, the visualization system comprises a monitor or display device configured to display one or more images captured by the visualization scope. The visualization system can comprise a storage medium configured to preserve or record one or more images obtained or captured by the visualization scope. The monitor and the storage medium can be coupled to the visualization scope via a wired or wireless connection. In some embodiments, the visualization scope and/or camera are coupled to the monitor via an optical connection and not an RF connection. In one embodiment, the visualization scope and/or camera are coupled to the monitor (or corresponding control unit coupled to the monitor) via a Universal Serial Bus (USB) connector or other connector. In some embodiments, the monitor or display device comprises a touch screen or graphical user interface. In some embodiments, the touch screen can be configured to allow for immediate capture of an image using a prompt on the touch screen.

In some embodiments, the coupling assembly comprises one or more coupling members. For example, the coupling assembly can comprise a coupling member having one or more inlet ports. In one embodiment, the coupling member comprises a main in-line device insertion port and one or more branched inlet ports. The branched inlet ports can comprise, for example, an oxygen port configured to connect to an oxygen line or ventilator and an access port configured to receive a stylet (e.g., a malleable obturator).

In some embodiments, the window of the visualization tube comprises a visual marking to indicate the orientation of the visualization device. In some embodiments, the visualization tube comprises one or more sensors to provide feedback to an operator of the visualization device. In some embodiments, the visualization tube comprises two separate fiber bundles or chips to provide spacing and angle of view suitable for 3D imaging. The enclosed visualization tube can comprise a bend radius that approximates the bend radius of a standard endotracheal tube.

In accordance with several embodiments, a method of confirming proper positioning or facilitating placement of an endotracheal tube within a patient is provided. In one embodiment, the method comprises providing a visualization device and coupling the visualization device to an endotracheal tube inserted or residing within a patient. The visualization device can comprise a visualization tube having a sealed distal end and an open proximal end. In one embodiment, the sealed distal end comprises a window. In some embodiments, the visualization device comprises a scope retention assembly. In some embodiments, the visualization device is used to confirm proper insertion after intubation. In some embodiments, the visualization device is used to facilitate proper positioning during intubation.

In some embodiments, the method comprises inserting a visualization scope within the visualization tube of the visualization device. In one embodiment, the visualization scope comprises a locking or retention member configured to couple with the scope retention assembly of the visualization device. In one embodiment, the method comprises advancing the visualization device within the visualization tube until the distal end of the visualization device is pressed against the distal end of the visualization tube. In one embodiment, the method comprises coupling the scope retention assembly of the visualization device with the locking member of the visualization scope, thereby exerting a static force on the visualization scope in the direction of the window at the distal end of the visualization tube. In one embodiment, the method comprises confirming a position of the distal end of the endotracheal tube within the airway of the patient. The position can be confirmed by viewing one or more images captured by the visualization scope. In some embodiments, the captured images can be displayed on a monitor in real-time. In some embodiments, the method comprises recording an image of the position of the distal end of the endotracheal tube (e.g., for later viewing). In some embodiments, the method comprises storing the recorded image in a storage medium. For example, one or more captured images can be stored in a patient's medical record files (e.g., in a physical file or in electronic medical records on a computer database).

Some embodiments disclosed herein are particularly advantageous because they avoid or reduce the likelihood of the need for "blind" suctioning of debris or secretions from the lungs or native distal airways of a patient. When blind suctioning is performed, there is no way of knowing where an inserted suction catheter tip is located within the tracheobronchial tree. The tracheobronchial tree contains a number of segments and under blind suctioning, the suction catheter may not go into all of the segments or branches in which pooled secretions exist, leaving segments of the lung with residual pooled secretions. Retained pooled secretions can lead to prolonged ventilation, which is an important risk factor for a patient to acquire VAP. Furthermore, when blind endotracheal suctioning is used to obtain quantitative cultures upon which antibiotic treatment is to be based, the cultures obtained may not be indicative of the actual area of the lung involved in the infectious process.

In one embodiment, an airway cleaning device comprises a disposable, steerable suction catheter guided by an enclosed visualization member that can be configured for suctioning, irrigating, culturing, pathologically evaluating, administering medications or other pulmonary therapeutics to, and/or generally treating the native airways of a patient under direct imaging in a safe, effective and efficient manner. According to several embodiments, the suction catheter is capable of one-handed operation.

Some embodiments disclosed herein are particularly advantageous because they do not require performance by a physician and do not require sedation, short acting paralytics, increased intravenous fluid administration, and/or vasopressors. Some embodiments of the inventions are advantageous because they are minimally invasive and they minimize pain and discomfort to the patient and minimize the overall time of cleaning. Some embodiments of the inventions reduce the number of times that suctioning must be performed in a twenty-four hour period.

In accordance with several embodiments, a cleaning device is provided. In some embodiments, the cleaning device comprises a steerable suction catheter comprising a main suction lumen defined therein and a pre-bent, distal end configured to facilitate steering of the suction catheter within a distal airway of the patient. In some embodiments, the cleaning device comprises a visualization channel configured to removably receive a visualization scope. In some embodiments, the visualization scope comprises a fiber optic scope having imaging and light delivery elements. In one embodiment, one or more lights are included to enhance visualization, wherein said lights do not generate significant heat, thereby protecting delicate membrane tissue. In some embodiments, the visualization channel comprises a transparent or a substantially transparent window at its distal end. In some embodiments, the cleaning device comprises an irrigation channel configured to deliver fluid to at least partially clean the transparent window of the visualization channel and/or to deliver fluid to the distal airways of the patient. In some embodiments, the cleaning device comprises an inflation channel configured to provide inflation of a balloon disposed near the distal end of the suction catheter.

In some embodiments, the cleaning device comprises an expandable endotracheal tube cleaning member disposed on the outer surface of the steerable suction catheter. In some embodiments, the cleaning member is configured to expand upon inflation of the balloon and to remove biofilm deposited on the inner walls of the endotracheal tube as the cleaning device is withdrawn from the endotracheal tube. The balloon or other inflatable means can extend beyond a proximal end of the cleaning member (e.g., umbrella-like scaffold). The proximal end of the cleaning member can be deployed to contact the inner surface of an endotracheal tube by the balloon or other inflatable means. An outer sleeve, O-ring, or other biofilm removal member can be mounted over the cleaning member (e.g., scaffold) to facilitate collection of biofilm or secretions. The balloon or other inflatable means can span about 25% of the proximal portion of the cleaning member (e.g., scaffold frame) to create a collection area capable of collection of organized secretions and biofilm that is adhered to the wall of an endotracheal tube or other tubular structure. In some embodiments, the balloon is cone-shaped, with attachments to the outer sleeve.

In several embodiments, the cleaning device is particularly advantageous because it rejuvenates endotracheal tubes that have been clogged or otherwise contaminated with biofilm. In one embodiment, the cleaning device removes biofilm such that endotracheal tube resistance is decreased by at least 90% after cleaning, thus enhancing the functionality of the endotracheal tube. In some embodiments, the cleaning device removes greater than 99% of bacteria (as determined by colony counts in the biofilm) from the endotracheal tube. Thus, in several embodiments, the cleaning device offers significant economic and clinical benefits.

In some embodiments, the cleaning member can be mechanically expanded (e.g., using an actuation assembly) or is self-expanding and the cleaning device does not comprise an inflation channel. In some embodiments, the cleaning device comprises a control handle configured for one-handed operation of the cleaning device. In some embodiments, the cleaning device provides an "all-in-one" device configured to provide visualized cleaning of body-inserted medical tubes (e.g., endotracheal tubes) and visualized suctioning of distal airways (e.g., portions of lungs).

In some embodiments, the cleaning device comprises a scope retention assembly configured to exert a static backward force on a visualization scope inserted within the visualization channel to press the visualization scope against a window at the distal end of the visualization channel, thereby advantageously reducing glare and providing protection for the scope. In some embodiments, the scope retention assembly comprises an elastomeric sleeve and a scope retention member configured to interact with a locking or retention member coupled to the visualization scope to exert the static backward force. In some embodiments, the lens of the visualization scope is kept in constant contact or near contact with the viewing window of the visualization tube, or sheath, using the scope retention assembly.

According to several embodiments, a self-contained distal airway cleaning system for removing debris from one or more distal airways of a patient comprises a suction catheter comprising a main suction lumen and a pre-bent, distal end configured to facilitate steering of the suction catheter within the distal airways of the patient. The system can further comprise a standalone suction control unit configured to control a level of suction applied to the suction catheter. The system can also comprise an irrigation channel defined within the main suction lumen of the suction catheter, the irrigation channel configured to deliver fluid to the distal airways of the patient, and a standalone irrigation control unit configured to control the delivery of fluid to the distal airways of the patient. In some embodiments, the system comprises a control handle configured for one-handed control of the suction control unit and the irrigation control unit. The irrigation channel (or other optional delivery channel) may also be used to deliver medicaments, biologically active agents and/or other compounds to a patient. Ultraviolet (e.g., UVC), germicidal and/or antimicrobial treatment may be incorporated in several embodiments. Therapeutic modalities are included in some embodiments, including but not limited to, radiofrequency, ultrasound, laser, microwave, heat, and cryotherapy, or combinations thereof. In one embodiment, the therapy is used to effect fibrosis, stiffening and/or ablation.

In accordance with several embodiments, a distal airway cleaning device for removing debris from one or more distal airways of a patient comprises a steerable suction catheter comprising a main suction lumen defined therein and a pre-bent, distal end configured to facilitate steering of the suction catheter within the distal airways of the patient.

In some embodiments, an angling or articulating mechanism is incorporated into the distal airway cleaning device to facilitate steering of the distal end of the cleaning device. In some embodiments, the angling or articulating mechanism is built into a tubular structure of the airway cleaning device, which may comprise a suction catheter. The angling or articulating mechanism can be constructed of material that is substantially harder (e.g., hard plastic or metal) than the tubing of the device to facilitate steering of the distal end by balloon expansion. In other embodiments, the angling or articulating mechanism comprises one or more articulating wires within the tubing of the device. The distal angling or articulating (e.g., deflecting) mechanism can facilitate access to all areas of the bronchus and lungs.

The distal airway cleaning device can also comprise a visualization channel configured to removably receive a visualization scope or device having imaging and light delivery elements. The visualization channel can comprise a transparent window at its distal end. In some embodiments, the distal airway cleaning device comprises an irrigation channel configured to deliver fluid to at least partially clean the transparent window of the visualization channel and/or to deliver fluid to the distal airways of the patient. In some embodiments, the distal airway cleaning device comprises a control handle configured for one-handed operation of the distal airway cleaning device.

In some embodiments, the suction lumen of the distal airway cleaning device comprises an outer diameter of 4 mm or larger. The distal airway cleaning device can also comprise a standalone suction control unit configured to provide variable suction control and a standalone irrigation control unit configured to provide variable irrigation control.

According to several embodiments, a distal airway management system comprises a distal airway cleaning device comprising a steerable suction catheter having a suction line, an irrigation line, and a visualization channel. The distal airway cleaning device can comprise a control handle configured for one-handed operation of the distal airway cleaning device. The distal airway management system can further comprise a visualization member configured to be removably inserted within the visualization channel of the distal airway cleaning device, wherein the visualization member is configured to provide direct visualization of at least a portion of a distal airway of a patient to be cleaned by the distal airway cleaning device. In some embodiments, the distal airway management system comprises a monitor configured to display images obtained by the visualization member.

In some embodiments, the distal airway management system comprises a standalone suction control unit and an automated irrigation control unit. The distal airway management system further comprises a storage device configured to store images captured by the visualization member. The captured images can be stored with the patients' electronic medical records. In some embodiments, the distal airway management system comprises one or more remote devices communicatively coupled to the monitor via a communications network. The remote devices can be used for monitoring, storing of data, controlling the various devices of the distal airway management system, and/or other purposes. In some embodiments, the one or more remote devices are configured to enable active remote management of a patient and supervision of clinical personnel responsible for in-person care of the patient. In one embodiment, the distal airway management system further comprises one or more robotic controls configured to enable an operator to remotely manipulate the one or more remote devices.

In some embodiments, the distal airway management system comprises a non-inflatable mechanically-actuated endotracheal tube cleaning device for removing biofilm from an interior wall of an endotracheal tube and/or an endotracheal tube having a visualization channel defined therein for removably receiving the visualization member. In accordance with several embodiments, the distal airway management system can be used in conjunction with, or is compatible with, any commercially available endotracheal tube. In some embodiments, the distal airway management system comprises an endotracheal tube cleaning device, such that the device is compatible with both open and closed suction systems, and the endotracheal tube can be visualized and wiped clean, and the distal airway can be viewed, irrigated and suctioned, and pooled secretions sampled using a single device or system.

According to some embodiments, a method for visualizing a patient's distal airway (e.g., branches of the tracheobronchial tree) comprises introducing a visualization member into a sealed lumen incorporated into the wall of a suction tube, thereby advantageously preventing against contamination of the visualization member and thereby allowing the visualization member to be reusable for a single patient or multiple patients. In other embodiments, a method for visualizing mucus and/or other debris in a patient's lungs comprises introducing a visualization member into a sealed lumen within a suction lumen of a suction tube or catheter. The method can further include suctioning out the visualized mucosal secretions and/or other debris within the lungs.

According to some embodiments, a device for removing debris or secretions from the lungs or other native airway comprises a suction tube having a visualization lumen less than one and a half millimeters in diameter and closed at the distal end. The visualization lumen can be configured to receive a visualization member and the closed distal end can comprise a cap having a transparent window that enables visualization of the lungs or other native airway and/or a body-inserted device located within a native airway of the patient. The device can also include a suction lumen configured to suction out or aspirate debris or secretions from the lungs or native airway. The device can further include an irrigation lumen configured to deliver a fluid to enable cleaning of the closed end of the visualization lumen and/or to deliver a fluid, gel, or solid substance to the lungs or other native airway of the patient.

In some embodiments, a system for visualizing and suctioning debris comprises a catheter that includes a suction lumen, an enclosed visualization lumen having a transparent window at its closed distal end, and an irrigation lumen to deliver a fluid to clean the window of the visualization lumen. In some embodiments, the irrigation lumen can be configured to spray the window with a minimal amount of fluid. A visualization member, such as a visualization scope, can be inserted within the visualization lumen and the visualization member can be communicatively coupled (e.g., via a wired or wireless connection) to a camera, a light source, and/or a monitor or control unit. In some embodiments, all of the visualization components except for the visualization scope are located completely out of the operative area to facilitate a one-handed procedure, and to protect the scope from contamination. In some embodiments, the irrigation lumen can be configured to simultaneously deliver fluid to break down or dissolve debris for removal through the suction lumen. In some embodiments, a thickness of a sheath around the visualization member is advantageously thin (e.g., approximately 0.1 mm, 0.001 inches to 0.005 inches, etc.) and the lumen of the suction catheter provides an outer support member for the visualization member for protection.

In accordance with some embodiments, a method to improve weaning of a patient from a ventilator comprises providing a suction catheter with a visualization member and identifying debris that, if removed, would enable the patient to breathe better and to be removed from the ventilator. In some embodiments, an x-ray, fluoroscopic, MRI, CAT scan, ultrasonic, and/or like image or set of images can be used to guide the device to the location where the debris is located within the patient.

According to some embodiments, an airway cleaning device and/or an endotracheal tube can include a lumen suitable for receiving a visualization member, wherein performance of the catheter or endotracheal tube is not compromised and the overall outside dimension of the catheter or endotracheal tube is not substantially and/or clinically increased by incorporating at least a portion of the visualization lumen into the wall of the suction catheter or the endotracheal tube. The closed distal end of the lumen can be covered with a transparent window designed to improve the view of materials that could be removed by suction. The window can have anti-glare properties such as window glazing, optimized or improved geometric properties, and optimized or improved distances and angles with respect to the visualization system (e.g., fiber optic visualization scope) and/or other features to improve the quality of the images obtained by the visualization system.

In accordance with some embodiments, an airway cleaning device comprises a suction catheter having a "pre-bent" or "pre-curved" distal portion. The pre-bent distal portion can be rigid or flexible. In some embodiments, the distal portion is substantially straight when inserted within an endotracheal tube and configures itself to the bend of the endotracheal tube and then assumes the "pre-bent" configuration as soon as it exits the endotracheal tube to allow the operator to steer it into the desired location (e.g., a particular branch of the tracheobronchial tree). In some embodiments, the distal portion comprises shape memory material. In other embodiments the "pre-bent" configuration comprises a gentle curve by utilizing an angled entrance and/or exit.

According to some embodiments, an airway cleaning device comprises a steerable suction catheter with visualization guidance and a control handle configured for one-handed insertion into an endotracheal tube within a patient and then into the bronchus, and lungs of a patient. The control handle can be configured to direct the distal tip of the pre-bent catheter to a desired location within the lungs via single-hand operation. In some embodiments, the control handle includes a strain relief at its proximal and/or distal end. In some embodiments, the control handle, a strain relief element, and the stiffness of the suction catheter work in conjunction to permit the steerability of the pre-bent distal portion of the suction catheter.

According to several embodiments, a suction/irrigation device comprises a control handle, wherein the handle is constructed so that the distal portion of the device permits one handed suction and irrigation of a patient's lungs. The suction/irrigation device can have a visualization lumen that allows for the introduction of a readily available endoscope. The visualization lumen terminates with a closed window at its distal end so that the endoscope can be used on multiple patients without cleaning. The window can have glazing features.

According to several embodiments, an endotracheal tube for facilitating intubation of an airway as the endotracheal tube is inserted within said airway comprises an elongate body having a proximal end and a distal end, a lumen defined within the elongate body extending from the proximal end to the distal end, and a visualization channel extending along at least a portion of the length of the elongate body. In some embodiments, the visualization channel is sized and shaped to temporarily receive a visualization member. The closed, distal end of the visualization channel can comprise a transparent viewing window. In some embodiments, the visualization channel is configured to selectively alternate between an expanded configuration and a collapsed configuration.

In some embodiments, the visualization channel is defined at least partly within a wall of the elongate body such that the visualization channel does not significantly affect the flow of gases or fluids through the endotracheal tube. In one embodiment, the visualization channel transitions to the collapsed configuration when suction is applied to the visualization channel. In some embodiments, the expanded configuration is achieved by temporary inflation of the visualization channel. In other embodiments, the expanded configuration is achieved by insertion of the visualization member within the visualization channel. In some embodiments, the visualization channel is configured to return to its collapsed configuration upon removal of the visualization member from the visualization channel.

According to several embodiments, a method for facilitating proper positioning of an endotracheal tube within an airway of a patent comprises providing an endotracheal tube having a visualization channel defined at least partly within or adjacent to a wall of the endotracheal tube, wherein a distal end of the visualization channel comprises a closed, transparent window. The method can also comprise providing a visualization member having at least one imaging element and at least one light delivery element. At least one image obtained by the visualization member can be configured to be displayed, in real-time, on a monitor or other output device. The method can further comprise inserting the visualization member within the visualization channel of the endotracheal tube such that the visualization member extends to the distal end of the endotracheal tube. In some embodiments, the method comprises inserting the endotracheal tube within a native airway of a patient to a predetermined position with respect to a carina of the patient under direct visualization provided by the visualization member. The method can also comprise withdrawing the visualization member from the visualization channel.

In some embodiments, the method further comprises recording an image of the predetermined position of the inserted endotracheal tube on a storage device. According to several embodiments, the method also comprises removing any portion of the visualization channel extending outside of the exterior wall of the endotracheal tube after withdrawing the visualization member.

According to several embodiments, a system for facilitating proper positioning of an endotracheal tube within an airway of a patient comprises an endotracheal tube having a visualization channel defined at least partly within or adjacent to a wall of the endotracheal tube, wherein a distal end of the visualization channel comprises a closed window. The closed window of the visualization channel can be at least partially transparent. The system can also include a visualization member comprising at least one imaging element and at least one light delivery element. Images obtained by the visualization member can be configured to be displayed, in real-time, on a display. The system can further comprise a storage device configured to record or store images obtained by the visualization member, wherein the images recorded on the storage device are configured to be used, at least in part, as part of the electronic medical records of a patient.

According to several embodiments, a system for verifying proper positioning of an endotracheal tube within an airway of a patient comprises an endotracheal tube comprising an elongate body having a proximal end and a distal end, a lumen defined within the elongate body extending from the proximal end to the distal end, and a visualization channel extending along at least a portion of the length of the elongate body, wherein a closed, distal end of the visualization channel comprises a viewing window. The system can also comprise a visualization scope configured to be removably inserted within the visualization channel, wherein the visualization scope comprises visualization elements and imaging elements and a lens. The system can further comprise a monitor configured to display images obtained by the visualization scope within the visualization channel. In some embodiments, the system further comprises a storage device configured to selectively store one or more of the images obtained by the visualization scope.

In some embodiments, the visualization member comprises a visualization scope (e.g., an endoscope, a bronchoscope, or any other type of scope). According to several embodiments, the visualization channel comprises material that is collapsible upon application of suction to the visualization channel. The optical properties and positioning of a lens of the visualization member can be matched to the transparent window to improve quality of the images. In some embodiments, the system further comprises a tongue elevator device configured to facilitate insertion of the endotracheal tube, wherein the soft tongue elevator device is configured for single-hand operation and comprises one or more soft materials.

In some embodiments, an endotracheal tube comprises an additional "accessory" lumen on the exterior of the tube to rapidly place a probe suitable of determining the placement location of the endotracheal tube immediately after introduction, confirm placement and remove the probe, such that there are no additional devices that encumber the area around the patient. In some embodiments, the endotracheal tube is constructed such that the function of the endotracheal tube is uncompromised, and the placement of the endotracheal tube is carried out with improved safety and accuracy. The accessory lumen can be fitted with a low-cost, collapsible window at the distal end, positioned on the outer perimeter of the endotracheal tube that is configured to protect the probe for quick confirmation of location of placement of the endotracheal tube and quick withdrawal of the viewing probe to keep the area clear of accessory devices. In some embodiments, the window comprises a flap/valve that permits both viewing and biopsy or other procedures through the accessory lumen. In some embodiments, a simple catheter with a lumen configured to facilitate placement of a visualization system to verify the positioning of an endotracheal tube comprises a pre-bend to self-direct the distal tip of the catheter by manipulation of a handle to provide sufficient torque to the distal tip of the catheter.

According to several embodiments, a method of intubation and extubation comprises providing a temporary guiding introducer (e.g., a tongue elevator) and using the temporary guiding introducer to facilitate intubation and extubation. The temporary guiding introducer can advantageously replace the use of a rigid laryngoscope. In some embodiments, the temporary guiding introducer comprises a semi-rigid polyurethane or other material and is placed adjacent to the endotracheal tube to help guide the tube into or out of the trachea.

In some embodiments, a method for improved intubation comprises the use of a soft supporting member to generally direct an endotracheal tube with a temporary guiding member placed in a secondary lumen of the endotracheal tube, for intubation in a mammal, and then a visualization probe is used to confirm the placement of the endotracheal tube. In one embodiment, the temporary guiding member comprises a malleable stylet or similar member or feature. In some embodiments, the temporary guiding member is replaced with a guiding and visualization member, which can advantageously limit or eliminate the use of a rigid laryngoscope.

According to some embodiments, a system for verifying proper positioning of an endotracheal tube within an airway of a patient includes a endotracheal tube comprising an elongate body having a proximal end and a distal end, a lumen defined within the elongate body extending at least partially from the proximal end to the distal end, and a visualization channel extending along at least a portion of the length of the elongate body, wherein a closed, distal end of the visualization channel comprises a viewing window. The system further includes a visualization scope configured to be removably inserted within the visualization channel, wherein the visualization scope comprises visualization elements, imaging elements and a lens. In one embodiment, the system comprises a display configured to display images obtained by the visualization scope within the visualization channel.

According to certain embodiments, a system for removing debris from one or more distal airways of a patient includes a self-contained distal airway cleaning device for removing debris from one or more distal airways of a patient. The distal airway cleaning device comprises a suction catheter having a main suction lumen and a distal end configured to facilitate steering of the suction catheter within an airway of the patient. In one embodiment, the distal airway cleaning device comprises a suction control unit configured to control a level of suction applied to the suction catheter. In some embodiments, the system additionally includes an endotracheal tube cleaning device configured to be inserted into an endotracheal tube of a patient either before or after the self-contained distal airway cleaning device has been positioned and subsequently removed from one or more distal airways of the patent. In several embodiments, the endotracheal tube cleaning device includes an elongated member having a proximal end and a tip along its distal end, such that the elongated member comprises at least one lumen extending within its interior along at least along a portion of a length of the elongated member. The endotracheal tube cleaning device can further include an expandable structure positioned along the elongated member, wherein the structure is adapted to be selectively moved between a radially-collapsed position and a radially-expanded position. In one embodiment, the endotracheal tube cleaning device additionally includes an actuation assembly coupled to the proximal end of the elongated member. In some embodiments, one or more removal members of the cleaning device are configured to engage an interior surface of an endotracheal tube when the expandable structure is in the radially-expanded position. In some embodiments, one or more removal members are configured to contact and remove debris collected on an interior surface of the endotracheal tube when the cleaning device is moved relative to the endotracheal tube.

According to some embodiments, a method for cleaning one or more airways of a patient comprises providing a cleaning device configured to remove biofilm from an interior wall of an endotracheal tube. In one embodiment, the cleaning device includes an elongate body, an expandable structure, a removal member, and an actuation assembly. In one embodiment, the removal member comprises a generally smooth outer surface that contacts the inner surface of the endotracheal tube. The method additionally includes inserting the cleaning device into the endotracheal tube while the expandable structure is in a collapsed position and actuating the expandable structure using the actuation assembly to expand the expandable structure from the collapsed position to an expanded position, thereby expanding the removal member to contact the biofilm. In some embodiments, the method further comprises withdrawing the cleaning device from the endotracheal tube while maintaining contact between the removal member and the biofilm to dislodge said biofilm and removing the cleaning device from the patient. In several embodiments, the method comprises providing a suction catheter system having a main suction lumen and distal end configured to facilitate steering of the suction catheter within one or more distal airways of the patient. In one embodiment, the suction catheter system comprises a suction control unit configured to control a level of suction applied to the suction catheter. The method additionally includes activating the suction control unit so as to provide suction through the main suction lumen to remove debris from one or more airways of the patient. In one embodiment, the suction catheter system is inserted into and removed from the one or more distal airways of the patient either before or after the cleaning device is used to remove biofilm from the interior wall of the endotracheal tube.

According to some embodiments, a method of removing debris from one or more airways of a patient includes providing an airway cleaning device comprising a steerable suction catheter having at least one suction lumen defined therein and a distal end configured to facilitate steering of the suction catheter within the airways of the patient. In one embodiment, the airway cleaning device comprises a visualization channel configured to removably receive a visualization scope having imaging and light delivery elements, wherein the visualization channel comprises a transparent window at its distal end. In several embodiments, the method of removing debris further comprises inserting the airway cleaning device within an airway of the patient, positioning the distal end of the airway cleaning device within a target region of a patient's airway and inspecting the target region for accumulated debris using the visualization scope positioned within the visualization channel. In some embodiments, the method additionally includes activating a suction force within the suction lumen of the suction catheter to remove accumulated debris from the airway of the patient and removing the airway cleaning device from the patient's distal airway.

According to some embodiments, a kit (e.g., system or collection of items for a common purpose) for removing debris that has collected within one or more airways (e.g., native airway, oral cavity, nasal passages, pharynx, larynx, trachea, and/or any portion of the lungs, including any of the branches of the tracheobronchial tree, endotracheal tube, etc.) of a patient is provided. The term "kit" as used herein should be given its ordinary meaning and should include any system, grouping and/or collection of devices, systems, components, features, materials and/or the like provided for a common goal. In one embodiment, the kit comprises one or more of the following, depending on the needs or clinical situations handled by the patient care facility: an endotracheal tube (e.g., having standard or non-standard size, shape, etc.), an endotracheal tube with built-in visualization channel, another type of endotracheal tube or other body-inserted tube or device, a visualization member (e.g., a visualization scope), a visualization device (e.g., tube or sheath) adapted to receive a visualization member, an endotracheal tube cleaning device, a tongue elevator, an airway cleaning device and/or any other system, device or component. The kit can further comprise instructions for using the various devices, components and/or other features of the kit for a particular cleaning protocol or procedure. For example, such instructions for use can include details regarding the order in which the devices, systems or other components are used, the duration of use and/or the like.

In accordance with several embodiments of the invention, a kit is provided that comprises a visualization device and one or more scope retention sleeves, wherein said scope retention sleeves are configured for retaining an off-the-shelf or conventional visualization scope.

According to several embodiments of the invention, a kit is provided that comprises a visualization device, a visualization scope configured to be removably inserted within the visualization device, and a cleaning device. The cleaning device can comprise an endotracheal tube cleaning device or a distal airway cleaning device. In some embodiments, the cleaning device comprises features configured to provide both visualized suctioning of the distal airways of a patient and cleaning of the interior surfaces of an endotracheal tube that is facilitating the patient's breathing. In some embodiments, the kit comprises an endotracheal tube. In some embodiments, the kit comprises one or more adapters or connectors configured to couple the component parts of the kit together.

In accordance with several embodiments of the invention, the visualization scope or other visualization member (e.g., fiber optic scope) is reusable and can be used with one or more disposable components, devices, or systems. The reusable visualization scope can be combined with disposable components, for example, to view and verify the placement of an endotracheal tube and/or to view and clean an already-placed endotracheal tube. In some embodiments, the reusable visualization scope can be used with a disposable or reusable system that provides viewing combined with suctioning and irrigating of the lungs. In some embodiments, a visualization system that includes a sealed member around a flexible, non-articulating fiber optic scope or other member that is pressed against the viewing window at the distal end of the sealed member for optimal view and reusability without the need for sterilization creates a more efficient cost effective delivery of airway viewing and maintenance. Mineral oil, silicone oil, and/or other suitable fluids or substances can be used between these members to act as an optical coupling agent if there is not continuous and/or complete intimate contact between two adjacent mating surfaces. The fluids or other substances can create an approximately equivalent refractive index between the two materials (e.g., refractive index matching). The use of optical coating or optical coupling agents and/or other refractive index matching techniques can reduce reflection and/or improve the contrast of the images captured by the visualization system.

In accordance with several embodiments, an endotracheal tube adapter is provided that connects or couples to any standard endotracheal tube (e.g., via a standard universal endotracheal tube connector or plug). In some embodiments, the endotracheal tube adapter comprises multiple ports or branches (e.g., 2 ports, 3 ports, 4 ports, or more). The adapter can include one or more inlet ports and one or more outlet ports. The endotracheal tube adapter can be configured to receive a device (e.g., the visualization devices, suction devices, distal airway cleaning devices described herein or off-the-shelf devices, such as bronchoscopes, endoscopes, suction catheters, etc.) to be inserted within the endotracheal tube through one of the inlet ports (e.g., a central in-line inlet port). In some embodiments, the ports comprise a sealing member (e.g., an O-ring) to provide a seal when a device is received by (e.g., introduced within) the ports of the adapter. In some embodiments, the endotracheal tube adapter includes at least two inlet ports, with a first inlet port (e.g., in-line port) configured to receive a visualization or cleaning device and a second inlet port (e.g., off-center port) to be coupled to oxygen tubing via a removable oxygen tubing connector or to be coupled directly to a ventilator. The adapter advantageously can provide continuous oxygen ventilation while a device is inserted within the endotracheal tube. In one embodiment, the adapter comprises a generally cylindrical body comprising an outlet port and at least two inlet ports, wherein the outlet port is coaxially aligned with a longitudinal axis of the generally cylindrical body and is dimensioned to be coupled to a universal endotracheal tube connector inserted within an endotracheal tube, and wherein a first one of the inlet ports is a device insertion port that is coaxially aligned with a longitudinal axis of the generally cylindrical body and is configured to receive a visualization or cleaning device dimensioned for insertion within an endotracheal tube. In one embodiment, a second one of the inlet ports is an oxygen port that extends at an angle offset from the longitudinal axis of the cylindrical body and is configured to be coupled to oxygen tubing or directly to a ventilator, thereby facilitating continuous oxygen flow while the visualization or cleaning device is inserted within the endotracheal tube. In some embodiments, at least one of the two inlet ports is removable (e.g., a removable collection port to facilitate collection of biofilm for microbiology testing). In some embodiments, the inlet ports comprise a removable cap or seal configured to provide a ventilation seal.

In some embodiments, one or more ports of the adapter can be shaped, angled or curved in a similar manner as the device being introduced through the port to aid in the ease of introduction, removal and collection of organized secretions or biofilm. The adapter can be connected to any tube-like structure, including, but not limited to, endotracheal tubes, percutaneous tracheostomy devices, urinary catheters, or dialysis catheters, chest tubes, or other catheters and tubes.

In accordance with some embodiments of the invention, the adapter can be used with "closed suction" systems. The adapter can include three ports, with one port or tube for connection to oxygen tubing or directly to a ventilator, one port or tube for a "closed suction" catheter, and one port or tube for introduction of visualization, distal airway cleaning device, endotracheal tube cleaning device, suction device, bronchoscope and/or the like. Any ports or tubes not in use can be sealed and capped. The device adapter can be configured to be used multiple times.

For purposes of summarizing the disclosure, certain aspects, advantages and novel features of embodiments of the inventions have been described herein. It is to be understood that not necessarily all such advantages can be achieved in accordance with any particular embodiment of the inventions disclosed herein. Thus, the embodiments disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

FIGS. 4A and 4B illustrate another embodiment of a visualization device.

FIGS. 5A-5C illustrate an embodiment of a coupling assembly of the visualization device of FIGS. 4A and 4B.

FIG. 5D illustrates one embodiment of a coupling member of a coupling assembly.

FIGS. 6A-6E, 7A-7D, and 8A-8E illustrate embodiments of centering assemblies that can be incorporated into the visualization devices of FIGS. 3A, 3B, 4A and 4B.

FIGS. 9A-9D illustrate a radially compressible and expandable sheath section, or coupling adapter, of a visualization device.

FIGS. 14A-14C, 15A-15C, 16A-16C, 17A-17U, 18A-18P, 19A and 19B, 20A and 20B and 21A and 21B illustrate embodiments of an airway cleaning device for removal of debris or secretions from one or more distal airways of a patient.

FIG. 26A is a schematic illustration of an embodiment of an airway cleaning device comprising an expandable endotracheal tube cleaning member.

FIGS. 26B-26F illustrate various embodiments of the expandable endotracheal tube cleaning member of the airway cleaning device of FIG. 26A.

FIGS. 27A-27D illustrate an embodiment of an endotracheal tube cleaning device.

FIGS. 28C and 28D illustrate the mechanism of retention of the scope retention assembly of FIGS. 28A and 28B.

FIGS. 29A-29F illustrate an embodiment of a toggle safety stop of the endotracheal tube cleaning device of FIGS. 27A-27D.

DETAILED DESCRIPTION

Figure 1:
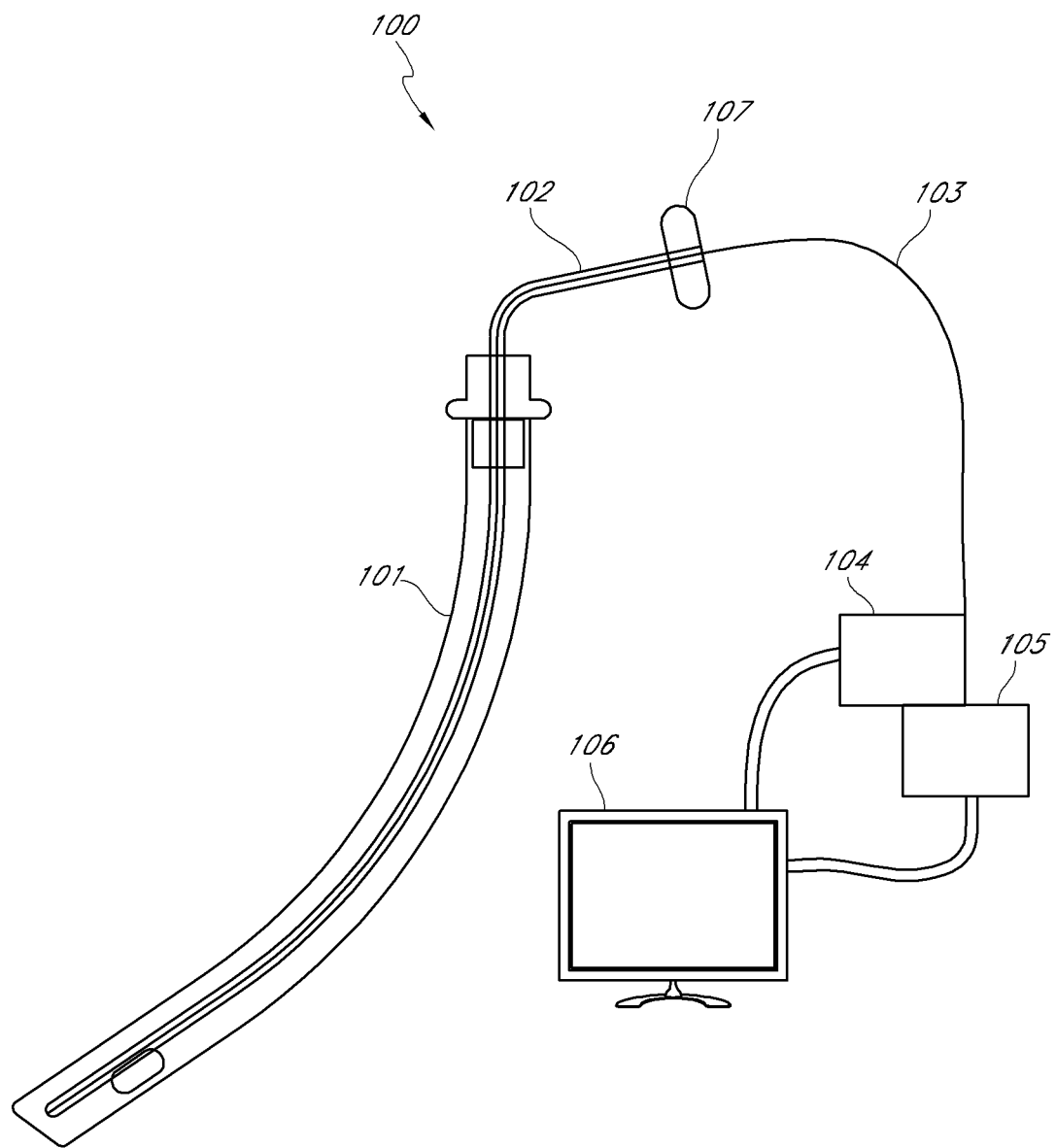
FIG. 1 illustrates an embodiment of a visualization system for facilitating proper positioning of an endotracheal tube within a native airway of a patient.

Several embodiments of cleaning systems, devices and methods described herein are particularly well-suited to remove secretions, debris and/or other materials from the lungs or native airways of a patient while a patient is intubated with an endotracheal tube. Several embodiments of visualization systems, devices and methods described herein are particularly well-suited to facilitate positioning of an endotracheal tube within a patient's native airway. The various devices, systems, methods and other features of the embodiments disclosed herein may also be utilized or applied to other types of apparatuses, systems, procedures, and/or methods, whether medically-related or not. For example, the embodiments disclosed herein can be utilized for, but are not limited to, bronchoscopes, chest drainage tubes, gastrostomy drainage tubes, abdominal drainage tubes, other body drainage tubes, feeding tubes, endoscopes, percutaneous dialysis catheters, and any other percutaneous or per os catheters or body-inserted tubes. In addition, the various embodiments disclosed herein can be used to facilitate positioning of other body-inserted members or devices. The visualization features described herein can be used to visualize the internal features of any anatomical structure, such as the colon, esophagus, nasal passages, ear passages, lungs, abdominal cavity, blood vessels, and/or any other anatomical passage or location.

The materials used for the various components of the cleaning and/or visualization devices and systems described herein can advantageously comprise one or more biocompatible materials. Such materials can be rigid or semi-rigid and/or flexible, as desired or required for a particular application or use. The materials used can include, but are not limited to, polyether ether ketone (PEEK), Nylon 6/6, polyethylene, polypropylene, polyethylene terephthalate (PET), glycol-modified PET, polyvinyl chloride (PVC), thermoplastic elastomers (TPEs), other natural or synthetic polymers (e.g., KRATON polymers), silicone, natural rubber, latex, polycarbonate, K resin, acrylonitrile butadiene styrene (ABS), styrenes and/or other thermoplastic elastomers or polymers.

The terms "debris" and "secretions" as used herein shall be given their ordinary meaning and shall include, without limitation, biological fluids, solids, gels, deposits, films, debris, and/or secretions, such as mucosal secretions, blood, bacteria, biofilm, viruses, other microorganisms, protein, feces, urine, albumin and/or any other biological or biologically-related materials. The term "native airway(s)" as used herein shall be given its ordinary meaning and shall include, without limitation, the oral cavity, nasal passages, pharynx, larynx, trachea, and/or any portion of the lungs, including any of the branches of the tracheobronchial tree.

The term "biofilm" as used herein shall be given its ordinary meaning and shall include, without limitation, biological fluids, solids, gels, deposits, films, debris, and/or secretions, such as mucosal secretions, blood, bacteria, viruses, other microorganisms, protein, feces, urine, albumin and/or any other biological or biologically-related materials.

The term "scaffold" as used herein shall be given its ordinary meaning and shall include, without limitation, support members, collapsible members, expandable members, distensible members, solid structures, mesh structures, braided devices, porous structures, struts, polymeric structures, membranes, mechanically actuated bellows, bladders, stents, umbrella-type devices, ribs, spokes, frames, and the like, and combinations thereof. Scaffolds may be fully or partially covered or may be uncovered. Covered scaffolds may comprise skeletons that are partially or fully covered by membranes, fabrics, films, multiple layers, and/or coated. Scaffolds may function as the cleaning member and/or may be used for supporting a cleaning member. Scaffolds can be mechanically actuated, self-actuated, inflated, and/or combinations thereof.

I. Visualization

FIG. 1 illustrates an embodiment of a visualization system 100 for verifying or confirming proper positioning of an endotracheal tube 101 or other body-inserted tube within a native airway of a patient. The visualization system 100 comprises a visualization tube, or sheath 102, a visualization member (e.g., a visualization scope) 103, a light source 104, a camera 105, and a monitor 106.

The visualization tube 102 can be sized to extend along the entire length of any standard endotracheal, tracheostomy, or other body-inserted tube. The outer diameter of the visualization tube 102 can be dimensioned and otherwise configured to fit within the inner diameter of any standard body-inserted tube. For example, the outer diameter of the visualization tube 102 can range from approximately 0.1 mm to 15 mm. However, in other embodiments, the outer diameter of the visualization tube 102 can be smaller than approximately 0.1 mm or greater than 15 mm, as desired or required. The visualization tube 102 can be closed on its distal end (e.g., further away from the operator) and open on its proximal end (e.g., near the operator). The cross-section of the visualization tube 102 can be circular, substantially circular, elliptical, oval, and/or any other shape. The visualization tube 102 can include a depth stop 107 to control the depth of insertion within the endotracheal tube 101. The depth stop can facilitate proper positioning of the tube within an anatomy and/or help prevent damage due to over-insertion. In one embodiment, the depth stop 107 is adjustable and/or lockable. In some embodiments, the visualization tube 102 can be inserted to extend to the distal tip of the endotracheal tube 101 and/or to extend beyond the distal tip of the endotracheal tube 101.

The closed distal end of the visualization tube 102 can comprise one or more windows configured to provide visualization of the patient's native airway through the window. The window can be configured to focus light (e.g., through a lens or similar member) and/or can provide a transparent cover for protection of the visualization member without focusing light. The window can be configured to act as a fisheye, advantageously increasing the field of view. For example, in some embodiments, such a fisheye or other type of features of the window allows for about 100 degrees or greater field of view. In some embodiments, the window is not a lens in that it does not focus light or alter optical properties or characteristics. In some embodiments, the window can have optical properties to provide magnification and/or angular correction. The window can also comprise one or more filters, coatings, layers and/or any other mechanism to reduce glare or flashback from a light delivery element (e.g., a light fiber) and/or to provide other visualization aids. In some embodiments, the window comprises one or more anti-reflective and/or anti-glare optical coatings, layers and/or other features.

In some embodiments, the window comprises one or more visible markings or indicia to indicate orientation of the device to a patient care provider. For example, markings at 12 o'clock and/or 6 o'clock can be used to orient the user to the patient anterior and/or posterior. In some embodiments, a marking on the window or visualization tube can be matched to the radiopaque line or other detectable feature of the endotracheal tube. In some embodiments, the window comprises markings arranged in a circular pattern to help indicate the percentage of occlusion of the endotracheal tube. In some embodiments, in addition, or as an alternative to, the markings, a camera can be rotated to provide north/south orientation. Similarly, a user can rotate an image on the display of a tablet, personal digital assistant (PDA), smartphone, pad, computer monitor, other display and/or any other device to achieve the desired orientation for viewing. In some embodiments, software executed by a control unit or processing device coupled to the monitor or display device can indicate to the user anterior and posterior positions.

The window can comprise polypropylene, polycarbonate, polyurethane, styrene, K resin, polysulphone, PETG, acrylic, cyclic olefin, and/or other like material and can have a thickness of between about 0.01 and 0.1 mm. In some embodiments, the window can have a thickness between about 0.001 inches and 0.015 inches (e.g., less than or equal to about 0.009 inches, 0.012 inches, 0.015 inches). However, in other arrangements, the thickness of the window can be less than 0.001 inches or greater than 0.015 inches, as desired or required. The window can be injection molded and can be adapted to provide high quality, low cost optics, consistent with a disposable device. In other embodiments, the device in which the window is included can be reusable. In some embodiments, one or both sides of the window are glazed with metal hydrides, such as magnesium fluoride and/or the like. In one embodiment, the window comprises multiple panes. In some embodiments, the window is insulated with krypton, argon, xenon, and/or another gas or other fluid, or comprises other materials having properties that help protect the window against conducted heat or other potentially dangerous conditions. In one embodiment, the window does not comprise a lens.

The visualization tube 102 can comprise flexible and/or rigid materials. The visualization tube 102 can comprise one or more metals (such as, for example, aluminum or titanium) and/or one or more plastics, polymers, elastomers and/or the like (such as, for example, PVC, polypropylene, polyethylene, polyurethane, polyester, polyamide, silicone, latex and/or the like) or combinations thereof. Multiple layers of the same or different materials can also be used. In some embodiments, the visualization tube 102 comprises an inner layer and an outer layer or an inner layer, an outer layer, and one or more middle layers. In some embodiments, at least a portion of the visualization tube 102 comprises a malleable or flexible material (for example, such that the visualization tube can permit use with flexible scopes). The visualization tube 102 can be pre-bent or otherwise pre-shaped to facilitate insertion within the endotracheal tube 101. Variable regions of stiffness and flexibility are provided in some embodiments. In some embodiments, the visualization tube 102 comprises an inner tube or sheath and an outer tube or sheath. In one embodiment, the visualization tube 102 comprises an inner tube, an outer tube, and one or more middle tubes or sheaths. In some embodiments, different components or instruments can be provided in the various tubes or layers (e.g., in between tubes, sheaths, or layers). For example, a fluid irrigation channel can be provided between component tubes or sheaths of the visualization tube 102. In some embodiments, a fluid irrigation channel can be used to clean the viewing window (e.g., remove biofilm, secretions, condensation), such as described in connection with the irrigation line or channel of the airway cleaning devices described herein. However, cleaning of the window can be provide by other suitable devices or methods; fore example, in one embodiment, the visualization tube 102 comprises a channel within a wall of the visualization tube that has an opening through which fluid can be delivered to clean the window.

The visualization member 103 can comprise any structure or device capable of providing visualization or imaging of the patient's internal body structures, such as a charge-coupled device (CDD) imaging element, a complementary metal oxide semiconductor (CMOS) imaging element, a very large scale integrated (VLSI) chip imaging element, one or more optical fibers, photodynamic therapy (PDT) elements, ultrasonic imaging elements, combinations of the same, and/or the like. In some embodiments, the visualization member 103 includes one or more imaging elements and one or more light delivery elements. In one embodiment, the imaging elements and the light delivery elements comprise optical fibers (e.g., myriad fiber imaging). In some embodiments, the visualization member comprises a visualization scope. The visualization scope can comprise a standard "off-the-shelf" endoscope, bronchoscope, or other scope, fiber optic, chip or "chip on a stick" or a proprietary scope configured for use with the embodiments described herein.

Figure 2A:
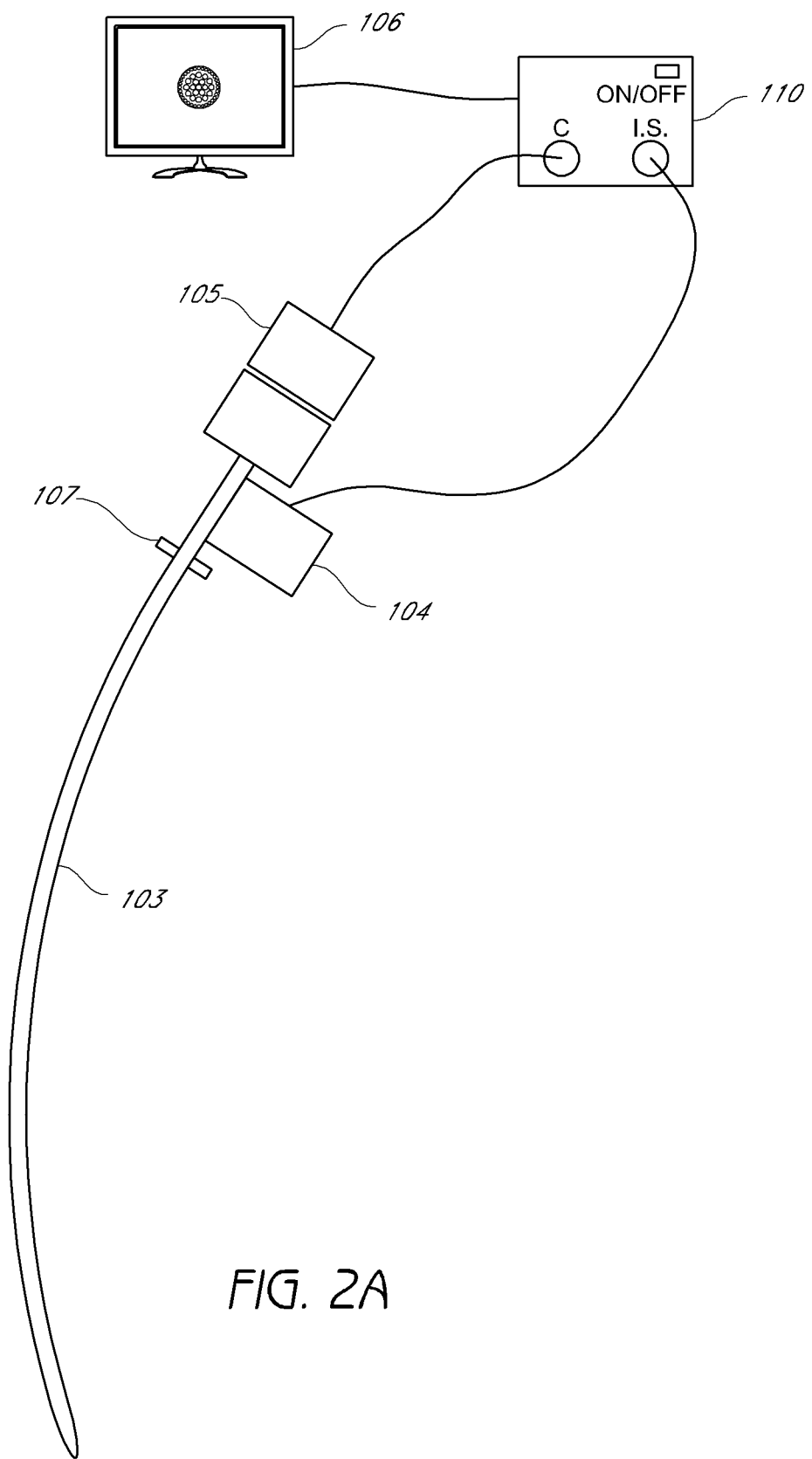
FIGS. 2A-2C illustrate embodiments of a visualization member.
Figures 2B, 2C:
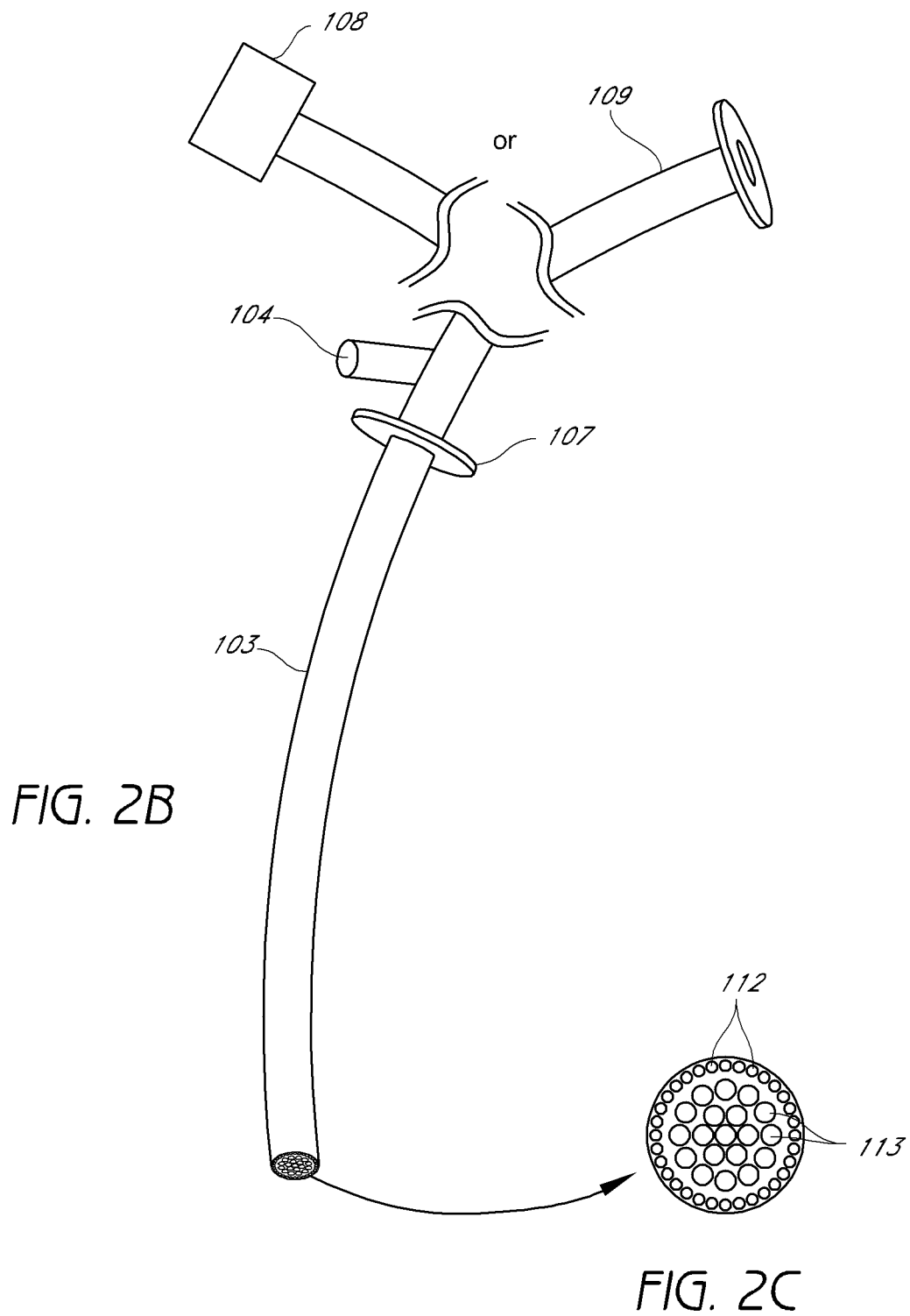

As shown in FIGS. 2A and 2B, the visualization member 103 (e.g., a visualization scope) can comprise a sheath or jacket that is pre-bent and/or substantially straight. In some embodiments, the sheath or jacket has a thickness between approximately 0.01 mm and approximately 0.5 mm, e.g., between about 0.01 mm and about 0.05 mm, between about 0.05 mm and about 0.1 mm, between about 0.1 mm and about 0.2 mm, between about 0.2 mm and about 0.5 mm, or greater than about 0.5 mm, and/or overlapping ranges thereof. The visualization member 103 can be coupled to a direct camera connection 108 or an optical connector 109 and to a light source 104. In some embodiments, the camera 105 and light source 104 are located within a control unit 110, which can be coupled to a monitor 106 for display. In several embodiments, the visualization member 103 comprises a length and/or is otherwise configured so that all of the components except for the visualization scope itself are located completely out of the operative area to facilitate a one handed procedure and/or to protect the scope from contamination. In some embodiments, the direct camera connection 108 and an integral light source can be coupled to the monitor 106 or control unit 110 for display via an electrical cable and USB connector.

In some embodiments, the optical properties of the optical fibers within the visualization member 103 can be matched to the one or more windows or lenses to provide a clear image by avoiding "stray light," reflected light, and/or other reflections or conditions that may limit the clarity of the image. In some embodiments, preventing or reducing stray light or glare can be accomplished by placing the window at about a 30 to 60-degree angle relative to a perpendicular plane of the optical fiber axis. In one embodiment, the window is placed at or about a 45-degree angle relative to a perpendicular plane of the optical fiber axis. In some embodiments, the optical fibers are generally arranged in a figure eight configuration such that illumination fibers are in one segment of the "eight" and visualization fibers are in another segment of the "eight." In some embodiments, the outside surface of the window can be designed with a parabolic or a convex shaped geometry.

In some embodiments, the window can be coated on one or both sides with metal hydrides, such as magnesium fluoride, in one or more layers. The coatings can be used by themselves and/or with one or more other materials, features and/or approaches. According to some embodiments, the coatings are designed to have a refractive index that is generally between that of air and plastic. For instance, air has refractive index of approximately 1.0, and plastic has a refractive index of approximately 1.55. According to one embodiment, a coating has a refractive index that is approximately halfway between the respective refractive indexes of air and plastic (e.g., from about 1.25 to about 1.30). The coatings can be placed on one or more surfaces of the fiber optic lens(es) and/or window(s). Mineral oil, silicone oil, and/or other suitable fluids or substances can be placed on one or more surfaces of the window to act as an optical coupling agent that may create an approximately equivalent refractive index between the window and the scope (e.g., refractive index matching). In some embodiments, such optical coupling agents reduce the difference in refractive index between the window and the scope. The use of optical coating or optical coupling agents and/or other refractive index matching techniques can reduce reflection and improve the contrast of the images captured by the visualization system 100. Precise and uniform intimate contact of the scope lens with the window can also provide an optical coupling. For example, this contact can be accomplished by precisely guiding the fiber optic scope through the tip by assuring that the L/D ratio is at least 60%.

In some embodiments, the visualization system 100 includes a scope retention assembly (not shown) to keep the distal end of a visualization member 103 (e.g., scope) inserted within the visualization tube 102 against the window at the distal end of the visualization tube 102. The scope retention assembly can include the components and features of the scope retention assemblies described herein (e.g., scope retention assembly 123) and be coupled to the visualization tube 102 in a similar manner as described herein in connection with the visualization device 120.

In some embodiments, the visualization systems 100 (e.g., camera 105) can be tuned or otherwise adjusted by modifying the illuminate color. For example, in one embodiment, more red color can be selected so that the amount of white color received is reduced. This can help to prevent, minimize or otherwise reduce saturation of the visualization systems caused by glare from the illuminated objects. In one embodiment, a polarization filter is utilized to reduce glare. The camera's image capture gain can be increased or decreased and/or the camera's virtual shutter open time can be shortened to reduce exposure and thus prevent or reduce glare. According to some embodiments, the camera's internal white balance can be manipulated by lopping off the brightest portions. In addition, the camera's gamma stretch function can be adjusted to reduce the amount of white color that is received.

One or more elements to reduce condensation (e.g., anti-fogging) are provided in several embodiments. For example, a heating element can be thermally coupled to the viewing window of the visualization tube. The heating element can heat up periodically, or as needed (e.g., as determined by a sensor), thereby warming the lens and preventing condensation or fog from forming on the viewing window. In some embodiments, suction can be applied to the window even in the absence of view-obstructing fluids because the application of suction would tend to cool the window or remove vapor that might otherwise tend to condense on the window of the visualization tube.

The light delivery elements and the imaging elements can be arranged in any suitable pattern within the visualization member. In one embodiment, as shown in FIG. 2C, the light delivery elements 112 and the imaging elements 113 are arranged in a "halo" or annular pattern, with the imaging elements 113 bundled in the center of the visualization member 103 and the light delivery elements 112 arranged spaced around the periphery of the visualization member 103 near the wall of the visualization member 103. In some embodiments, the light delivery elements 112 and the imaging elements 113 can be arranged to minimize or reduce the glare of the light, or otherwise shield the imaging elements 113 such that the illumination from the light delivery elements 112 does not interfere with the images received by the camera. In some embodiments, the light delivery elements 112 and the imaging elements 113 can be delivered through separate windows at the distal end of the visualization tube 102 to enhance the balance of imaging and light delivery. In some embodiments, a collimator or other opaque or partially opaque element can be positioned around the window corresponding to the imaging elements 113 to shield the imaging elements from direct illumination by the light delivery elements 112. In other embodiments, the quality of the lens, the positioning of the lens, and/or anti-glare properties of the lens of the visualization member 103 and/or window of the visualization channel can improve the quality of the images obtained.

Figure 7A:
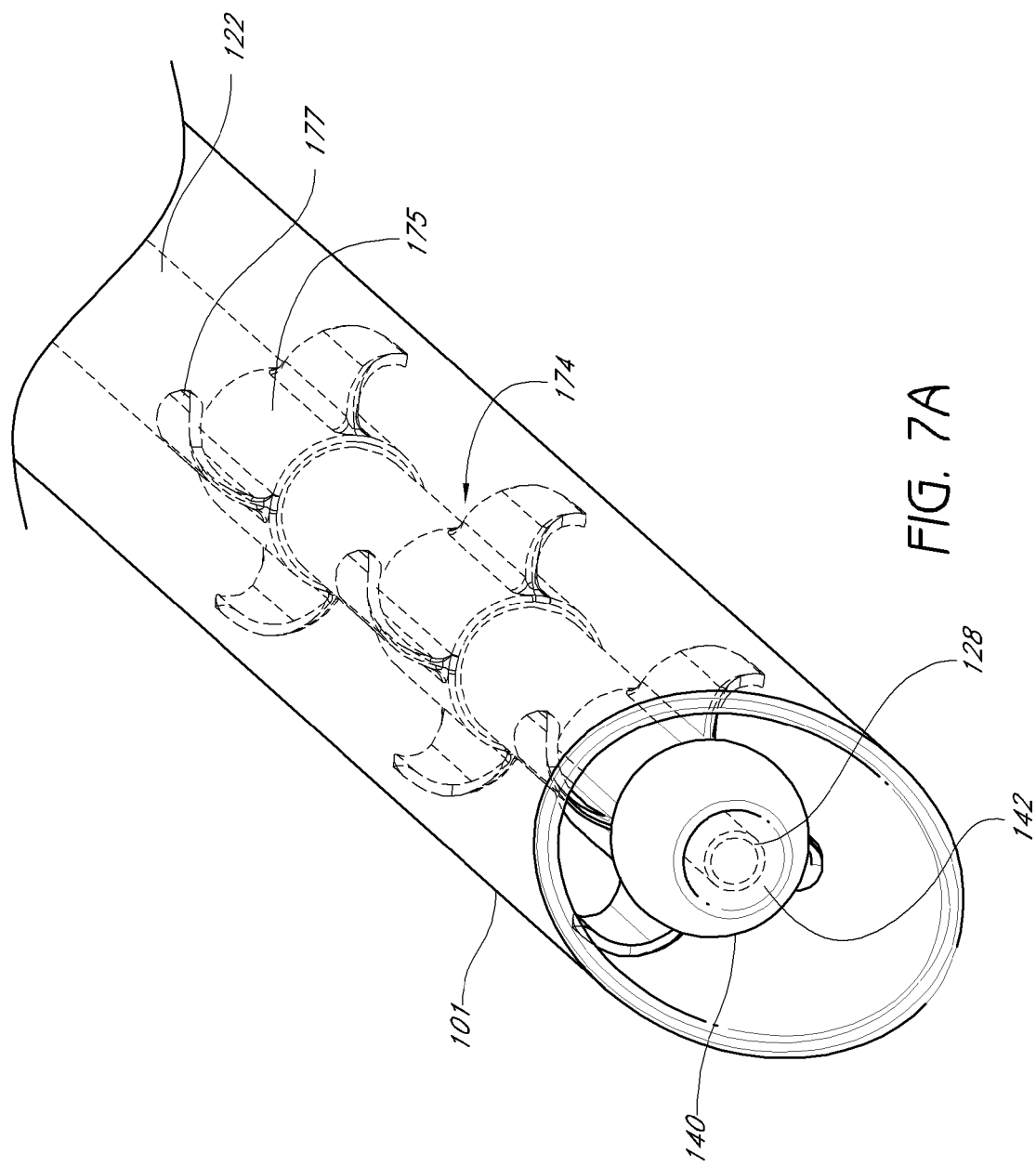

According to some embodiments, glare can also be reduced by moving the distal ends of the outside light delivery elements 113 (e.g., illumination fibers) proximally from the distal ends of the inside imaging elements 112 (e.g., visualization fibers) such that they are offset by between about 0.05 inches to about 0.5 inches (e.g., between 0.05 inches and 0.1 inches, between 0.1 inches and 0.3 inches, between 0.2 inches and 0.5 inches, between 0.06 inches and 0.08 inches, 0.07 inches, or overlapping ranges thereof). In some embodiments, the light delivery elements 113 can be recessed by about 1 or 2 mm. With reference to FIGS. 7A-7C, in one embodiment, the offset lighting facilitates delivery of a majority of the light at an angle through the side of the tip 140 of the visualization device 120 (e.g., lateral delivery with respect to a longitudinal axis of the tip 140) rather than through the window 142 at the center of the tip 140 (e.g., in contrast to standard bronchoscopes, which deliver light straight out of the distal end along the longitudinal axis of the scope). The offset lighting elements can create diffuse lighting. In some embodiments, light directed at the window of the tip can cause glare. The offset or recessed light delivery elements can provide adequate or sufficient light with minimal or reduced glare to the images and enhanced color definition (e.g., as compared with standard bronchoscopes or endoscopes).

In some embodiments, a small doughnut-like or annularly shaped member is placed over the exposed imaging elements 112 (e.g., visualization fibers) near or at the distal tip of the visualization member 103, thereby reducing glare. At least a portion of the proximal end of the doughnut-like member can be shiny and mottled. In some embodiments, the light from the light delivery elements 113 (e.g., illumination fibers) is reflected (e.g., the angle of incidence equals or substantially equals the angle of reflection) and is generally diffused because of the mottled surface of the doughnut-like member. In some embodiments, the distal tip 140 of the visualization device 120 comprises a diffusing tip. For example, in some embodiments, the distal tip 140 of the visualization device 120 comprises a protective ferrule to additionally diffuse light and protect the light elements and/or imaging elements (e.g., optical fibers). The protective ferrule can block stray light from reflecting off the window and thus causing glare. In some embodiments, the side lighting provided by the offset light elements and the diffusing tip illuminated with a light source results in low or reduced glare and/or high definition imaging (e.g., enhanced color definition) as compared with standard bronchoscopes or endoscopes that provide central lighting in a straight line out of the distal end of the scope (e.g., along a longitudinal axis of the scope). In some embodiments, the side lighting of the visualization device is combined with therapeutic light (delivered by the same visualization device or another device) to reduce bacteria or other microbe counts. The distal tips of any of the devices described herein (e.g., the visualization devices, the distal airway cleaning devices, the endotracheal tube cleaning devices) can include the structural features and elements configured to provide diffused or side lighting as described above.

The light source 104 can comprise any element capable of producing optical output. In some embodiments, the light source 104 comprises a non-coherent light source whose light is configured to be transmitted via one or more optical fibers. In some embodiments, the light source 104 comprises one or more high intensity light sources. In other embodiments, the light source 104 comprises one or more incandescent electric lights or fluorescent lights or UV light sources. In other embodiments, the light source 104 comprises one or more halogen and/or xenon light sources. In yet other embodiments, one or more laser diodes or light-emitting diodes are used. The light source(s) 104 can be positioned externally to the visualization tube 102 to reduce weight and/or otherwise facilitate one-handed operation. Alternatively, such light source(s) can be located at any position within the visualization tube 102.

The camera 105 can comprise any suitable image collection or capture device, such as, for example, a CCD camera or other digital or analog camera. In some embodiments, the camera 105 is replaced with another imaging element, such as a viewing lens or an optical connector. In some embodiments, the visualization system 100 comprises more than one camera (e.g., for stereoscopic imaging). The camera 105 can be positioned externally to the visualization tube 102 or within the visualization tube 102. The camera 105 can have one or more lenses to focus the images. The light source 104 and the camera 105 can be communicatively coupled to a monitor 106 (as shown, for example, in FIG. 1), to a control unit 110 and/or to any other device or component, which in turn may be coupled to the monitor 106 (as shown in FIG. 2A). The monitor 106 can enable the person positioning the endotracheal tube 101 or confirming the position of the endotracheal tube 101 to view the location of the distal end of the endotracheal tube 101 within the native airway (e.g., trachea) of the patient. The monitor 106 can comprise any suitable display device, such as a liquid crystal display (LCD), cathode ray tube (CRT), plasma display device and/or the like. In some embodiments, the fiber optics, camera and/or other components of the visualization system 100 can include one or more visible markings to indicate orientation (e.g., relative to anterior or posterior of the patient) of the displayed image.

In accordance with some embodiments of the visualization system 100, the percent occlusion of the endotracheal tube 101 caused by deposited biofilm can be calculated or determined by a processor coupled to the monitor 106 based at least in part on the images captured by the visualization member 103. In some embodiments, the calculated percentages can be displayed on the monitor in real-time as the visualization member 103 (e.g., scope) is advanced within the endotracheal tube 101. In some embodiments, a visual indication (such as a colored indicia) is displayed to indicate proper placement of the endotracheal tube 101, to indicate the need to clear an endotracheal tube clogged with biofilm, and/or to indicate a target location in the lungs with pooled secretions. For example, green, yellow and red colored indicia can be displayed on the monitor to indicate various levels of conditions. In some embodiments, a suction catheter, such as the suction catheters described herein, can be sterotactically or robotically directed to a target location identified or determined by X-ray, MRI, echo, or other diagnostic, visualization, or imaging modality, and/or using the visualization member. The identification of the target location in the lungs with pooled secretions can advantageously allow the best sample of bacteria to be obtained from the lungs to aid in the diagnosis and treatment of VAP or other lung diseases. By more precise sampling of the lungs, the most effective antibiotic can be selected for the specific bacteria identified, thereby improving the clinical effectiveness and cost effectiveness of treatment. In some embodiments, the tools and process of sampling bacteria and prescribing optimized antibiotics comprise a method for detecting, analyzing and transforming an endotracheal tube (and the patient's lungs) to their pre-operative state. In some embodiments, an endotracheal tube that is 20-80% blocked is cleared and transformed into an endotracheal tube functioning as if the endotracheal tube were brand new, or unused, by the distal airway management systems (including the cleaning devices or members) described herein.

In some embodiments, the monitor 106 or control unit 110 is communicatively coupled to one or more storage devices configured to record one or more images of the position of the endotracheal tube within the patient. Such recorded images can be advantageously used to document the proper positioning of the endotracheal tube 101, which can serve an evidentiary purpose in the future (e.g., for billing purposes, for defending a patient care facility and/or a medical professional against medical malpractice claims, etc.). The captured image can include one or more visible indicia or marking to indicate orientation of the image to a patient care provider. The monitor 106, control unit 110, and/or one or more storage devices can be communicatively coupled via a wired and/or wireless connection. The control unit 110 can comprise a processor configured to execute machine-executable instructions. The control unit can be communicatively coupled to other external processing and/or display devices or systems via one or more networks, thereby allowing visualization by persons (e.g., nurses, doctors, experts, etc.) in remote locations (e.g., a nursing station or other remote location outside an ICU area or outside a hospital). The remote communication can facilitate the obtaining of a second opinion, for example. In some embodiments, the recorded images, which may be stored with or otherwise tied to the patient's electronic medical records, can automatically be sent to a hospital billing department, a quality assurance department, and/or other departments or entities.

Power can be provided to the one or more light sources 104, the one or more cameras 105, the monitor 106 and/or any other component of the system 100 by an external power supply (e.g., a standard electrical wall socket) and/or by an internal power source (e.g., a replaceable, rechargeable or disposable battery). In some embodiments, the one or more light sources 104 and the one or more cameras 105 can be powered by one or more pins of an optical or electrical cable connecting the one or more light sources 104 and the one or more cameras 105 to the monitor 106 or control unit 110. In some embodiments, power can be provided by a Universal Serial Bus (USB) port and/or another type of standard or non-standard port or access point on the control unit 110 and/or other computing device (e.g., computer, tablet, pad, smartphone, PDA, other handheld, etc.). In some embodiments, power to the visualization system is delivered through a USB and/or other type of power-enabled connection to the camera 105, or by a single wire or cable electrically coupled to the back of the camera 105 that splits near its connection to the control unit 110 or other computing device into two USB connectors. One of the USB connectors (and/or other connector types) can provide power for illumination and the other USB connector can allow for visualization and storage of digital images captured by the camera 105.

In some embodiments, the visualization member 103 is inserted within the visualization tube 102, which is then inserted into the endotracheal tube 101. The visualization system 100 can be inserted within an indwelling endotracheal tube to confirm the position of the endotracheal tube or within an endotracheal tube that was just inserted within the patient's mouth to facilitate the initial positioning of the endotracheal tube. In some embodiments, the visualization system 100 is configured to provide immediate (e.g., real-time) and reliable confirmation of the position of the distal tip of an endotracheal tube in relation to the carina of a patient who has been intubated. In some embodiments, the visualization system 100 is used to confirm or rule out significant airway obstruction. In some embodiments, the visualization tube 102 comprises one or more sensors to provide feedback to a clinician or other patient care provider (e.g., physiological sensors, contact sensors, pressure sensors, moisture sensors, etc.). One or more parameters measured or detected by the sensor(s) can be displayed on a monitor or display coupled to the visualization system 100. In some embodiments, the sensors comprise RF, infrared or other types of sensors. The sensors can be used to detect carbon dioxide levels, the presence of selected bacteria of interest, moisture levels within the endotracheal tube or the adjoining trachea and lungs, other respiratory parameters, and/or other physiologic measurements that can aid in the treatment and recovery of the patient.

In some embodiments, the visualization member 103 (e.g., visualization scope) never contacts the patient or any fluid during use, and thereby, is advantageously configured for reuse without requiring sterilization or other form of cleaning or treatment. However, in other embodiments, a visualization member 103 can continuously or intermittently contact the patient. The visualization tube 102 can be disposable or reusable. In some embodiments, the visualization system, such as, for example, the visualization system 100 illustrated in FIG. 1, does not provide for suctioning or irrigation, thereby making the visualization system relatively simple, inexpensive, and easy to use. The visualization member and system described above can be used in conjunction with any of the devices, methods, and/or systems described herein.

Figure 3A:
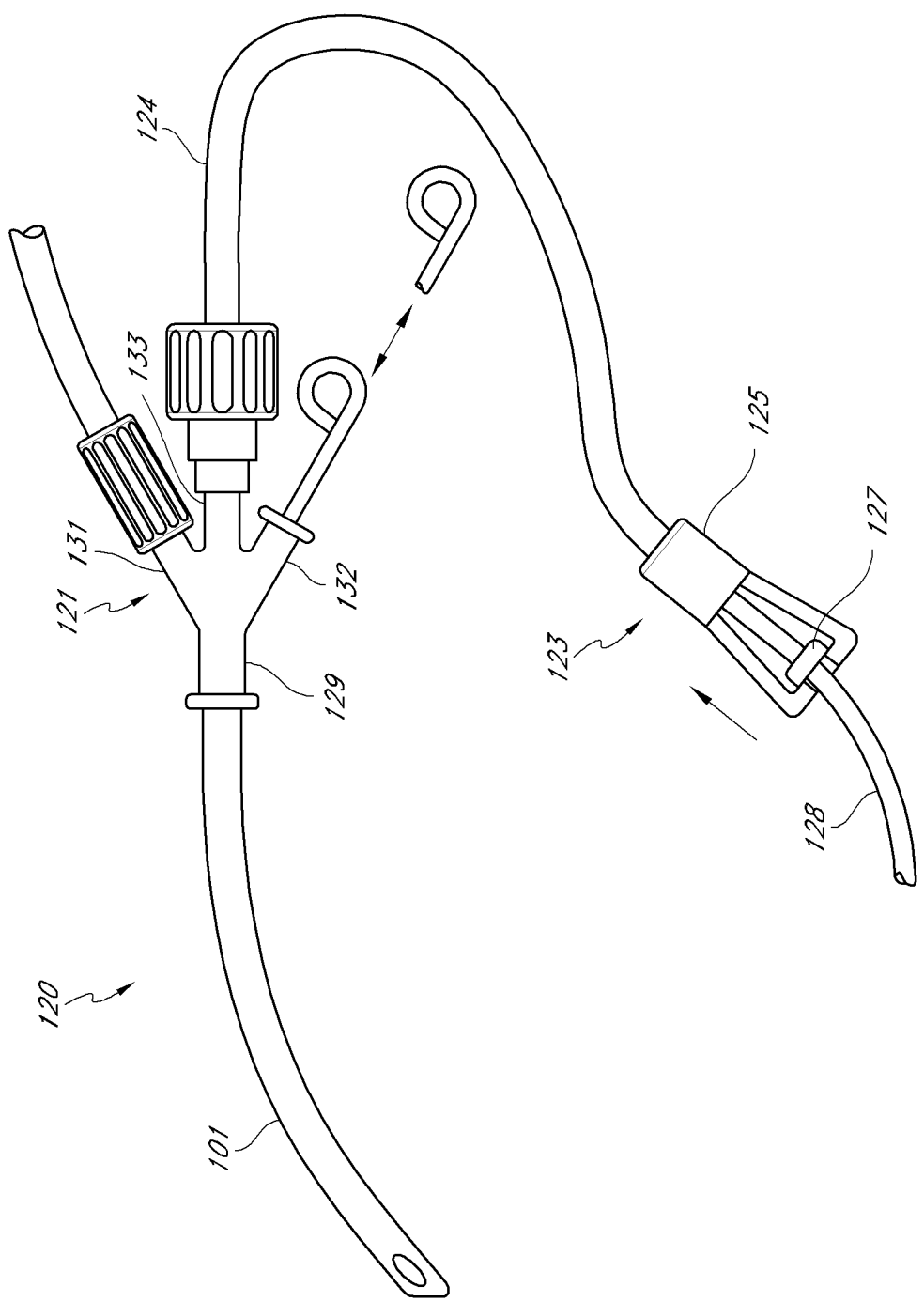
FIGS. 3A and 3B illustrate an embodiment of a visualization device.
Figure 3B:
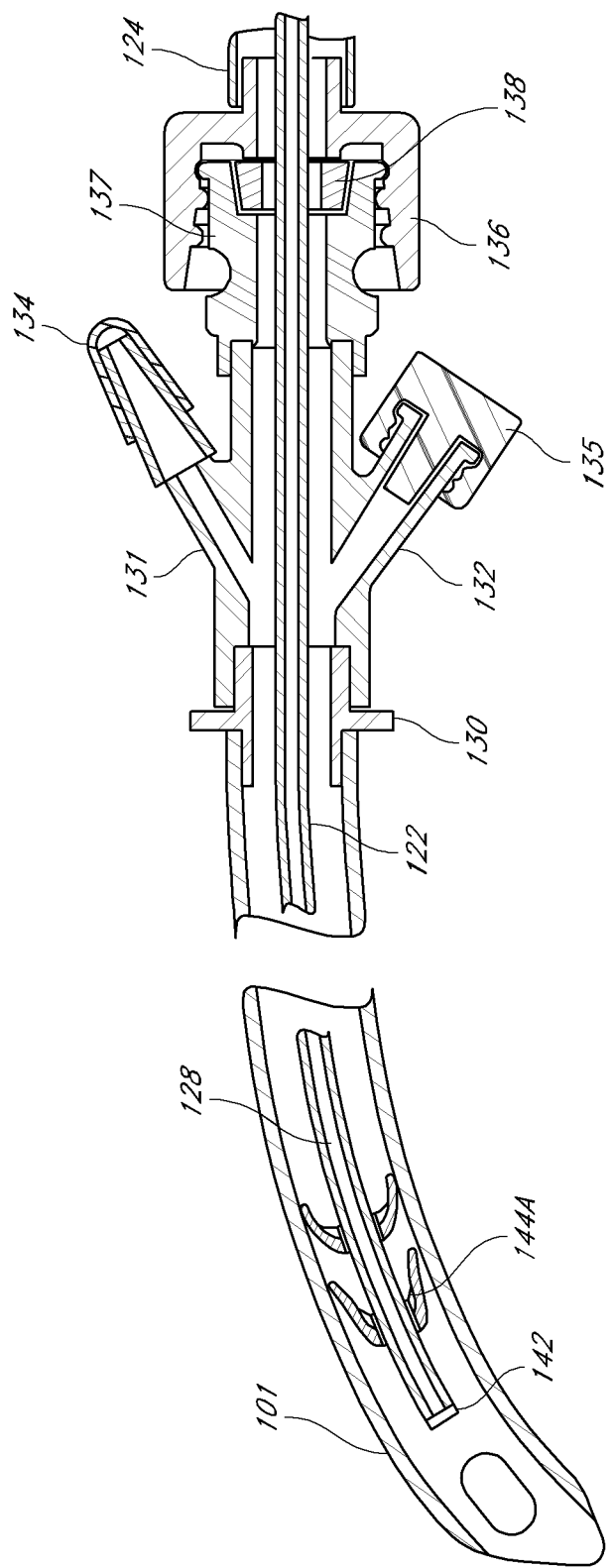

FIGS. 3A and 4A illustrate embodiments of a visualization device 120 that can be used in conjunction with any of the visualization systems disclosed herein, such as, for example, those discussed with reference to FIGS. 1, 2A and 2B (e.g., visualization system 100), and/or with any of the visualization members (e.g., visualization scopes) described herein. FIGS. 3B and 4B illustrate cross-sectional side views of the visualization devices 120 of FIGS. 3A and 4A, respectively. The visualization device 120 can be used to, among other things, verify or confirm proper positioning of an endotracheal tube or other body-inserted tube within a native airway of a patient, visualize the interior of a body-inserted tube, visualize the native airway of a patient beyond the body-inserted tube and/or for any other purpose. The visualization device 120 can provide visualization of the entire airway from the mouth to the carina, as well as other locations in the patient, without requiring the use of a laryngoscope or bronchoscope. For example, the visualization device 120 can provide visualization of one or more of the uvula, the vocal cords, the trachea, the carina, and/or the right and left main bronchi or stems of the lungs, other portions of a patient's airways and/or the like using a single device. In some embodiments, the visualization device 120 (or one or more of its component parts) is intended to be a single-use, sterile or sterilized, disposable medical device, while a visualization scope inserted therein is intended to be reused without requiring a sterilization procedure between patients or uses because it never comes into contact with the patient or any fluids because it is inserted within the visualization device 120, which is sealed to prevent contamination of the visualization scope. In other embodiments, however, the visualization device 120 (or one or more of its component parts) can be sterilized and reused and/or the visualization scope can be disposable.

In some embodiments, the visualization device 120 comprises a coupling assembly 121, a visualization tube 122, and a scope retention assembly 123. The scope retention assembly 123 can comprise one or more sleeves 124 (e.g., an elastomeric sleeve) and a scope retention member 125. The sleeve 124 can be located generally between the coupling assembly 121 and scope retention member 125. Thus, in some embodiments, as illustrated in FIGS. 3A, 4A and 4B, the distal end of the sleeve 124 is secured to or near the proximal end of the coupling assembly 121, and the proximal end of the sleeve 124 is secured to or near the distal end of the scope retention member 125. In some embodiments, the sleeve 124 (e.g., elastomeric sleeve) is coupled to the visualization tube 122, or sheath, using an adapter 126, as shown generally in FIGS. 4A and 4B, and in more detail in FIGS. 9A-9D.

According to some embodiments, the sleeve 124 (e.g., an elastomeric sleeve) comprises one or more stretchable materials. When such materials of the sleeve 124 are stretched, corresponding retention features of the scope retention member 125 and of a visualization scope inserted within the sleeve 124 contact one another or otherwise interact to provide a backwardly-oriented static force. As discussed in greater detail herein, in some embodiments, such a configuration causes a distal lens of the visualization scope to be pressed against a window at the distal end of the visualization tube 122, thereby reducing glare, reflectivity, and/or otherwise improving the quality of visualization and providing one or more other benefits to the clinician. In some embodiments, the scope retention assembly 123 is configured to provide increased or enhanced color definition (alone or in combination with the optical properties of the window and/or with the arrangement of optical fibers in a fiber optic scope).

According to some embodiments, the sleeve 124 comprises an inner diameter of between 0.005 inches and 0.025 inches (e.g., between 0.005 inches and 0.010 inches, between 0.008 inches and 0.016 inches, between 0.012 inches and 0.015 inches, between 0.015 inches and 0.025 inches, overlapping ranges thereof, or 0.014 inches). In some embodiments, the inner diameter is less than 0.005 inches or greater than 0.025 inches. The sleeve 124 can have an outer diameter of between 0.0150 inches and 0.0250 inches (e.g., between 0.0150 inches to 0.0200 inches, between 0.0185 inches and 0.0195 inches, between 0.0190 inches and 0.0220 inches, between 0.0200 inches and 0.0250 inches, overlapping ranges thereof, or 0.0192 inches). In some embodiments, the outer diameter can be less than 0.0150 inches or greater than 0.250 inches. In some embodiments, the wall of the sleeve 124 has a thickness of between 0.020 inches and 0.060 inches (e.g., between 0.020 inches and 0.040 inches, between 0.030 inches and 0.050 inches, between 0.040 inches and 0.060 inches, overlapping ranges thereof, or 0.044 inches). In some embodiments, the wall thickness is less than 0.040 inches or greater than 0.060 inches.

With reference to FIG. 3A, a locking member 127 (e.g., ring) on the visualization scope 128 can be received within a groove, slot, recess and/or other opening in the scope retention member 125. In some embodiments, the sleeve 124 can be stretched up to 1 inch or more (e.g., ¼ inch, ½ inch, 1 inch, 1½ inches, 2 inches, 3 inches, more than 3 inches, etc.) from its relaxed (e.g., without any external forces exerted upon it), non-stretched state. However, in other embodiments, the sleeve 124 can only be stretched to a distance of less than 1 inch. In some embodiments, the sleeve 124 comprises one or more bellows, expansion zones or members and/or other features that are configured to stretch or expand, either in addition to or in lieu of the materials.

Figures 5C, 5D:
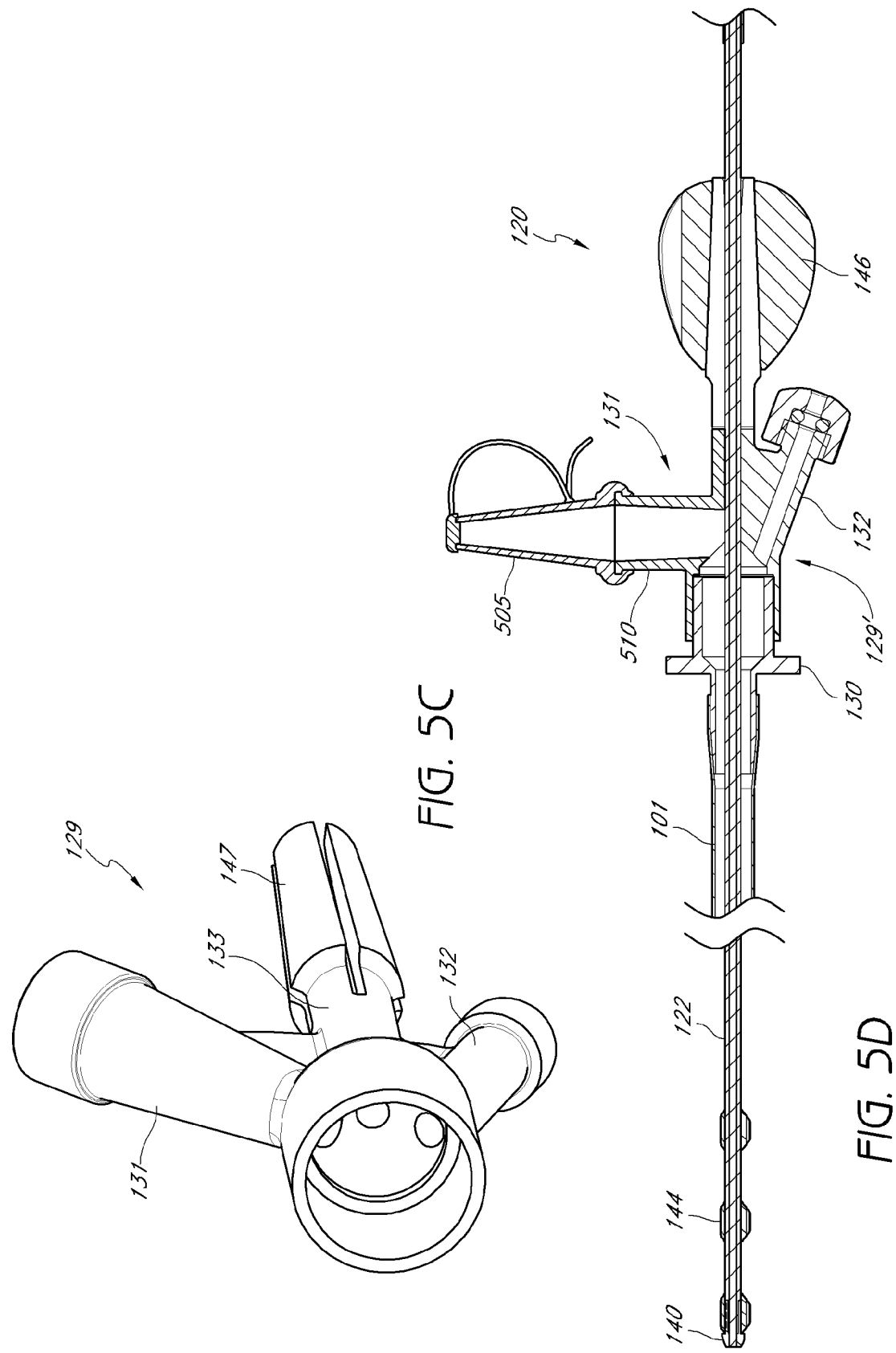

The coupling assembly 121 can comprise one or more coupling members. In some embodiments, the coupling assembly 121 comprises a coupling member 129 having multiple inlet ports; however, in one embodiment, the coupling member 129 comprises a non-branched connector having a single inlet port. The coupling member 129 can be removably or permanently attached (or otherwise coupled) to a universal connector 130 of an endotracheal tube or other body-inserted tube. The coupling member 139 can be configured to receive any device configured for insertion within an endotracheal tube (e.g., the visualization and cleaning devices described herein, bronchoscopes, endoscopes, and/or the like) The coupling member can advantageously provide continuous ventilation or oxygen supply to a patient while the device is inserted within the endotracheal tube. In some embodiments, the coupling member 129 comprises a branched connector having three inlet ports: an oxygen port 131, a stylet access port 132, and a visualization port 133 (as shown, for example, in FIGS. 3A and 3B and in FIGS. 5A-5C. In some embodiments, the coupling member 129 can include more or fewer ports or branches (e.g., one, two, four, five, more than five, etc.) or different types of ports, as desired or required. The oxygen port 131 can be configured to connect to a standard or non-standard oxygen line, such as, for example, a ³⁄₁₆-inch diameter oxygen line. The oxygen port 131 can comprise a male connector configured to mate with a corresponding female oxygen line connector or a female connector configured to mate with a corresponding male oxygen line connector (as shown in FIG. 3B and FIGS. 5A and 5B, respectively). A flexible or rigid cap 134 can be attached to the oxygen port 131 when the visualization system is not in use. The size, shape and/or other characteristics of the ports, connectors and/or items or devices configured to attach or otherwise use the coupling member 129 can be different than disclosed herein.

Further, the stylet access port 132 can be sized and configured to receive a stylet (e.g., an obturator) or similar device. In some embodiments, the obturator is malleable and is used to reshape the endotracheal tube. For example, the obturator can be used to alter the radius or bend angle of the distal end of the endotracheal tube and/or visualization tube depending on the anatomical characteristics of the patient or as desired and/or required by a patient care provider. In one embodiment, the obturator comprises a malleable metal sheathed, either partially or completely, in an elastomeric material. The obturators inserted into the stylet access port 132 can be smaller in diameter or other cross-sectional dimension than standard obturators, because the working space within the endotracheal tube may be decreased due to the presence of the visualization scope within the visualization tube. As shown in FIGS. 4B, 5A and 5B, the stylet access port 132 can be a female luer lock-like port with a slit flexible membrane configured to seal against the stylet (e.g., obturator) when it is inserted into the stylet access port 132. However, the stylet access port 132 can comprise any other type of standard or non-standard port. In some embodiments, the seal comprises an O-ring, as shown in FIG. 5A, or a duck-bill valve. One or more of the ports, or branches, can be threaded.

The size, shape, spacing, arrangement general orientation and/or other details regarding a device's inlet ports can vary, as desired and/or required. In some embodiments, the oxygen port 131 and/or the stylet access port 132 extend out from the main body at any one of a variety of angles relative to the longitudinal centerline of the main passage of the coupling assembly 121 and the visualization scope 128 positioned therethrough. For example, in some embodiments, the relative angle between the port (e.g., the stylet port, oxygen port, etc.) and the main longitudinal centerline or axis of the system varies between 5 and 90 degrees (e.g., 5, 10, 20, 30, 45, 50, 60, 70, 80, 85, 90 degrees, angles between such values, etc.). In other embodiments, at least one of the inlet ports extends out from the main body at a right angle or a substantially right angle. In configurations wherein the coupling member 121 comprises multiple branches, the branches can extend out at different angles or at substantially similar angles. In some embodiments, such a relative angle of a port can be varied by a clinician either before or during use. In one embodiment, the oxygen port 131 or any of the inlet or outlet ports can be aligned with one or more orientation indicia (e.g., colored line, notch, groove, projection, arrow, other protrusion, text, etc.) on the endotracheal tube 101.

FIG. 5D illustrates an alternative embodiment of a coupling member 129'. In some embodiments, the coupling member 129' can comprise a tri-port connector (e.g., two inlet ports and one outlet port). The oxygen port 131 can comprise a removable male oxygen tubing connector 505 and a male ventilator connector 510. The oxygen port 131 can be configured to allow either oxygen tubing to be connected using the oxygen tubing connector 505 or the oxygen tubing connector 505 can be removed to allow direct connection to a ventilator via the ventilator connector 510. In some embodiments, the oxygen tubing connector 505 includes a removable cap that can be coupled to the oxygen tubing connector 505 by a tether. The oxygen tubing connector 505 can comprise a generally tapered or cone-shaped profile. In some embodiments, the oxygen tubing connector 505 comprises one or more annular ridges or rings. In one embodiment, the oxygen tubing connector 505 comprises a "christmas tree" oxygen tubing connector. The oxygen tubing connector 505 can comprise ABS or other suitable plastic materials. In one embodiment, the oxygen port 131 extends perpendicularly or substantially perpendicularly to the center-line of the visualization port 133 of the visualization device 120; however, in other embodiments, the oxygen port 131 extends at an acute angle. In some embodiments, the removable oxygen tubing connector 505 can be coupled to the ventilator connector 510 such that when the oxygen tubing connector 505 is removed it does not get lost or misplaced.

The coupling member 129 of the coupling assembly 121 can comprise one or more materials, such as, for example, clear or opaque polycarbonate, nylon, PETG, K resin, polypropylene, PVC, ABS, polysulfone, other injection moldable resins or polymers and/or any other material. In one embodiment, the cap 134 for the oxygen port 131 comprises a dipped PVC plastisol vented cap. In some embodiments, the cap 134 for the oxygen port 131 comprises one or more injection moldable resins, such as polyethylene, polypropylene, PVC, and/or the like. A cap 135 for the obturator port 132 can comprise one or more injection moldable resins, such as polyethylene, polypropylene, PVC, and/or the like. The flexible membrane of the obturator port 132 can comprise urethane, latex, TPE, silicone, and/or other suitable elastomeric materials. The O ring seal can include 10 to 80 Shore A injection moldable silicone, urethane, TPE and/or other elastomeric or polymeric materials.

The materials for the sleeve 124 can include extruded silicone, urethane, TPE, latex, and/or other elastomeric or polymeric materials. In some embodiments, the maximum elongation of the sleeve 124 can range from approximately 150% to 750% (e.g., from about 250% to 500%, from about 150% to 600%, from about 300% to 550%, from about 350% to 600%, from about 400% to 450%, overlapping ranges thereof, or 425%) The Shore A hardness of the elastomeric sleeve can be between 20 to 80 Shore A (e.g., between 20 to 60, between 50 to 70, between 40 to 75, between 60 to 80, overlapping ranges thereof, or 60). Materials for the scope retention member 125 can include nylon, urethane, polypropylene, ABS, TPE, polycarbonate, and/or the like. Materials for the locking member 127 (e.g., ring) can include ABS, polycarbonate, urethane, TPE, silicone, K resin and/or other injection moldable resins. UV cure adhesives, silicone adhesives, or other adhesives can be used to assemble (e.g., adhere, otherwise attach, etc.) the sleeve 124 to the scope retention member 125 and to the proximal end of the central inlet port of the coupling member 129.

FIG. 3B and FIG. 5B illustrate cross-sectional views of embodiments of the coupling assembly 121 attached to an endotracheal tube 101, with a visualization tube 122 inserted within the endotracheal tube 101. As shown, a visualization scope 128 has been removably inserted within the visualization tube 122 to allow for visualization of the distal tip of the endotracheal tube 101 for any one of a variety of reasons (e.g., to confirm proper positioning of the endotracheal tube 101 within the patient). The distal end of the visualization tube 122 can include a bend radius (e.g., of between about 2 to 16 inches) that matches or approximates the bend radius of any standard or non-standard endotracheal tube. In some embodiments, the visualization device 120 can be used with other tubular structures (such as laryngeal masks, laryngeal mask airways, tracheostomy tubes, and/or the like).

In some embodiments, the visualization tube 122 is non-integral with or not built into the endotracheal tube 101. In some embodiments, the visualization tube 122 is a separate (e.g., not integral) component or structure from the endotracheal tube 101. In some embodiments, the visualization tube 122 is non-integral with or otherwise a separate component or structure from, the visualization scope 128. In some embodiments, the visualization tube 122 may comprise a wire for security, shaping, and/or other purposes that can aid in the placement of the visualization tube within the endotracheal tube and the visualization device or system within the patients. The visualization tube 122 can comprise any of the materials or features described above with respect to visualization tube 102 (e.g., flexibility, multiple layers, multiple tubes).

With continued reference to FIG. 3B, the proximal end of the visualization tube 122 can be held in place, or otherwise retained or compressed, using a compression member, such as a cinching nut, adjustable knob, or other suitable fastening device or method. In some embodiments, the coupling assembly 121 provides adjustable coupling such that the coupling assembly 121 can be removed and/or can accommodate tubes of various diameters. As shown in FIG. 3B, the coupling assembly 121 can comprise a cinching nut 136 that acts against an anvil 137 with a built-in living hinge and a stopper 138 (e.g., an elastomeric stopper) to provide retention of the visualization tube 122. The cinching nut 136 can comprise "fast threads," or multiple steep threads, to minimize or reduce the amount of turning necessary for engagement (e.g., approximately ¼ to ½ turn). In some embodiments, the threads of the cinching nut 136 are sloped. Thus, when engaged, such threads can contact the anvil 137 with increased radial force and can travel when the cinching nut 136 is turned. As a result, the anvil 137 bends and engages the stopper 138. In some embodiments, the stopper 138 bulges or otherwise deforms when force is applied against it (radially and/or longitudinally). In such configurations, the stopper 138 can create a seal and provides a means of retention for the visualization tube 122 relative to the endotracheal tube 101. In one embodiment, the stopper 138 comprises one or more O-rings and/or other sealing members (e.g., gaskets).

In FIG. 5A and FIG. 5B, the coupling assembly 121 comprises a cinching nut, or adjustable knob 146, that acts against a collet or other compressible gripping feature 147 (e.g., illustrated in FIG. 5C) that moves radially and seals and/or retains the visualization tube relative to the endotracheal tube. The anvil may not be included in this embodiment. The cinching nut, or adjustable knob 146, can comprise "fast threads" or multiple steep threads, to minimize or reduce the amount of turning necessary for engagement (e.g. approximately ¼ to ½ turn). The travel of the collet 147 when engaged by the adjustable knob 146 can range from 1° to 8° in an inclusive angle. In some embodiments, as the knob 146 is rotated in one direction, the collet 147 is radially compressed and as the knob 146 is rotated in the other direction, the collet 147 is radially expanded. In some embodiments, the collet 147 is threaded to engage with the threads of the knob 146.

Other retention features, devices or methods can be used to maintain, couple, retain, fixate, adhere, attach, compress, and/or anchor the visualization tube 122 relative to the endotracheal tube 101, as desired and/or required without departing from the spirit and/or scope of the disclosure herein. In some embodiments, the coupling assembly 121 is configured to temporarily couple the visualization tube 122 to the endotracheal tube 101. In other embodiments, the coupling assembly 121 can permanently couple the visualization tube 122 to the endotracheal tube 101.

The visualization tube 122 can extend beyond the proximal end of the stopper 138 (e.g., elastomeric stopper) or beyond the proximal end of the compression member (e.g., cinching nut 136, adjustable knob 146). The visualization tube 122 can be used to protect and isolate the visualization scope 128 from the surrounding environment when inserted through an endotracheal tube.

In some embodiments, the visualization tube 122 is approximately 25 inches in length (e.g., 15 to 45 inches, 20 to 40 inches, 20 to 30 inches, etc.); however, the visualization tube 122 can be longer than 25 inches or shorter than 25 inches as desired and/or required. Beyond the proximal end of the stopper 138 or collet 147, the visualization tube 122 adds extra protection to the visualization scope 128. The visualization tube 122 can comprise any of the materials and/or properties or characteristics described herein with respect to the other tubes, sheaths, channels and/or other members.

According to some embodiments, the distal tip 140 of the visualization tube 122 comprises one or more windows 142 or other viewing areas or features. The window 142 can comprise clear polycarbonate, clear nylon, clear PETG, clear styrene, clear K resin and/or any other clear, substantially clear injection moldable resin and/or any other suitable material. In some embodiments, the entire distal tip 140 comprises clear, transparent or substantially transparent material. The window 142 can comprise a thickness of less than about 0.012 inches (for example, about 0.002 inches, 0.003 inches, 0.004 inches, 0.005 inches, 0.006 inches, 0.007 inches, 0.008 inches, 0.009 inches, 0.010 inches, 0.011 inches, 0.012 inches, etc.). In one embodiment, the thickness of the window is about 0.005 inches. In some embodiments, the thickness of the window does not exceed about 0.008 inches. The window injection mold can be highly polished (e.g., with an SPE #1 finish and/or optical finish) or otherwise treated in order to ensure optical clarity of the molded parts. The lens of the visualization scope 128 can be indented by a few thousandths of an inch (e.g., about 0.001 to about 0.004 inches) in order to prevent or reduce the likelihood of scratches and damage to the lens. The window 142 can comprise any of the materials and/or properties or other characteristics described with respect to other windows and/or lenses disclosed herein.

A reverse bias or force can be exerted on the visualization scope 128 by the scope retention feature 125 to advantageously press the lens end of the visualization scope 128 against the window 142 of the visualization tube 122. In some embodiments, such a configuration results in minimal or no air gap between the lens end of the visualization scope 128 and the window 142 of the visualization tube 122. In some embodiments, the window thickness combined with the lens indentation is less than about 0.010 inches in order to reduce glare and/or halo effects and otherwise improve the quality of visualization. This can be particularly helpful during a treatment procedure because glare may make it difficult to view one or more anatomical features. However, in other embodiments, the clearance between the lens end of the visualization scope 128 and the window 142 of the visualization tube 122 and/or the combined thickness of the window 142 and lens indentation can be different than disclosed herein. One or more antireflective coatings, layers or other features can be applied to the outside of the window to further reduce glare. The terms "backward" or "reverse" as used herein shall be given their ordinary meanings and shall be used, without limitation, to refer to a force or pressure in the general direction of the distal end of the endotracheal tube.

The total length of the visualization scope 128 can vary, as desired or required. For example, in some embodiments, the length of the visualization scope 128 is about 20-50 inches, 40-80 inches or 50-70 inches. In other embodiments, the length of the visualization scope 128 can be different than disclosed herein (e.g., less than about 20 inches, more than about 80 inches, etc.). The visualization scope 128 can comprise a sheath having a thickness that varies along its length. For example, the thickness of the sheath surrounding the portion of the visualization scope 128 configured to reside within the visualization device 120 can be ultra thin to minimize or reduce the overall diameter or other cross-sectional dimension of the device. The thickness of the sheath surrounding the portion of the visualization scope 128 configured to reside proximal to the proximal end of the visualization tube 122 can be relatively larger to provide more resiliency and protection and/or other benefits and advantages. In other embodiments, the thickness of the sheath is generally constant along its length.

The window 142 can be attached to the visualization tube 122 with a gap filling or standard UV cure adhesive, quick curing silicone adhesive, standard silicone adhesive or the like that have an enhanced shear strength. In some embodiments, the window 142 can be attached to the visualization tube 122 with a cement, solvent or other adhesive that comprises one or more non-volatizing ingredients. The visualization tube 122 can comprise extruded polyetherketone (PEK), polyethylene, polypropylene, another suitable extruded material and/or any other material. In some embodiments, an optical coupling material, such as, for example, mineral or silicone oil or any fluid that has an approximate refractive index of 1.55 or thereabout (e.g., 1.30 to 1.80), can be coated at least partially on the window 142 to reduce reflections, image contrast and/or otherwise improve visualization properties.

With continued reference to the embodiments illustrated in FIG. 3B and FIG. 4A, the distal region of the visualization tube 122 comprises one or more centering or stabilizing assemblies or features 144. The centering assemblies 144 can advantageously be used to accommodate and generally center the visualization tube 122, and therefore the visualization scope 128, within the endotracheal tube 101. The centering assemblies 144 can be automatically adjustable to accommodate endotracheal tubes of any size or type (including, but not limited to, tubes having a diameter between 7 and 9 mm). The centering of the visualization tube 122 and visualization scope 128 can help improve the quality of visualization beyond the distal tip of the endotracheal tube. In some embodiments, the distal-most centering assembly 144A is located about one to two centimeters from the distal tip of the visualization tube 122 (for example, to avoid interference with a Murphy's eye of the endotracheal tube). In other embodiments, the distal-most centering assembly 144A is positioned over the distal tip of the visualization tube 122. In some embodiments, the centering assembly 144A is located flush with the distal tip or within one centimeter of the distal tip of the visualization tube 122. If multiple centering assemblies 144 are used, the centering assemblies 144 can be spaced apart, e.g., by about one to five centimeters. By centering the visualization scope 128 and visualization tube 122 within the endotracheal tube 101, viewing of patient anatomical features beyond the tip of the endotracheal tube 101 can be preserved and/or enhanced.

The quantity, spacing, orientation, location (e.g., relative to the distal end of the visualization tube), shape, size, general configuration and/or other details of the centering assemblies or features 144 can be different than illustrated and discussed herein, as desired or required. Further, the centering assemblies or features 144 can be configured to maintain the visualization scope 128 and tube 122 at or near the longitudinal centerline of the endotracheal tube 101. In other embodiments, such centering assemblies or features 144 can be configured to maintain the visualization tube 122 closer to one interior wall of the endotracheal tube 101 and generally away from the endotracheal tube centerline (e.g., off-center).

The centering assemblies 144 can be frictionally fitted to the outer surface of the visualization tube 122 with an interference fit and/or can be adhered to the visualization tube 122 with UV cure adhesive or any other suitable nonvolatizing cement, solvent, welding, molding, or other adhesion or coupling device or method. The transitions from the centering assemblies 144 to the visualization tube 122 can be filled with heat shrink tubing. The heat shrink tubing can serve an aesthetic function and/or can further enhance retention strength for such centering assemblies or features 144. In some embodiments, heat shrink stretchable tape or other types of stretchable tape is employed.

FIGS. 6A-6C illustrate an embodiment in which a centering assembly 154 is formed using a cantilever design. FIGS. 6A and 6B illustrate cross-sectional views, while FIG. 6C illustrates a distal end view of such a configuration. The centering assemblies 144 illustrated in FIGS. 6A-6C comprise a base 145, a strengthening rib 146 and a flexible arm 147. As shown, the base 145 can be attached to the outer surface of the visualization tube 122. In some embodiments, the strengthening rib 146 increases stiffness and provides an outward bias to the flexible arm 147 such that the arm 147 engages the inner surface of the endotracheal tube 101. The portion of the flexible arm 147 that contacts the inner surface of the endotracheal tube 101 can comprise a hemispherical protuberance configured to minimize or reduce contact with the inside wall when inserted into the endotracheal tube 101. This can help reduce or minimize drag as the adjacent surfaces are moved relative to one another. Two to four arms, wings, or tines, can be equally spaced around the diameter of the visualization tube 122 to form the centering assembly. FIG. 6C illustrates an embodiment having three tines 148 separated radially by about 120 degrees. In other embodiments, the quantity, shape, size and/or other details regarding the arms, wings, or tines, varies. For instance, a visualization tube can include more than four arms, wings, or tines, as desired or required. In some embodiments, the spacing between the arms, or tines, is sufficiently large to enable a stylet, catheter, or other element to be passed through adjacent arms in order to access a region (within the endotracheal tube or outside the endotracheal tube) that is distal to the centering assembly.

FIGS. 6D and 6E illustrate an embodiment in which a centering assembly 154 is formed using a radially distending design. The centering assemblies 154 of FIGS. 6D and 6E comprise a base 155 with a cored-out section 159 (or cavity) and a flexible arm Thus, as shown, the flexible arm 157 can move radially (e.g., inwardly) due to the cored-out section or cavity 159. According to one embodiment, this can advantageously allow for flexing of the resilient membrane above the cored-out section or cavity 159. The portion of the flexible arm 157 that contacts the inner surface of the endotracheal tube can comprise a hemispherical protuberance configured to minimize or reduce contact with the inside wall when inserted into the endotracheal tube. As noted above, such a configuration can help reduce overall drag when the visualization tube 122 is moved relative to the endotracheal tube.

In some embodiments, the centering assemblies comprise an engagement member that provides continuous contact around the entire circumference of the endotracheal tube (e.g., a disc-like, ring-like or substantially circular or cylindrical member). The centering assemblies can be self-expanding (e.g., comprised of shape memory material or flexible material), mechanically expandable, or inflatable.

FIGS. 7A-7D illustrate an embodiment of a visualization tube 122 in which the one or more centering assemblies 174 are formed using a radially distended design. The centering assemblies 174 of FIGS. 7A-7C comprise a base 175 with "rudder" shaped fins 177 that are injection molded with a slightly curved bias (e.g., 1° to 15° from each fin's radial orientation). FIG. 7D illustrates a close-up perspective view of one of the centering assemblies 174 in FIGS. 7A-7C. The slightly curved bias can allow easier entrance into an endotracheal tube when inserted. Once inserted, the fins 177 can bend, or unfold, to accommodate the internal diameter of the endotracheal tube yet can be sufficiently stiff to maintain centering of the visualization tube 172 within the endotracheal tube. In some embodiments, the fins 177 are 0.010 to 0.090 inches thick and 0.10 to 0.50 inches wide. In some embodiments, all of the fins 177 are configured to curve in the same direction (e.g., counter-clockwise or clockwise). The front and back edges of the fins 177 can be ramped, thereby allowing for equal insertion and withdrawal as expansion is in a different direction than scope movement (e.g., rotary instead of axial).

In some embodiments, the centering assemblies 174 automatically adjust to accommodate endotracheal tubes of varying diameters (e.g., 9 mm for FIGS. 6A and 6D, and 7 mm for FIGS. 6B and 6E). Other stabilization designs are also possible, as long as the centering assemblies are sufficiently rigid to center the visualization tube 172 and sufficiently flexible to reduce friction during insertion of the shaft within the endotracheal tube. For example, FIGS. 8A-8E illustrate alternative embodiments of centering assemblies.

Figure 8C:
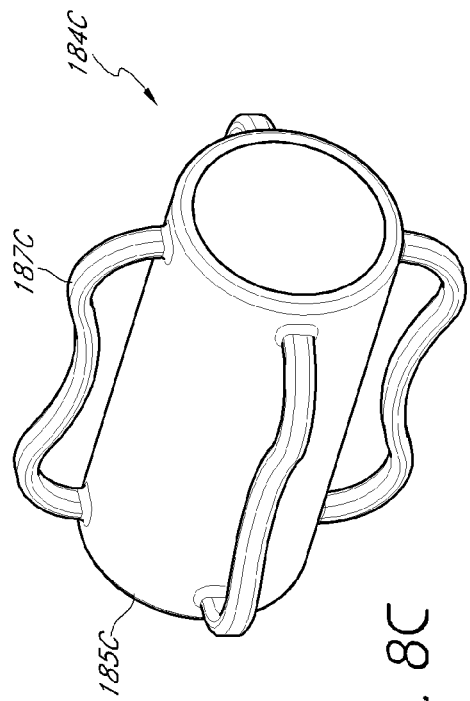
Figure 8E:
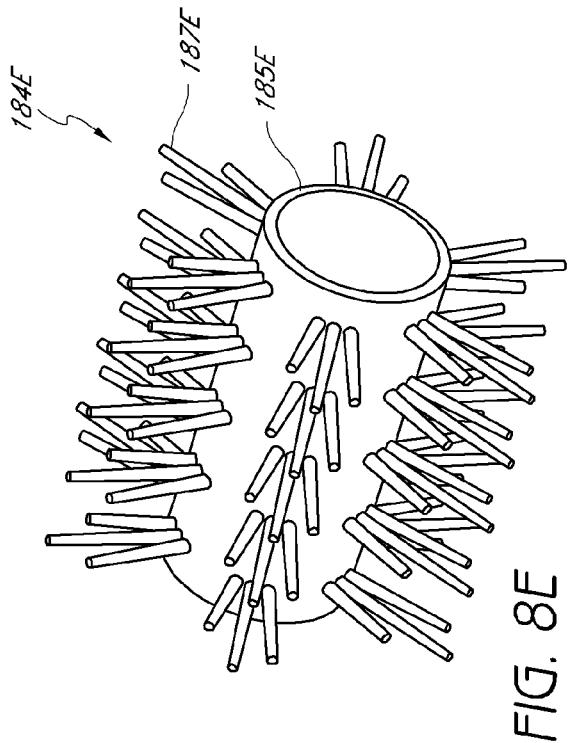
Figure 8B:
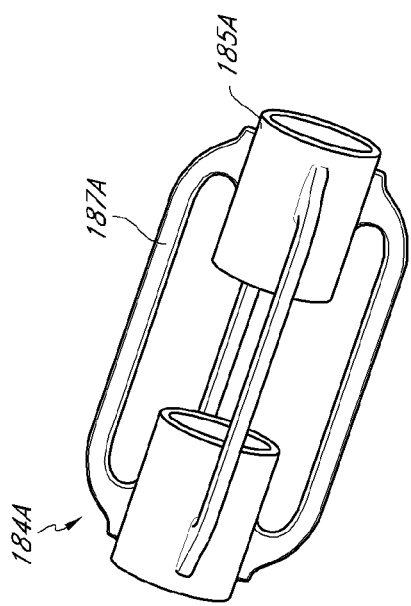

FIGS. 8A and 8B illustrate embodiments of centering assemblies 184A comprising compressible arches 187A on sliding rings 185A (a proximal ring and a distal ring). As shown, one or more springs 188 and/or other biasing or resilient members can be positioned between adjacent centering assemblies 184A to exert a spring force on the sliding rings 185A. Such a spring or resilient force can drive the arches 187A outwardly to generally conform to the inner diameter of the endotracheal tube. The distal ring of the most distal centering assembly and the proximal ring of the most proximal centering assembly can be fixed on the visualization tube (e.g., using any attachment device or method, including, for example, an interference fit, heat shrink tubing, adhesive, epoxy, molding, welding and/or the like). FIG. 8C illustrates a centering assembly 184C comprising a closed loop design. In some embodiments, if uncompressed, the flexible arms 187C of the centering assembly 184C can generally form semicircles or other curved shapes. The flexible arms 187C can be sized and configured to remain in a semicircular shape for larger diameter endotracheal tubes (e.g., tubes having a diameter or about 9 mm or more). In some embodiments, the flexible arms 187C of the centering assembly 184C can be configured to fold inwardly at the center of the arms 187C (e.g., when compressed) upon entering a smaller diameter endotracheal tube (e.g., endotracheal tubes having a diameter of about 7 mm or smaller).

Figure 8D:
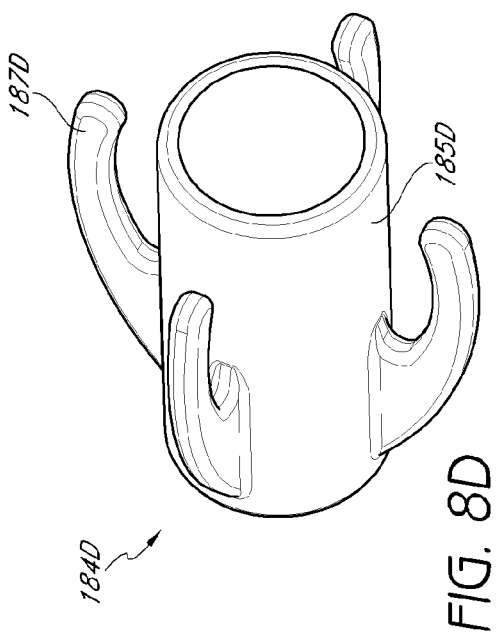

FIG. 8D illustrates an embodiment of centering assemblies 184D having a cantilevered arm design. As shown, such centering assemblies 184D can comprise an attached end and a free end. The cantilever arms 187D can be adapted to spring open in order to generally conform to the inner diameter of the endotracheal tube. Each centering assembly 184D can include two or more cantilever arms 187D (e.g., two, three, four or more arms). FIG. 8E illustrates a centering assembly 184E having a bottle brush design with sets of flexible bristles of varying lengths. The varying length bristles can accommodate different sized endotracheal tubes with a single visualization tube. For example, in some embodiments, the centering assembly 184E comprises sets of bristles having three different lengths (one set for 7 mm endotracheal tubes, one set for 8 mm endotracheal tubes, and one set for 9 mm endotracheal tubes). In other embodiments, the centering assembly can include bristles of different shapes and/or sizes. In some embodiments, the set of bristles corresponding to the diameter of the endotracheal tube are in contact with the inner diameter of the endotracheal tube when in a generally straight orientation so that they retain their column strength for group support. Bristles that are sized to accommodate larger diameter endotracheal tubes will be bent over for smaller diameter endotracheal tubes.

Suitable materials for the centering assemblies or features 144, 154, 174, 184 shown in FIGS. 6A-6E, FIGS. 7A-7D, and/or FIGS. 8A-8E can include polypropylene, nylon, ABS, polycarbonate, urethane, TPE, silicone, other injection or otherwise moldable resins or polymers and/or the like. The centering, or stabilization, assemblies can comprise one or more polymeric materials having a hardness between 15 Shore A and 90 Shore A. In some embodiments, the centering assemblies comprise unitary, contiguous molded structures. In some embodiments, the centering assemblies comprise a single flexible material. In other embodiments, the centering assemblies comprise two or more materials, one or both of which may be flexible, semi-rigid, or substantially rigid.

As described above, in some embodiments, the sleeve 124 (e.g., stretchable elastomeric sleeve) enables the scope retention member 125 and a corresponding member on the visualization scope 128 to create a static backward force on the visualization scope 128. Such a configuration can help maintain the scope 128 pressed against the window 142 of the visualization tube 122, thereby improving visualization (e.g., by reducing glare and increasing color definition). In some embodiments, the visualization scope 128 comprises a scope retainer sleeve that fits over a portion of the visualization scope 128. The scope retainer sleeve can include a locking ring or other retention member that interfaces with the scope retention member at the proximal end of the elastomeric sleeve 124. The scope retainer sleeve can be permanently or temporarily (e.g., detachably) adhered or otherwise coupled to the visualization scope. For example, the scope retainer sleeve can be integrally molded or otherwise coupled with the visualization scope 128.

In some embodiments, the scope retainer sleeve is interchangeable between visualization scopes, such that the scope retainer sleeve can be used on any visualization member or scope. In some embodiments, the scope retainer sleeve comprises elastomeric or other material that can be stretched to accommodate scopes having varying diameters.

FIGS. 9A-9D illustrate a radially compressible and expandable sheath section, or coupling adapter 190, of the visualization device 120 of FIG. 4A that can serve one or more purposes. FIG. 9A illustrates a perspective view, FIGS. 9B and 9C illustrate cross-sectional views and FIG. 9D illustrates the sheath section or coupling adapter with the outer layer removed. The compressible sheath section 190 can allow the cinching nut, or adjustable knob 146, of FIG. 5A or other coupling member to more evenly engage and retain and/or seal against itself. As shown in FIGS. 9B and 9D, the compressible sheath section 190 can also be extruded with embedded wires that can act as a strain relief, thus protecting the visualization scope 128 or other visualization member from kinking and/or being destroyed. In some embodiments, the embedded wires are configured to allow radial compression while increasing bending resistance. The compressible sheath section 190 can be attached over or to a standard extruded sheath or it can be extruded or manufactured as one continuous length or extension of the visualization tube, or sheath.

As shown in the cross-section view of FIG. 9C, the compressible sheath section 190 can overlap adjoining portions of the sleeve 124 on both ends. In some embodiments, adhesive joints can be used to make the sleeve 124 a generally continuous structure. In embodiments wherein the compressible sheath section 190 is used, the compressible sheath section 190 can be of sufficient length and be positioned so that it can be engaged by the coupling member (e.g., cinching nut 136 or adjustable knob 146) in any configuration. In some embodiments, the compressible sheath section 190 extends the entire length of the visualization tube 122. In some embodiments, the compressible sheath section 190 extends approximately the length of the adjustable knob 146 or other coupling member surrounding the compressible sheath section 190 to provide the compression. The compressible sheath section, or coupling adapter 190, can be used to couple the sleeve 124 (e.g., elastomeric sleeve) to the visualization tube 122.

The locking ring or other retention member 127 can be positioned on the visualization scope 128 at a predetermined distance from the distal end of the visualization scope 128 (e.g., approximately 25 inches, less than 25 inches, more than 25 inches, etc.). Such a predetermined distance can be selected based on the length of the visualization tube 122 of the visualization device 120 and the length of the scope retention assembly 123. In other embodiments, the visualization scope 128 comprises a locking ring or other retention member 127 that is integral with or molded to the visualization scope without a separate scope retainer sleeve element. The locking ring 127 can comprise a circular elastomeric or plastic ring; however, other shapes and/or materials can be used, as desired and/or required without departing from the spirit and/or scope of the disclosure.

Figure 10A:
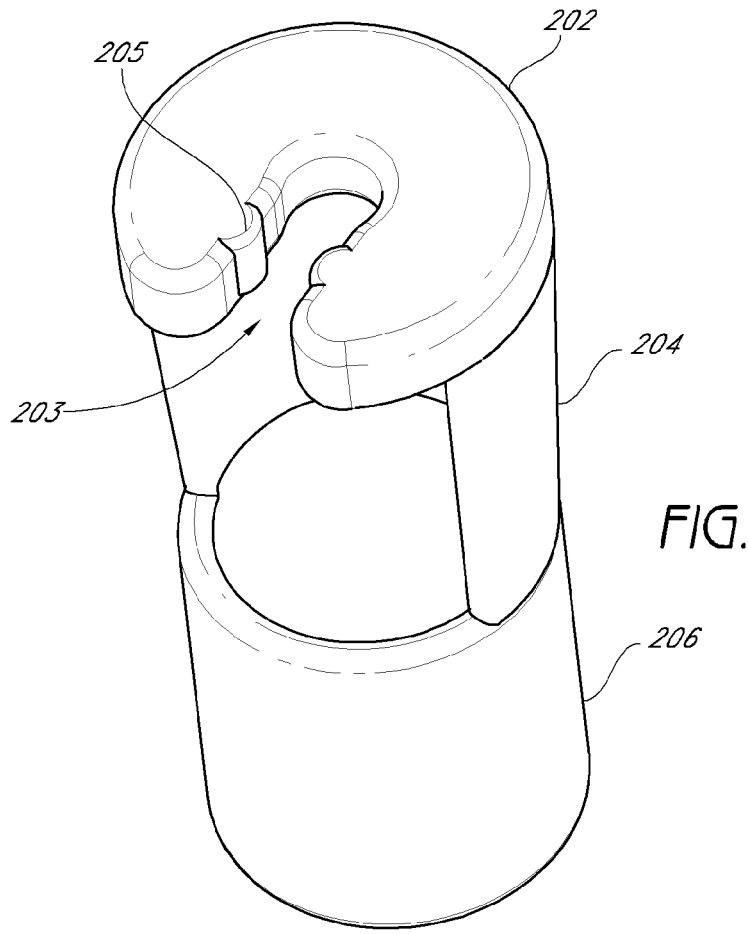
FIGS. 10A, 10B, 11A and 11B illustrate embodiments of scope retention assemblies of the visualization devices of FIGS. 3A, 3B, 4A and 4B.
Figure 10B:
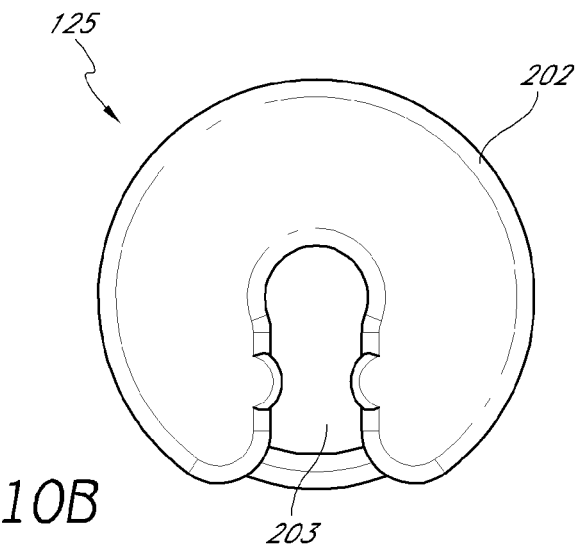
Figure 11A:
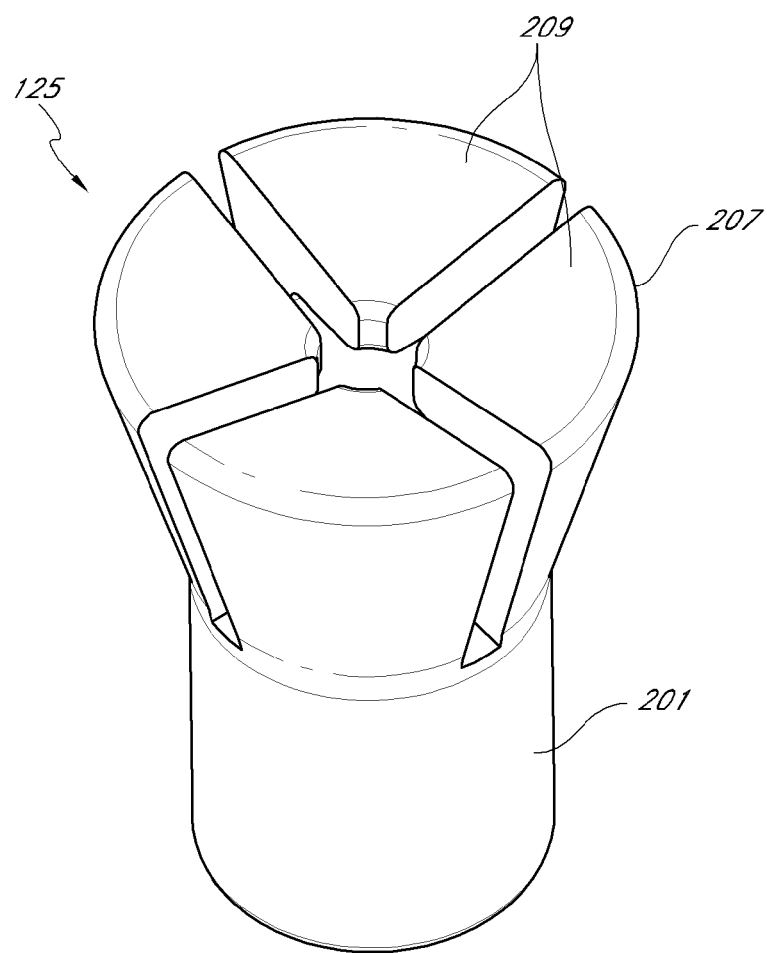
Figure 11B:
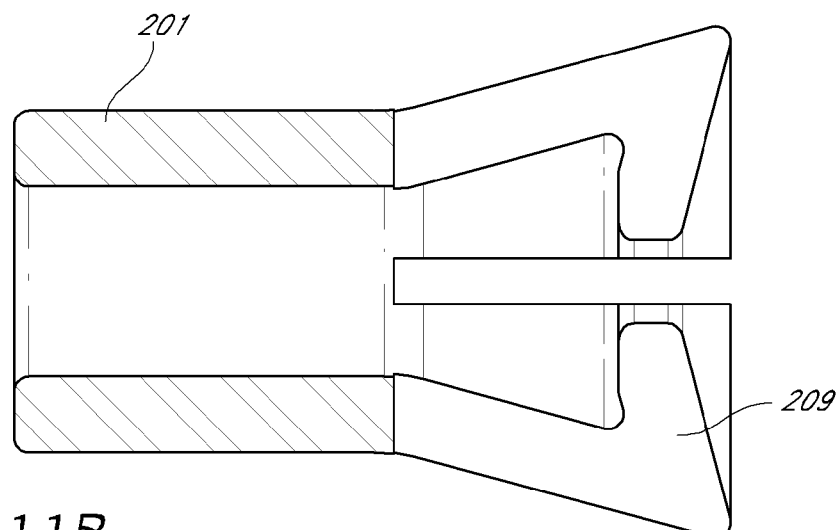

FIGS. 10A, 10B, 11A and 11B illustrate two embodiments of the scope retention member 125. FIGS. 10A and 10B illustrate a perspective view and a top view of a "Slide" embodiment of the scope retention member 125, and FIGS. 11A and 11B illustrate a perspective view and a cross-sectional view of a "Snap" embodiment of the scope retention member 125.

In the "Slide" embodiment shown in FIGS. 10A and 10B, the scope retention member 125 comprises a C-shaped proximal end 202, a substantially hollow body 204, and a substantially cylindrical distal end 206. In some embodiments, the body 204 comprises ridges, grooves, or other surface features (e.g., to improve gripping). In some embodiments, the visualization scope 128 is received coaxially within the scope retention member 125. In order to provide the backward force on the visualization scope 128, the scope retention member 125 is advanced (while stretching the elastomeric sleeve 124) until the lower surface of the C-shaped proximal end 202 is proximal to a ring or circumferential protrusion disposed on the visualization scope 128. A side slot 203 of the C-shaped proximal end 202 is then slid over the ring such that the ring abuts against the lower surface of the C-shaped proximal end 202. In some embodiments, the lower surface of the C-shaped proximal end 202 includes a groove or recess that receives the ring or an annular ridge disposed on the upper surface of the ring to further secure the ring within the scope retention member 125. In one embodiment, the side slot 203 comprises a pair of hemispherical protuberances or ridges 205 extending towards each other on opposite sides of the side slot 203 to aid in retention of the visualization scope 128 within the side slot 203.

In the "Snap" embodiment shown in FIGS. 11A and 11B, the scope retention member 125 comprises a cylindrical distal end 201 and an outwardly-tapered receiving sleeve 207 at its proximal end. The proximal sleeve, for example, can comprise a collet-like assembly of two or more leaflets or fingers. As shown in the perspective view of FIG. 11A, the proximal end comprises four leaflets or fingers 209. With reference to the cross-sectional view of FIG. 11B, the leaflets or fingers 209 can be substantially cored out or at least partially hollowed such that the ring or circumferential protrusion disposed on the visualization scope can be received within the scope retention member 125. As the elastomeric sleeve 124 with the scope retention member 125 is pulled over the ring 127 of the visualization scope 128, the leaflets 209 of the scope retention member 125 bend out of the way to allow the ring 127 to move through and then seat in place in abutment against the lower surfaces of the wedged heads of the leaflets 209.

Other designs and approaches of creating a static reverse force on the visualization scope 128 to improve the quality of visualization are possible without departing from the spirit and/or scope of the disclosure herein. In some embodiments, other shapes or geometry can be used for the scope retention members 125, such as a proximal end that is not C-shaped or non-cylindrical distal ends without departing from the spirit and/or scope of the disclosure herein.

In one embodiment, the visualization device 120 can be used to intubate a patient according to the following steps; however, one or more of the steps can be excluded in other embodiments. A visualization scope (e.g., fiber optic scope) can be inserted into the visualization tube. Then, the fiber optic scope is reversibly coupled to the visualization device 120 utilizing a locking member (e.g., ring or circumferential protrusion) on the visualization scope (e.g., on a sheath or sleeve over the visualization scope) and the scope retention member 125 at the proximal end of the sleeve 124. The visualization device 120 can then be inserted into an endotracheal tube and reversibly connected to the coupling member 129 (e.g., a tri-port connector). The visualization device 120 can then be positioned with the visualization window at the distal end of the visualization tube, or sheath, 122 positioned at or near the distal tip of the endotracheal tube. The compression member (e.g., cinching nut 136 or knob 146) is then actuated to compress the visualization tube, or sheath, 122 onto the visualization scope so that the distal tip of the visualization device 120 cannot move axially in relation to the endotracheal tube and so that the visual orientation of the visualization scope is maintained.

If the clinician desires to use a malleable obturator at this point, the malleable obturator can optionally be inserted through the stylet access port 132 and manipulated so that the endotracheal tube attains the desired shape. If the clinician chooses, standard oxygen tubing can be connected to a removable oxygen tubing connector (e.g., a "christmas tree" adapter) so that oxygen is flowing during the intubation process.

In one embodiment, a camera (e.g., camera 105) is then connected in wired or wireless fashion to a visualizing monitor (e.g., monitor 106). The monitor or a storage device coupled to the monitor can store video or still images obtained and/or transmit the images to a remote location. A standard laryngoscope or specialized tongue elevator can optionally be placed to provide exposure to the posterior oropharynx of the patient being intubated. The visualization device 120 can then be inserted into the oral cavity and manipulated through the vocal cords utilizing the images on the monitor for guidance. If a malleable obturator was used, it can be removed after insertion of the visualization device through the vocal cords. Alternatively, if nasal intubation is performed instead of intubation through the mouth, the visualization device 120 can be inserted through the nose into the posterior nasopharynx and oropharynx and manipulated through the vocal cords utilizing the images on the monitor for guidance.

In one embodiment, the endotracheal tube, still coupled to the visualization device 120, is advanced down to satisfactory visualization of the carina. The clinician can then secure the endotracheal tube in the desired position at the mouth and inflate the endotracheal tube balloon. Alternatively, if nasal intubation is performed, the clinician can then secure the endotracheal tube at the nose and inflate the endotracheal tube balloon. If the clinician chooses, the oxygen tubing connector, or adapter, can then be removed and the patient can be connected directly to a ventilator with the visualization device 120 still in place. The clinician can then fine-tune the endotracheal tube tip position while the patient is being ventilated or the visualization device 120 (including the coupling member 129 (e.g., a tri-port connector such as shown in FIGS. 5C and 5D)) can be decoupled from the endotracheal tube and the patient can be connected directly to the ventilator.

FIGS. 12A-12I illustrate embodiments of an endotracheal tube 1001 having a visualization channel 1002 built into the wall of the endotracheal tube 1001. In some embodiments, the camera 1005, light source 1004, and/or monitor 1006 include a location and/or an orientation such that they do not encumber the area around the patient. The visualization channel 1002 can extend, at least partially, along any length of the endotracheal tube 1001. In some embodiments, the visualization channel 1002 advantageously extends to the distal tip of the endotracheal tube 1001.

Figure 12A:
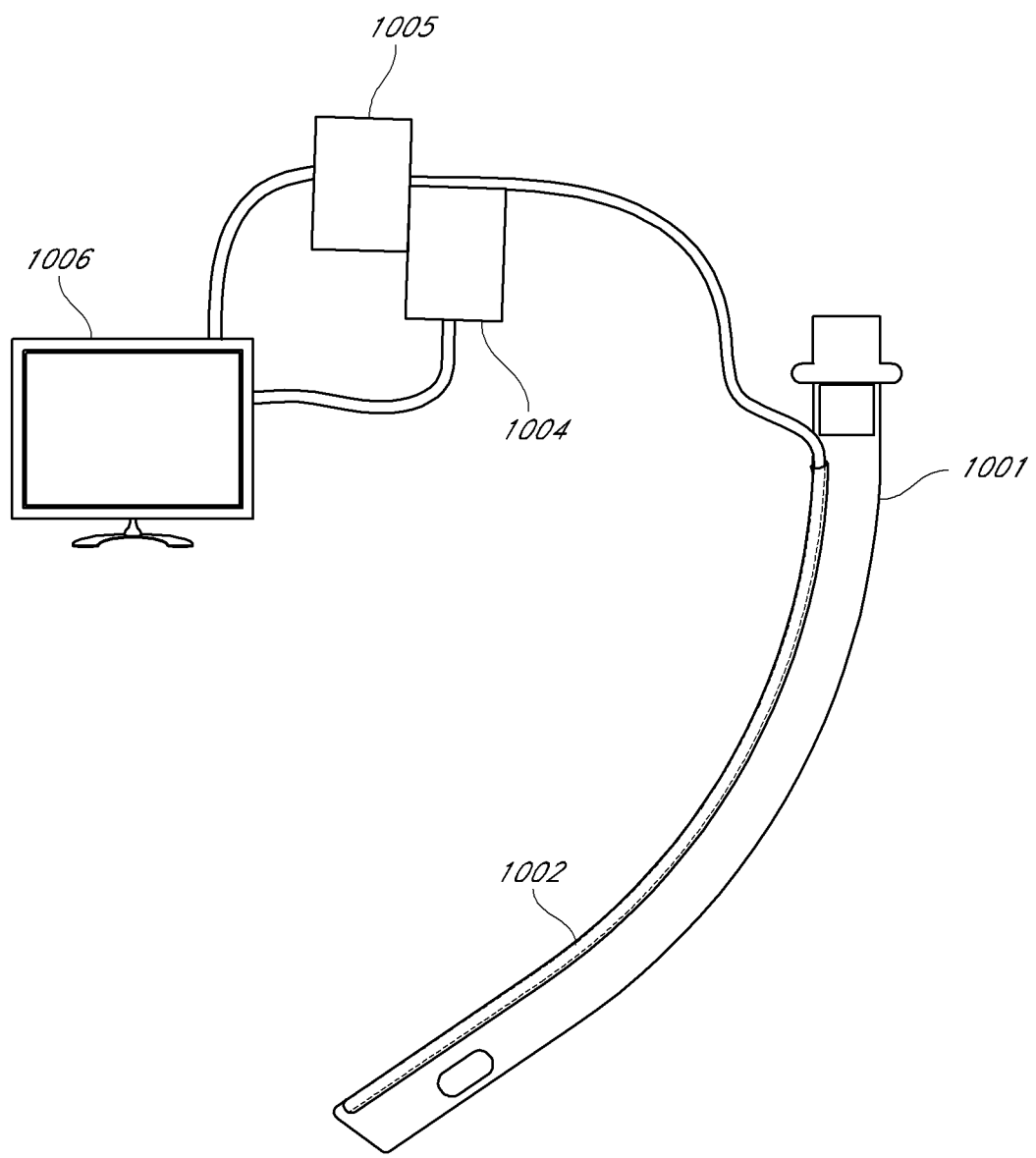
FIGS. 12A-12I illustrate embodiments of an endotracheal tube having a built-in visualization channel.
Figure 12B:
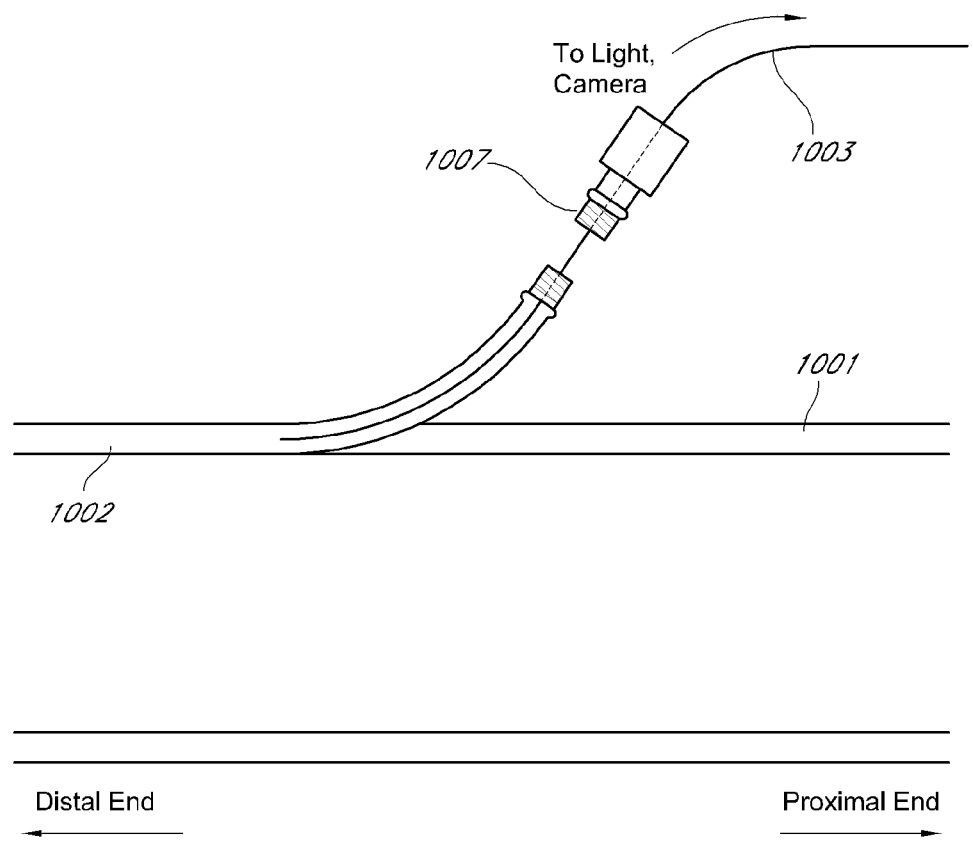
Figure 12C:
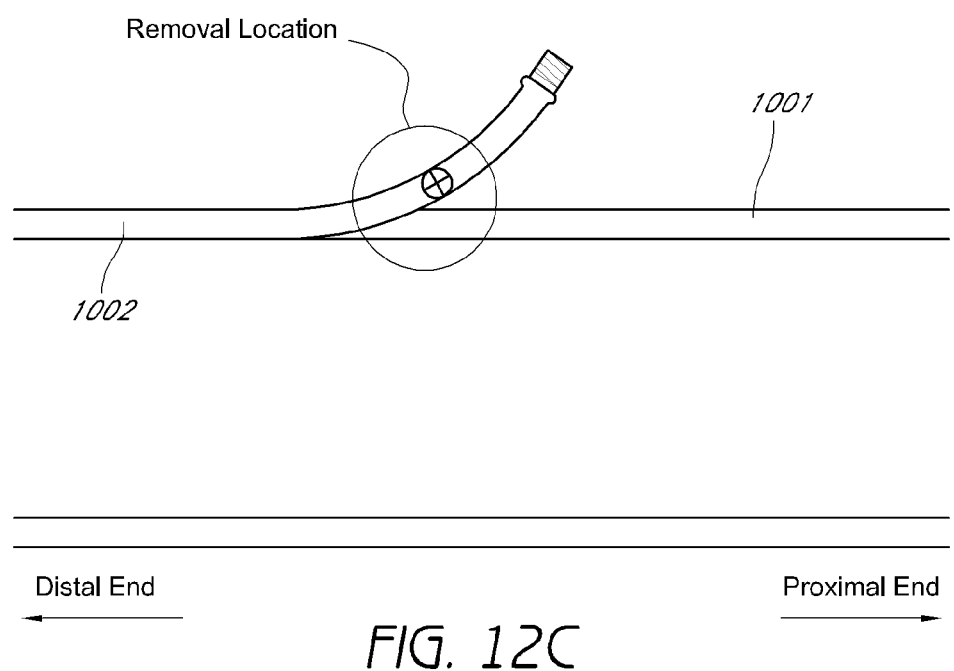

In accordance with several embodiments, the visualization channel 1002 can be configured to control the depth of insertion of a visualization member 1003 within the visualization channel 1002 (e.g., via a depth stop, a luer tip connector and/or any other positioning feature or device). FIG. 12B illustrates an embodiment of a visualization channel 1002 comprising a luer tip connector 1007 to atraumatically keep the visualization member 1003 advanced to its desired position within the visualization channel 1002.

Figure 12D:
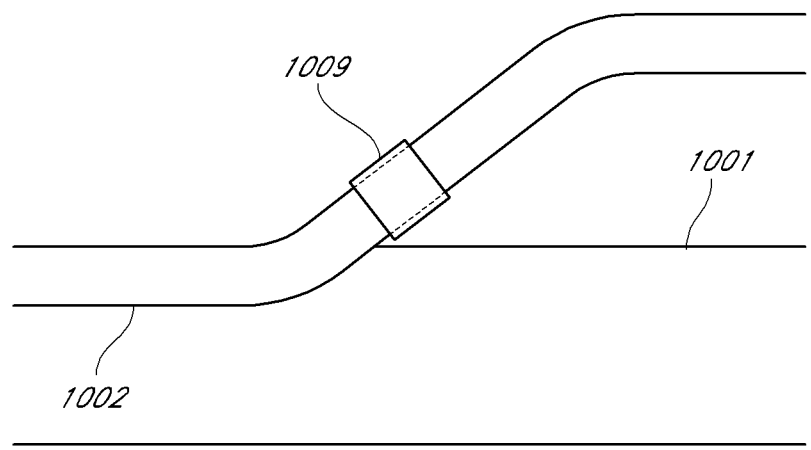
Figure 12E:
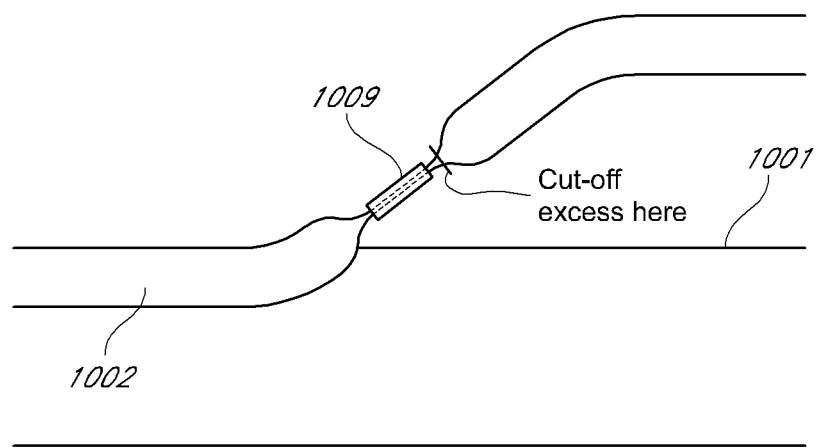

In some embodiments, the portion of the visualization channel 1002 external to the endotracheal tube 1001 can be removed after intubation for safety, comfort, convenience and/or other reasons as desired and/or required. The external portion of the visualization channel 1002 can be removed (at the location marked with an X in FIG. 12C, for example) using scissors or a scalpel blade, by heat sealing and transection, by crimping a metal sleeve 1009 around the tubing and dividing the tubing proximally as shown in FIGS. 12D and 12E, and/or by other methods of sealing and dividing a conduit.

The visualization channel 1002 can be closed at its distal end and open at its proximal end. The distal end can comprise a window or lens. The window can be transparent, substantially transparent, or substantially translucent. The window can serve as a protective cover and/or can help to focus light as a lens. The proximal end can be configured to receive a visualization member 1003, such as, for example, one or more of the visualization members described herein. For example, the visualization member 1003 can comprise a fiber optic, CCD, and/or other imaging element. In some embodiments, the visualization member 1003 is configured to avoid contact with the patient, thereby facilitating cleaning and reuse of the visualization member 1003. In some embodiments, the window is not a lens configured to focus light.

Figure 12F:
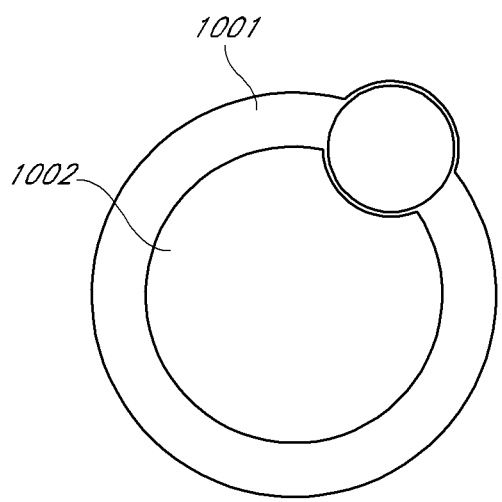
Figure 12G:
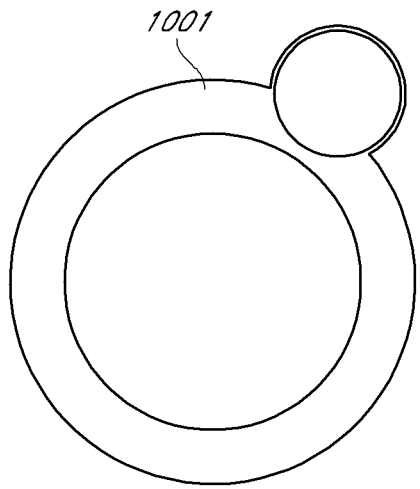
Figure 12H:
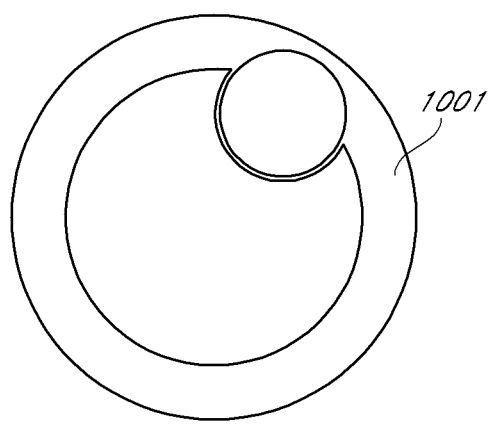
Figure 12I:
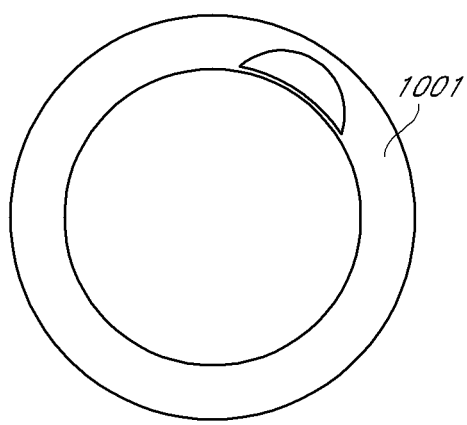

FIGS. 12F-12I illustrate various embodiments of cross-sections of an endotracheal tube 1001 with a built-in visualization channel 1002. The visualization channel 1002 can be located within any portion of the wall of the endotracheal tube 1001. In some embodiments, the visualization channel 1002 is formed wholly or partially within the wall of the endotracheal tube 1001. In other embodiments, the visualization channel 1002 is located on and/or within the exterior wall. As shown in FIG. 12G, the visualization channel 1002 can extrude from the exterior wall of the endotracheal tube 1001. In some embodiments, the visualization channel 1002 is wholly within the pre-existing boundary of the endotracheal tube wall (as shown in FIG. 12I), whereas in other embodiments, the visualization channel 1002 protrudes beyond a pre-existing interior and/or exterior wall of the endotracheal tube (as shown in FIGS. 12F and 12H). The inner diameter of the visualization channel 1002 can be sized, shaped and/or otherwise configured to receive one or more optical fibers or other visualization members. In some embodiments, the inner diameter of the visualization channel 1002 ranges from about 0.05 mm to about 3 mm (e.g., from about 0.05 mm to about 0.1 mm, from about 0.1 mm to about 1 mm, from about 1 mm to about 2 mm, from about 0.5 mm to about 2 mm, from about 1.5 mm to about 3 mm, or greater than 3 mm and/or overlapping ranges therein.

The visualization channel 1002 can be advantageously added to, or can be configured to be compatible with, existing, currently commercially available endotracheal tubes. In some embodiments, the endotracheal tube 1001 illustrated in FIGS. 12A-12I comprises an inflatable cuff at its distal end having a connection for inflation of the cuff (not shown). In some embodiments, the visualization channel 1002 and/or other components or features described herein are compatible with some or all currently commercially available modifications of the "basic" endotracheal tube. The endotracheal tube 1001 of FIGS. 12A-12I can optionally include other modifications to facilitate assisted breathing of a patient and/or insertion within the airway of a patient (e.g., a modification for subglottic aspiration).

The wall of the visualization channel 1002 can be advantageously thin such that the wall can collapse when the visualization member 1003 is removed and/or sufficient suction is administered to the lumen defined within the visualization channel 1002 (e.g., via a vacuum applied to the luer lock tip). The collapse of the visualization channel 1002 can return the endotracheal tube 1001 to its normal internal diameter. The window at the closed end of the visualization channel 1002 can comprise a portion that is capable of collapsing on itself when suction is applied to the visualization channel 1002. For example, such a portion can include one or more materials, including, but not limited to, latex, KRATON polymer, urethane, silicone, TPE, other thin-walled low durometer elastomeric material and/or any other natural or synthetic materials. The collapsing of the visualization channel 1002 can be reversed by applying air or any other fluid to the visualization channel 1002 and/or by inserting the visualization member 1003 within the channel 1002. In some embodiments, the window comprises a flap or valve that permits both viewing and biopsy or other procedures through the visualization channel 1002. The flap or valve can comprise urethane, nylon, TPE, latex, polypropylene, silicone and/or other thin-walled thermoplastic, thermoset plastic, elastomeric materials and/or the like.

According to some embodiments, the endotracheal tube 1001 with the visualization channel 1002 advantageously facilitates the process of endotracheal intubation and allows for immediate (e.g., real-time) and reliable confirmation, under direct imaging, of the position of the tip of an endotracheal tube in relation to the carina of the patient being intubated. In some embodiments, the visualization member 1003 (e.g., scope) is not permanently embedded within the endotracheal tube 1001, but can be quickly removed after intubation and/or confirmation of position after intubation. In some embodiments, the visualization channel 1002 comprises an accessory channel that can be used for other purposes besides visualization.

In some embodiments, the use of the endotracheal tube 1001 with a built-in visualization channel 1002 can advantageously prevent the need to use a laryngoscope made of metal or another hard material to elevate the base of the tongue and epiglottis. Such devices can injure the soft tissues of the oropharynx as well as chip or dislodge patient dentition.

In embodiments where the endotracheal tube 1001 comprises one or more built-in visualization channels, simplified versions of a laryngoscope can be used, as illumination and visualization of the oropharynx, vocal cords, and trachea can be performed using the channels of the endotracheal tube 1001. Therefore, a softer material can advantageously be used to elevate the tongue base and epiglottis that does not injure the soft tissues, or chip or dislodge healthy dentition.

Figure 13:
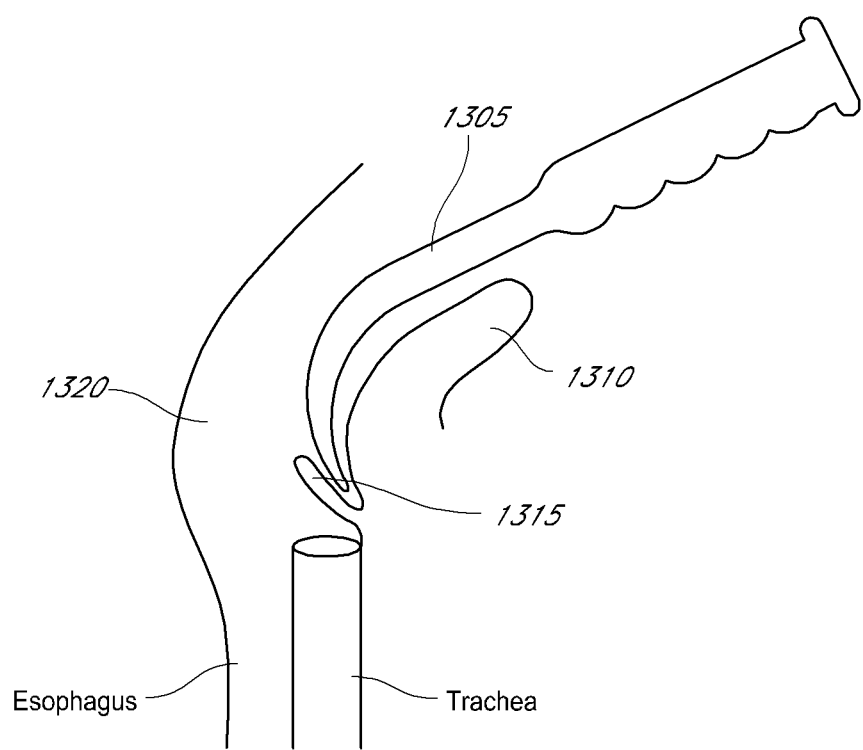
FIG. 13 illustrates an embodiment of a tongue elevator device.

FIG. 13 illustrates an embodiment of a tongue elevator 1305 comprising soft material. Such a device can be held and manipulated in one hand by the intubating practitioner, while the endotracheal tube is inserted with the other hand. The tongue elevator 1305 can comprise a handle attached to the portion of the device that elevates the base of the tongue 1310 and epiglottis 1315.

The distal portion of the tongue elevator 1305 can be configured to conform to the natural curve of the tongue base and to be inserted into the space between the base of the tongue 1310 and the epiglottis 1315. Elevation of the device exposes the posterior oropharynx 1325 and allows visualization of the posterior oropharynx and the vocal cords using the illumination and visualization provided by the endotracheal tube.

In some embodiments, the tongue elevator device 1305 is wider than the standard laryngoscope to prevent portions of the tongue from not being adequately anteriorly displaced. This can help prevent obscuring of the posterior oropharynx 1325 during intubation. The tongue elevator device 1305 can be approximately the width of the adult tongue with its distal-most portion conforming to the anatomy of the base of the tongue 1310 as it transitions to the epiglottis 1315. The surface of the device 1305 can be irregular to accentuate traction on the tongue 1310. The tongue elevator 1305 can also be coated with a material to provide temporary adhesion to the tongue 1310.

II. Airway Cleaning

FIGS. 14A-14C, 15A-15C, 16A-16C, 17A-17U, 18A-18P, 19A and 19B, 20A and 20B and 21A and 21B illustrate embodiments of an airway cleaning device for removal of biofilm, secretions, debris and/or other materials from a patient. The features or elements of any of the embodiments described herein can be compatible with or combined with the features or elements of any of the other embodiments. In some embodiments, the airway cleaning device comprises a disposable, steerable suction catheter guided by an enclosed visualization member for suctioning, irrigating, culturing, pathologically evaluating, administering medications or other pulmonary therapeutics, and generally treating the distal airways of a patient under direct imaging.

The airway cleaning device can be used on patients who breathe unassisted but have impaired cough or secretion clearance mechanisms, as well as on patients receiving assisted ventilation. The airway cleaning device can advantageously be inserted via the natural airway of the patient and/or while the patient undergoes assisted ventilation utilizing an endotracheal or tracheostomy tube. The airway cleaning device can assist in the reliable diagnosis and treatment of pulmonary infection by imaging-directed irrigation and culturing (e.g., bronchoalveolar lavage (BAL)), and/or can allow for microscopic evaluation of tracheobronchial tissue for pathology. With precise diagnosis of bacteria and prescribing the best antibiotic, patients can receive optimized or improved care.

Any of the embodiments of an airway cleaning device described herein can advantageously be configured to remove some or all tracheobronchial secretions or other debris under direct imaging without the need for invasive fiber optic bronchoscopy performed by a physician. In some embodiments, procedures using such cleaning devices are performed regularly, using inexpensive, disposable components. However, in other embodiments, one or more components or portions of device can be reusable. The airway cleaning device can advantageously decrease intubation times and decrease the incidence of ventilator associated pneumonia. This can result in a decrease of hospital stay costs and/or other benefits.

In some embodiments, the airway cleaning device can be used for any unexplained adverse change in airway or ventilation in the intubated patient during surgery. In some embodiments, the airway cleaning device is used to periodically remove pooled secretions from the native airways (e.g., the tracheobronchial tree) of a patient. The airway cleaning device can be used to provide immediate, reliable confirmation of single lumen or multi-lumen (e.g., double lumen) endotracheal tube placement. In some embodiments, the cleaning device is configured to identify acute obstruction of the endotracheal tube (e.g., by hemoptysis or bloody secretions), which can prompt the introduction of an endotracheal tube airway cleaning device, such as the endotracheal tube cleaning devices described herein.

The airway cleaning device can comprise a suction catheter and a control handle. The suction catheter can comprise one or more accessory channels or liners to facilitate removal of the secretions. In some embodiments, the suction catheter comprises a suction line, a visualization/imaging channel and/or an irrigation line. The airway cleaning device can comprise a self-contained system. In some embodiments, the airway cleaning device can operate without visualization and/or irrigation.

The suction line can be used to remove debris or secretions from within the patient (e.g., pooled secretions within the tracheobronchial tree, biofilm lining the trachea, and/or biofilm lining the endotracheal tube). The suction line can be coupled to a wall suction unit and/or to a Lukens trap or other culturing or sampling device for pathological analysis of the removed secretions or debris. In some embodiments, the suction line can advantageously be coupled to a stand-alone suction control unit. The suction control unit can be configured to control suction from about 0.1 cc/sec to about 50 cc/sec (e.g., from about 0.1 cc/sec to about 1.0 cc/sec, from about 1.0 cc/sec to about 10.0 cc/sec, from about 10.0 cc/sec to about 15 cc/sec, from about 5.0 cc/sec to about 15 cc/sec, from about 15 cc/sec to about 50 cc/sec, or greater, and/or overlapping ranges thereof) and to provide for a collection chamber for analysis of infectious bacteria and/or disposal of contaminated debris. In some embodiments, the suction control unit can provide higher levels of suction than a wall suction unit. An in-line detachable suction chamber just proximal to the handpiece or integral with the handpiece can have a capacity of up to 8 ccs. In some embodiments, the suction chamber is designed so that it is relatively free from features that can "hang up" the suctioned material and cause clogging and surging in the suction line. In some embodiments, the suction chamber is different from the Lukens traps that may have angled connections. In some embodiments, the fluid passageways are smooth, uniform and unobstructed. The suction control unit can be configured to remove debris having a cross-sectional dimension of up to about 4 or 5 mm, or greater. In some embodiments, the amount of suction applied to the cleaning device can range from about 30 mmHg to about 250 mmHg (e.g., from about 30 mmHg to about 100 mmHg, from about 50 mmHg to about 180 mmHg, from about 100 mmHg to about 200 mmHg, from about 200 mmHg to about 250 mmHg, from about 100 mmHg to about 250 mmHg, or greater, and/or overlapping ranges thereof).

The suction line can be open at its distal end. In some embodiments, the suction line comprises a "safety slot" or "safety valve" located near the most distal portion of the device (e.g., smaller than the Murphy Eye, and closer to the tip of the device) to reduce or minimize tissue damage when high volume suction is used to remove large amounts of mucus or other debris. For example, this can be advantageous when the distal tip of the airway cleaning device is up against the wall of the lung.

The visualization/imaging channel can be used to locate the pooled secretions or debris collections within the patient's airway for removal, to confirm removal of the secretions or debris, and/or to confirm the position of the endotracheal or other body-inserted tube within the patient. The visualization channel can include a window or transparent lens at its closed distal end, similar to the windows or lenses described above. The visualization channel can be configured to receive a visualization member, such as, for example, the visualization member described above. The visualization member can comprise a "chip on a stick" or a visualization scope configured to obtain images of the internal anatomical structures of the patient. The visualization member can be coupled to one or more cameras, light sources, monitors or other output devices for display of the images, as described above. The visualization member can comprise any of the features or elements described herein.

The irrigation line can be used to administer air or other fluid to a window or lens at or near the distal end of the visualization channel in order to remove obstructions from or otherwise clean the window or lens. The irrigation line can be open at its distal end. In one embodiment, the irrigation line is coupled to a pressurized saline irrigation bag or other fluid source. In some embodiments, an irrigation control system is coupled to the airway cleaning device that is configured to drive a syringe (e.g., having a capacity of about 10 cc to 200 cc, smaller than about 10 cc, greater than about 200 cc) or other device in order to deliver a selected bolus of irrigation or medication. In some embodiments, the control system comprises an automated irrigation system capable of variable control. The irrigation line can also be used to administer medications or other pulmonary therapeutics to the patient's native airway. In some embodiments, the irrigation line administers substances that help dissolve or otherwise break up larger debris or secretions. In one embodiment, the irrigation line comprises a distal end with a "flap" or some other backflow prevention valve or feature that allows irrigation to be delivered, but prevents reverse flow of mucus or other debris through the tube.

FIGS. 14A-14C illustrate an embodiment of a distal airway cleaning device 1500. FIG. 14A illustrates a side view of the distal airway cleaning device 1500. FIG. 14B illustrates a close-up view of the distal end 1502 of the airway cleaning device 1500 of FIG. 14A and FIG. 14C illustrates a cross-sectional view of the distal airway cleaning device 1500 of FIG. 14A. As shown in FIG. 14A, the distal airway cleaning device 1500 comprises a control handle 1505 and a suction catheter 1510. In some embodiments, the suction catheter 1505 can be substantially straight. However, in other embodiments, the suction catheter 1505 can have any other shape (e.g., non-straight, curved, etc.).

The suction catheter 1505 can comprise one or more rigid or semi-rigid, stiff, substantially stiff, flexible and/or substantially flexible materials. These materials include, but are not limited to, PEEK, TPE, polyethylene, polypropylene, PET, PETG, silicone, latex, KRATON polymers and/or any other natural or synthetic materials. The varying degrees of rigidity, stiffness and flexibility of the suction catheter 1505 can be provided by materials selected to aid in steerability and angulation of the distal end. The main body of the suction catheter 1505 can comprise one or more stiff or substantially stiff materials. In some embodiments, the distal end 1502 of the suction catheter 1505 can comprise one or more pre-curved and/or flexible materials. For example, the distal end 1502 of the suction catheter 1505 can comprise one or more flexible materials that aid in the steerabilty of the catheter 1505.

According to several embodiments, the distal end 1502 of the suction catheter 1505 comprises the distal one to five centimeters of the catheter. In alternative embodiments, the distal end 1502 comprises more or less of the distal portion. In a pre-curved embodiment, the distal end 1502 can be curved through an angle of between about 1 degree and 60 degrees, e.g., between about 1 degree and 15 degrees, between about 15 degrees and 45 degrees, between about 45 and 60 degrees, between about 10 degrees and 20 degrees, between about 15 degrees and 30 degrees, between about 30 degrees and 60 degrees, greater than 60 degrees, less than 1 degree, and overlapping ranges thereof. In a flexible, non-pre-curved embodiment, the distal end 1502 can be guided or manipulated to curve at an angle between about 0 degrees and 60 degrees. The distal end 1502 can be controlled by the operator and pivotable in one, two or more directions. The distal end 1502 of the suction catheter can be curved or dimensioned differently for different anatomies.

In some embodiments, the distal end 1502 of the suction catheter 1505 comprises one or more shape memory materials such that the suction catheter 1505 can be configured to conform to the straight lumen of the endotracheal tube upon insertion, can be configured to conform to the bend of the endotracheal tube upon further insertion, can be configured to assume its "pre-bent" or angled configuration upon exiting the endotracheal tube and/or the like. In some embodiments, the distal end 1502 comprises one or more hydrophilic or hydrophobic materials.

The distal end 1502 of the suction catheter 1505 can be open or patent at its distal tip and can include one or more Murphy's eyes 1530. The distal end 1502 of the suction catheter 1505 depicted in FIGS. 14A-14C comprises the distal approximately two centimeters of the suction catheter 1505 and is curved at about a 45 degree angle.

The length L of the suction catheter 1505 from the control handle 1510 to the distal tip can range from approximately 4 inches to approximately 24 inches, e.g., from approximately 4 inches to approximately 12 inches, from approximately 6 inches to approximately 10 inches, from approximately 8 inches to approximately 16 inches, from approximately 12 inches to approximately 24 inches, or greater, and overlapping ranges thereof. The inner diameter of the suction catheter 1505 can range from approximately 1 mm to approximately 10 mm, e.g., from approximately 1 mm to approximately 3 mm, from approximately 3 mm to approximately 6 mm, from approximately 6 mm to approximately 10 mm, or greater, and overlapping ranges thereof. In some embodiments, the inner diameter of the suction catheter 1505 is dimensioned to be able to receive debris having a cross-sectional diameter or other dimension of about 4 to 5 mm. In other embodiments, however, the inner diameter of the suction catheter 1505 is configured to receive debris of greater or lesser size. The outside diameter of the suction catheter 1505 can advantageously be smaller in dimension than existing bronchoscopes. For example, the outside diameter of the suction catheter 1505 can range from about 1 mm to 12 mm, from about 3 mm to about 6 mm, can be smaller than 1 mm, can be larger than 12 mm and/or can have any other dimension. The dimensions of the suction catheter 1505 can be adjusted to accommodate various uses or various body-inserted tubes without departing from the spirit and/or scope of the disclosure.

The control handle 1510 can be rotated by the operator to "steer" or direct the angled or curved distal portion of the suction catheter 1505 into specific anatomical locations (e.g., branches of the tracheobronchial tree) under direct visualization following insertion of the distal airway cleaning device 1500 through the endotracheal tube or other body-inserted tube.

As shown in FIGS. 14B and 14C, the suction catheter 1505 can comprise a suction line 1515, a visualization channel 1520, an irrigation line 1525, and/or any other passage. The visualization channel 1520 can be extruded on the outside of the suction line 1515. The outer diameter of the visualization channel 1520 can range from approximately 0.1 mm to approximately 5 mm, e.g., from about 0.1 mm to about 1 mm, from about 1 mm to about 3 mm, from about 3 mm to about 5 mm, or greater, and overlapping ranges thereof. As shown in FIG. 14B, the distal tip of the visualization channel 1520 can be positioned at or near the proximal boundary of the distal portion (e.g., just before the curve or bend). The distal tip of the visualization channel 1520 can be positioned at any position along the length of the suction catheter 1505 (including along the curved or flexible distal portion or along the straight main portion).

The irrigation line 1525 can be extruded within the lumen of the suction line 1515. The inside diameter of the irrigation line 1525 can range from approximately 0.1 mm to approximately 3 mm, from approximately 0.5 mm to approximately 2 mm, or smaller or larger. The distal tip of the irrigation line 1525 can be positioned at any location along the length of the suction line 1515. In some embodiments, the irrigation line 1525 is positioned at a location corresponding to the distal tip of the visualization channel 1520 to facilitate cleaning of a window or lens of the visualization channel 1520.

FIGS. 15A-15C illustrate another embodiment of a distal airway cleaning device 1500A. FIG. 15A illustrates a side view of the distal airway cleaning device 1500A. FIG. 15B illustrates a close-up section side view of the distal end 1502A of the distal airway cleaning device 1500A of FIG. 15A and FIG. 15C illustrates a cross-sectional view of the distal airway cleaning device 1500A of FIG. 15A. The visualization channel 1520 and the irrigation line 1525 can be extruded within the lumen of the suction line 1515. The visualization channel 1520 and the irrigation line 1525 can be positioned anywhere along the circumference of the suction line 1515. In some embodiments, the visualization channel 1520 and the irrigation line 1525 are adjacent each other (for example, to facilitate cleaning of a window or lens of the visualization channel 1520). In other embodiments, the visualization channel 1520 and the irrigation line 1525 can be spaced farther apart, as desired or required.

FIGS. 16A-16C illustrate an embodiment of a distal airway cleaning device 1500B (e.g., suction catheter) as described herein, wherein the closed distal end of the visualization channel 1520 ends proximally to the angulation and distal tip of the cleaning device 1500B. FIG. 16A illustrates a side view of the distal airway cleaning device 1500B. FIG. 16B illustrates a magnified side view of the distal end 1502 of the distal airway cleaning device 1500B of FIG. 16A. Further, FIG. 16C illustrates a magnified top view of the distal end 1502 of the distal airway cleaning device 1500B of FIG. 16A. In some embodiments, the visualization channel 1520 and the irrigation line 1525 are adjacent to each other (for example, to facilitate cleaning of a viewing window or lens of the visualization channel 1520 as described in more detail below).

With continued reference to FIG. 16B, a diameter of the distal airway cleaning device 1500B can be increased adjacent to the angulation to allow the visualization channel 1520 to be angled at or near its distal end. For instance, positioning the distal end of the visualization channel 1520 on an angle can increase visualization of the location of the distal end of the distal airway cleaning device 1500B within the native airways of the patient and of the native airways themselves. The visualization channel 1520 and irrigation channel 1525 can be parallel and/or be positioned adjacent to one another within the suction catheter portion 1505 of the cleaning device 1500B for at least a portion of its length, outside the suction catheter portion 1505 for at least a portion of its length, or within the wall of the suction catheter portion 1505 for at least a portion of its length. As shown in FIG. 16C, deflectors 1508 can be positioned distally to the window at the end of the visualization channel 1520 in order to, among other things, keep secretions off the window. In some embodiments, the angulated visualization channel is incorporated into the designs of other distal airway cleaning devices or any other tubular structures.

Figure 17E:
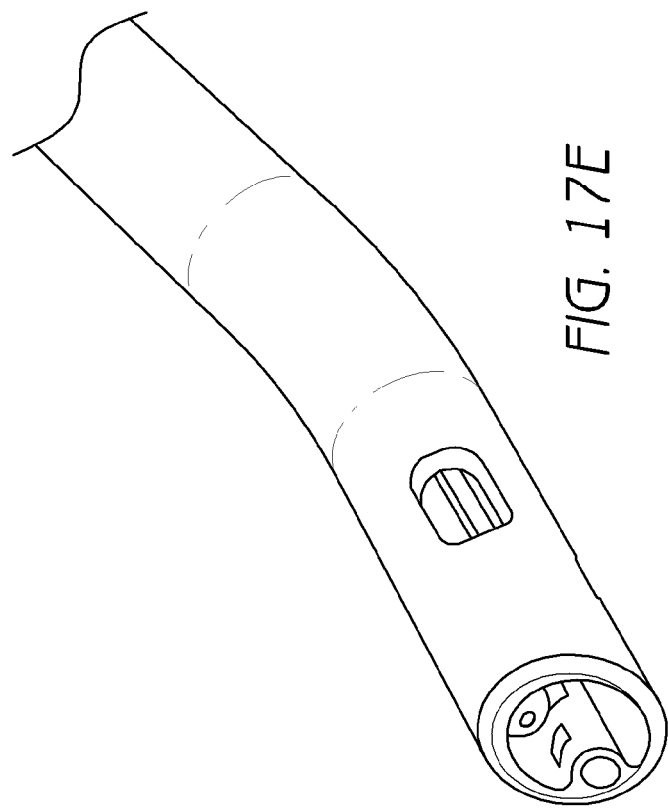
Figure 17D:
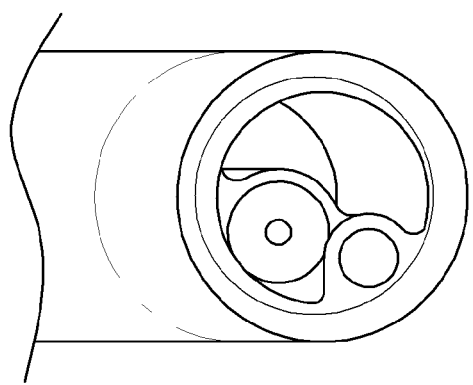
Figure 17F:
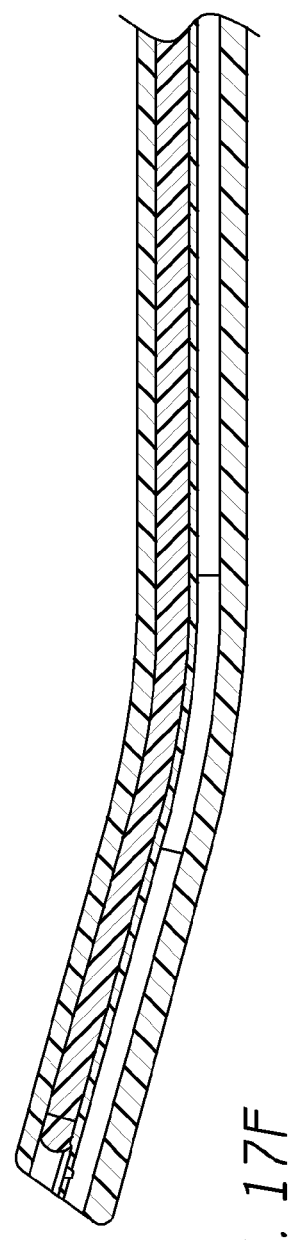
Figure 17I:
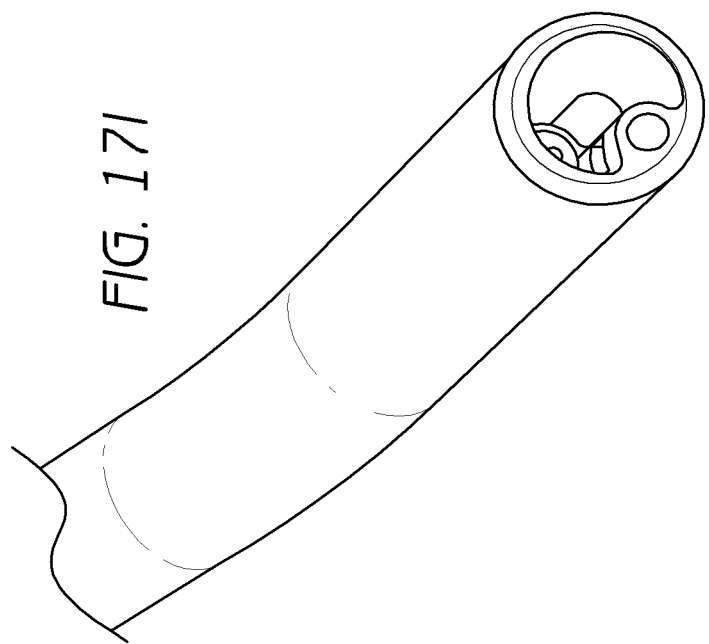
Figure 17G:
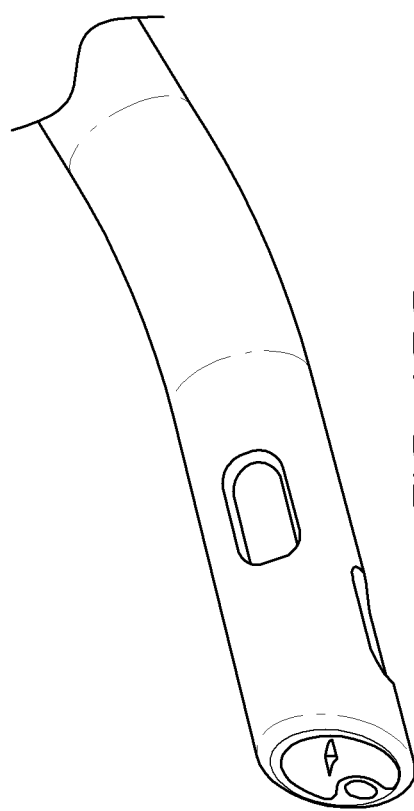
Figure 17H:
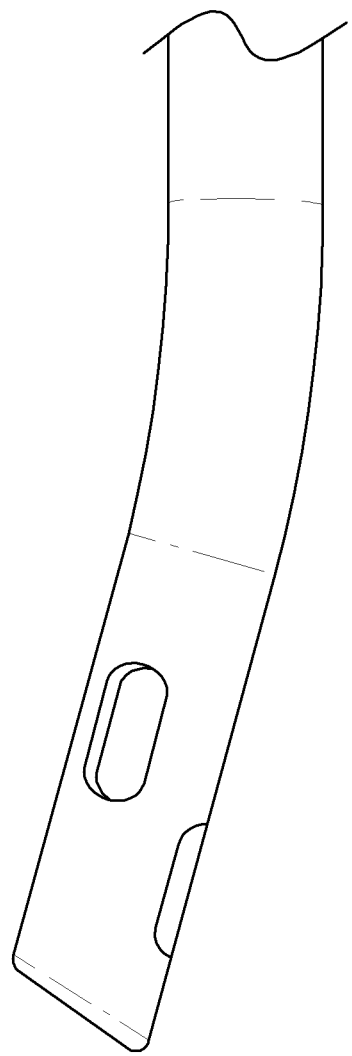
Figure 17K:
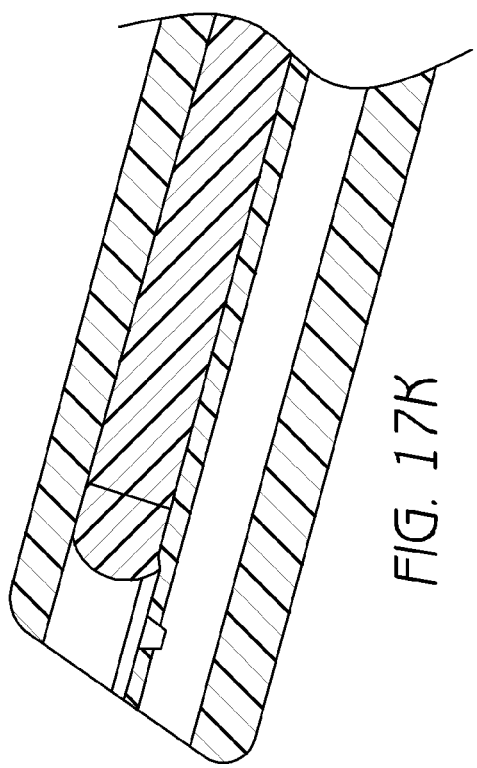
Figure 17L:
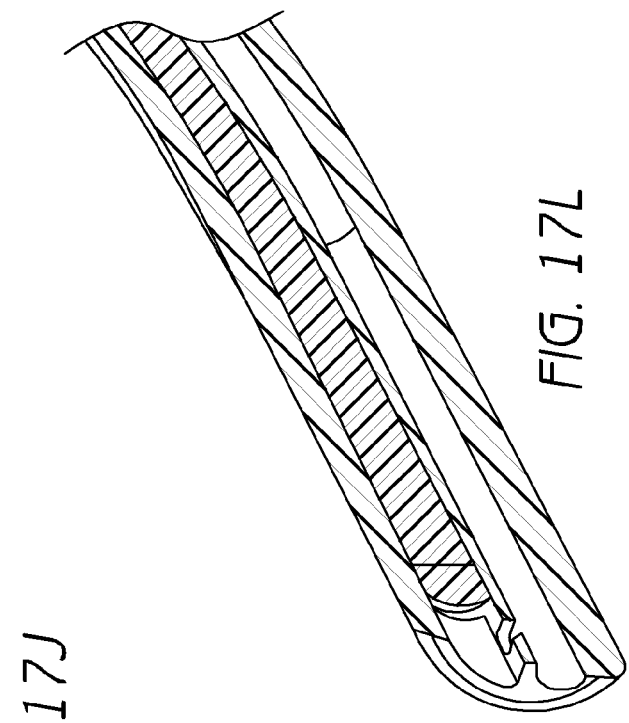
Figure 17J:
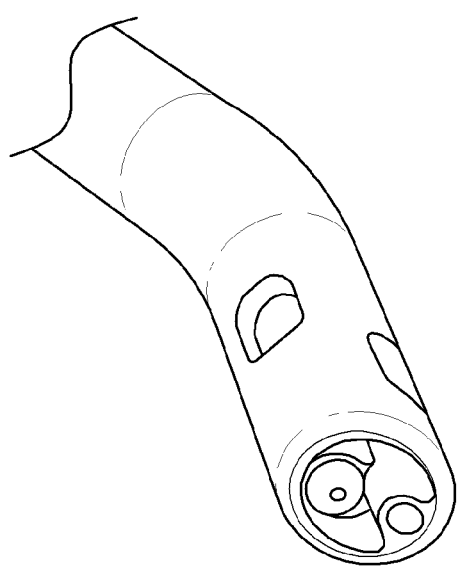
Figure 17M:
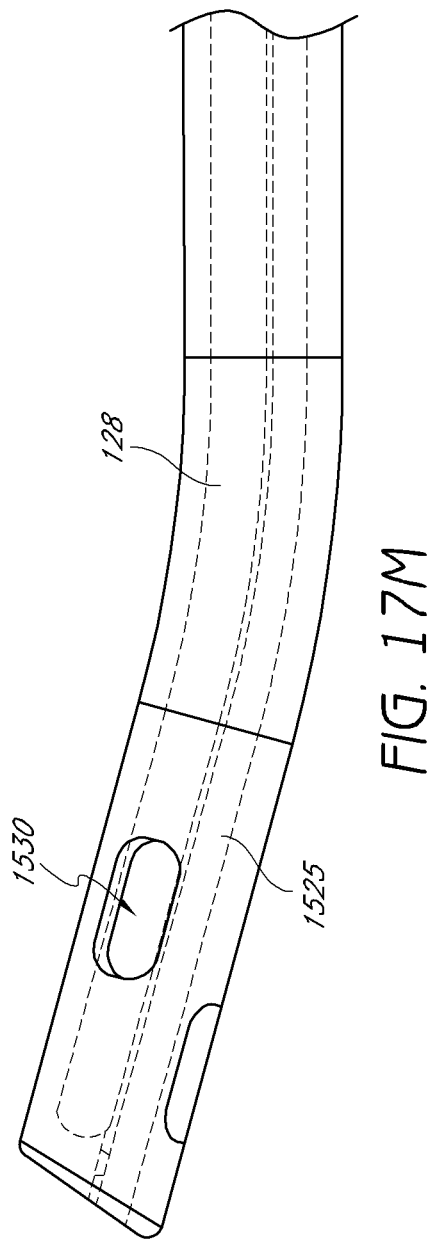
Figure 17N:
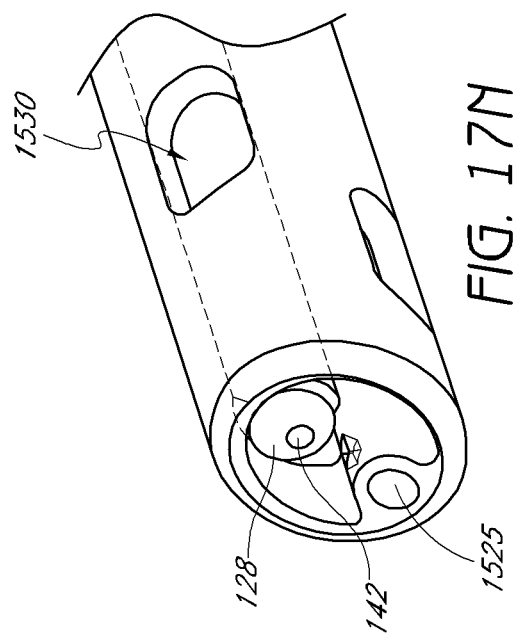

FIGS. 17A-17U illustrate another embodiment of a distal airway cleaning device 1500C in which the distal ends of the visualization channel 1520 and the irrigation line 1525 extend all the way to the distal tip of the suction catheter 1505. The distal end of the suction catheter 1505 in the embodiment of FIGS. 17A-17C comprises approximately the distal 2 cm of the suction catheter 1505 and is curved to a lesser degree (e.g., a 15 degree angle) than the embodiment of FIGS. 15A-15C. FIG. 17A illustrates a side view of the distal airway cleaning device 1500C. FIG. 17B illustrates a close-up section side view of the distal portion of the distal airway cleaning device 1500C of FIG. 17A and FIG. 17C illustrates a cross-section view of the distal airway cleaning device 1500C of FIG. 17A. FIGS. 17D-17P illustrate various views of the distal end 1502 of the distal airway cleaning device 1500C of FIG. 17A. FIGS. 17M and 17N illustrate transparent views.

Figure 17O:
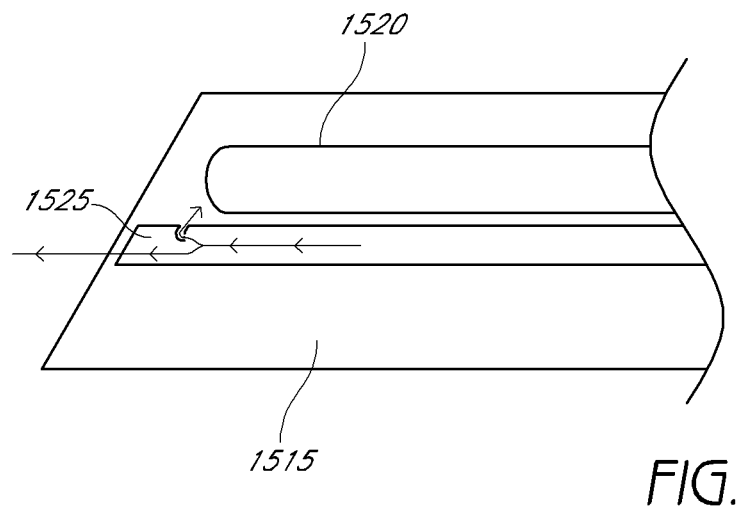
Figure 17P:
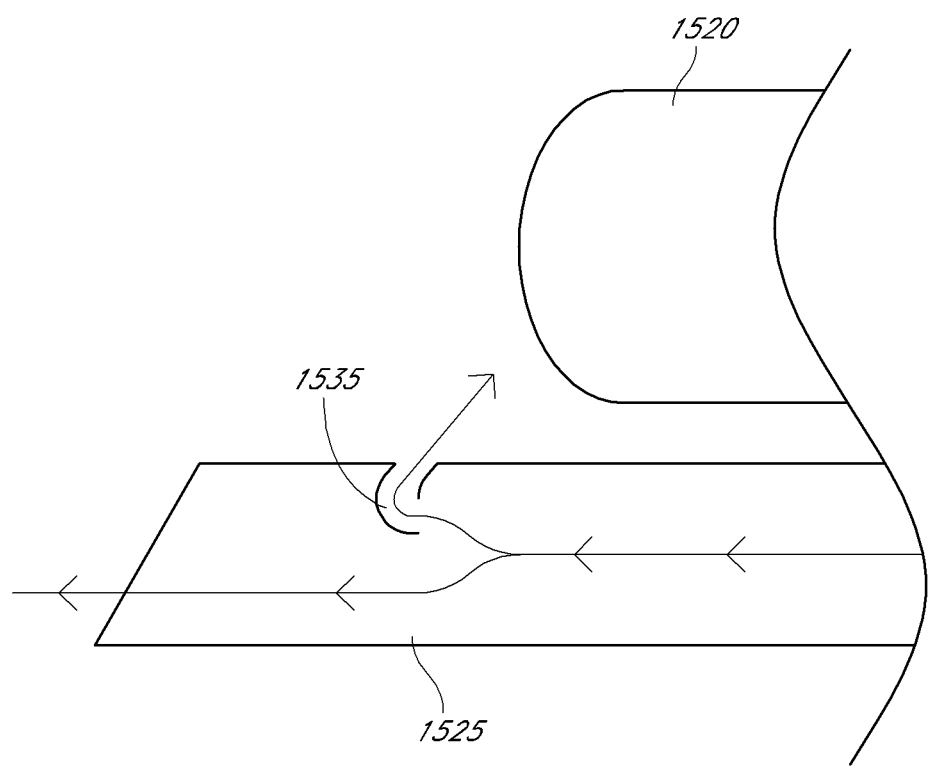
Figure 17Q:
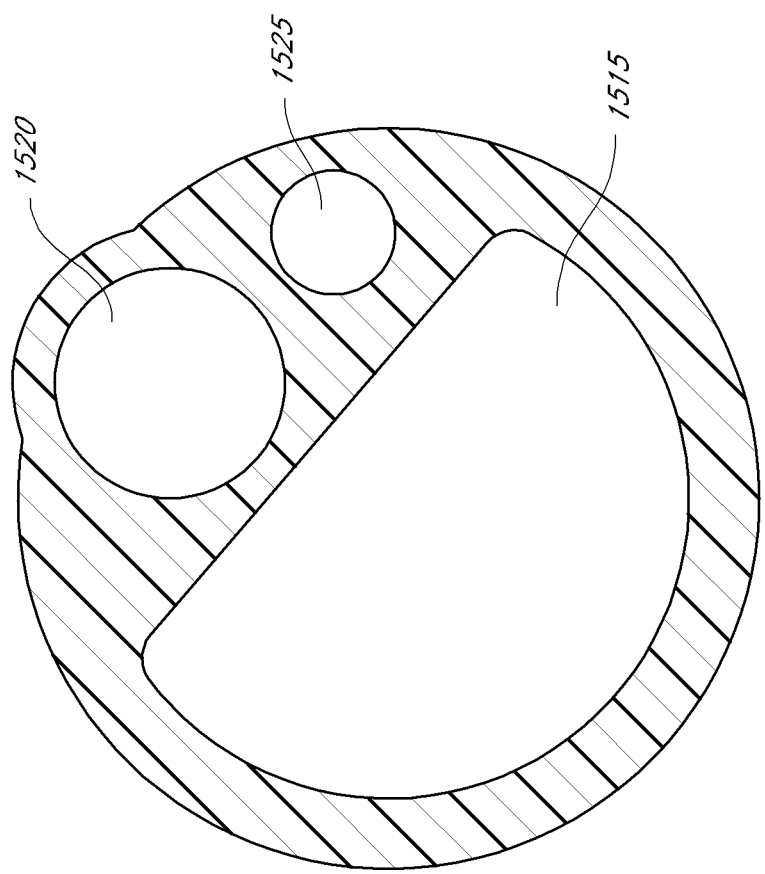

As shown in FIGS. 17A-17Q, the visualization channel 1520 and the irrigation line 1525 of the distal airway cleaning device 1500C can be located within the suction catheter 1505. The visualization channel 1520 and the irrigation line 1525 extend to or near the distal tip of the suction catheter 1505. The distal edges of the suction catheter 1505 can comprise one or more soft materials and/or can be rounded to prevent injury to the patient's native airways (e.g., trachea or tracheobronchial tree) or to the endotracheal or other body-inserted tube. As best shown in FIGS. 17E, 17G, 17K, and 17L, the irrigation line can comprise one or more slits, openings, recesses, or other apertures, adjacent to its distal end to facilitate cleaning of a lens or window at the distal tip of the visualization channel 1520. In some embodiments, as shown in FIG. 17O, the slit 1535 comprises a "blow-back" cutout shaped and dimensioned to direct irrigating fluid backward toward the window of the visualization channel 1520 or visualization member. FIG. 17P is a detailed close-up view of FIG. 17O.

In some embodiments, the slit 1535 can include one or more nozzles configured to provide a wash jet and/or air jet at an appropriate pressure to wash the outside surface of the lens or window of the visualization channel 1520. In other embodiments, the slit 1535 comprises a diffusing opening configured to spray the outside surface of the lens or window while simultaneously delivering a sufficient amount of fluid to assist in the breakdown of biomaterials such that they can be suctioned by the suction line. In some embodiments, the distal tip of the visualization channel 1520 can be covered with a cap comprising a window or lens. In some embodiments, the cap comprises multiple windows and/or lenses. FIG. 17Q illustrates an alternative embodiment of a cross-section of a suction catheter 1505 of the distal airway cleaning device 1500C.

FIGS. 17R-17U schematically illustrate mechanical methods for selectively deflecting the distal end of the distal airway cleaning devices described herein (e.g., distal airway cleaning devices 1500, 2600) or any suction catheter (e.g., standard, non-standard, etc.). In some embodiments, with reference to FIGS. 17R and 17S, a non-bendable material 1590 (e.g., hard plastic, metal) is positioned at or near an elbow 1592 of a suction catheter portion 1594 of the distal airway cleaning device 1500C. A distal portion 1596 of the non-bendable material can be secured to the suction catheter with the assistance of one or more attachment devices and/or methods, such as, for example, interference or friction fits, heat shrink tubing, adhesives, epoxies, molding, welds, mechanical fasteners and/or the like. As shown, one or more inflation channels 1598 can be positioned along at least a portion of the suction catheter portion 1594. Such inflation channels can be routed inside the suction catheter portion 1594, outside the suction catheter portion 1594, and/or within the wall of the suction catheter portion 1594. One or more actuators and/or other control devices for regulating balloon inflation can be located at the proximal end of the distal airway cleaning device 1500C, on a control handle 1510 that is an integral part of the distal airway cleaning device 1500C and/or at any other location. In some embodiments, a balloon 1599 is insufflated by a syringe type mechanism or by manipulating a controller (e.g., depressing a button, turning a lever, etc.), thereby compressing a bladder within the control handle 1510 that contains a predetermined amount of air connected to the distal balloon 1599 in a closed system. As the balloon 1599 is inflated, the angulation of the distal tip 1502 of the suction catheter portion 1594 changes so that the elbow 1592 of the bend subtends or otherwise assumes a more obtuse angle. The suction line or conduit can also be used with a visualization channel as described herein, an irrigation channel as described herein and/or another inflation channel that may be used to deploy an endotracheal tube cleaning device positioned on or near the catheter.

With reference to FIGS. 17S and 17T, an angulation or deflection wire 1597 can be inserted within one or more channels (e.g., visualization channel or separate angulation or deflection channel) of the distal airway cleaning device 1500C in order to change the angulation of the distal end of the distal airway cleaning device 1500C. Such channels can be positioned inside the suction line 1515, outside the suction line 1515, and/or within the wall of the suction line 1515. For example, in the nominal orientation or position (as shown in FIG. 17S), the elbow 1592 of the suction catheter portion 1594 subtends an obtuse angle suitable for general use.

With reference to FIG. 17T, when traction is placed on the wire 1597 backwards toward the proximal portion or control handle 1510 of the distal airway cleaning device 1500C, the elbow 1592 subtends a less obtuse angle and the distal tip of the catheter is deflected. The backward traction on the wire 1597 can be performed at the control handle 1510 by exerting backward traction on a protuberant, moveable portion of the control handle 1510 (e.g., using a thumb or other finger). This mechanism for tip deflection may also be used in conjunction with a visualization channel, balloon inflation channel, and/or irrigation channel in the suction catheter 1594 (as described herein).

FIGS. 18A-18P, 19A and 19B, 20A and 20B and 21A and 21B illustrate embodiments of a control handle 1510 of the distal airway cleaning device 1500C. The control handle 1510 comprises one or more user inputs configured to control the operation of the irrigation line 1525 and the suction line 1515 of the airway cleaning device 1500. The one or more user inputs can comprise buttons, ports, switches, touch-sensitive elements, pressure-sensitive elements, and/or the like. The user inputs can be configured to actuate two or more operational states (e.g., on and off) or can be configured to provide variable control of the irrigation and suction lines (e.g., variable pressure, variable inflow/outflow rates, and/or the like). The embodiments illustrated in FIGS. 18A-18P, 19A and 19B, 20A and 20B and 21A and 21B illustrate various embodiments of an irrigation control input 1540 (e.g., on/off button) and a suction control input 1545 (e.g., on/off port) for controlling the operation of the irrigation line 1525 and the suction line 1515, respectively. In some embodiments, a single user input can be used to actuate both the irrigation line 1525 and the suction line 1515.

Figure 18E:
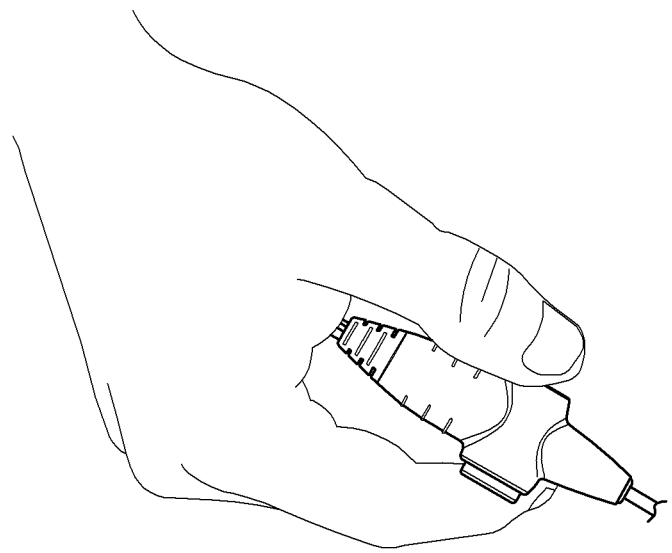
Figure 18D:
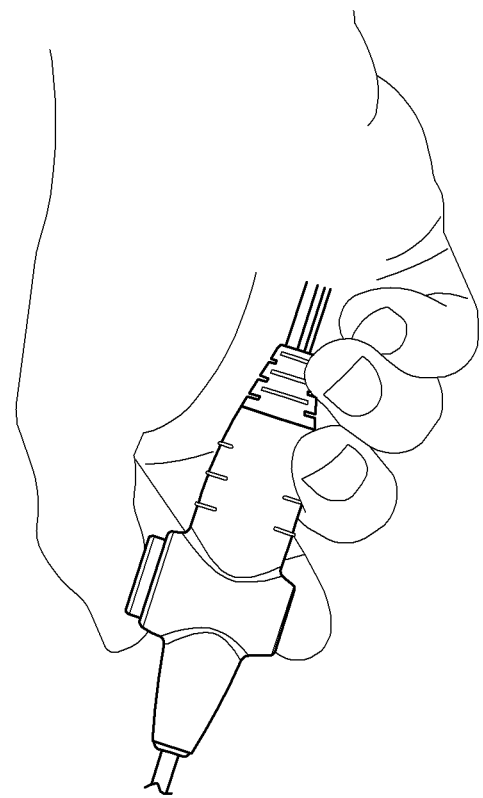
Figure 18F:
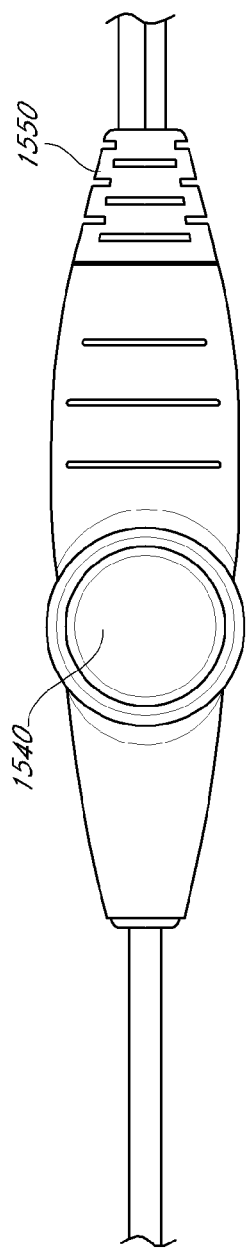
Figure 18G:
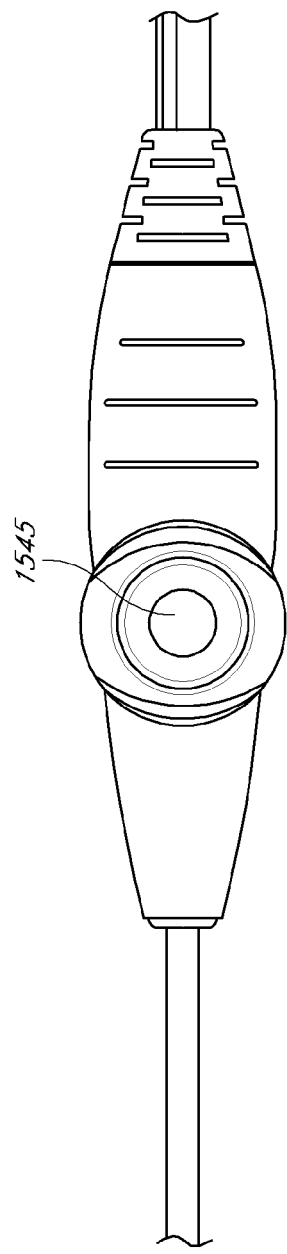
Figure 18H:
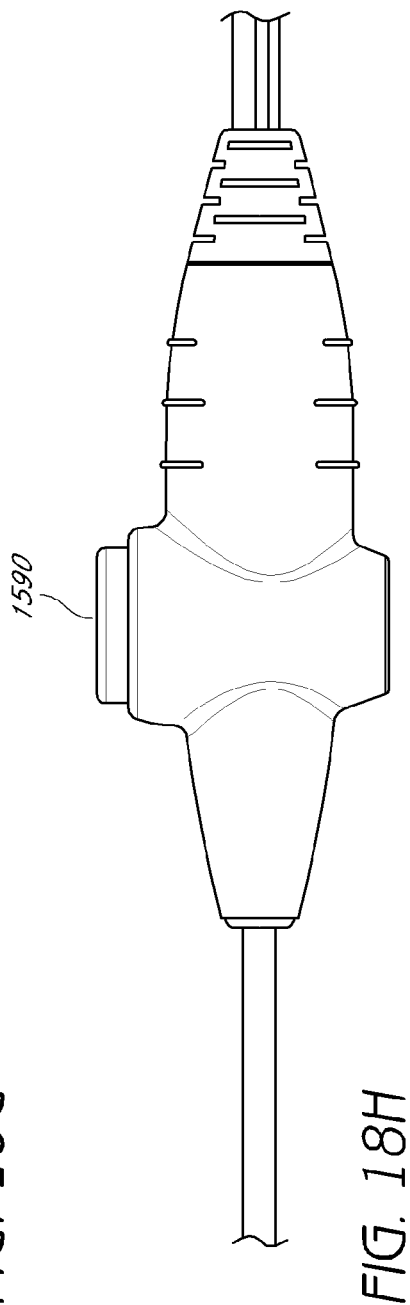
Figure 18O:
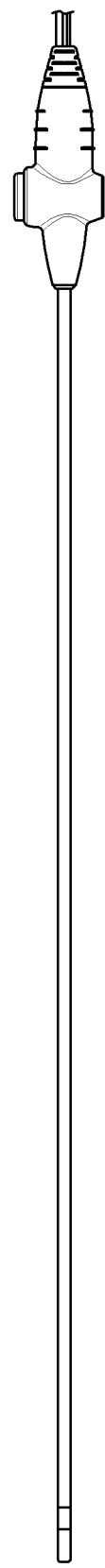
Figure 18P:
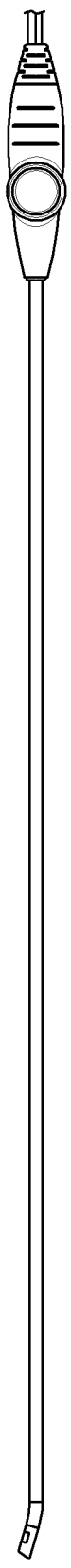
Figure 19B:
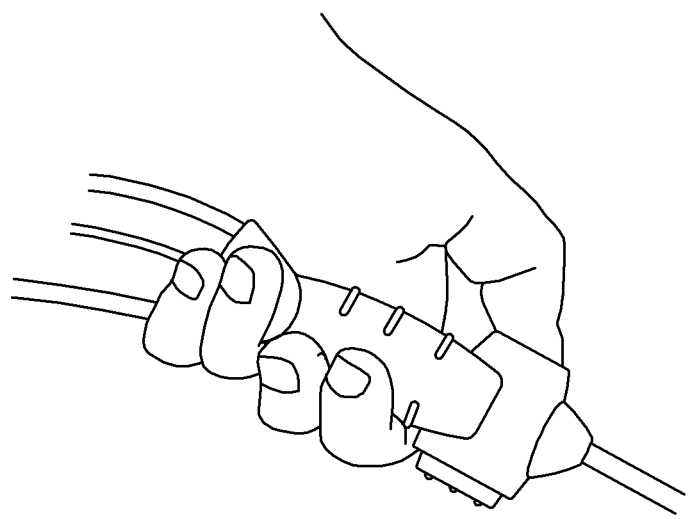
Figure 19A:
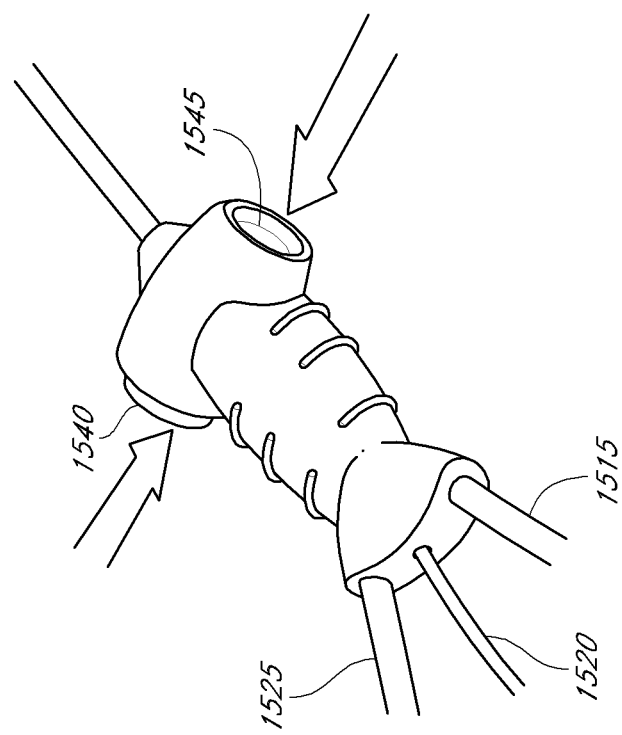
Figure 20B:
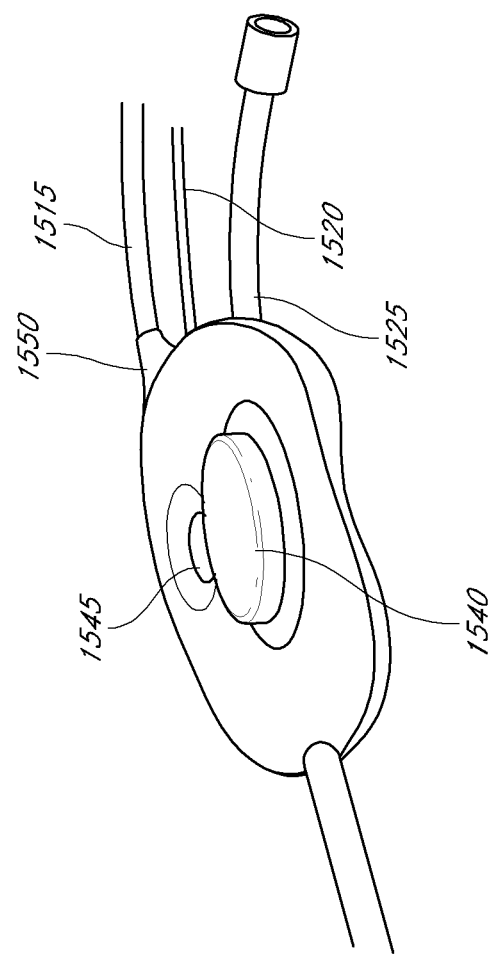

As shown in FIGS. 18A-18P, the control handle 1510 can comprise a strain relief member 1550 at the proximal end of the control handle 1510. In some embodiments, the control handle 1510 advantageously allows for one-handed operation of the distal airway cleaning devices 1500. FIGS. 18C-18E illustrate three different examples of how the control handle 1510 illustrated in FIGS. 18A and 18B can be held and manipulated by an operator using a single hand. FIGS. 19B, 20B and 21B illustrate examples of how the control handles of FIGS. 19A, 20A and 21A, respectively, can be held by an operator using a single hand. In some embodiments, a first user input is configured to be actuated using a thumb of the operator, and a second user input is configured to be actuated by an index finger or a middle finger of the operator. The user inputs can be located on opposite sides of the control handle 1510, as shown in FIGS. 18A-18P and 19A and 19B. As shown in FIGS. 18A-18E, the control handle 1510 can comprise a smooth, generally cylindrical body that gradually tapers from the midpoint of its length to the proximal and distal ends of the control handle 1510. In addition, the control inputs can extend laterally outward from the cylindrical body (e.g., in a cross-like shape). Alternatively, the control handle can include one or more ergonomic features to facilitate the gripping and/or manipulation of the control handle by an operator. For example, as illustrated in FIGS. 18F-18P and FIGS. 19A and 19B, the control handle 1510 can include one or more gripping ridges 1555. In some embodiments, the control handle 1510 can include grooves, recesses, and/or other surface features configured to receive different portions of the hand of the user.

Figure 20A:
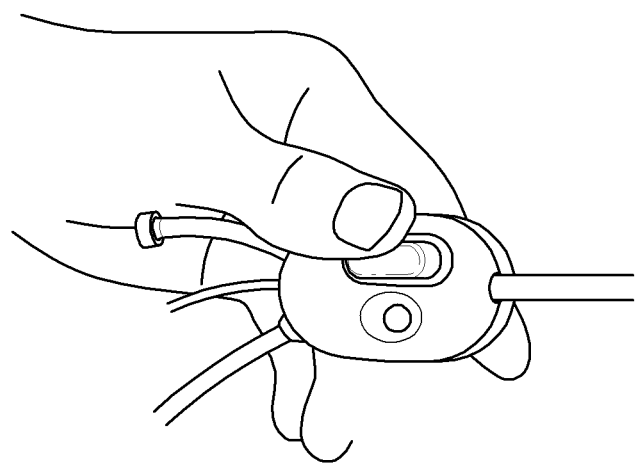

FIGS. 20A and 20B illustrate another embodiment of the control handle 1510. As shown, the control handle 1510 can comprise a generally flat, oval-shaped body. As shown in FIGS. 20A and 20B, the user inputs can be located adjacent to each other on a top side of the control handle 1510. The user inputs (e.g., buttons) can also comprise surface features to enhance grip and reduce slipping, as shown.

FIGS. 21A and 21B illustrate another embodiment of an ergonomic control handle 1510 configured for single-handed operation. The suction control input 1545 is located within a side port extending outwardly from the main body of the control handle 1510. In some embodiments, the suction control input 1545 and the irrigation control input 1540 are offset by approximately ninety degrees. As shown in FIGS. 21A and 21B, the control handle 1510 can comprise a generally-cylindrical body that is tapered from the proximal end to the distal end of the control handle 1510. However, in other embodiments, the control handle 1510 can include any other shape, as desired or required.

Figure 22:
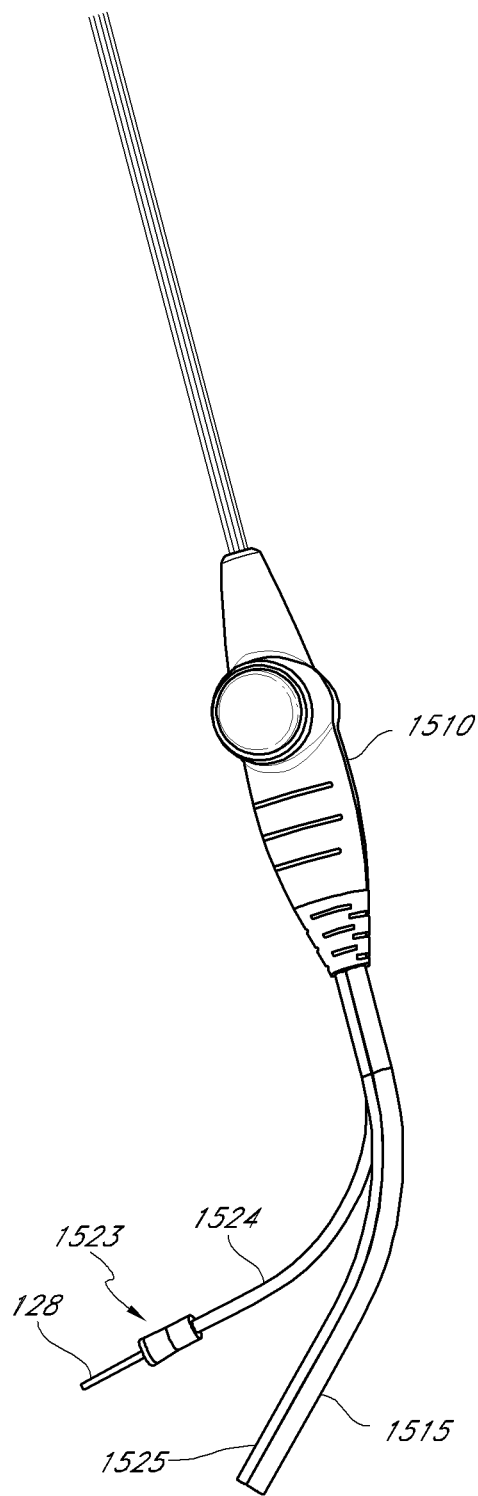
FIG. 22 illustrates an embodiment of an airway cleaning device comprising a scope retention assembly.

The distal airway cleaning devices 1500 described herein can include a scope retention assembly 1523 as shown in FIG. 22. The scope retention assembly 1523 of FIG. 22 can operate in a similar manner as the scope retention assembly 123 described above with respect to the visualization devices to exert a static backward force on a visualization scope inserted within the visualization channel 1520 or line of the distal airway cleaning device 1500.

In some embodiments, the distal airway cleaning device 1500 can be configured to operate in a sterile, "closed" system such that the distal airway cleaning device 1500 is used more than once on the same patient (e.g., over a twenty-four hour period or longer or shorter depending on applicable patient care guidelines, protocols, or regulations).

Figure 23:
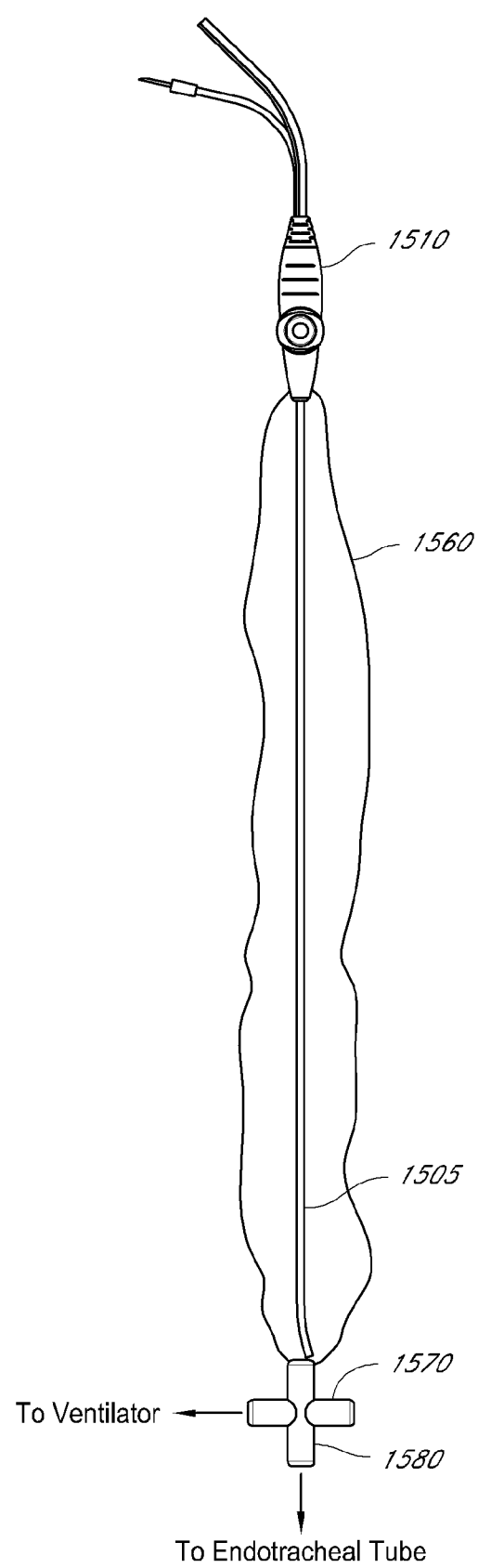
FIG. 23 is a schematic illustration of an embodiment of an airway cleaning device operating in a "closed" environment.

With reference to FIG. 23, in the "closed" system, a substantially clear, collapsible sheath 1560 extends from a distal end of the control handle 1510 to an in-line port 1565 of a T-connector 1570 that can be connected to an endotracheal tube inserted within a patient. The T-connector 1570 can also include a ventilation port 1575 and a lavage port (not shown). The collapsible sheath 1560 can comprise plastic, latex, other polymeric or elastomeric materials and/or any other material. Such materials can be relatively thin to permit the sheath to easily collapse or otherwise move during use. In some embodiments, the collapsible sheath 1560 comprises clear or substantially clear materials to allow for enhanced visualization of the suction catheter portion of the airway cleaning device 1500. The suction catheter 1505 can include one or more markings to indicate depth of insertion and/or to indicate that the suction catheter 1505 has been completely removed from the patient.

In some embodiments, the suction catheter portion of the distal airway cleaning device 1500 is enclosed within the collapsible sheath 1560 until deployed out of an outlet port 1580 of the T-connector 1570 and into the endotracheal tube within the patient. Therefore, the suction catheter 1505 remains within a closed suction environment during use and can be re-used within the same patient. The T-connector 1570 can include a user control button or other controller to regulate the initiation and termination of suction. Such a button or other controller can include a lock or other safety feature to prevent accidental suctioning.

In use, the suction catheter portion of the distal airway cleaning device 1500 can be advanced through the endotracheal tube and into a targeted region of the tracheobronchial tree to provide visualized suctioning of the distal airways of a patient (as described in more detail herein) in a closed suctioning environment. The collapsible sheath 1560 is axially collapsed as the suction catheter 1505 is advanced and is axially expanded as the suction catheter 1505 is withdrawn. In one embodiment, a clinician or other patient care provider can hold the T-connector 1570 with one hand while advancing and retracting the suction catheter 1505 with the other hand, allowing for single-person operation of the system.

Figure 24A:
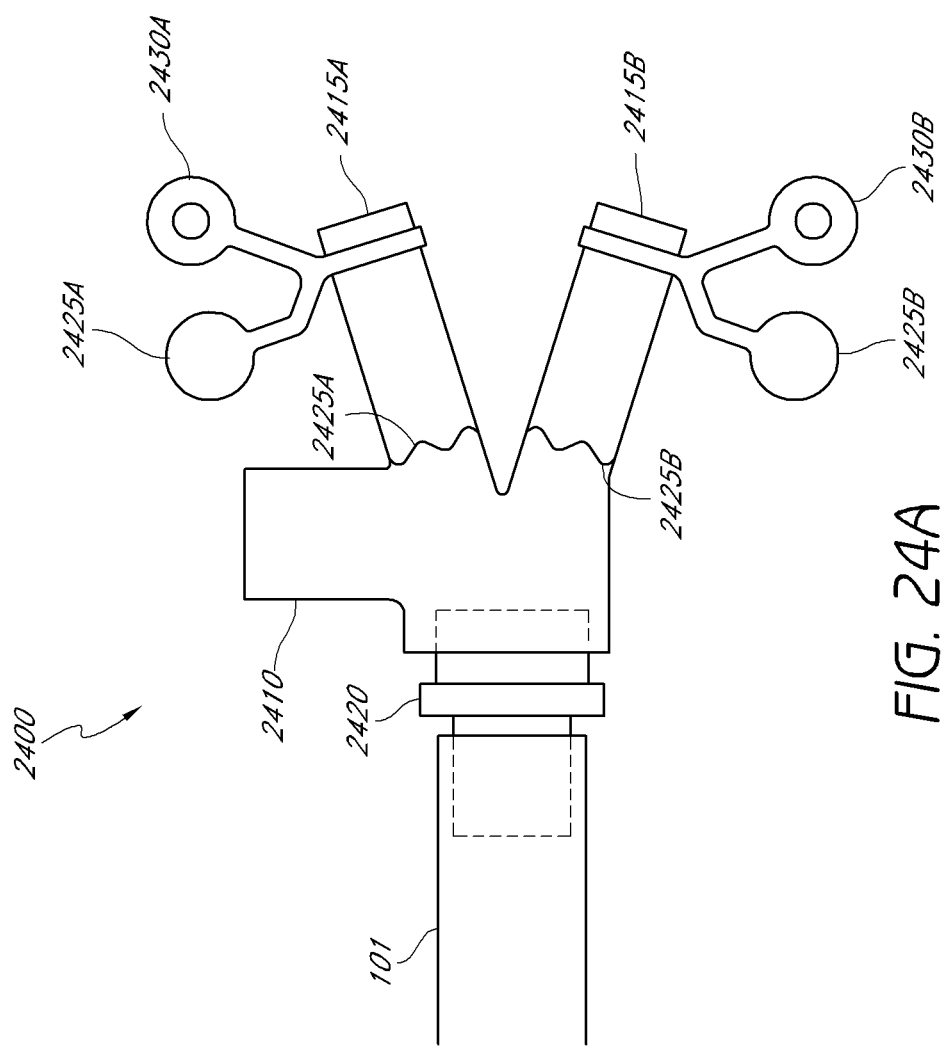
FIGS. 24A and 24B illustrate an embodiment of an endotracheal tube adapter.
Figure 24B:
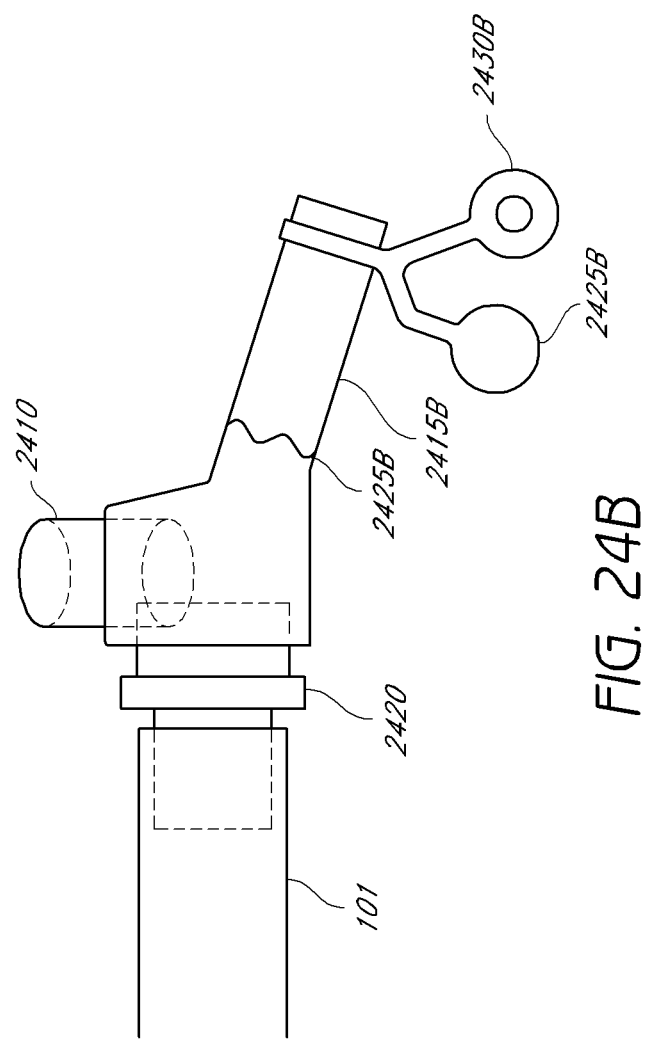

FIGS. 24A and 24B illustrate a top view and a side view, respectively, of an endotracheal tube adapter 2400 that facilitates insertion of endotracheal tube cleaning devices, distal airway cleaning devices (e.g. distal airway cleaning devices 1500), visualization devices (e.g., visualization devices 120), and/or other devices while the patient continues to be ventilated. In some embodiments, the adapter comprises one or more clear, substantially clear, transparent, substantially transparent, translucent, substantially translucent materials and/or other materials to allow visualization of the devices or instruments inserted within. As shown, the endotracheal tube adapter 2400 can include an endotracheal tube connector 2405 at its distal end, a side ventilator connector 2410, and two proximal extensions 2415A, 2415B. The endotracheal tube connector 2405 can be sized and shaped to fit snugly over the universal connector or plug 2420 typically used for all endotracheal tubes. The ventilator connector 2410 at the side of the adapter 2400 is provided to connect to the ventilator for continuous, ongoing ventilation of the patient during cleaning procedures.

With continued reference to FIGS. 24A and 24B, the two proximal extensions 2415 can comprise individual passages for insertion of endotracheal tube cleaning devices, distal airway cleaning devices (e.g., suction catheters), visualization devices, and/or any other devices or items (e.g., catheters, probes, scopes), either alone or in combination with one another, in accordance with a particular procedure or protocol. Each proximal extension 2415 may include a solid end plug 2425 to occlusively plug the connector and/or an end plug with a diaphragm 2430 in order to permit insertion of a device while simultaneously maintaining a ventilation seal (e.g., preventing or reducing loss of ventilator tidal volume). Such a configuration can also advantageously prevent or reduce the likelihood of contamination and promote sterilization. The proximal extensions 2415 can be between about 1 and 10 cm long (e.g., between 1 and 6 cm, between 2 and 4 cm, between 3 and 8 cm, between 4 and 10 cm, or overlapping ranges thereof) and between about 5 and 25 mm wide (e.g., between 5 and 20 mm, between 10 and 15 mm, between 15 and 25 mm, or overlapping ranges thereof).

In some embodiments, the proximal extensions 2415 are removable. For example, one or both of the proximal extensions 2415 can be removed, for example, at lines 2425A, 2425B illustrated in FIGS. 24A and 24B. One or both of the proximal extensions 2415 can be removed and an occlusive cap can be placed over the site of removal (e.g., the distal end of the proximal extension). The removed proximal extension(s) can then be evaluated (e.g., subjected to laboratory testing) to determine the nature of the secretions contained therein. In some embodiments, the proximal extensions 2415 (either attached to the adapter 2400 or as removed and capped units) are configured to connect directly or indirectly to a bedside analysis unit (e.g., for PCR and/or other analytical or diagnostic tools or methods), as desired or required. In some embodiments, one or more proximal extensions 2415 can be added to a suction device (such as the cleaning devices 1500 described herein) to function as a collection port to facilitate the collection of secretions collected as part of a bronchoalveolar lavage. In some embodiments, one or more of the proximal extensions 2415 can be added to a device used for aspiration of subglottic secretion. The proximal extensions 2415 can collect the secretions, which can then be delivered to a microbiology diagnostic tool (either in a separate lab or in a beside diagnostic unit (e.g., PCR)).

With reference to FIG. 24B, the proximal extensions 2415 can have a generally downward angulation. Thus, such a configuration can take advantage of gravity to trap any removed secretions or specimens within the extensions 2415 as one or more cleaning, suctioning, visualization and/or other devices or instruments are withdrawn. The diaphragm of the end plug 2430 can be adapted to scrape or otherwise removably contact the specimen from the cleaning and/or other device so that the specimen remains within the extension 2415. The diaphragm can comprise one or more elastomeric materials, such as, for example, urethane, latex, silicone, other polymeric or elastomeric materials, and/or the like. The thickness of the diaphragm can range from about 0.002 inches to about 0.030 inches. In some embodiments, the thickness of the diaphragm is about 0.005 inches to about 0.20 inches. However, in other embodiments, the diaphragm thickness is greater than 0.030 inches or smaller than 0.002 inches, as desired or required.

The central opening of the diaphragm can be sized, shaped and otherwise configured to accommodate devices or instruments from about 4 to 6 mm in diameter with a seal that allows the patient to continue to be ventilated without significant gas escape from the insertion site. In some embodiments, the central opening of the diaphragm is sized to accommodate devices or instruments less than about 4 mm or greater than about 6 mm in diameter. As shown in FIG. 24B, the ventilator connection 2410 can angle slightly upwardly, thereby helping to prevent or reduce the likelihood of biofilm from getting into the ventilator connection 2410. In some embodiments, the endotracheal tube adapter 2400 is configured to be used multiple times (e.g., two, three or more times). In such embodiments, the endotracheal tube adapter can be termed a "multiple use" endotracheal tube adapter. In other embodiments, the endotracheal tube adapter 2400 is discarded after a single use.

Figure 25:
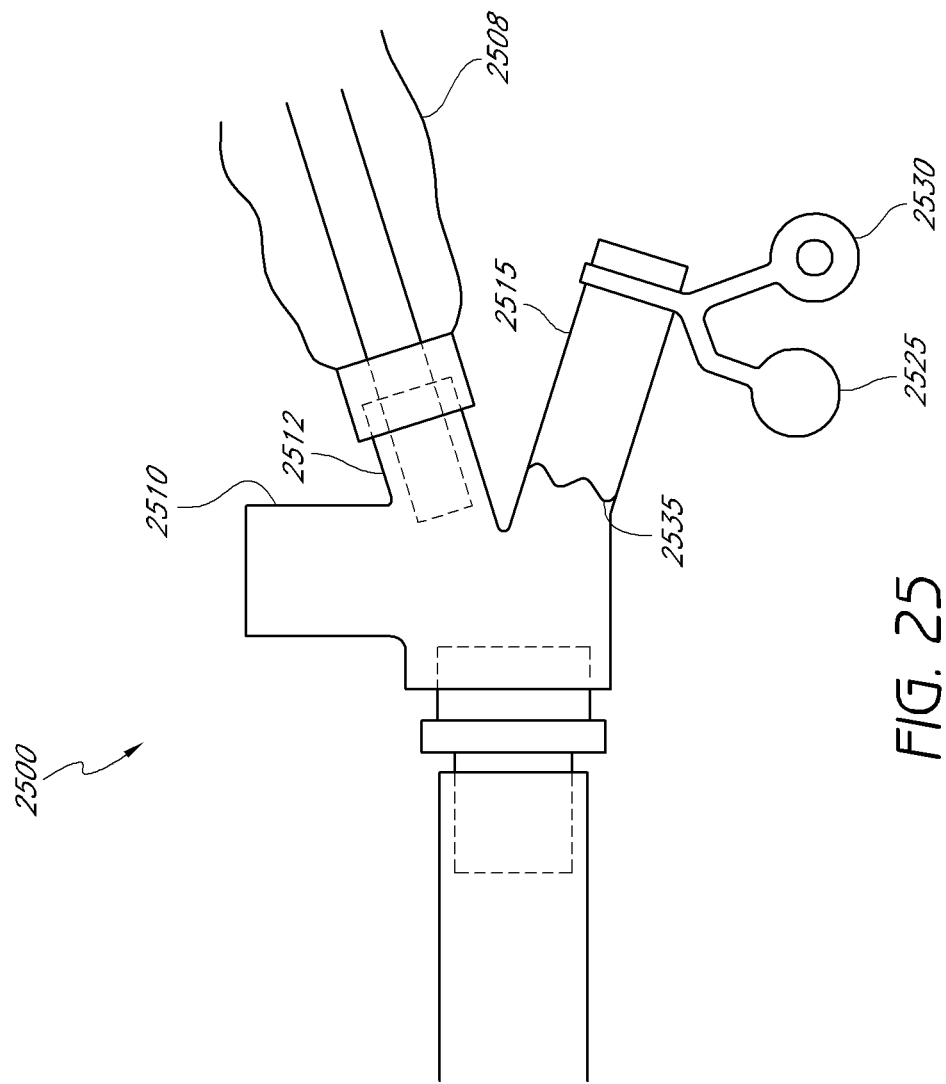
FIG. 25 illustrates an embodiment of an endotracheal tube adapter that can be used with any closed suction system.

According to some embodiments, an endotracheal tube adapter 2500 is configured to be used with any closed suction system 2508, such as Ballard® and Portex® closed suction systems. As illustrated in FIG. 25, the endotracheal tube adapter 2500 can include one or more elements, dimensions, and features of other endotracheal tube adapters disclosed herein (see, for example, the adapters 2400 depicted in FIGS. 24A and 24B). In some embodiments, however, one of the proximal extensions 2415 of the endotracheal tube adapter is replaced by a closed suction system connector 2512. The endotracheal tube adapter 2500 can advantageously allow for insertion of a cleaning or visualization device and a closed suction system while the patient is ventilated. In some embodiments, insertion of the cleaning or visualization device into a proximal extension 2515 does not require disconnection of the closed suction system and/or does not generally disturb the closed suction system.

As discussed above in connection with the endotracheal tube adapter 2400 of FIG. 24, the proximal extension 2515 of the endotracheal tube adapter 2500 can be removed (e.g., at or near line 2535) to allow debris and/or other materials recovered from within the endotracheal tube and/or lungs to be isolated in the removable extension. In some embodiments, such materials can be subsequently collected (e.g., as a sterile specimen) for further testing and analysis. The removable extension 2515 can be configured to connect to any bedside analytical tool such as PCR or any other analytical or diagnostic system. Also as discussed above, the ventilator connection 2510 can be angled slightly upwardly relative to the closed suction system connector 2512 or the removable extension 2515 so that removed biofilm is less likely to enter into the ventilator circuit. The endotracheal tube adapters 2400, 2500 can include fewer than two proximal extensions or more than two proximal extensions as desired or required.

FIG. 26A illustrates an embodiment of a distal airway cleaning device 2600 having an endotracheal tube cleaning member 2605. In some embodiments, the distal airway cleaning device 2600 with the endotracheal tube cleaning member 2605 is configured to provide the ability to clean the endotracheal tube and suction the distal airways with a single cleaning device. The cleaning device 2600 of FIG. 26A can include the same or similar structure and provide the same or similar function as the distal airway cleaning devices described herein (e.g., a control handle 2610, a suction line 2615, a visualization channel 2620, and an irrigation channel 2625). In some embodiments, the cleaning device 2600 includes an inflation channel 2630 to inflate, or otherwise expand, the endotracheal tube cleaning member 2605. In other embodiments, the endotracheal tube cleaning member 2605 comprises a self-expanding material or a mechanically-expandable member or structure. The distal airway cleaning device 2600 can be used in a "closed" suction environment, as described above, or in an open suction environment.

After expansion, the endotracheal tube cleaning member 2605 can be moved relative to an endotracheal tube to scrape or otherwise dislodge biofilm that has collected along the interior surface of the endotracheal tube as a suction catheter portion of the distal airway cleaning device 2600 is removed from the endotracheal tube. In some embodiments, at least a portion of the dislodged biofilm is collected within or on a collection member or area (e.g., through a mesh structure, along a scraping member, etc.) during removal of the cleaning member 2605. Additional details regarding endotracheal tube cleaning members and similar devices and features are provided below.

FIGS. 26B-26E illustrate various embodiments of inflatable endotracheal tube cleaning members 2605. The endotracheal tube cleaning member 2605B of FIG. 26B comprises an umbrella-like mechanism with expandable struts 2602. In some embodiments, the struts 2602 are configured to expand about living hinges positioned at the distal ends of the struts as a balloon 2604 positioned within the endotracheal tube cleaning member 2605B is inflated. In the depicted embodiment, the proximal ends of the struts 2602 are connected to an expandable O-ring or other scraping member 2606. According to some embodiments, the outer surface of the O-ring or other scraping member 2606 presents a generally smooth, continuous, regular surface to remove the biofilm without damaging the endotracheal tube.

The endotracheal tube cleaning member 2605C can comprise an expandable mesh and/or membrane 2608 that surrounds a low-profile inflatable balloon 2604. The expandable mesh and/or membrane 2608 can comprise one or more porous and/or non-porous materials. For example, the expandable mesh and/or membrane 2608 can comprise a braided weave and/or a resilient elastomeric material. However, an expandable membrane 2608 can be used without a mesh. The expandable membrane 2608 can comprise a smooth, regular exterior contact surface or a ribbed, abrasive exterior contact surface.

The endotracheal tube cleaning member 2605D of FIG. 26D comprises a low-profile inflatable balloon 2604 having two elastomeric circumferential ridges, rings or other members 2609 configured to remove the biofilm from the endotracheal tube. In other embodiments, the endotracheal tube cleaning member 2605D comprises one circumferential ridge or more than two (e.g., three, four, five, more than five, etc.) circumferential ridges 2609. The circumferential ridges 2609 can exhibit any of the profiles described herein in connection with the cleaning members of the endotracheal tube cleaning devices. According to some embodiments, the endotracheal tube cleaning member of FIG. 26D can be rapidly cleaned for re-use.

FIGS. 26E and 26F illustrate an inflatable endotracheal tube cleaning member 2605E in generally compressed (or closed) and expanded (or open) configurations, respectively. The inflatable endotracheal tube cleaning member 2605E can be configured for use with the distal airway cleaning device 2600 or the other distal airway cleaning devices described herein; however, the inflatable endotracheal tube cleaning member 2605E can be applicable for use with any suction catheter. According to some embodiments, the inflatable endotracheal tube cleaning member 2605E comprises a sleeve 2640 (e.g., elastic sleeve) that is attached by adhesive or other coupling methods at its distal portion 2645 to the suction catheter portion of the distal airway cleaning device 2600. The remainder of the sleeve 2640 can extend proximally by a certain distance, in the direction of the control handle of the device 2600, depending on the dimensions of the balloon or other inflatable member being used to create the necessary deployment. The remainder of the sleeve 2640 can comprise a free or non-adhered portion. In some embodiments, the sleeve 2640 comprises stiffening elements 2650 that allow the sleeve 2640 to expand at its proximal most edge 2655 as a cone. The balloon 2604 can expand slightly beyond (e.g., several millimeters, 1-10 mm, more than about 10 mm, etc.) the most proximal edge 2655 of the sleeve 2640 to contact the inside of the endotracheal tube. The balloon 2604 can be compressible, thereby changing shape and allowing the leading edge 2655 of the stiffened sleeve 2640 to contact and at least partially clean the inside of the endotracheal tube as the distal airway cleaning device 2600 is withdrawn. The balloon inflation channel 2630 can be located inside the suction line 2615, outside the suction line 2615, or within the wall of the suction line 2615. Inflation of the balloon or other expandable member can be controlled by a syringe-like mechanism at the proximal end or handle area of the distal airway cleaning device 2600 and/or any other type of regulation or control device (e.g., valve).

In accordance with some embodiments, with the endotracheal tube cleaning member 2605E in the closed position (e.g., as shown in FIG. 26E), the distal airway cleaning device 2600 can be used to suction biofilm, debris and/or other materials within the endotracheal tube and/or to suction deeper segments of the lungs. In some embodiments, a reusable visualization device or system, such as those described herein, is inserted into the closed-end visualization channel 2620 within the distal airway cleaning device 2600 to assist in visually identifying the areas of the lungs requiring suction. Such visualization devices or systems can also be used to identify the specific segment or segments from which a bronchoalveolar lavage (BAL) is desired. As described herein, the closed-end visualization channel 2620 can be positioned on the inside of the suction line 2615, the outside of the suction line 2615, or within the wall of the suction line 2615.

The distal airway cleaning device 2600 with an endotracheal tube cleaning apparatus 2605 as described herein may be inserted and used through an open proximal end of an endotracheal tube, through a standard bronchoscopic adapter, or through one of the adapters described herein (e.g., endotracheal tube adapters 2400, 2500, T-connector 1570). Centimeter or other distance markings may be provided on the outside of the suction catheter portion of the distal airway cleaning device 2600 that correspond to the centimeter markings on an endotracheal tube. These markings can allow proper positioning for deployment of the described cleaning members 2605.

In accordance with several embodiments, the distal airway cleaning device 2600 is intended to remove material from desired portions of a patient's airway. The portions for material removal include all sites from the proximal portion of an endotracheal tube to the distal arborizations of the native airway. Removal of the material can be performed for therapeutic, diagnostic and/or any other purpose. The various embodiments of a distal airway cleaning device 2600 described herein, and variations thereof, can be utilized in a closed suction system where the distal airway cleaning device 2600 is the only catheter in the system. Alternatively, such embodiments can be used with one or more adapters to be introduced (e.g., intermittently) together within a suction catheter provided in separate closed suction systems.

III. Endotracheal Tube Cleaning Devices

The discussion and the figures illustrated and referenced below describe various embodiments of body-inserted tube cleaning systems and devices, as well as methods related thereto. A number of these embodiments of tube cleaning systems, devices and methods are particularly well suited to remove biofilm from an interior surface of an endotracheal tube. However, the various devices, systems, methods and other features of the embodiments disclosed herein may be utilized or applied to other types of apparatuses, systems, procedures, and/or methods, whether medically-related or not. For example, the embodiments disclosed herein can be utilized for, but are not limited to, cleaning bronchoscopes, chest drainage tubes, gastrostomy drainage tubes, abdominal drainage tubes, other body drainage tubes, feeding tubes, endoscopes, percutaneous dialysis catheters, and any other percutaneous or per os catheters or body-inserted tubes. Tubes, lumens and conduits may have a circular, square, rectangular or other cross section.

The materials used for the various components of the endotracheal tube cleaning devices and systems described herein can advantageously comprise one or more biocompatible materials.

A. General System

1. Endotracheal Tube

An endotracheal tube can include a proximal end and a distal end. The endotracheal tube includes a hollow, central lumen extending through the endotracheal tube from the proximal end to the distal end. In some embodiments, the endotracheal tube includes a hole at the tip of its distal end and a hole on a side of the endotracheal tube near the tip of the distal end known as a Murphy eye. In other embodiments, an endotracheal tube can include more or fewer holes or openings.

The endotracheal tube can include one or more balloon cuffs at or near the distal end of the endotracheal tube. The balloon cuff is inflated during mechanical ventilation to prevent air leaks back around the endotracheal tube. In some embodiments, the proximal end can include a coupling element for connection with a mechanical ventilator. The inner diameter of the endotracheal tube can range from about 1 mm to about 20 mm or from about 5 mm to about 10 mm. The length of the endotracheal tube can range from about 10 cm to about 40 cm; however, endotracheal tubes of any length can be cleansed by the cleaning devices described herein. The endotracheal tube can be manufactured to have a slight curve or pre-bend for facilitating insertion into a patient's native airway (e.g., trachea).

The endotracheal tube can be configured to be inserted within a patient temporarily or permanently. In some embodiments, the endotracheal tube is inserted within a patient orally or nasally via an intubation procedure. In other embodiments, the endotracheal tube is inserted via a tracheotomy or tracheostomy procedure.

Biofilm can build up on the interior surface of the endotracheal tube over time. If not removed, biofilm can restrict the airflow through the endotracheal tube. In addition, biofilm can harbor harmful bacteria or other microbes and undesired organisms (e.g., staph aureus, pseudomonas, streptococcus, candida) that can eventually lead to the development of pneumonia and/or other ailments or conditions. The layer of biofilm on the interior surface of the endotracheal tube can be substantially uniform or can vary substantially in thickness (e.g., peaks and valleys) along the length of the endotracheal tube.

The biofilm can be present anywhere along the interior surface of the endotracheal tube. In some embodiments, the majority of the biofilm collects in a main collection region that extends from a point proximal to the Murphy eye (e.g., about 2.5 cm from the tip of the distal end) and for approximately another 15 cm toward the proximal end. In some embodiments, approximately 80% of the total biofilm found in the endotracheal tube is found within this main collection region. The remaining biofilm can be found from the proximal end of the main collection region to the ventilator coupling element. The biofilm can have the consistency of rubber cement or nasal secretions. The amount of biofilm present in the endotracheal tube can range anywhere from zero to about thirty cubic centimeters or more at the time of cleaning, depending on the dimensions and/or properties of the endotracheal tube, patient conditions or factors, the length of time within the body before cleaning, and/or other factors. In some embodiments, the internal surface of the endotracheal tube cleaning device can be coated with a bactericide before insertion within a patient to help prevent or reduce the likelihood of bacterial growth within the biofilm. The endotracheal tube cleaning devices described herein can reduce endotracheal tube resistance by about 90% or more after cleaning. In some embodiments, the endotracheal tube cleaning devices remove about 99% of bacteria from the endotracheal tube during cleaning.

2. Endotracheal Tube Cleaning Device

An endotracheal tube cleaning device can include an elongate body, an actuation assembly at the proximal end of the elongate body, and a cleaning member generally at the distal end of the elongate body. In other embodiments, the cleaning member is positioned anywhere along the length of the elongate body (e.g., near the proximal end of the elongate body, generally between the distal and proximal ends of the elongate body, etc.). In some embodiments, the actuation assembly is a syringe-like mechanism that actuates expansion, or deployment, of the cleaning member. The actuation assembly can be configured to provide single action deployment of the cleaning member. As discussed in greater detail herein, the cleaning member can be configured to remove and collect or trap some or all of the biofilm lining the endotracheal tube.

The endotracheal tube cleaning device can be sized, shaped, or otherwise adapted so as to be inserted within any commercially available endotracheal tube (e.g., the endotracheal tube) or other body-inserted tube for cleaning. In some embodiments, the endotracheal tube cleaning device can be sized, shaped, or otherwise adapted so as to be inserted within a specially-designed, proprietary endotracheal tube. In some embodiments, the outside diameter of the elongate body of the endotracheal tube cleaning device ranges from about 0.05 mm to about 10 mm, e.g., from about 1 mm to about 5 mm, about 2 mm to about 4.5 mm, about 2.5 mm to about 3.5 mm, about 5 mm to about 8 mm, about 8 mm to about 10 mm, or greater, and overlapping ranges thereof. The length of the elongate body distal to the actuation assembly can range from about 10 cm to about 70 cm, or greater, e.g., from about 10 cm to about 20 cm, about 20 cm to about 30 cm, about 30 cm to about 40 cm, about 40 cm to about 50 cm, about 50 cm to about 70 cm, and overlapping ranges thereof. In one embodiment, the length of the elongate body is about 29 cm to about 45 cm. The dimensions can be adjusted to accommodate various uses or various body-inserted tubes without departing from the spirit and/or scope of the disclosure.

In some embodiments, the endotracheal tube cleaning device is manufactured with a slight curve to match or substantially conform to the curve of commercially available endotracheal tubes. The curvature of the endotracheal tube cleaning device can advantageously reduce the friction between the outer surface of the endotracheal tube cleaning device and the inner surface of the endotracheal tube and can avoid disruption of the biofilm during insertion of the endotracheal tube cleaning device. The curvature of the endotracheal tube cleaning device can range from about a 5 cm to a 50 cm radius or from about a 10 cm to about a 30 cm radius. In one embodiment, the radius of the curvature of the endotracheal tube cleaning device is approximately 17.5 cm. However, in other embodiments, the radius of curvature of the endotracheal tube cleaning device can be greater or smaller than disclosed herein without departing from the spirit and/or scope of the disclosure. The endotracheal tube can comprise an S shape, question mark shape, or other curved shape upon insertion into a patient airway. In some embodiments, the endotracheal tube cleaning device is generally straight in order to facilitate efficient insertion.

The elongate body of the endotracheal tube cleaning device can include an inner shaft or sheath and an outer shaft or sheath. In some embodiments, the inner shaft and the outer shaft connect the actuation assembly to the cleaning member. The inner shaft is coupled to the distal end of the cleaning member and is configured to transmit the motive force necessary to expand the cleaning member by compressing the distal end of the cleaning member. The outer shaft is coupled to the proximal end of the cleaning member and holds the proximal end of the cleaning member in place while the distal end is compressed or deployed. In this manner, the cleaning member can be selectively expanded radially so as to impart a radial force against the inside wall of the endotracheal tube and/or biofilm collected thereon. This and other embodiments of the expansion mechanism of the cleaning member will be described in further detail below.

3. Endotracheal Tube Cleaning System and General Operation

In some embodiments, the endotracheal tube is disconnected from a ventilator and a distal tip of the endotracheal tube cleaning device is inserted through the ventilator coupling member. The distal tip of the cleaning device can be advanced until the distal tip is positioned just proximal to (e.g., between about 1 mm and 20 mm, such as 1 mm-5 mm, 5 mm-10 mm, 10 mm-15 mm, 15 mm-20 mm), within, or just distal of (e.g., between about 1 mm and 20 mm, such as 1 mm-5 mm, 5 mm-10 mm, 10 mm-15 mm, 15 mm-20 mm) the Murphy eye. In other embodiments, the ventilator coupling member is removed before insertion of the endotracheal tube cleaning device.

The cleaning member can include a removal member and a collection member. In some embodiments, the cleaning member includes more than one removal member and/or more than one collection member. The removal member can be configured to contact or engage the inside wall of the endotracheal tube upon radial expansion of the cleaning member. The removal member can be positioned within a region just proximal of the Murphy eye (e.g., within about 0.5 cm to about 2 cm). However, the removal member can be positioned at any position within the endotracheal tube depending upon a determination of where the biofilm accumulation begins (e.g., via the visualization means described herein) and/or any other factor. Mechanisms for controlling the depth of insertion will be further described below.

After proper positioning of the endotracheal tube cleaning device within the endotracheal tube, the cleaning member is expanded by the actuation assembly such that the removal member contacts the inside wall of the endotracheal tube and/or the biofilm layer situated thereon. After expansion of the cleaning member by the actuation assembly, the endotracheal tube cleaning device can be withdrawn from the endotracheal tube by a clinician. As the endotracheal tube cleaning device is withdrawn from the interior of the endotracheal tube, the removal member removes biofilm from the inside of the endotracheal tube, and the collection member advantageously traps and collects the removed biofilm. Upon completion of a cleaning procedure or as otherwise desired, the clinician can manipulate the actuation assembly of the cleaning device to return the cleaning member to its collapsed configuration. Additional details regarding the expansion and collapse of the cleaning member, as well as the manner in which the collection member traps and collects removed biofilm, are provided below.

4. Side Port

In some embodiments, a side port is coupled to the proximal end of the endotracheal tube cleaning device. The side port can branch off from the main body of the actuation assembly. The side port can branch off of at any location along generally the proximal end of the endotracheal tube cleaning device. For example, in other embodiments, the side port can branch off of the elongate body at a location distal to the actuation assembly.

The side port can be constructed without sharp edges and corners to enhance safety and/or to provide one or more other benefits. The length of the side port can be sufficiently long so as to prevent contamination of the scopes, probes, catheters, and/or other instruments inserted therein due to contact or exposure to the endotracheal tube or the biofilm removed from the endotracheal tube. The length of the side port can be just a few inches to avoid patient contact or as much as ten feet to avoid proximity to the patient. In some embodiments, the length of the side port ranges from about 0.5 inches to about 24 inches.

In some embodiments, the side port includes an elastomeric diaphragm to reduce or eliminate airflow bypass. The elastomeric diaphragm can have a slit, valve, or flap to allow insertion of scopes, catheters, and/or other instruments. The elastomeric diaphragm can comprise any suitable material, such as, for example, latex, silicone, urethane, other elastomeric or polymeric materials and/or the like. The thickness of the diaphragm can range from about 0.001 inches to about 0.1 inches or from about 0.005 inches to about 0.020 inches.

The side port can be used for the introduction of a visualization scope. In some embodiments, the visualization scope comprises an endoscope or boreoscope. However, the visualization scope can include any other scope or viewing element configured to provide visual feedback to the clinician or other user of the cleaning device. The visualization scope can include one or more light delivery elements (e.g., light fibers) and an imaging or visualization element (e.g., an ultrasound probe, a fiber optic camera, a CCD camera, optical imaging fibers, etc.), thereby providing a clinician with simultaneous illumination and viewing of selected portions within the endotracheal tube, such as, for example, the biofilm along the endotracheal tube walls, possible tube obstructions, and/or the like. Accordingly, such a visualization scope or similar tools can assist in the proper placement of the endotracheal tube cleaning device within the endotracheal tube.

In some embodiments, the visualization scope includes a bundle of fiber optic cables, with at least some of the fibers configured to provide light and at least some of the fibers configured to provide viewing capabilities. In some embodiments, the light fibers can extend around the periphery of the visualization scope (e.g., along the inner wall) and the viewing fibers can extend through the central portion of the visualization scope. In some embodiments, the light fibers are coupled to a light source and the viewing fibers are coupled to a direct camera connection and/or to an optical connector. The visualization scope can advantageously provide the clinician with an assurance that the endotracheal tube cleaning device is placed properly and does not unintentionally disrupt the biofilm. In some embodiments, the visualization scope is configured to extend beyond the distal end of the endotracheal tube.

The visualization scope can include an integral or removable sheath, sleeve, or jacket that extends along all or a portion of its length and that is configured to prevent against contamination and to allow relatively easy reuse of the visualization scope for multiple patients and/or procedures. In some embodiments, the visualization scope and/or its sheath is pre-curved to assist in positioning the visualization scope within the endotracheal tube cleaning device.

In some embodiments, the visualization scope and/or its sheath includes a stopper (fixed or adjustable) that is configured to help position the distal tip of the visualization scope at a predetermined or adjustable position within the endotracheal tube cleaning device (e.g., in a viewing window at the distal tip of the endotracheal tube cleaning device). The stopper can be configured to abut against the proximal end of the side port. The side port can have visible markings that correspond to markings on the visualization scope to aid in the positioning of the distal end of the visualization scope and/or to aid in the application of the stopper. The visible markings or indicia can comprise lines, numbers, and/or text labels.

The thickness of the sheath of the visualization scope can range from about 0.05 mm to about 0.5 mm, such as, for example, about 0.1 mm. The outer diameter of the visualization scope can range from about 0.5 mm to about 2 mm, depending on the size of a lumen or channel of the endotracheal tube cleaning device, as described in further detail below.

The visualization scope can be coupled to a visualization unit (e.g., via a coupling element of a camera head). In some embodiments, the visualization unit includes a light source for delivery of light to the endotracheal tube, the endotracheal tube cleaning device, and/or the patient's native airway via light delivery elements. The light delivery elements can provide illumination, activation of drugs delivered within the endotracheal tube (e.g., in conjunction with photodynamic therapy) and/or other capabilities. In other embodiments, the visualization unit includes a display for enhanced viewing. For example, the display can include a monitor capable of displaying high-quality, high-resolution images. In other embodiments, the visualization unit can include one or more other types of output devices. Moreover, the visualization unit can be configured to store in memory (temporarily and/or permanently) images obtained by a scope during a cleaning procedure. In some embodiments, the visualization unit can transmit the images over a network (wired or wireless) to remote storage, display, and/or processing devices. These embodiments advantageously enable a supervising physician to observe and monitor the cleaning procedure and direct further intervention or treatments from a remote location (for example, outside the ICU). In some embodiments, the visualization scope or other visualization member or element can be coupled to the visualization unit via an optical connection and not an RF connection. In such configurations, the images captured by the visualization scope can be optically coupled to the monitor and are not transmitted by RF communication devices or methods. In accordance with some embodiments of the visualization system, the percent occlusion of the endotracheal tube caused by deposited biofilm can be calculated or determined by a processor coupled to the monitor based at least in part on the images captured by the visualization member. In some embodiments, the calculated percentages can be displayed on the monitor in real-time as the visualization member (e.g., scope) is advanced within the endotracheal tube. In some embodiments, a visual indication (such as colored indicia) is displayed to indicate the need to clear an endotracheal tube clogged with biofilm. For example, green, yellow and red colored indicia can be displayed on the monitor to indicate various levels of conditions.

In other embodiments, the side port can be used for the introduction of diagnostic and/or therapeutic catheters or other instruments. Example catheters include, but are not limited to, ultrasonic catheters, radio frequency (RF) catheters, irrigation catheters, aspiration catheters, drug delivery catheters, catheters for delivering light for photodynamic or other light-based therapy, and/or the like. In yet other embodiments, diagnostic and/or therapeutic catheters can be introduced in conjunction with the endotracheal tube cleaning methods, procedures, and/or devices described herein but are not inserted within the endotracheal tube cleaning device itself. Visualization and other facilitative and/or supplementary modalities will be described in further detail below.

B. Structural Components and Connection Interfaces

1. Actuation Assembly

The actuation assembly can include a handle and a trigger. The actuation assembly can comprise a one-part assembly or a multi-part assembly (e.g., two, three or more parts). The distal end of the handle can be coupled to the outer shaft of the endotracheal tube cleaning device using any mechanical fastener, adhesive, and/or other coupling device or method, including, for example, interference fits, ultrasonic welding, UV cure adhesives, epoxy, and/or the like. The proximal end of the handle can include a grip that is sized, shaped, or otherwise adapted to receive an operator's thumb or other finger. The grip can be formed in line with the longitudinal axis of the elongate body or can be offset with respect to the longitudinal axis of the elongate body. In some embodiments, the distal end of the handle is integral with the outer shaft.

The distal end of the trigger can be coupled to the inner shaft using any mechanical fastener, adhesives, and/or other coupling device or method, including, for example, interference fits, ultrasonic welding, UV cure adhesives, epoxy, and/or the like. In some embodiments, the distal end of the trigger is integral with the inner shaft. In the illustrated embodiment, the proximal end of the trigger includes two grips that may be symmetrically positioned about the longitudinal axis of the handle. Each of the two grips can be sized, shaped, or otherwise adapted to receive an operator's finger. The grips can comprise fully-closed grips (e.g., circular grips or non-closed grips (e.g., substantially semi-circular grips. The handle thumb loop may be shaped and sized to be more natural or ergonomic to grip with the thumb, the finger grips can be easier to access, and a trumpet-like, or flared, opening on the proximal end of the handle can prevent or reduce the possibility of kinking.

Materials for the handle and trigger can include any suitable materials, such as, for example, acrylonitrile-butadiene-styrene (ABS), polycarbonate, K-RESIN, other polymeric or elastomeric resins (e.g., rigid or semi-rigid resins, generally stiff resins, etc.) and/or the like. In some embodiments, the materials are tough, non-brittle, injection-moldable, plastic resins. In other embodiments, the materials include one or more modifiers to improve stiffness and/or other physical properties so that actuation of the trigger and/or other functionality of the endotracheal tube cleaning device is not compromised. The modifiers can include glass fiber, calcium carbonate, titanium oxide, carbon, combinations of the same, and/or the like. In some embodiments, the handle and the trigger include internal ribs to improve stiffness.

The actuation assembly advantageously allows for single person, single-handed operation of the endotracheal tube cleaning device. In order to actuate the endotracheal tube cleaning device so that the cleaning member transitions from the collapsed configuration into a desired deployed configuration, manual force can be applied to the trigger and handle to move the trigger proximally with respect to the handle. As the trigger moves with respect to the handle, the inner shaft and the outer shaft are driven to move relative to one another. Accordingly, the relative movement of the inner and outer shafts can apply compressive and tensile forces to the cleaning member to selectively expand and collapse, respectively, the cleaning member. As discussed in greater detail below, the extent of expansion of the cleaning member can be advantageously controlled by the actuation member. In some embodiments, the actuation assembly enables single-hand operation and/or single action deployment of the cleaning member.

2. Main Elongate Body

As described above, the main elongate body of the endotracheal tube cleaning device can include an inner shaft and an outer shaft.

a. Outer Shaft

In some embodiments, the outer shaft of the main elongate body extends from the handle of the actuation assembly to the proximal end of the cleaning member. The proximal end of the outer shaft can be assembled into an opening located at the distal end of the handle. As described above, the outer shaft can be coupled to the handle by any suitable mechanical and/or adhesive method or device, such as interference fits, mechanical fasteners, ultrasonic welding, UV cure adhesives, epoxy, and/or the like. The distal end of the outer sheath can be coupled to the proximal end of the cleaning member by any suitable attachment method or device, including, but not limited to, adhesives, crush ribs, heat shrink tubing, other low-profile mechanical fasteners, other attachment methods or devices, ultrasonic bonding, interference fits, and/or the like.

The outer shaft can comprise a central lumen or channel in which the inner shaft is slidably retained. In some embodiments, the cross-section of the outer shaft is circular, substantially circular, elliptical, oval and/or any other shape. In some embodiments, the outer diameter of the outer shaft ranges from about 1.5 mm to about 4 mm; however the outer diameter of the outer shaft can be smaller than 1.5 mm or larger than 4 mm, as desired and/or required. In some embodiments, the outer shaft is an extrusion comprising polyolefin and/or one or more other plastic materials, such as, for example, polypropylene, PEPAX, polyester, nylon, polyimide, polyethylene terephthalate (PET), polyethylene terephthalate glycol (PETG), and/or the like.

b. Inner Shaft

In some embodiments, the inner shaft is located within an inner lumen of the outer shaft and is configured to move with respect to the outer shaft in a direction along the longitudinal axis of the outer shaft. In some embodiments, the inner shaft extends from the trigger to the distal tip of the endotracheal tube cleaning device. The inner shaft can be coupled to the distal tip by any suitable attachment method or device, such as, for example, adhesives, crush ribs, heat shrink tubing, mechanical fasteners, other mechanical devices or methods, low-profile mechanical connection means, ultrasonic bonding, interference fits, and/or the like. The inner shaft can be coupled to the distal tip and to the cleaning member with heat shrink tubing. In other embodiments, the inner shaft and the distal tip are integrally formed as a single molded component.

In some embodiments, the inner shaft is a hollow sheath or tube. In some embodiments, the outer diameter of the inner shaft is less than 4 mm and the inner diameter of the inner shaft is greater than 1 mm; however, the inner shaft can have any other diameter, as desired and/or required. For example, the outer diameter of the inner shaft can range from about 0.85 mm to about 2.5 mm and the inner diameter of the inner shaft can range from about 0.5 mm to about 2 mm. The inner shaft can include a central lumen or channel for the introduction of a visualization scope and/or one or more diagnostic or therapeutic catheters or other instruments. In some embodiments, a visualization element (e.g., fiber optic camera) of a visualization scope (e.g., visualization scope) can be inserted into the central lumen or channel. The central lumen or channel can have a diameter ranging from about 0.5 mm to about 1.5 mm (e.g., about 1 mm). However, the diameter of the central lumen or channel can be smaller than 0.5 mm or larger than 1.5 mm as desired and/or required by the dimensions of the inner shaft. A depth stop can be included to position a visualization scope for desired or required optical characteristics, thereby resulting in maximum viewing potential.

In other embodiments, the inner shaft includes one or more internal and/or external channels adapted to selectively receive scopes and/or other instruments or devices for visualization and/or any other purpose. For example, the one or more channels can be used for light delivery, photodynamic therapy, fluid delivery (e.g., air, therapeutic agents, saline), irrigation, aspiration, and/or the like. In some embodiments, the one or more channels can comprise an equilibrium channel to reduce or alleviate the any negative pressure or suction effect created distal to the expandable cleaning member as the endotracheal tube cleaning device is being withdrawn from the endotracheal tube. The channels can extend through any length of the inner shaft. For example, one or more channels can extend from generally the proximal end to generally the distal end of the endotracheal tube cleaning device. In some embodiments, the one or more channels can include an inlet in communication with the side port and one or more outlets in the distal tip, in or adjacent to the removal member, in the side wall of the endotracheal tube cleaning device. In other embodiments, the one or more channels can include inlets or outlets at other locations of the endotracheal tube cleaning device.

In other embodiments, the inner shaft is a solid, central rod. The inner shaft can have a circular, substantially circular, elliptical, oval, and/or any other cross-sectional shape. In some embodiments, the inner shaft comprises an extrusion having polyolefin and/or other plastic materials, such as, for example, polypropylene, PEPAX, polyether ether ketone (PEEK), polyester, nylon, polyimide, polyethylene terephthalate (PET), polyethylene terephthalate glycol (PETG), and/or the like.

c. Distal Tip

In some embodiments, the distal tip is a closed tip to prevent against exposure of the internal structure of the endotracheal tube cleaning device, and any instruments or devices inserted therein, to the biofilm or other potential contaminants within the patient's body. The distal tip of the endotracheal tube cleaning device can comprise one or more injection-moldable plastics, polymeric resins, including, but not limited to, polycarbonate, PET, PETG, nylon, polypropylene, K-RESIN, and/or the like. In some embodiments, at least a portion of the distal tip can comprise a clear, transparent or semi-transparent material to form a viewing "window." In some embodiments, the entire distal tip comprises transparent or semi-transparent material. According to some embodiments, the window comprises a thickness of less than about 0.012 inches (for example, about 0.001 inches to about 0.002 inches, about 0.003 inches to about 0.004 inches, about 0.005 inches to about 0.006 inches, about 0.007 inches to about 0.008 inches, about 0.009 inches to about 0.010 inches, about 0.011 inches to about 0.012 inches, and overlapping ranges thereof). The injection mold of the distal tip can be polished (e.g., using an SPE/SPI A1 "high polish" finish of the injection mold) such that at least the distal end of the distal tip is optically transparent or partially optically transparent. In some embodiments, the transparent material can be configured to enable a "fish eye" view for enhanced viewing of the endotracheal tube itself, any biofilm that could be accumulating in the tube, and/or the like. Magnifying capabilities may also be included.

In some embodiments, the viewing window can have optical properties to provide magnification and/or angular correction to correct for the natural tendency for the device to follow the outer bend of the endotracheal tube. For example, the optical properties can enable the scope to provide a view of the lumen in the middle of the endotracheal tube and not a view of the side of the visualization scope or the biofilm itself. The viewing window can also comprise a filter, coating, layer and/or other mechanism to reduce glare of flashback from a light delivery element (e.g., an endoscope light). In some embodiments, the viewing window comprises one or more anti-reflective coatings, including but not limited to magnesium fluoride and oxides, such as silicone oxide, titanium oxide, zirconium oxide. One or more of these (or other) coatings or layers can be applied to one and/or both sides of the window. In some embodiments, the viewing window comprises a hydrophobic material. In several embodiments, the viewing window is scratch resistant and/or comprises a slick surface that repels biofilm and smudges. In some embodiments, the window includes a convex or angled shape with a refractive index that reduces or limits glare. In one embodiment, the window comprises anti-fogging properties.

In some embodiments, the distal end of the distal tip is sized, shaped, and/or otherwise adapted to facilitate introduction into, or penetration of, the biofilm without dislodging the biofilm. In one embodiment, the distal tip comprises a bullet shaped tip with a relatively small diameter instead of a flat, large diameter tip like a bronchoscope. For example, the distal end of the distal tip can have a radius from about 0.005 R to about 0.050 R, or from about 1 mm to about 15 mm. The distal tip can be radiused using a radio frequency tool, by injection molding and/or any other suitable forming technologies. In arrangements wherein a visualization scope is to be used in conjunction with the endotracheal tube cleaning device, the optically clear distal end of the distal tip can be relatively thin (for example, from about 0.010 inches to about 0.20 inches thick) to improve the optical qualities of the distal tip for enhanced visualization. In other embodiments, the optical properties of the clear, transparent or semi-transparent materials used to form the distal tip (e.g., an extrudable grade of clear polypropylene) may help reduce or eliminate the need of the relatively thin tip. In some embodiments, the inside of the distal tip at the junction of the window includes a radius of about 0.005 R to 0.015 R to facilitate and improve injection molding and ultimately optical clarity without imperfections.

In some embodiments, the distal tip can include one or more outlets or ports to provide access to the interior of the endotracheal tube and/or to the patient's airway (e.g., the tracheobronchial tree) through the endotracheal tube cleaning device. Such outlets can provide openings for airflow through the endotracheal tube cleaning device. For example, an outlet can be in communication with an inner lumen or channel of the endotracheal tube cleaning device into which diagnostic and/or therapeutic instruments (e.g., aspiration, irrigation, and/or drug delivery mechanisms) can be inserted. In some embodiments, the one or more outlets can permit the escape of a fluid, such as air or therapeutic agents, from the endotracheal tube cleaning device. In other embodiments, the one or more outlets can permit the escape of a catheter or conduit inserted through an internal channel of the endotracheal tube cleaning device. The outlet can include a diaphragm, slit, one-way valve and/or the like to substantially seal off the inner lumen or channel, thereby preventing or reducing the likelihood of contamination of the interior of the endotracheal tube cleaning device and/or the therapeutic and/or diagnostic instruments inserted therein. In some embodiments, the distal end allows for airflow across the cleaning device. In one embodiment, the distal end of the cleaning device is configured for the introduction of anti-bacterial agents, bactericides, antiviral agents, mucolytic agents, saline solution, sterilant, enzymatic cleaner, germicide, antimicrobial fluid, detergents, combinations thereof and/or any other fluid or material. The distal tips of the visualization devices and visualization channels of the airway cleaning devices can comprise the structural and/or functional elements and features described herein with respect to the distal tip of the endotracheal tube cleaning devices.

3. Cleaning Member

As described above, the cleaning member can include a removal member and a collection member. In some embodiments, the removal member and the collection member can be two separate members. In other embodiments, a single, integral removal/collection member can perform removal and collection of accumulated biofilm. In yet other embodiments, the cleaning member may not include a removal member (e.g., an O-ring, wiper, etc). In some embodiments, the cleaning member comprises a distensible scaffold that removes and collects the deposited biofilm. In some embodiments, the cleaning member comprises a distensible mesh scaffold covered by an expandable (e.g., elastomeric) sleeve.

According to some embodiments, the removal member and/or any other portion of the cleaning member is configured to be actively mechanically actuated between an expanded configuration and a collapsed configuration. In several embodiments, the removal member and/or any other portion of the cleaning member are actively mechanically actuated without the use of a sheath, sleeve, covering and/or the like. In another embodiment, the removal member and/or any other portion of the cleaning member are non-bristled and/or non-sheathed.

In some embodiments, the removal member and/or the collection member of the cleaning member can elute and/or be coated with a fluid, drug, therapeutic agent, and/or other medicament or substance that is configured to clean, disinfect, decontaminate, sterilize, and/or prevent future contamination of the endotracheal tube and/or to degrade, disperse, and/or dissolve biofilm deposited along the interior surface of the endotracheal tube. Such materials can include, for example, an anti-bacterial agent, a mucolytic agent, a saline solution, a sterilant, an enzymatic cleaner, a germicide, and antiviral drug, an antimicrobial drug, and/or a detergent. A coated removal member and/or collection member can be configured to deliver the fluid, drug, therapeutic agent, and/or other materials upon contact with the inside wall of the endotracheal tube. A coating of the cleaning member can also comprise one or more absorbent materials, such as, for example, super-absorbent polymers (e.g., polyacrylimide and/or the like).

a. Collection Member

As described above, the collection member can be adapted to collect and/or trap biofilm removed by the removal member. In some embodiments, the collection member effectuates expansion of the removal member as it is expanded by the relative movement between the inner and outer shafts. However, any other method of selectively expanding and contracting the removal member can be used. The collection member can advantageously be constructed to allow sufficient airflow through the endotracheal tube during use. For example, the air flow rates can range from about 0.08 liter per minute to about 10 liters per minute, from about 1 liter per minute to about 5 liters per minute or from about 0.1 liter per minute to about 1 liter per minute.

In some embodiments, the collection member comprises a distensible scaffold that can be mechanically actuated (e.g., actively mechanically actuated) between an expanded configuration and a collapsed configuration. In some embodiments, the scaffold comprises a mesh or braided scaffold. In several embodiments, the scaffold is non-sheathed and/or non-bristled. The scaffold can comprise a woven tubular braided material. The fibers of the braid can range in diameter (or other cross-sectional dimension) from about 0.001 inches to about 0.04 inches, or greater, e.g., about 0.001 inches to about 0.005 inches, about 0.005 inches to about 0.010, about 0.010 inches to about 0.020 inches, and overlapping ranges thereof. However, the diameter or other cross-sectional dimension of the fibers can be smaller than 0.001 inches or greater than 0.040 inches, as desired or required. The braided material can be comprised of PET, nylon, polyester, polypropylene and other extrudable plastic resins that are flexible in the extruded state. The pick count (e.g., which in some embodiments is the number of fibers or picks crossing per inch) of the braided material can range from 5 to 25 picks per inch, or greater, e.g., from about 5 to 8 picks per inch, about 8 to 12 picks per inch, about 12 to 14 picks per inch, about 14 to 16 picks per inch, about 16 to 18 picks per inch, about 18 to 20 picks per inch, about 20 to 25 picks per inch, and overlapping ranges thereof.

According to some embodiments, the scaffold, the collection member and/or any other portion of the cleaning device is configured to be actively mechanically actuated between an expanded configuration and a collapsed configuration. In several embodiments, the scaffold, the collection member and/or any other portion of the cleaning device are actively mechanically actuated without the use of a sheath, sleeve, covering and/or the like. In another embodiment, the scaffold, the collection member and/or any other portion of the cleaning device are non-bristled and/or non-sheathed.

In other embodiments, the collection member is a scaffold comprising a porous elastomeric polymer material, such as silicone, urethane, and/or latex, or a porous foam material. In some embodiments, the collection member has a generally uniform construction from one end to the other end. In other embodiments, the collection member can have varying constructions for different portions of the collection member to serve different purposes. For example, a distal section of the collection member can have a construction just large enough to allow air flow (e.g., high pick count, fine weave, small pore size, etc.), which advantageously results in the efficient trapping and storage of biofilm, and the proximal section of the collection member can have a construction with larger openings (e.g., low pick count, loose weave, large pore size, etc.) to facilitate collection of the biofilm while still allowing expansion of the removal member. In some embodiments, the pick count of the distal section of the collection member can range from about 10 to about 25 picks per inch and the pick count for the proximal section can range from about 5 to about 10 picks per inch. In some embodiments, the distal section can have a construction that is impermeable or substantially impermeable to fluids or permeable so as to allow fluids to filter through while catching solid and semi-solid debris.

In some embodiments, the collection member comprises two or more layers of braided or mesh material. The two or more layers can have varying pore size or pick count constructions. In some embodiments, the proximal section of the collection member comprises a first mesh layer having a relatively large pore size (e.g., greater than about 0.1 inch opening) and the distal section of the collection member comprises the first mesh layer having the relatively large pore size as an inner mesh layer and a second outer mesh layer having a relatively small pore size (e.g., about 0.05 inch opening). The inner mesh layer and outer mesh layer can be ultrasonically welded or otherwise coupled together at various locations (e.g., the proximal and distal ends of the outer mesh tube). For example, the distal ends of the two mesh layers can be coupled together and/or to the inner shaft using heat seal, silicone or other suitable adhesive or heat shrink band clamps. In other embodiments, the two mesh layers are coupled by sutures, epoxy, adhesive, other low-profile attachment devices, and/or the like. The outer mesh layer can include an outer mesh ring having the relatively large pore size that is ultrasonically welded or otherwise connected to the inner mesh layer at one or more locations adjacent to the removal member. The outer mesh ring can have a conical or substantially conical shape. In some embodiments, both the proximal section and the distal section of the collection member comprise two or more mesh layers.

In some embodiments, the length of the collection member ranges from about 0.2 inches to about 1 inch. In one embodiment, the length of the collection member is about 0.4 inches. In some embodiments, the length is selected to effectuate a "tent-like" configuration when deployed instead of a "sausage-like" configuration. The "tent-like" configuration advantageously focuses the radial force along a perpendicular plane through the removal member.

In some embodiments, the collection member is expanded generally uniformly across its length. For example, in its expanded configuration, the collection member can exhibit a "tent-like" form, wherein the distal half and the proximal half have a convex shape. In other embodiments, a proximal portion (e.g., the proximal half) of the collection member can be configured to expand in a concave fashion and a distal portion (e.g., the distal half) of the collection member can be configured to expand in a convex fashion. The proximal and distal portions can be integral or separate.

In some embodiments, the collection member can have a convex distal section and a concave proximal section. The concave profile of the proximal portion can advantageously keep the surface of the collection member away from the inner wall of the endotracheal tube, thereby ensuring that the outer surface of the removal member is the only surface that comes in contact with the inner wall of the endotracheal tube. In some embodiments, the concave profile advantageously results in more efficient biofilm collection than the convex profile. For example, the concave profile can create more surface area and volume for collection of biofilm. In some embodiments, the collection member is formed of two separate elements. A slight wave pattern of the removal member can advantageously improve radial deployment of the collection member, can improve collection due to its greater surface area, and/or can increase the expandability of the removal member.

The concave profile of the proximal section of the collection member can be effected by attaching one or more rings about the proximal section of the collection member to constrain the expansion. If multiple rings are used, the rings can be spaced apart and can be configured to expand to different diameters to effectuate a desired profile. In some embodiments, the length of the collection member can be increased with the inclusion of the rings to constrain the expansion of the proximal section of the collection member. For example, the length of the collection member can range from about 0.15 inches to about 2 inches. The collection member can be constructed to have a capacity of about 15 cubic centimeters (ccs) of biofilm or other material; however a capacity of less than or more than 15 ccs can be used as desired and/or required.

b. Removal Member

In general, the removal member is configured to be expanded during use to come in contact with the interior surface of the endotracheal tube (or other conduit) and to remove the deposited debris (e.g., biofilm) therefrom as the cleaning device is withdrawn from the endotracheal tube. In some embodiments, the removal member is configured to engage the interior surface of the endotracheal tube with a smooth, regular outer surface. In other embodiments, the surface profile of the removal member can have an irregular shape. In one embodiment, the removal member is flush with the outside periphery of the scaffold (which, in some embodiments can serve as a collection member). In other embodiments, the removal member protrudes beyond the outside periphery of scaffold by about 0.05 mm to about 4 mm, such that, in some embodiments, only the removal member contacts the interior surface of the endotracheal tube (or other conduit).

In some embodiments, the removal member comprises one or more soft, flexible, expandable materials, such as, for example, silicone, UV curable silicone, ethylene vinyl acetate (EVA), thermoplastic elastomer (TPE), KRATON polymers, polyisoprene, urethane, silicone rubber, other suitable flexible and low-tear materials, and/or the like.

In some embodiments, the removal member has a material softness that enables optimum deployment of the collection member and reduces or prevents "hydroplaning" of the removal member as it is withdrawn, thereby ensuring that the biofilm is removed in an efficient manner. If the material is too soft, the removal member can gradually tear or pull away from the collection member over time. In some embodiments, the removal members described herein facilitate removal of a sufficient amount of biofilm such that endotracheal tube resistance is decreased by about 90% or more after cleaning. In some embodiments, the removed biofilm removes about 99% of microbes (e.g., bacteria) from the endotracheal tube during cleaning.

In some embodiments, the use of materials that are too hard can retard the deployment of the collection member, because the removal member exerts a backward force on the collection member as it is expanded. Failure to adequately deploy the removal member can prevent the removal member from adequately engaging the inside wall of the endotracheal tube with sufficient radial force to effectively remove biofilm. In other embodiments, if the material is too soft, then the removal member "hydroplanes," thereby failing to adequately remove the biofilm as the endotracheal tube device is withdrawn.

The softness of the removal member, as measured on a durometer scale, can range from 20 Shore A to 60 Shore A when silicone is used or from about 0 Shore A to about 40 Shore A when urethane or other materials are used. In one embodiment, the softness of the removal member is 30 Shore A when silicone or a similar material is used. The removal member can be configured to expand to approximately 200 to 250 percent of its nominal diameter. In some embodiments, the removal member can be configured to expand to accommodate endotracheal tubes having a diameter between about 1 to about 10 mm.

The removal member can be removably or integrally coupled to the collection member using any suitable attachment method or device, including but not limited to, adhesive, epoxy, suture, welding, casting, mechanically connected interference fit, overmolding, and/or the like. In one embodiment, such as when the removal member comprises urethane material, the removal member becomes chemically bonded to the collection member (e.g., a PET or nylon braid scaffold) when overmolded. In some embodiments, the removal member is coupled to the outer surface of the collection member. In other embodiments, the removal member is coupled to the inner surface of the collection member. In yet other embodiments, the removal member is detachable or separable from the collection member. In still other embodiments, the removal member is integral with the collection member. In one embodiment, an integral well is formed underneath and through the collection member when the removal member is overmolded or formed with an applicator. The integral well design can advantageously prevent or reduce the likelihood of the removal member being sheared from the collection member during operation.

In one embodiment, the removal member comprises an expandable O-ring wiper that generally circumscribes the collection member. The O-ring wiper can be circular, substantially circular, elliptical, oval, and/or any other shape. The O-ring wiper can be a single, smooth, regular, continuous bead that is in a perpendicular plane to the collection member. In another embodiment, the removal member comprises a wavy, or undulating, pattern. The peaks of the wave pattern can vary from between about 0.05 inches to about 0.5 inches peak to peak, or e.g., about 0.1 inches to about 0.35 inches.

In some embodiments, the portion of the removal member that contacts or engages the inner surface of the endotracheal tube provides a smooth, regular contact surface. In other embodiments, the contact portion of the removal member comprises an irregular contact surface. In one embodiment, the O-ring has a substantially triangular cross section. The concave slope and radius of the edges of the substantially triangular O-ring can be varied as desired and/or required. In one embodiment, the O-ring has a quarter-circle cross section. The quarter-circle O-ring can be tapered on the distal side for minimal disruption of biofilm on introduction and optimal wiping of biofilm on removal of the device. In some embodiments, the proximal side of the quarter circle O-ring is concave, thus forming an O-ring having a "wave-like" or "fin-like" cross section.

In one embodiment, the O-ring has a U-shaped cross section. In one embodiment, the O-ring has a half-circle or half-moon shaped cross section. The radius of the half-circle can range from about 0.001 inches to about 0.1 inches, or greater, e.g., about 0.005 inches to about 0.01 inches, about 0.01 inches to about 0.025 inches, about 0.025 inches to about 0.05 inches, about 0.05 inches to about 0.1 inches, and overlapping ranges thereof. In one embodiment, the O-ring has a "squeegee-like" cross section with a steep slope and a narrow wiping or scraping edge. In one embodiment, the O-ring has a half-circle cross section with a parting line. The parting line can be a natural or intentional result of the molding process in forming the O-ring. In one embodiment, the O-ring has a squared-off contact portion. In one embodiment, the O-ring has an X-shaped cross section.

The removal member can be constructed of two or more materials of an expandable nature. In some embodiments, the majority of the body of the removal member comprises a material having a suitable durometer for expansion and the contact portion comprises a more rigid material to provide sufficient strength and rigidity for the effective wiping or removal of biofilm.

In some embodiments, the removal member has a helical or "barber pole" configuration. Other embodiments of removal member configurations include, but are not limited to, a ribbed O-ring, an O-ring having a full circle cross-section, and an O-ring having a varying cross-section about its circumference. In still other embodiments, the removal member can comprise shaving members, bristles, or other protrusions. In various embodiments, the removal member can comprise bumpy, ribbed, saw-like, abrasive, rough, textured, slotted, and/or smooth or substantially smooth materials. In some embodiments, the removal member can range from about 0.015 inches to about 0.050 inches in height and from about 0.015 inches to about 0.1 inches in width.

In some embodiments, the cleaning member can include multiple removal members. The multiple removal members can have the same or different profiles. Different profiles can be used to accomplish various purposes, as will be described in further detail below. In some embodiments, the multiple removal members include partial O-rings that extend around a partial circumference of the collection member and are rotationally staggered.

In some embodiments, the removal member can include holes or apertures for fluid delivery, for suction, and/or for any other purpose. The removal member can be connected to a fluid delivery channel or a suction/aspiration conduit within the endotracheal tube cleaning device. For example, the removal member can be configured to deliver fluid and/or other materials that help to disperse, degrade, or loosen hardened, more adherent biofilm and/or to deliver drugs to the accumulated biofilm and/or the internal surface of the endotracheal tube.

c. Multiple Cleaning Members

In some embodiments, the endotracheal tube cleaning device includes multiple cleaning members. The multiple cleaning members can be constructed to serve different purposes. For example, the removal member of each of the multiple cleaning members can be constructed with a different profile or cross section. In other embodiments, each of the removal members can have the same profile or cross section.

For example, the cleaning member can include a round or half-circle O-ring for removing the mucous and other easy-to-remove secretions deposited on the outer surface of the biofilm layer. The cleaning member can include an O-ring having a scraping edge for removing the tenacious, more adherent, older biofilm deposits. Other scraping edge profiles can be used without departing from the spirit and/or scope of the disclosure. The cleaning member can include a round, half-circle, or quarter-circle O-ring configured to remove and collect any remaining biofilm. As described above, the O-ring removal members can be constructed of more than one material to enhance the scraping or wiping action of the O-rings. The O-rings of the cleaning members can have any of the cross-sectional profiles described above or any other cross-sectional profiles as desired and/or required.

Each of the cleaning members can include a collection member (e.g., braided or mesh scaffold) for collecting biofilm while still allowing sufficient airflow through the endotracheal tube. The multiple cleaning members can be separated by a non-expandable attachment device or method, such as, for example, a heat shrink clamp band, sutures, adhesives, epoxy, welding, other low-profile mechanical attachment methods or devices, and/or the like. For example, the multiple cleaning members are separated by clamp bands that constrain the expansion of the mesh collection members but are not attached to the inner shaft, thereby allowing for simultaneous deployment of the multiple cleaning members.

d. Separate Collection Member

The endotracheal tube cleaning device can include a removal member and a collection member. The removal member can include an O-ring wiper and a scaffold (e.g., mesh scaffold) for selectively effectuating deployment of the O-ring wiper. In one embodiment, the collection member comprises a biofilm collection basket. The collection member can be spaced proximally from the removal member at a distance ranging from about 0.1 inches to about 0.5 inches; however other separation distances can be used as desired and/or required.

The collection member can comprise a mesh or other porous material having openings that are small enough to collect solid or semi-solid biofilm deposits but large enough to allow for sufficient airflow through the collection member. In some embodiments, the maximum cross-sectional dimension of the openings ranges from about 0.010 inches to about 0.050 inches. The collection member can be sized and shaped to hold up to about 20 ccs of biofilm. The collection member can advantageously have a width or diameter that is less than the diameter of the endotracheal tube so as not to contact the inner wall of the endotracheal tube. The endotracheal tube cleaning device can include an internal channel for insertion of scopes (e.g., a visualization scope), catheters, probes, and/or other instruments, as described in greater detail herein.

e. Outer Sleeve Surrounding Expansion Member

FIG. 27A illustrates another embodiment of an endotracheal tube cleaning device 2720. As shown, the endotracheal tube cleaning device 2720 can comprise an elongate body 2722 having a pre-defined curvature that approximates the curvature of an endotracheal tube. However, the endotracheal tube cleaning device 2720 can also comprise an elongate body 2722 that is generally straight, thereby facilitating introduction into a patient-inserted endotracheal tube that conforms to the patient airway in an S shape. In one embodiment, the cleaning member 2726 at the distal end of the endotracheal tube cleaning device 2720 comprises an expansion member and an outer sleeve (e.g., an elastomeric sleeve) 2705. Expansion of the expansion member using the actuation assembly 124 can cause the expansion of at least a portion of the outer sleeve. The endotracheal tube cleaning device 2720 can include a scope retention assembly 2725, which is described in more detail below with respect to FIGS. 28A-28D. FIG. 27B illustrates a close-up perspective view of the distal end of the endotracheal tube cleaning device 2720 of FIG. 27A. In some embodiments, the outer sleeve 2705 surrounds the expansion member (not shown) in a concentric fashion. The expansion member can comprise an expandable scaffold that includes one or more expandable and collapsible struts. In other embodiments, the expansion member comprises an expandable and collapsible mesh or braided scaffold. In some embodiments, the expansion member is non-inflatable and mechanically actuated. Such expandable scaffolds can be air permeable or non-air permeable. In some embodiments, the expansion member is not self-expandable upon removal of a surrounding sheath. In some embodiments, the outer sleeve is not a sheath that is withdrawn to cause an expandable member to be deployed. The terms expandable member, expansion member, expansion structure, and expandable structure are used interchangeably herein.

With continued reference to FIG. 27B, the cleaning member 2726 can comprise one or more cutouts, air gaps, holes, or vents 2715 at or near the proximal and distal ends of the outer sleeve 2705. In several embodiments, 1, 2, 3, 4, 5, 6-8, 8-10, and 10 or more cutouts, air gaps, holes or vents are provided at the ends or along the sleeve. Such features can allow for air exchange through the cleaning member 2726 during expansion. The sleeve may comprise breathable or porous material to facilitate air exchange. For example, in embodiments wherein a mesh scaffold is used, the mesh scaffold is exposed to the air through the air gaps and air can flow through the interstices of the mesh scaffold from one air gap to the other. The air gaps or vents 2715 can advantageously prevent formation of a vacuum effect during removal of the cleaning device 2720 (e.g., within an endotracheal tube, along the distal end of the cleaning member), which can result in hydroplaning and/or increase the pull-out force required to remove the cleaning device. The width of the air gaps 2715 can range from 0.005 inches to 0.500 inches, from 0.050 inches to 0.250 inches, from 0.060 inches to 0.180 inches, and/or overlapping ranges thereof to allow for adequate air exchange through the cleaning member 2726.

In some embodiments, the endotracheal tube cleaning device 2720 optionally comprises a distal heat-shrink tubing cover 2735A between the distal air gap and the distal tip 2745 and a proximal heat-shrink tubing cover 2735B disposed over the outer shaft 2729 proximal to the proximal air vent 2715B. The heat-shrink tubing covers 2735A, 2735B can be provided for aesthetic purposes. In other embodiments, the heat-shrink tubing covers 2735A, 2735B can aid in retention of one or more components and/or provide additional benefits or advantages. In some embodiments, the heat-shrink covers 2735 comprise heat shrink stretchable tape or other type of stretchable tape.

Figure 27C:
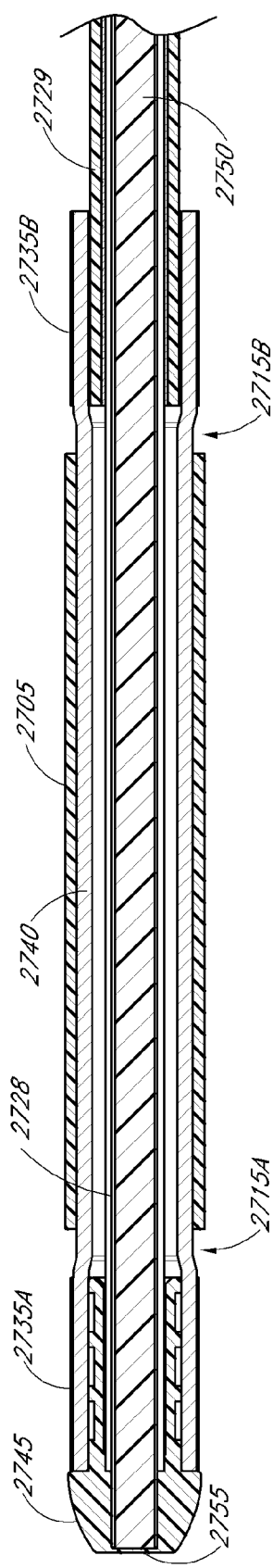

FIG. 27C illustrates a cross-sectional view of the distal end of the endotracheal tube cleaning device 2720. The depicted assembly of the endotracheal tube cleaning device 2720 is similar to the assemblies described above. In the illustrated embodiment, the expansion member comprises a mesh or braided scaffold 2740. The distal end of the mesh scaffold 2740 can be adhered or otherwise secured to the distal tip 2745 of the endotracheal tube cleaning device 2720, which is in turn adhered or otherwise secured to the distal end of the inner shaft 2728. In some embodiments, the proximal end of the mesh scaffold 2740 is adhered to the distal end of the outer shaft 2729. The mesh scaffold or other expansion member 2740 can be adhered with any suitable coupling and/or attachment device or method, such as, for example, interference fits, ultrasonic welding, heat shrink tubing, heat shrink stretchable tape, stretchable tape, adhesive, epoxy, NuSil MED2-4013 silicone adhesive, other low-profile mechanical attachment means, and/or the like. As shown, a visualization scope 2750 can be inserted within the inner shaft 2728 such that the distal end of the visualization scope 2750 is pressed against a viewing window 2755 of the distal tip 2745. Such a configuration can allow for visualization beyond the distal end of the endotracheal tube.

The sleeve 2705 can vary in length from approximately 0.25 inches to approximately 3 inches, from approximately 0.5 inches to approximately 1.5 inches from approximately 0.75 inches to approximately 1 inch, greater, and/or overlapping ranges thereof. In some embodiments, the sleeve is partially or fully elastomeric. In some embodiments, the sleeve 2705 comprises thermoplastic elastomer (TPE), silicone; however, other elastomers, polymers and/or other materials can be used, either in lieu of or in addition to silicone, as desired and/or required. The sleeve 2705 can comprise elastomeric materials having a Shore A durometer of between 15 and 50 and a wall thickness of between 0.005 inches and 0.05 inches. For example, in some embodiments, the elastomeric sleeve 2705 comprises a material having a 20 to 25 Shore A durometer and a 0.010 to 0.015-inch wall thickness; however, other durometer values and thicknesses can be used as desired and/or required. In some embodiments, the wall thickness or durometer value of the outer sleeve 2705 varies across its length to improve the shape upon expansion. For example, the wall thickness can be thinner and/or have a lower durometer value in the center of the sleeve 2705. The outer diameter of the outer sleeve 2705 can be sized to receive a visualization scope of less than 2 mm. In some embodiments, the outer diameter of the outer sleeve 2705 is between about 0.1 inches and 0.2 inches (e.g., about 0.100 inches, 0.125 inches, 0.150 inches, 0.175 inches, 0.200 inches).

The outer sleeve 2705 (e.g., elastomeric sleeve) can be assembled to the mesh scaffold 2740 with a slight interference (inner diameter of the sleeve to the outer diameter of the scaffold). For example, the interference can vary from 0.001 inches to 0.025 inches per side. The outer sleeve 2705 can be attached to the mesh scaffold 2740 with an adhesive and/or any other connection material, device or method. The adhesive can be applied underneath the sleeve 2705 and circumferentially for a distance of approximately 0.25 inches on each side. Advantageously, the adhesive comprises quick setting properties, has a sufficiently high viscosity to prevent running during setting, and is flexible when set. The flexibility of the adhesive can permit the adhesive to move with the movement of the fibers during distension of the mesh scaffold 2740. In some embodiments, the adhesive comprises a NuSil MED2-4013 silicone adhesive or equivalent. The adhesive can be selected to accommodate a shear force of approximately three to six pounds; which, in some embodiments, can provide a significant safety factor of two to four times when compared to the required pull force. The adhesive can be configured to retain the elastomeric sleeve 2705 on both sides so that the outer sleeve 2705 can distend to the preferred shape upon expansion of the expansion member 2740 (e.g., mesh scaffold). Alternatively, the outer sleeve 2705 can be assembled to the device tip and outer sheath with stretchable tape or stretchable heat shrink tape.

In embodiments wherein a mesh scaffold is used, the scaffold can comprise a mesh having four to fourteen picks per inch, eight to twelve picks per inch, six to ten picks per inch, and/or overlapping ranges thereof. In other embodiments, the mesh of the scaffold can a pick count of less than four picks per inch or greater than fourteen picks per inch (e.g., 22 to 24 picks per inch). The mesh scaffold 2740 can comprise fibers having a diameter of between 0.002 inches and 0.050 inches, between 0.005 inches and 0.020 inches, less than 0.002 inches, greater than 0.050 inches and/or overlapping ranges thereof. The mesh scaffold 2740 can comprise, for example, between ten and sixty strands of fibers (e.g., 12 end, 24 end, 48 end); however fewer than ten and greater than sixty strands of fibers can be used as desired and/or required. In one embodiment, the mesh scaffold 2740 comprises a 48 end (meaning 48 fibers), 0.010-inch fiber diameter scaffold having 22-24 picks per inch. In one embodiment, the mesh scaffold 2740 has a weaving pattern of one fiber over two under two fibers and wound on a 0.093" core or 0.110" core. In one embodiment, a sleeve is placed over the mesh scaffold 2740 that is a silicone 20 Shore A 0.010" to 0.015" thick sleeve. The mesh fiber ends can be fused with an adhesive to prevent the mesh from unraveling when the mesh is cut to size. In some embodiments, the mesh is cut to 25-27 mm and constrained on each side so that 8-10 mm of the mesh becomes the working width. However, other parameters can be selected to alter the radial force exerted on the outer sleeve 2705 and the shape of the outer sleeve 2705 formed upon expansion. The mesh scaffold 2740 can comprise one or more mesh layers. In some embodiments, the fibers comprise nylon fibers; however, other fiber materials can be used, such as PET, nylon, polyester, polypropylene and/or other extrudable plastic resins that are flexible in the extruded state, either in lieu of or in addition to nylon fibers.

Figure 27D:
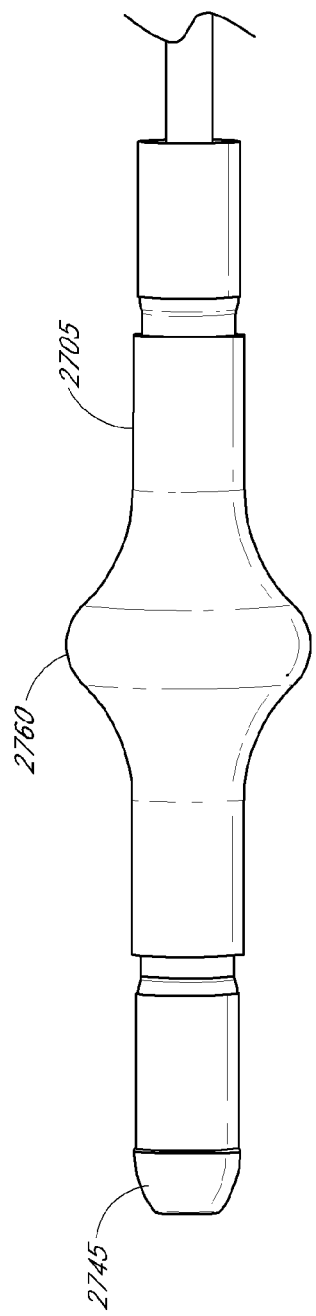

FIG. 27D illustrates the outer sleeve 2705 upon expansion of the expansion member 2740 by manipulation of the actuation assembly 2724. As shown, the material properties of the expansion member 2740 (e.g., mesh scaffold) and the outer sleeve 2705 can be selected such that the central portion of the outer sleeve 2705 forms a removal member 2760 upon expansion of the expansion member 2740. In some embodiments, the removal member 2760 comprises a disc-like or disc-shaped removal member. The terms disc-like and disc-shaped as used herein can be used interchangeably. Disc-shaped, as used herein, shall be given its ordinary meaning and shall include shapes that are generally circular in geometry, including, but not limited to, frisbee-shaped, plate-shaped, ellipse-shaped, and oval-shaped. Disc-shaped structures shall also include, but not be limited to, structures that have two opposing ends (e.g., flat or planar), wherein each end has a length and a width (for example in a circular disc, the length and width would both be diameters), and wherein the structure has a thickness or height between the two opposing ends, wherein the thickness or height is less than (e.g., by at least 30%, 50%, 75%, 90% or more) at least one of the length and width of each end. In one embodiment, the disc-shaped structure is non-cylindrical. In one embodiment, the disc-shaped structure has one or more axes of symmetry. In one embodiment, the disc-shaped structure is asymmetrical. In one embodiment, the two ends are substantially identical, while in other embodiments, the two ends are sized and/or shaped differently. In several embodiments, the disc-shaped structure has one or more openings (or apertures) that extends from one end through the other end (e.g., as in an O-ring), or through one end only. In several embodiments, the disc-shaped structure does not have an opening. Other shapes are also provided in some embodiments. In some embodiments, the side cross-section (cut along the longitudinal axis of the elongate body of the cleaning device from the proximal end to the distal end) is contoured, concave, oblong, triangular or square.

In some embodiments, the removal member 2760 has an apex and a base (e.g., on one side of a two-sided structure), wherein the ratio of the apex:base is about 1:2, 1:3, 1:4, 1:5, 1:6, 1:7, 1:8, 1:9 and 1:10, or higher. For example, the apex is about 0.02-0.5 inches and the base is about 0.04 to about 2 inches in some embodiments, (e.g., about 0.1-0.2 inches at the apex and about 0.3 to about 0.8 inches at the base). Smaller or larger apices and/or bases may be used depending on the size of the tube that needs cleaning. The apex may be rounded, squared, or pointed. In one embodiment, the removal member 2760 has a single base with two apices. In some embodiments, the ratio of the width of the removal member 2760 to the overall length of the outer sleeve 2705 in the radially-expanded position is about 1:10 to about 2:5 (e.g., about 1:10, 1:9, 1:8.5, 1:8, 1:7, 1:6, 1:5.5, 1:5 1:4, 1:3, 2:5, etc.). In some embodiments, the ratio of the width of the removal member 2760 to the overall length of the outer sleeve 2705 in the radially-expanded position is between about 1:8.5 and about 1:5.5. In other embodiments, the ratio of the width of the removal member 2760 to the overall length of the outer sleeve 2705 is less than about 1:10 or greater than about 2:5. In some embodiments, the width of the removal member 2760 is about 1 mm to about 10 mm (e.g., 4 mm to 7 mm, 4.5 to 6.3 mm, 3 mm to 6 mm, etc.). However, in other embodiments, the width of the removal member 2760 is less than about 1 mm or greater than about 10 mm. In some embodiments, the length of the outer sleeve 2760 when the expandable structure is in the radially-expanded position is about 63% (e.g., about 50-85%, about 55-75%, about 60-70%, etc.) of the length of the outer sleeve 2705 when the expandable structure is in the radially-collapsed position. In some embodiments, the length of the outer sleeve 2705 when the expandable structure is in the radially-expanded position is greater than about 85% or less than about 50% of the length of the outer sleeve 2705 when the expandable structure is in the radially-collapsed position. In some embodiments, the length of the outer sleeve 2705 decreases by about 15 to about 50% upon expansion of the expandable structure. In some embodiments, the length of the outer sleeve 2705 decreases by between about 4 to 24 mm (e.g., 4 to 20 mm, 8 to 16 mm, 10 to 14 mm) upon expansion of the expandable structure. However, in other embodiments, the length of the outer sleeve 2705 decreases by less than about 4 or more than about 24 mm upon expansion of the expandable structure. In accordance with some embodiments, a mesh scaffold working length of 8 to 10 mm produces a 9.5 mm to 10.0 mm distension. The mesh scaffold with the outer sleeve 2705 can provide a uniform wiping action that successfully clears the endotracheal tube of the biofilm such that endotracheal tube resistance is reduced by about 90% after cleaning.

According to some embodiments, for a diamond-shaped or disc-shaped removal member, the top and bottom apexes can be generally rounded. Further, for any of the sleeve embodiments disclosed herein, the removal member 2760 can have generally vertical and/or sloped sides along one or both sides of the top or bottom apex. In addition, for any of the embodiments disclosed herein, the removal member 2760, as viewed from the side or in cross-section, can be generally symmetrical about an axis perpendicular to the adjacent wall of the endotracheal tube or other medical tube being cleaned. In other embodiments, the removal member 2760 can be asymmetrical about such an axis.

As discussed in greater detail herein, in other embodiments, the removal member comprises shapes other than generally disc shapes. The removal member 2760 can comprise a steep, substantially vertical slope on each side of the removal member 2760. The disc-like shape can advantageously provide a smooth, regular contact surface over a highly concentrated distance against the inner wall of the endotracheal tube. In some embodiments, the material properties of the expansion member and the elastomeric sleeve 2705 provide an increased radial pressure at a centralized, concentrated location. This concentrated increased radial pressure can help form the removal member 2760 which, as shown in FIG. 27D, can have a more disc-like profile than a convex, "football-shaped" profile (e.g., as viewed from the side).

In some embodiments, the removal member 2760 is generally symmetrical about the longitudinal axis of the cleaning member and/or about a transverse axis or plane of the removal member 2760 (e.g., along an axis perpendicular to the longitudinal axis of the cleaning member or any other axes or planes). In other embodiments, the removal member 2760 is asymmetrical about one or more axes of the cleaning member. In some embodiments, the removal member 2760 formed on the sleeve 2705 comprises a bell curve-like cross-section (e.g., Gaussian curve) or an A-frame or tent-shaped cross-section on each side of the longitudinal axis of the removal member 2760 when viewed from the side of the cleaning device 2720, or forms a smooth apex having a relatively steep slope. In some embodiments, the apex of the removal member 2760 comprises a generally narrow, rounded profile. In other embodiments, the apex is generally squared or pointed. The width of the removal member 2760 can range from about 0.10 to about 0.80 inches (e.g., about 0.10 to about 0.60 inches or about 0.15 to about 0.75 inches). In other embodiments, the width can be less than about 0.10 inches or greater than about 0.80 inches. The width of the removal member 2760 formed generally near the center of the outer sleeve 2705 can comprise about 10 to 40% of the total length of the outer sleeve 2705 in the expanded, or distended, configuration. In other embodiments, the width of the removal member 2760 can comprise less than 10% or greater than 40% of the total length of the outer sleeve 2705 in the expanded, or distended, configuration. In one embodiment, the removal member 2760 advantageously allows an operator to remove at least about 90% or 95% of the biofilm in one or two passes with approximately 1.5 lbs of pull force. However, in alternative embodiments, the percentage of biofilm removed for any particular pulling force can vary (e.g., less than about 90%, more than about 95%, etc.).

According to some embodiments, as discussed in greater detail herein, the outer sleeve 2705 can be configured to selectively form a removal member 2760 having a side cross-sectional or side view (when viewed from the side of the cleaning device) that is bell-shaped (e.g., in half-section or the portion that extends along only one side of the sleeve), tent-shaped or triangular-shaped (e.g., half-section), diamond-shaped (e.g., in full-section or as it extends along both sides of the sleeve), or disc-shaped (e.g., full-section). The side cross-sectional view can be taken by cutting the removal member formed on the outer sleeve 2705 in half from the proximal end to the distal end along the longitudinal axis of the elongated body and viewing the removal member from the side of the cleaning device. In some embodiments, bell-shaped and tent-shaped refers to the shape of the upper half-section or lower half-section of a generally diamond-shaped removal member.

In one embodiment, the removal member 2760 is dimensioned to exert sufficient pressure against the interior wall of a tube (including, but not limited to, a medical tube such as an endotracheal tube) so as to remove debris from the tube without causing significant (or any) invagination. The removal member may or may not be disc-shaped. In some embodiments, the removal member comprises a non-sharp and smooth surface. In some embodiments, the removal member comprises a non-sharp and roughened surface. In one embodiment, the removal member allows a single operator to remove at least about 90% or 95% of debris (such as biofilm) in less than 3 passes with about 0.5-3 lbs of pull force (e.g., 0.5 lbs, 1 lb, 1.5 lbs, 2 lbs, 2.5 lbs, 3 lbs). Removal of at least 90% of all debris is accomplished in less than 90 seconds in some embodiments (e.g., less than about 60 seconds, 30 seconds, 15 seconds, 10 seconds, and 5 seconds). In one embodiment, the cleaning device increases the lifespan of an endotracheal tube by enhancing its functionality. For example, in one embodiment, at least 75% (e.g., 90%) of airflow is restored after cleaning. In one embodiment, at least 75% (e.g., 90%) of patency or working diameter is restored after cleaning. In some embodiments, a patient's exertion (e.g., work of breathing) is reduced by at least 75% (e.g., 90%). In one embodiment, at least 90% (e.g., 99%) of microbes, such as bacteria or fungus which may be present in the biofilm, are removed or rendered inactive.

C. Mechanical Expansion

As described above, according to some embodiments, the cleaning member can be configured to transition from a collapsed configuration to an expanded configuration by the relative movement of inner and outer members (e.g., inner shaft 128 and outer shaft). In some embodiments, the inner member moves axially while the outer member remains stationary. In other embodiments, the outer member moves axially while the inner member remains stationary. In yet other embodiments, the inner and outer members are both configured to move axially.

1. Mechanical Struts

In some embodiments, the cleaning member can be mechanically expanded by multiple deploying struts. The proximal section of the collection member can comprise multiple "umbrella-like" deploying struts to effectuate radial expansion of the removal member and the distal section of the collection member comprises a mesh scaffold, or collection basket, constructed to collect and trap biofilm removed by the removal member. The deploying struts can be coined to provide flexibility for a desired expansion angle. The expansion angle can range from about 5 degrees to about 45 degrees or from about 20 degrees to about 35 degrees. The deploying struts can extend from the outer shaft to the removal member. The deploying struts can be mechanically coupled and/or adhered to the outer shaft and the removal member by any suitable coupling and/or adhesive device or method, such as interference fits, ultrasonic welding, heat shrink tubing, adhesive, epoxy, other low-profile mechanical attachment means, and/or the like. The deploying struts can be coupled to the outer shaft by a heat shrink band clamp. The deploying struts can comprise one or more metallic and/or plastic materials. Nitinol can be used in several embodiments to form expanding components, such as the struts, scaffold, removal member, etc.

In some embodiments, a "living hinge" endotracheal tube cleaning device comprising deployment struts for mechanical expansion of a cleaning member is provided. The cleaning member can comprise a scaffold having deployment struts and longitudinal slits and an O-ring wiper. In some embodiments, the distal tip of the endotracheal tube cleaning device is integrally formed with distal end of the cleaning member. The distal tip of the endotracheal tube cleaning device can be coupled to the inner shaft and the proximal end of the cleaning member can be coupled to the outer shaft by any suitable coupling and/or adhesive device or method, such as interference fits, ultrasonic welding, heat shrink tubing, adhesive, epoxy, other low-profile mechanical attachment means, and/or the like. In some embodiments, the connections between the distal end of the cleaning member and the distal tip or inner sheath and/or the connection between the proximal end of the cleaning member and the outer sheath form living hinges about which the deployment struts expand. The O-ring wiper can be coupled and/or adhered to the deploying struts by overmolding, interference fits, ultrasonic welding, adhesive, sutures, epoxy, other low-profile mechanical attachment means, and/or the like. In some embodiments, movement of the inner shaft in a proximal direction causes the deploying struts to flex or bend outward, thereby radially expanding the O-ring wiper. The deploying struts can comprise a substantially rigid elastomeric material to prevent collapse due to the return force of the O-ring wiper.

2. Expanding Collet Assemblies

In some embodiments, mechanical expansion of the removal member can be controlled by a collet expansion assembly. The collet expansion assembly can include an expanding collet that can be radially expanded by a ram.

The expandable collet can comprise elastomeric material, such as polypropylene, polyethylene, nylon, polycarbonate, and/or the like. The elastomeric material can advantageously provide living hinge capability. The expandable collet can comprise multiple (e.g., four or more) struts, or leaves, and multiple longitudinal openings, or slits, to allow for radial expansion.

The ram can be fixedly attached to the outer shaft, thereby remaining stationary. The ram can have a circular, substantially circular, elliptical and/or other shaped cross section. The ram can have a uniform cross-sectional diameter across its length or a varying cross-sectional diameter. The distal end of the ram can have a tapered edge so as to reduce the likelihood that the expandable collet is snagged on the ram. The distal end of the expandable collet can be connected to and/or can be integral with the distal tip of the endotracheal tube cleaning device and the inner sheath can be connected to the distal tip.

As the inner shaft is pulled proximally, the expandable collet can be pulled toward the ram. As the inner surface of the struts engage and move over the ram, they can be expanded radially by the ram about living hinges formed between the distal ends of the struts and the distal tip. As the struts of the expandable collet expand, the removal member can also expand. Upon expansion, the open proximal side of the expandable collet can function as a collector of biofilm as the endotracheal tube cleaning device is withdrawn from the endotracheal tube. In some embodiments, a mesh or other porous material can be coupled to the expandable collet to facilitate collection of biofilm while still allowing airflow through the endotracheal tube cleaning device. In other embodiments, the ram can move with respect to the expandable collet.

The removal member can be overmolded, applicated, assembled, adhered, and/or otherwise coupled to the expandable collet. In some embodiments, the removal member sits within a circumferential groove of the expandable collet. The removal member can be an O-ring comprised of TPE, silicone, urethane, ethylene-vinyl acetate (EVA), polyisoprene, a KRATON polymer, and/or the like. The durometer of the O-ring can range from about 30 Shore A to about 90 Shore A. In other embodiments, the removal member is not included.

In one embodiment, the collet expansion assembly includes a center rod, a molded collet, a split tubing, an expanding netting, and a molded adhesion band. In some embodiments, the center rod replaces the inner shaft, the split tubing replaces the outer shaft, and the expanding netting replaces the collection member. The molded collet can be inserted over and attached to the center rod, which in turn is inserted within the split tubing, the expanding netting is placed over the split tubing, and the molded adhesion band is overmolded on the distal end of the expanding netting. The expanding netting can be connected to the center rod by the molded adhesion band. As the center rod moves proximally, the increasing diameter of the molded collet causes the split tubing to expand radially, thereby bringing the expanding netting into contact with the inner wall of the endotracheal tube. As the center rod is withdrawn, biofilm removed by the expanding netting can collect within the expanding netting, similar to the collection members described herein.

3. Vented Tube Design

In one embodiment, the endotracheal tube cleaning device comprises a vented tube assembly. The vented tube assembly can include a center rod, a vented tube, and a vented tip. The center rod can be inserted within the vented tube. The vented tip can be attached to the distal end of the center rod. The distal tip of the vented tube can be tapered such that when the center rod is moved proximally with respect to the vented tube, the rounded proximal edge of the vented tip slides over the tapered distal tip of the vented tube, and expands radially with the increasing diameter of the vented tube. The vents in the vented tube can allow the vented tube to expand. In some embodiments, the proximal edge of the vented tube comprises a circumferential ridge or protrusion configured to engage the inner surface of the endotracheal tube and to remove biofilm deposited thereon as the center rod is withdrawn from the endotracheal tube. In other embodiments, an O-ring can be overmolded or otherwise coupled about the circumference of the vented tube.

In some embodiments, the vented tip can be expanded by infusion of air and/or liquid through the vented tube. In some embodiments, therapeutic agents, drugs, and/or gases can be delivered through the vented tip and/or biofilm can be aspirated out of the endotracheal tube through the vented tube. The vented tip can comprise one or more durable elastomeric materials, such as silicone, urethane, polypropylene, polyethylene, and/or the like.

In one embodiment, a vented cleaning member can comprise a mechanically-expandable bellows-like expansion structure. The vented cleaning member can include one or more injection-moldable elastomeric materials, such as, for example, natural rubber, synthetic rubber, other elastomeric or polymeric materials and/or the like.

In some embodiments, the vented cleaning member is generally tubular and comprises a proximal end, a distal end and a body situated therebetween. The body of the vented cleaning member can comprise a varying cross-section along its length. For example, in one embodiment, the cross-sectional dimension is larger towards the proximal and distal ends and smaller near the center of the body. The connections between the body and the proximal and distal ends can comprise living hinges or similar features about which the body hinges to radially expand a removal member positioned in the center of the body. The removal member can comprise a tapered ring that presents a squeegee-like contact surface when expanded; however, other profiles or shapes can be used as desired and/or required.

According to some embodiments, the proximal and distal ends of the vented cleaning member comprise a plurality of vents, or openings, to allow for airflow through the vented cleaning member upon expansion. As noted above, such a feature can help prevent a vacuum effect from being created when the cleaning member is moved relative to the endotracheal tube. In some embodiments, the proximal end of the vented cleaning member abuts, but is not adhered to, the outer shaft. Likewise, the distal end of the vented cleaning member abuts, but is not necessarily adhered to the distal cap adhered at the distal end of the inner shaft. In some embodiments, the vented cleaning member is "free-floating" on (e.g., is not adhered to) the inner shaft.

As the inner shaft is pulled toward the actuation assembly, the vented cleaning member is axially compressed, thereby causing radial expansion of the body about the living hinges. Upon expansion, the removal member engages the inner surface of the endotracheal tube. As the cleaning device is withdrawn from the endotracheal tube, the removal member removes at least a portion of the biofilm adhered to the inner surface of the endotracheal tube. As discussed in greater detail herein, the level of radial expansion of the vented cleaning member, and thus the corresponding force imparted by the removal member along the interior wall of the endotracheal tube, can be selectively varied by the clinician or other user, as desired or required for a particular procedure.

In some embodiments, the length of the vented cleaning member in the relaxed or compressed configuration is between about 10 mm and 20 mm (e.g., between about 10 mm and 12 mm, between about 12 mm and about 15 mm, between about 14 mm and about 18 mm, between about 16 mm and about 20 mm, or overlapping ranges thereof). In other embodiments, the length of the vented cleaning member in the relaxed or compressed configuration is greater than 20 mm or less than 10 mm. The length of the vented cleaning member in the fully expanded configuration is between about 10 mm and 35 mm (e.g., between about 20 and 25 mm). In other embodiments, the length of the vented cleaning member is less than about 10 mm or greater than about 35 mm. In some embodiments, the length of the vented cleaning member decreases by about 20 to 50% (e.g., by about 28 to 43%) between the fully compressed configuration and the fully expanded configuration (depending on the inner diameter of the endotracheal tube).

4. Spring Assemblies

In some embodiments, the mechanical expansion mechanisms comprise helical springs. A distal end of a helical spring wireform can be attached to the inner sheath and a proximal end of the helical spring wireform can be attached to the outer sheath. The helical spring wireform can be attached to the inner sheath and the outer sheath by any suitable attachment method or device, such as, for example, heat shrink tubing, adhesive, epoxy, interference fits, other low-profile mechanical attachment methods and/or the like.

In some embodiments, the helical spring wireform is wound or otherwise manufactured such that the middle portion comprises a slightly unstable, naturally unfurled configuration. When the inner shaft is engaged by the trigger (thereby moving the inner sheath in a proximal direction, the inner sheath compresses or draws the helical spring wireform proximally, and the middle portion is distended radially. In other embodiments, the helical spring wireform is wound or otherwise manufactured such that the middle portion comprises a naturally distended configuration. Before insertion of the endotracheal tube cleaning device, the actuation assembly can be configured to move the outer sheath proximally to draw the middle portion of the helical spring wireform to an unfurled configuration. Once the middle portion has been properly positioned within the endotracheal tube, the trigger can be released to return the middle portion to its distended configuration for engaging the inner surface of the endotracheal tube.

The helical springs can comprise one or more metallic and/or plastic materials, such as, for example, stainless steel, spring steel, Nitinol, injection-molded polycarbonate and/or any other injection-molded plastic material that is capable of retaining spring qualities. In some embodiments, the diameter of the spring wire can range from about 0.001 inches to about 0.05 inches in diameter, or from about 0.005 inches to about 0.025 inches in diameter. The middle portion can comprise from about 1 to about 3 turns (e.g., 1⅛ to about 1¾ turns). In some embodiments, at least the outermost loop of the distended middle portion is coated with plastisol, silicone, other suitable elastomers, and/or the like, to aid in wiping and collecting biofilm as the endotracheal tube cleaning device is withdrawn from the endotracheal tube.

In some embodiments, a thin, flexible funnel extends from the distal end of the inner shaft or the distal tip of the endotracheal tube cleaning device to the middle spring of the middle portion of the helical spring wireform. The funnel can advantageously serve as a collector of biofilm when the endotracheal tube device is withdrawn from the endotracheal tube. The funnel can be attached to the inner shaft or the distal tip and to the helical spring wireform by any suitable attachment method or device, such as, for example, heat shrink tubing, adhesive, wound wire, suture, epoxy, other low-profile mechanical attachment method or device, and/or the like. The funnel can be attached to the helical spring wireform continuously or intermittently (e.g., at selected attachment locations) using any attachment method or device, such as adhesive, flexibly epoxy, sutures, and/or the like. The funnel can comprise latex, thin braid material, silicone, and/or other elastomeric or polymeric materials, flaccid materials and/or the like. The funnel can be draped over the helical spring wireform with enough spare material to allow for expansion of the helical spring to the distended configuration without substantially retarding or otherwise hindering deployment of the helical spring. In other embodiments, the helical spring can serve as its own collector without the funnel.

5. Self-Expanding

In some embodiments, the collection member can include one or more "self-expanding" materials that are configured to radially expand when a compressive force is exerted upon the materials in a longitudinal direction by the movement of the inner shaft. The radial expansion of the collection member causes the radial expansion of the removal member. The term "self-expanding" as used herein shall be given its ordinary meaning and shall mean, without limitation, that no additional mechanical structure (such as struts, collets, springs, pistons, and/or the like) other than the physical characteristics or properties of the materials of the collection member (e.g., scaffold), is used to expand the collection member. In several embodiments, the collection member comprises a sleeve (an elastomeric sleeve). For example, self-expanding materials can simply expand with the relative movement of the inner shaft with respect to the outer shaft. In some embodiments, self-expanding materials comprise Nitinol, other shape-memory metals, alloys or other materials and/or the like.

The cleaning member can include an expandable collection member or scaffold and a removal member having an angled rim for contacting the internal surface of the endotracheal tube. The angled rim can be angled about 2 to about 40 degrees (e.g., 5 to 25 degrees) from a vertical orientation.

The expandable collection member can comprise an outer scaffold member and an inner scaffold member. In one embodiment, the inner scaffold member is folded in on itself and forms a hinge about which it expands. In one embodiment, the distal end of the outer scaffold member is connected to the distal tip of the endotracheal tube cleaning device. The distal end of the outer scaffold member can be connected to the distal tip using heat shrink tubing, an interference fit, other fasteners, or other suitable low-profile mechanical devices and/or any other attachment method or device. The inner sheath can be assembled to or be formed integral with the distal tip. Likewise, a first end of the inner scaffold member can be connected to the distal end of the outer shaft using any attachment device or method, including, for example, an interference fit, heat shrink tubing, adhesive, epoxy, molding, welding and/or the like. The second end of the inner scaffold member and the proximal end of the outer scaffold member can be connected to the removal member using any attachment device or method, including, for example, an interference fit, heat shrink tubing, adhesive, epoxy, molding, welding and/or the like.

When the inner shaft is pulled back (i.e., moved proximally with respect to the outer shaft), a force can be exerted on the outer scaffold member by the inner shaft and the inner scaffold member that causes the angled rim of the removal member to distend radially against the inner wall of the endotracheal tube. In some embodiments, the inner scaffold member of the expandable collection member can also exert a radial expansion force on the removal member as the inner sheath moves in a proximal direction. The expandable collection member includes a collection area within the interior of the outer scaffold member and/or the inner scaffold member for collection of biofilm as the endotracheal tube cleaning device is withdrawn from the endotracheal tube. The scaffold of the expandable collection member can comprise one or more braid materials, elastomeric or polymeric materials, such as, for example, polyisoprene, TPE, silicone, urethane, and/or any other suitable material that has the desired or required softness and/or other characteristics (e.g., a softness of about 15 to about 40 Shore A durometer). The inner scaffold member of the expandable collection member can comprise strengthening materials to provide sufficient rigidity (e.g., larger diameter braided fibers or stiff porous elastomeric material).

The outer scaffold member and the inner scaffold member can be configured to have varying porosity to facilitate expansion and/or collection of biofilm. For example, in embodiments where braided material is used for the expandable collection member, a lower pick count (e.g., about 5 to about 10 picks per inch) can be used for the proximal side, while a higher pick count (e.g., about 10 to about 25 picks per inch) can be used for the distal side. In some embodiments, the diameters (or other cross-sectional dimensions) of the braid fibers vary from about 0.005 inches to about 0.010 inches. However, in alternative embodiments, such diameters or other cross-sectional dimension is less than about 0.005 inches or greater than 0.010 inches, as desired or required. In some embodiments, the expandable collection member comprises two or more layers of braid material. In some embodiments, the proximal portion and the distal portion of the braided collection member can be ultrasonically welded or otherwise attached to form a regular smooth continuous rim and the removal member is not included.

In embodiments where elastomeric material is used for the expandable collection member, the expandable collection member can be molded in a transfer press, an injection molding press, a compression molding press, a thermoforming press and/or using any other manufacturing device, system or method.

D. Alternate Modes of Expansion

In some embodiments, the collection member (e.g., scaffold) can comprise one or more shape memory or other materials that automatically expand from a compressed configuration maintained during insertion of the endotracheal tube cleaning device by a sheath to an expanded configuration when the sheath is withdrawn or the collection member is pushed out of the sheath. The shape memory material can include nickel titanium alloys and/or other shape memory materials. In some embodiments, the shape memory material can be temperature-activated, light-activated, and/or activated by liquid. In some embodiments, an expandable removal member (e.g., O-ring) adhered to the outer or inner surface of the collection member can automatically expand upon advancement out of a sheath.

For example, the collection member (e.g., scaffold) can be automatically expanded to an expanded configuration when a sheath is withdrawn or the collection member is pushed out of the sheath. In one embodiment, the cleaning device comprises a mesh collection member that is expanded by a spiral spring or other expandable member that automatically expands when not constrained by a sheath. In some embodiments, the distal end of the mesh collection member is adhered to a distal cap and the proximal end of the mesh collection member is adhered to the steel spiral spring. In use, the spiral spring is initially collapsed and inserted into the sheath. Then, the cleaning device is inserted within the endotracheal tube and advanced to a desired depth. Once the cleaning member has been properly inserted into the endotracheal tube, the sheath can be withdrawn toward the actuation assembly, thereby allowing the spiral spring or other expandable member to expand, generally to the size of the endotracheal tube. In one embodiment, the expansion of the spiral spring causes expansion of the mesh collection member. The cleaning device can be subsequently withdrawn from the endotracheal tube while the mesh collection member captures at least a portion of the removed biofilm.

In some embodiments, the cleaning device comprises a shuttlecock-like collection member made of material that automatically expands to about the diameter of the endotracheal tube when not constrained by a sheath. In one embodiment, the distal end of the shuttlecock-like collection member is adhered to a distal cap and the proximal end of the collection member is left unattached. In use, the shuttlecock-like collection member can be initially collapsed and fed into the sheath. Then, the cleaning device can be inserted within the endotracheal tube. Once the cleaning member is inserted to its proper depth, the sheath can be withdrawn (e.g., retracted toward the actuation assembly), thereby allowing the shuttlecock-like collection member to expand to the size of the endotracheal tube. In some embodiments, the cleaning device is withdrawn from the endotracheal tube while the shuttlecock-like collection member collects at least a portion of the removed biofilm.

In other embodiments, the collection member can be expanded using inflation. For example, the removal member can comprise an inflatable O-ring, which when inflated, causes the collection member to expand. The inflatable O-ring can be on the inside of the collection member (e.g., similar to an innertube) or on the outside of the collection member. In some embodiments, an inflatable balloon or other member is configured to selectively expand the cleaning member and/or any other portion of the cleaning device. In one embodiment, the removal member comprises a smooth or textured inflatable balloon or bladder.

E. Controlled Expansion

In some embodiments, the endotracheal tube cleaning device can provide for variable expansion of the cleaning member, depending on the tube's inside diameter, the amount of biofilm deposited on the internal surface of the endotracheal tube and/or one or more other factors or considerations. In other embodiments, the endotracheal tube cleaning device can selectively deploy the cleaning member with variable pressure depending on the endotracheal tube's inside diameter, the amount of biofilm deposited on the internal surface of the endotracheal tube and/or one or more other factors or considerations. In some embodiments, the actuation assembly is configured to expand the cleaning member about 0.1 mm to about 2 mm larger than the inside diameter of the endotracheal tube (e.g., from about 0.1 mm to about 1 mm, about 0.5 mm to about 1.5 mm, about 1 mm to about 2 mm, and overlapping ranges thereof).

In some embodiments, the actuation assembly includes features that provide for incremental expansion of the cleaning member. A détente half can include multiple détentes incrementally spaced along its length. The détentes can be formed as notches, slits, recesses, and/or the like within the molded material of the détente half. The détentes can be used to set a specific pressure and/or outer diameter of the expanded cleaning member. The détente half can include visible markings or indicia. The visible markings can aid the clinician in setting the initial position of the trigger with respect to the handle depending on the diameter of the endotracheal tube to be cleaned. The visible markings can also provide visible feedback to the clinician as to what diameter the cleaning member is currently expanded to. The visible markings can include color or pattern variations, text, varying line sizes or widths, numbers, and/or the like. In some embodiments, the visible markings provide tactile feedback to the clinician.

FIG. 21D illustrates one embodiment of a trigger for an actuation assembly. The trigger can include one or more bumps, ridges, projections and/or the like. In some embodiments, the bump is sized, shaped, or otherwise adapted to engage with, or be at least partially received by, the detents of the handle. In some embodiments, the trigger includes multiple bumps or similar features. The trigger can be captured by the assembly of the handle halves. Further, the handle halves can be coupled to each other or otherwise assembled using adhesives, crush ribs, snap fit connections, other mechanical fasteners, ultrasonic welding, and/or any other suitable attachment method or device.

The détentes can serve to provide a hard stop and gauge for the size of the endotracheal tube being to be cleaned. Accordingly, a single cleaning device can be used to clean endotracheal tubes having any of a range of inner diameters. For example, and not by way of limitation, the détentes can allow for cleaning of endotracheal tubes having an inner diameter between about 5 mm and about 10 mm. In other embodiments, the détentes can permit for cleaning of endotracheal tubes (or any other medical or non-medical tube) with inner diameter below 5 mm or above 10 mm, as desired or required. The détentes can be spaced to provide for incremental expansion in 0.5 mm or 1 mm increments. However, any other incremental expansion may be used. Engaging the appropriate détente for each endotracheal tube size can advantageously allow for the appropriate amount of scaffold deployment based on the inner diameter of the endotracheal tube. The détentes can comprise bumps or other protruding members to provide a tactile and/or an audible gauge or confirmation. The bumps along with suitable markings can allow the clinician to determine the inner diameter of the endotracheal tube.

The détente and bump profiles can be modified for smooth operation and reentry. For example, the edges and tips of the detents can be radiused such that the bumps do not hang up or otherwise serve as an obstruction. In some embodiments, the edges and tips of the détentes are generally smooth in order to reduce friction. In some embodiments, the handle can include visible indicia on the outside surface to indicate the correspondence between the detents and the inner diameter dimensions. Accordingly, a clinician can make sure that the cleaning member is appropriately expanded for the particular endotracheal tube being cleaned. In some embodiments, the radiusing of the détente tips and slight play in the trigger allows for "fine tuning" of the expansion during removal of the endotracheal tube cleaning device.

In other embodiments, the actuation assembly can be configured to provide for continuous controlled expansion of the cleaning member, such as a rotatable thumbwheel assembly. The handle of the rotatable thumbwheel assembly can be rotated to incrementally expand the cleaning member in a controlled manner.

Under some circumstances, the failure to contact the biofilm or inside wall of the endotracheal tube with the appropriate pressure can potentially result in invagination or cavitation. Accordingly, in some embodiments, the endotracheal tube cleaning device is configured to allow for manual fine tuning or adjustment of the expansion of the cleaning member. In some embodiments, the clinician can adjust the expansion of the cleaning member based upon an actual or estimated biofilm thickness (e.g., maximum biofilm thickness, average biofilm thickness, etc.) within the endotracheal tube and the known inner diameter of the endotracheal tube. For example, the estimated maximum biofilm thickness can be determined based on the endotracheal tube length, the inner diameter of the endotracheal tube, the reason for ventilation, one or more patient risk factors, the amount of biofilm removed at particular time intervals (e.g., 3, 8, 12, 24 hours, other time intervals, etc.).

In other embodiments, the clinician can adjust the expansion of the cleaning member based on, at least in part, a pressure sensor of the endotracheal tube cleaning device, tactile feedback, visualization of the biofilm using a visualization scope and/or one or more other factors or indicators.

In embodiments wherein a pressure sensor is used, the pressure sensor can be an electrical or nanotechnology sensor configured to sense the optimal pressure against the wall of the endotracheal tube. Thus, the clinician can selectively adjust the expansion of the cleaning member based upon the measured pressure and/or one or more other inputs. In other embodiments, the pressure sensor can be connected to a feedback mechanism to provide for automatic adjustment (e.g., expansion or contraction) of the cleaning member.

In some embodiments that incorporate visualization, expansion of the cleaning member can be manually or automatically set or adjusted based on an analysis of the diameter of the endotracheal tube, the amount of biofilm present in the endotracheal tube and/or one or more other factors or considerations.

In some embodiments, the removal member comprises one or more materials that automatically expand to independently apply pressure to the wall of the endotracheal tube, thereby providing automatic "fine-tuning" of the extent of expansion after a "rough" mechanical expansion of the actuation assembly and the collection member.

F. Depth Control

The endotracheal tube cleaning device can include features configured to control the depth of insertion of the endotracheal tube cleaning device within the endotracheal tube. In some embodiments, the endotracheal tube cleaning device includes visible indicia along the length of the outer shaft to indicate the depth of the endotracheal tube cleaning device in the endotracheal tube. In some embodiments, a lockable, movable stop is coupled to the outer shaft to prevent against over-insertion of the endotracheal tube cleaning device beyond the distal tip of the endotracheal tube. In other embodiments, the endotracheal tube cleaning device includes a visualization channel or lumen in which a visualization scope can be inserted to determine the exact positioning of the endotracheal tube cleaning device within the endotracheal tube. In still other embodiments, radiopaque markers can be used in combination with imaging modalities to determine the depth of insertion.

1. Mechanical Control

In some embodiments, the endotracheal tube cleaning device comprises a movable stop and visible depth markings. In some embodiments, the visible depth markings can be configured to align with corresponding depth measurements on the outside of the endotracheal tube. For example, if the endotracheal tube cleaning device is being inserted into an endotracheal tube having a length of 26 cm, the endotracheal tube cleaning device can be inserted until the 26 cm mark on the endotracheal tube cleaning device is aligned with the 26 cm mark on the endotracheal tube. The visible depth markings can be calculated such that when the corresponding depth marks are aligned, the distal tip of the endotracheal tube cleaning device is at the desired depth within the endotracheal tube (e.g., 1.5 cm proximal of the distal tip). Once the visible depth markings are aligned with the corresponding markings on the endotracheal tube, the movable stop can be locked in place at the proximal end of the endotracheal tube, thereby providing a positive check on the insertion of the endotracheal tube cleaning device within the endotracheal tube and advantageously preventing against or reducing the likelihood of inadvertent over-insertion.

In some embodiments, the endotracheal tube cleaning devices can comprise movable stops. For a movable stop having a locking clip design, the locking clip can slide freely along the length of the outer shaft. When the locking clip is moved to the correct position, as determined by the visible depth markings, the locking clip can be squeezed or otherwise manipulated to actuate the living hinge feature and engage the locking feature. Accordingly, the locking clip can be maintained in a fixed position. The locking clip design advantageously provides one-handed operation, a one-piece design, and a secure fastening feature. The materials for the locking clip design can comprise materials capable of providing "living hinge" capability, such as, for example, nylon, polypropylene, polycarbonate, and/or the like. In some embodiments the materials for the locking clip design can comprise flexible materials, such as, for example, urethane, silicone, and/or the like.

An internal oval design can provide a constant "lock" due to the interference of the internal oval opening with the radius of the outer shaft. In some embodiments, in order to temporarily "unlock" the movable stop and move the internal oval stop, manual force is used to overcome the friction fit connection of the internal oval design. The internal oval of the internal oval design can become substantially circular as it is moved along the outer shaft. Once in position, the internal oval can return to a substantially oval shape. In some embodiments, the internal oval design advantageously provides one-handed operation, a one-piece design, and a secure fastening feature. The materials for the internal oval design can comprise materials having desired or required physical and other properties, such as, for example, toughness, flexibility, short term creep resistance, and/or the like. Such materials can include, for example, urethane, polyisoprene, TPE, other polymeric or elastomeric materials and/or the like.

A spring lock design of the movable stop can be similar to the locking clips used on sweatshirt strings or drawstring bags. The bore or aperture of the illustrated spring lock can have a diameter slightly larger than the diameter of the outer shaft. The spring lock is maintained in a locking position by a spring-loaded feature. According to some embodiments, in order to unlock the device to move to a new position, the spring-loaded feature is compressed by pressing on the compression element. When the spring lock is positioned in the desired position, the compression element can be released, thereby releasing the spring-loaded feature to re-lock the spring lock. In other embodiments, the cylindrical features of the spring lock design can be substituted with flat, rectangular features. In some embodiments, the spring lock design advantageously provides one-handed operation. The spring lock design can comprise one or more materials including, but not limited to, ABS, polypropylene, nylon, filled polypropylene, polycarbonate, polyethylene, other suitable injection-moldable grade resins, other polymeric or elastomeric materials, and/or the like.

A double wing design of the movable stop can include a D-shaped opening and two symmetrical wings. In some embodiments, the flat-section of the D-shaped opening is configured to match a corresponding flat section of the cross-section of the outer shaft. When the corresponding flat sections are aligned, the double wing stop can move freely along the outer shaft. In one embodiment, in order to set the maximum depth, the double wing stop is turned either clockwise or counterclockwise using the wings so that the flat section of the D-shaped opening interferes with the radius of the outer shaft. The double wing design can advantageously provide one-handed operation and a one-piece design. The double wing design can comprise one or more materials such as, for example, ABS, polypropylene, nylon, filled polypropylene, polycarbonate, polyethylene, other suitable injection-moldable grade resins, other polymeric or elastomeric materials, and/or the like.

An oval design of the movable stop can include a D-shaped opening and operates in a similar manner to the double wing design. The oval design can advantageously provide one-handed operation and a one-piece design. The oval design can comprise one or more materials such as, for example, ABS, polypropylene, nylon, filled polypropylene, polycarbonate, polyethylene, other suitable injection-moldable grade resins, other polymeric or elastomeric materials, and/or the like.

In some embodiments, an elastomeric bag can be attached to the movable stop for containment of the collected biofilm after removal from the endotracheal tube. The elastomeric bag can be attached in a furled or rolled-up configuration. The movable stop with the attached elastomeric bag can be moved along the outer shaft in proximity to the biofilm that has been collected on the cleaning member. The elastomeric bag can then be rolled out, or unfurled, over the cleaning member, thereby containing the collected biofilm until it has been safely deposited into a biohazardous container. The elastomeric bag can comprise one or more materials, such as silicone, latex, other elastomeric or polymeric materials, and/or the like.

2. Visualization

According to some embodiments, mechanical depth control can be enhanced, supplemented, or replaced with the help of one or more visualization features. As described above, an endotracheal tube cleaning device can include a visualization channel or lumen configured to receive a visualization element (e.g., visualization scope). The visualization element can utilize ultrasound, infrared, CCD, fiber optic and/or any other type of imaging technology. For example, the visualization scope can comprise a fiber optic camera on the end of an endoscope. As discussed herein, the distal tip of the endotracheal tube cleaning device can include a transparent viewing "window" and/or other viewing area or region. The transparent viewing window or area of the visualization channel can advantageously enable a clinician to position the distal tip of the endotracheal tube cleaning device at a selected location with respect to the endotracheal tube. The window can advantageously have a thickness of less than about 0.012 inches (for example, 0.001 inches, 0.002 inches, 0.003 inches, 0.004 inches, 0.005 inches, 0.006 inches, 0.007 inches, 0.008 inches, 0.009 inches, 0.010 inches, 0.011 inches, 0.012 inches). The lens of the visualization scope can be indented by a few thousandths of an inch (e.g., 0.001 to 0.004 inches) in order to prevent or reduce the likelihood of scratches and damage to the lens. In some embodiments, the window thickness combined with the lens indentation is less than about 0.010 inches. This can help reduce glare and/or halo effects and can otherwise improve the quality of visualization. This can provide enhanced visualization to a clinician or other user as glare can make it difficult to view anatomical features. However, in other embodiments, other distances and/or thicknesses are used, as desired and/or required. One or more antireflective coatings, layers or features can be applied to the outside and/or inside of the window to further reduce glare.

In some embodiments, the proximal end of the visualization channel is constructed with a introducer sheath area suitable for preventing or reducing the likelihood of contamination of the visualization element, thereby enabling reuse of the visualization element from one patient to another without concern for cross-contamination.

In some embodiments, the visualization element can facilitate, optimize, and/or document the endotracheal tube cleaning procedures. In some embodiments, the images received from the visualization element scope can be transferred to remote locations over a network, as described above, to permit remote observation. In some embodiments, an endotracheal tube cleaning system comprises a visualization scope (e.g., endoscope with a fiber optic camera), an external camera for viewing the nurse and the patient from a control room outside the ICU environment. The images from the visualization scope and external camera can be transmitted, along with clinical test and/or patient data, such as oxygen saturation, heart rate, respiration rate, and/or the like, to facilitate the remote treatment of the ICU patient.

Figure 28A:
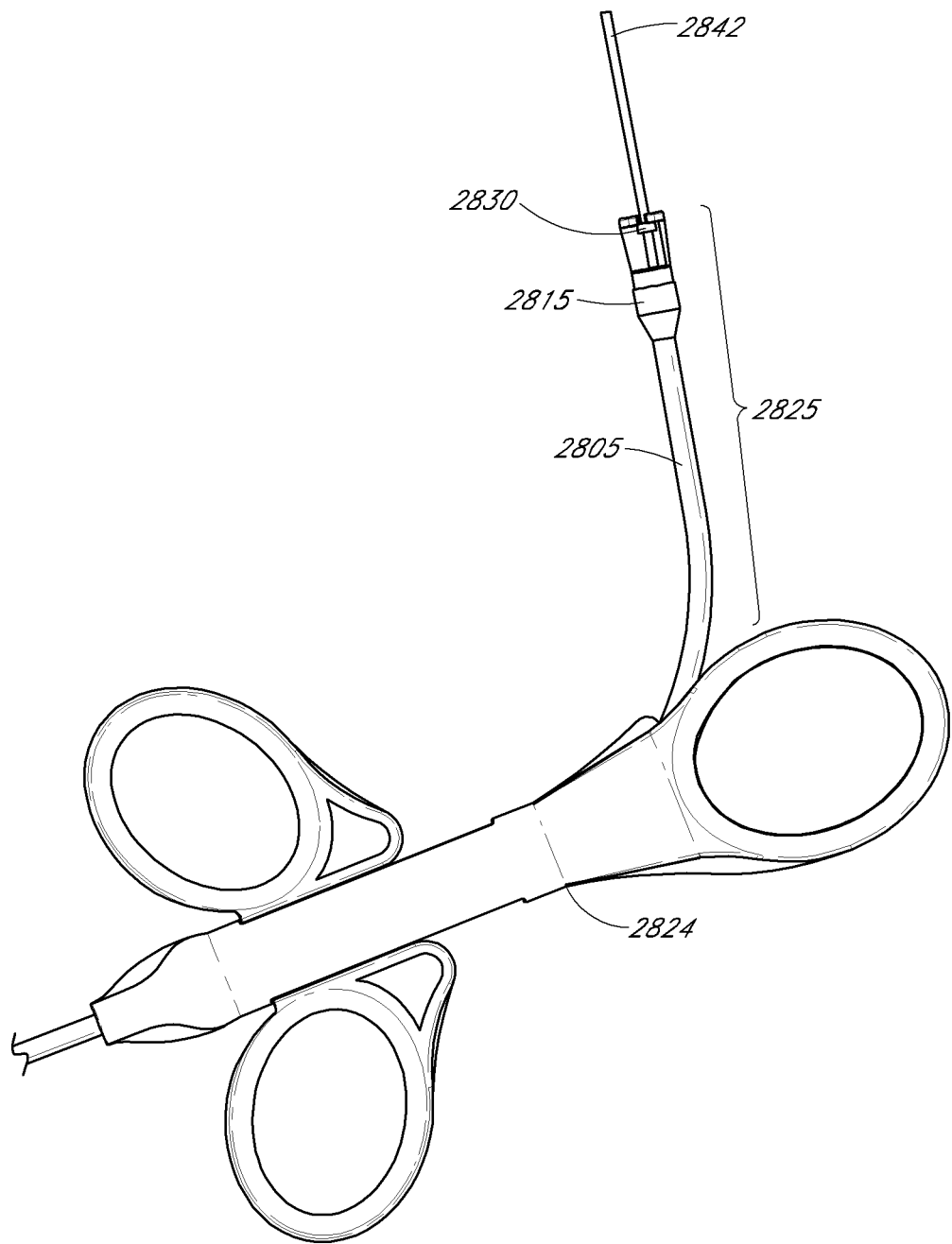
FIGS. 28A and 28B illustrate an embodiment of a scope retention assembly of the endotracheal tube cleaning device of FIGS. 27A-27D.

With reference to FIG. 28A, the endotracheal tube cleaning device 2720 can comprise a scope retention assembly 2825 configured to exert a static backward force on a visualization scope 2842 inserted within a visualization channel of the endotracheal tube cleaning device 2720. The scope retention assembly 2825 can comprise a stretchable elastomeric sheath 2805 and a scope retention member 2815. The elastomeric sheath 2805 can be attached to the actuation assembly 124 at its distal end and to the scope retention member 2815 at its proximal end. In some embodiments, the elastomeric sheath 2805 is advantageously coupled to the actuation assembly 124 in such a manner so as not to disrupt the operation of the actuation assembly 124.

In some embodiments, the elastomeric sheath 2805 comprises a stretchable material that can be stretched so that corresponding retention features of the scope retention member 2815 and of the visualization scope 2842 inserted within the elastomeric sheath 2805 interact to provide a backward static force. As described in greater detail herein, such a feature can cause the distal lens end of the visualization scope 2842 to be pressed against a window at the distal end of a visualization channel. For example, as shown in FIG. 28A, a stationary locking ring 2830 on the visualization scope 2842 can be received within a groove or slot in the scope retention member 2815.

Figure 28B:
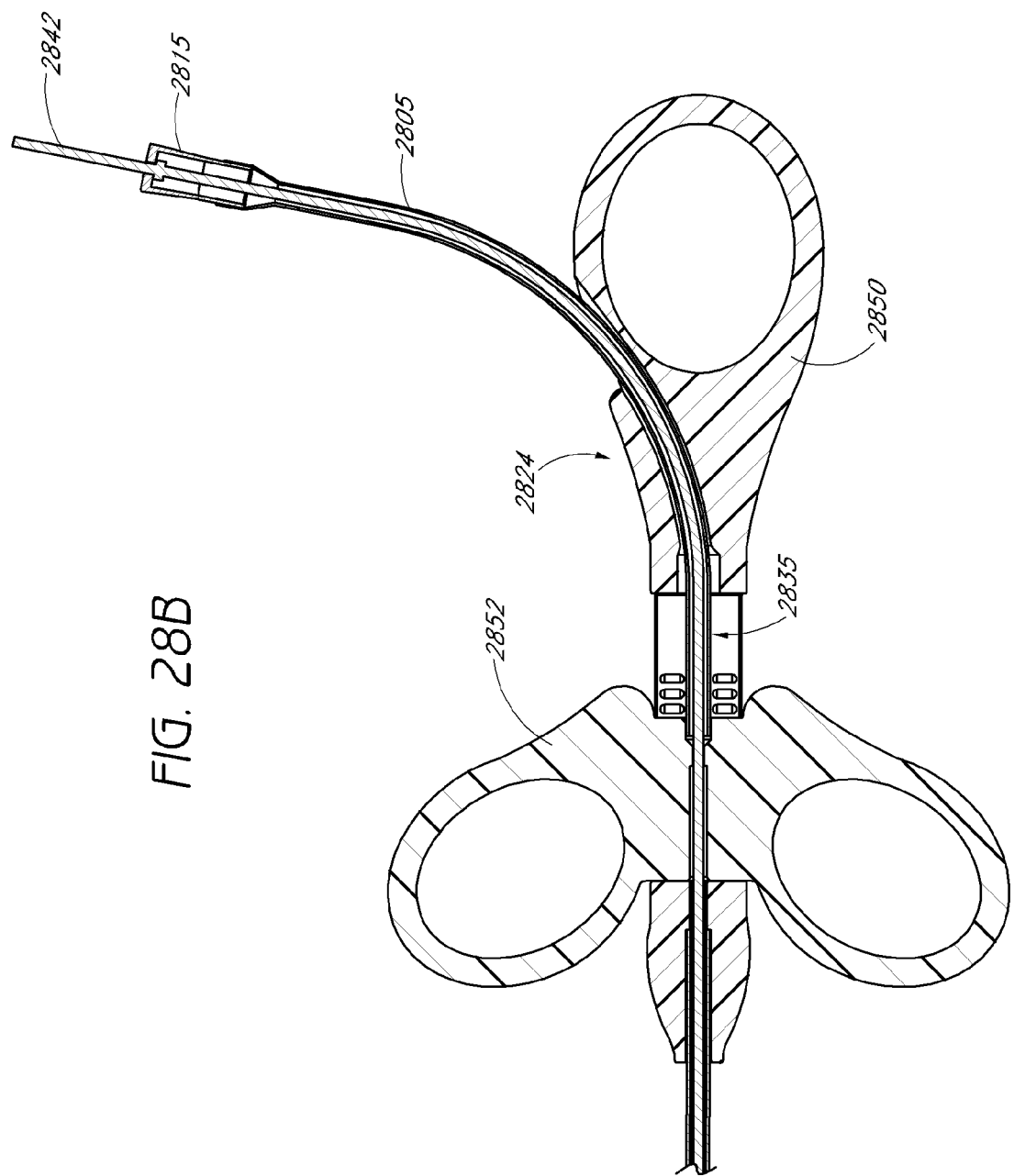

FIG. 28B illustrates a cross-sectional view of the proximal end of the endotracheal tube cleaning device 2820 and a visualization channel 2835 extending through the actuation assembly 2824 and into the elongate body 122 of the endotracheal tube cleaning device 2820. The distal end of the elastomeric sheath 2805 can be adhered, attached or otherwise coupled to a barb attachment of the trigger 2852 of the actuation assembly 2824. The elastomeric sheath 2805 can be adhered to the actuation assembly 2824 using one or more mechanical fasteners (e.g. low profile clip, other types of clips, etc.), adhesives, and/or other coupling device or method, including, for example, interference fits, ultrasonic welding, UV cure adhesives, epoxy, and/or the like. Although the endotracheal tube cleaning device and the sleeve are disposable in many embodiments, the elastomeric sheath, according to one embodiment, is or comprises a detachable disposable portion, while other portions of the endotracheal tube cleaning device remain reusable.

The visualization scope can comprise a scope retainer sleeve that fits over the visualization scope. The scope retainer sleeve can be permanently or temporarily adhered or otherwise coupled to the visualization scope. In one embodiment, the scope retainer sleeve comprises a stationary locking ring or other retention feature that is positioned on the visualization scope at a predetermined distance from the distal end of the visualization scope (e.g., approximately 25 inches, less than 25 inches, more than 25 inches, etc.). The predetermined distance can be selected based on the length of the visualization channel of the endotracheal tube cleaning device, the length of the scope retention assembly and/or any other factors or considerations.

The visualization channel can be entirely aligned with the longitudinal axis of the main elongate body of the endotracheal tube cleaning device by providing an actuation assembly having an offset thumb grip. By inserting the visualization scope along the longitudinal axis of the elongate body through a flared "trumpet-like" or substantially conical opening at the proximal end of the actuation assembly, kinking of the visualization scope can be advantageously prevented or minimized. In some embodiments, the visualization channel can have varying cross-sectional dimensions along its length. For example, the visualization channel can have one or more radial transitions for the visualization scope.

FIGS. 28C and 28D illustrate one embodiment of the interaction between the scope retention assembly 2825 and the visualization scope 2842 to create a desired static backward force on the visualization scope 2842. FIG. 28C illustrates the scope retention assembly 2825 and the visualization scope 2842 before loading, while FIG. 28D illustrates the scope retention assembly 2825 and the visualization scope 2842 after loading. In some embodiments, the elastomeric sheath 2805 can be stretched such that a corresponding receiving slot of the scope retention member 2815 is generally aligned and mated with the stationary locking ring 2830 of the scope retainer sleeve 2850 on the visualization scope 2842. The sheath 2805 can then be released to exert the necessary backward static force. In some embodiments, such a backward static force is due, at least in part, to the return force provided by the elastomeric characteristics of the elastomeric sheath 2805. In some embodiments, the elastomeric sheath 2805 can be stretched up to about one inch or more (e.g., ¼ inch, ½ inch, 1 inch, 1½ inches, 2 inches, 3 inches, more than 3 inches, etc.) from its relaxed, non-stretched state without requiring an excessive amount of pull force. However, in other embodiments, the sleeve can only be stretched to a distance of less than about 1 inch. In some embodiments, the sleeve comprises one or more bellows, expansion zones or members and/or other features that are configured to stretch or expand, either in addition to or in lieu of the stretch properties of the materials. The resulting backward force can advantageously press the lens end of the visualization scope 2842 against or near the window at the distal end of the visualization channel 2835, thereby reducing glare, improving the quality of visualization and providing one or more other benefits to the clinician.

A "Slide" embodiment of a scope retention member comprises a C-shaped proximal end, a substantially hollow body, and a substantially cylindrical distal end. In some embodiments, the body comprises ridges, grooves, or other surface features (e.g., to improve gripping). In some embodiments, the visualization scope is received coaxially within the scope retention member. In order to provide the backward force on the visualization scope, the scope retention member is advanced (while stretching the elastomeric sheath) until the lower surface of the C-shaped proximal end is proximal to the stationary locking ring or circumferential protrusion disposed on the visualization scope. The side slot of the C-shaped proximal end is then slid over the ring such that the ring abuts against the lower surface of the C-shaped proximal end. In some embodiments, the lower surface of the C-shaped proximal end includes a groove or recess that receives the ring or an annular ridge disposed on the upper surface of the ring to further secure the ring within the scope retention member. In one embodiment, the side slot comprises a pair of hemispherical protuberances or ridges extending towards each other on opposite sides of the side slot to aid in retention of the visualization scope within the side slot. In some embodiments, the C-shaped proximal end comprises a shape that is not necessarily C-shaped but still has the side slot. In some embodiments, the substantially cylindrical distal end comprises a non-cylindrical shape.

A "Snap" embodiment of a scope retention member comprises a generally cylindrical distal end and an outwardly-tapered receiving sleeve at its proximal end. The receiving sleeve, for example, can comprise a collet-like assembly of two or more leaflets or fingers. The proximal end comprises four leaflets or fingers. The leaflets or fingers are substantially cored out or at least partially hollowed such that the ring or circumferential protrusion disposed on the visualization scope can be received within the scope retention member. As the elastomeric sheath with the scope retention member is pulled over the stationary locking ring of the visualization scope, the leaflets of the scope retention member bend out of the way to allow the ring to move through and then seat in place in abutment against the lower surfaces of the wedged heads of the leaflets. The general shape and geometry of the scope retention member can vary without departing from the spirit and/or scope of the disclosure.

Other designs and approaches of creating a static reverse force on the visualization scope to improve the quality of visualization are possible without departing from the spirit and/or scope of the disclosure herein.

FIGS. 29A-29F illustrate embodiments of a safety toggle member 2910 that can be incorporated into any one of the endotracheal tube cleaning devices (e.g., endotracheal tube cleaning device 2720) described herein. The safety toggle member can comprise a mechanism that protects against premature or unintended deployment of the cleaning member (e.g., wiper) of the cleaning device. With the safety feature "off," the trigger 2852 of the endotracheal tube cleaning device can be activated, and the cleaning member of the device can be deployed. With the safety feature "on", the trigger 2852 of the endotracheal tube cleaning device cannot be activated, and the cleaning member of the device cannot be deployed. In some embodiments, the on-off positions of the safety toggle member 2910 can be visually (e.g., graphically, textually, etc.) indicated to the user. For example, the on-off positions can be indicated on a handle (e.g., handle 2850) of the cleaning device or on the safety toggle member 2910 itself. Visual toggle position indications can include color coding, such as red for stop (safety feature on) and green for go (safety feature off). The toggle safety member 2910 can be designed to be activated by a single finger or thumb of the user. In some embodiments, the toggle safety member 2910 is located on the superior or inferior aspect of the device handle 2850. The toggle safety member 2910 can be maintained in the on and off positions by détentes (not shown) in the handle 2850 and/or the toggle 2910 itself. The détentes can prevent or reduce the likelihood of the trigger 2852 from spontaneously or inadvertently changing from the "safe" (e.g., safety on) to the "ready to deploy" or deployed (e.g., safety off) position. The détentes can be adapted to be overcome intentionally utilizing a sufficient amount of pressure. In some embodiments, such pressure can be generated by one or more fingers (e.g., thumb) of the clinician or other user. In some embodiments, the toggle safety member 2910 is adapted to move about a pivot point 2911 so that the mechanism can be selectively rotated from the "safe" position to the "ready to deploy" position, and vice-versa.

Figure 29B:
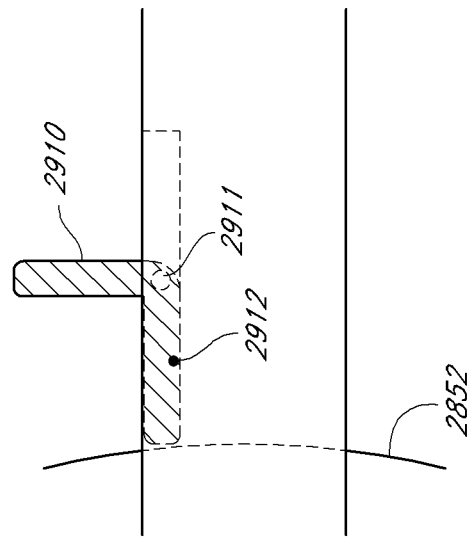
Figure 29A:
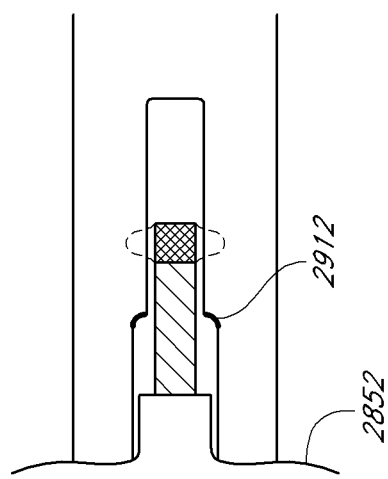

FIGS. 29A and 29B illustrate a top view and a side view, respectively, of the toggle safety member 2910 in a "safe" (e.g., safety on) position. In the "safe" position, the trigger 2852 cannot be retracted proximally, thereby preventing the expandable cleaning member from being deployed within the endotracheal tube. In some embodiments, the toggle safety member 2910 is configured to reside within a groove, notch or cutout portion of the handle 2850 or other portion of the actuation assembly in both of the toggled positions. The actuation assembly can include a trigger stop 2912, which may be incorporated into the handle 2850 or other portion of an actuation assembly (e.g., actuation assembly 2842) of the cleaning device.

FIGS. 29C-29E illustrate embodiments of the toggle safety member 2910 in a "ready to deploy" (e.g., safety off) position. FIGS. 29C and 29D illustrate a top view and a side view, respectively, before deployment of the cleaning member by proximal retraction of the trigger 2852. FIGS. 29E and 29F illustrate a top view and a side view, respectively, after deployment of the cleaning member. For example, the trigger 2852 in FIGS. 29E and 29F has been retracted proximally to the trigger stop 2912, generally corresponding to full deployment or expansion of the cleaning member. As shown, the toggle safety member 2910 in FIGS. 29C-29E has been rotated approximately ninety degrees about the pivot 2911 from the position of the toggle safety member 2910 in FIGS. 29A and 29B. Other implementations of safety mechanisms can be used without departing from the spirit and/or scope of the disclosure.

The endotracheal tube cleaning device can be provided to a user with the toggle safety member 2910 in the "safe" or "unable to be deployed" position. Accordingly, in some embodiments, a change in the toggle position by the user is required prior to the distal cleaning member of the cleaning device being able to deploy. After the cleaning device has been used in one cleaning pass, the toggle safety member 2910 may be placed in the "safe" position prior to reinsertion of the cleaning device for a second pass if a second pass is needed.

G. Supplementary and Preventative Modalities/Capabilities

In some embodiments, the endotracheal tube cleaning device can have one or more channels or lumens for visualization, aspiration or suction, ventilation, irrigation/infusion, light delivery, and/or the like. In some embodiments, the endotracheal tube cleaning device can have a single channel (e.g., a central lumen) for insertion of multiple catheters, probes, scopes, and/or other instruments. In other embodiments, the endotracheal tube cleaning device includes two or more channels. For instance, an endotracheal tube cleaning device can comprise a visualization channel, a suction channel, and an irrigation/infusion channel.

In arrangements including a side port, one or more channels or lumens of the endotracheal tube cleaning device can be in communication with such a side port. In some embodiments, the channels or lumens of the cleaning device can be sheathed to prevent contamination of the catheters, probes, scopes, and/or other instruments inserted therein.

The additional catheters, probes, scopes, and/or instruments providing additional features to supplement and/or facilitate the cleaning of the endotracheal tube can be configured for single-handed operation. The single-handed operation can be facilitated with the use of fibers, cables, conduits, and/or lines of sufficient length such that the bulky components of the additional diagnostic, visualization, and/or therapeutic instruments or systems are positioned remote from the patient. In some embodiment, user controls for the additional instruments or systems are located adjacent to the patient or adjacent to the actuation assembly of the endotracheal tube cleaning device to enable the single-handed operation by the user. The various mechanisms can be controlled by pressing one or more user input controls with a single finger. In some embodiments, a different finger can be used for each respective action (e.g., one finger for aspiration and another finger on the same hand for irrigation or drug delivery). In other embodiments, the additional instruments and/or capabilities can be controlled by multiple hands and/or multiple persons.

In some embodiments, the additional instruments and capabilities can be controlled by the clinician concurrently with cleaning of the endotracheal tube with the endotracheal tube cleaning device. In other embodiments, the additional instruments and capabilities can be activated before, concurrently with, and/or after the cleaning with the endotracheal tube cleaning device. In some embodiments, two or more instruments can be activated simultaneously (for example, for broncho-alveolar lavage).

1. Suction/Aspiration

In some embodiments, a suction or aspiration catheter, conduit, or line can be inserted into a channel of the endotracheal tube cleaning device. The suction catheter can be used to perform an initial pre-cleaning suctioning of the tracheobronchial tree, the endotracheal tube and/or any other item or region of the anatomy. The suction catheter can also be used to aspirate biofilm removed by the cleaning member of the endotracheal tube cleaning device. The aspiration catheter can be used for sampling and analysis of the biofilm within the endotracheal tube of a patient to determine the bacterial content or nature of the biofilm. The clinician can then implement more effective treatment, antibiotics and safeguards against cross-contamination based at least in part on the determination of the bacterial content, thereby advantageously reducing infections, conditions, and/or other ailments, including but not limited to VAP, and reducing the length of stay of the ICU patient. In some embodiments, the endotracheal tube cleaning device has a proximal seal at the entry of the tube for generally sealing the region during the application of suction, thereby helping to enhance the removal of material.

In some embodiments, the removal member (e.g., O-ring) can include one or more openings or ports spaced continuously or intermittently around its circumference or other outer region to facilitate in the aspiration of biofilm and/or other materials. The suction catheter, conduit, or line can provide suction to the removal member to facilitate removal of small amounts of biofilm that are not completely removed (e.g., wiped) from the inside surface of the endotracheal tube.

2. Irrigation/Fluid Delivery

In some embodiments, a delivery catheter can be inserted into a channel of the endotracheal tube cleaning device. Accordingly, the delivery catheter can be used to selectively deliver one or more fluids and/or other materials to a target region. In some embodiments, such fluids and/or other materials are adapted to disinfect, decontaminate, or sterilize the endotracheal tube. In some embodiments, such fluids and/or other materials are configured to loosen, break up, penetrate, degrade, disperse, dissolve and/or otherwise undermine or affect the biofilm deposited on the inside surface of the endotracheal tube. In some embodiments, such fluids and/or other materials can aid in removal of the biofilm and/or aid in the prevention of the future accumulation of biofilm. The delivery catheter can be configured and positioned to deliver one or more fluids and/or other materials to the inside wall of the endotracheal tube, tracheobronchial tree and/or any other region within a person's anatomy.

In some embodiments, fluids and/or other materials that are selectively delivered through a channel or lumen of the cleaning device include, without limitation: medicaments, biologically active agents, antibacterial or antimicrobial agents, bactericides, antiviral agents, mucolytic agents, saline solution, sterilant, enzymatic cleaner, germicide, antimicrobial fluid, detergent, combinations of the same, and/or the like. In some embodiments, the antiviral agents can be configured to prevent or treat ventilator assisted pneumonia or other maladies or conditions. Ultraviolet (e.g., UVC at about 254 nanometers) can provide a germicidal effect and/or a viracidal effect with a minor frequency modulation; however other germicidal and/or antimicrobial treatment may be incorporated in several embodiments. Therapeutic modalities are included in some embodiments, including but not limited to, radiofrequency, ultrasound, laser, microwave, heat, and cryotherapy, or combinations thereof. In one embodiment, the therapy is used to effect fibrosis, stiffening and/or ablation.

In some embodiments, an irrigation channel or lumen can deliver drugs, fluids and/or other materials via the removal member (e.g., O-ring), the collection member (e.g., mesh scaffold), a deployment member (e.g., struts) and/or any other component or portion of the cleaning device. In some embodiments, the irrigation channel or lumen includes multiple outlets that are in communication with the outside of the endotracheal tube cleaning device along the length of the channel. Accordingly, such embodiments can be used to selectively deliver fluids and/or other materials (e.g., antibiotics, antiviral substances, other pharmaceuticals, antiseptics, therapeutic agents, and/or the like) to the biofilm. In other embodiments, the irrigation channel or lumen includes a single outlet, either at the distal end of the endotracheal tube cleaning device (e.g., in the distal tip) or at any other location along the length of the device, in order to selectively deliver the desired fluids, agents, and/or other materials to the biofilm. The one or more outlets can comprise a one-way valve, slit, and/or diaphragm to substantially seal the outlet, thereby preventing or reducing the likelihood of contamination due to an influx of bacteria or materials from inside the patient.

In some embodiments, an irrigation channel or lumen can be used to deliver drugs in a spray pattern that will deliver the drugs in an acceptable amount or rate to the wall of the endotracheal tube. In some embodiments, a drug delivery catheter can deliver a "mist" of a prescribed amount of a therapeutic agent, other pharmaceutical or drug and/or other substance to at least partially coat the inside wall of the endotracheal tube and/or the biofilm attached thereto. In some embodiments, a drug delivery catheter can include a diffusing tip to enhance the spray of drugs to the wall of the endotracheal tube. For example, such tips or nozzles can help to more evenly diffuse the materials along a target region of the endotracheal tube or biofilm layer.

In other embodiments, an irrigation channel has a distal outlet directed at the "window," or distal tip, of the visualization channel to help clear debris and other materials away from the viewing window. Accordingly, the visualization features described herein can be improved.

3. Ventilation

In some embodiments, the endotracheal tube cleaning device has an internal lumen that facilitates or enables the continued delivery of air, pure oxygen and/or other gases to the patient while the endotracheal tube cleaning device is in place. This can help ensure that the patient's blood oxygen level is maintained above a threshold level during a particular procedure. However, in other embodiments, the cleaning device does not require supplemental oxygen or other gases to be delivered to a patient during a procedure. In some embodiments, the delivered gas or gases can be heated to a temperature of between about 120 degrees to about 180 degrees Fahrenheit.

4. Other Therapeutic Modalities

In some embodiments, one or more channels of the endotracheal tube cleaning device can be used to deliver therapeutic modalities, such as sonication, vibration, radiation, photodynamic therapy, light, electrical stimulation and/or the like.

For example, photodynamic therapy can be used to treat specific bacteria identified as being present within the endotracheal tube or within the tracheobronchial tree. In some embodiments, one or more drugs can be delivered through a channel (e.g., a drug delivery or infusion channel) of the endotracheal tube cleaning device or by a separate drug delivery catheter to the inner wall of the endotracheal tube. Then, one or more light delivery elements (e.g., LEDs, lasers) can be inserted within the same channel or a different channel to deliver light at an appropriate wavelength (e.g., visible, infrared, UV wavelengths) to activate the one or more drugs delivered to the inner surface of the endotracheal tube. For example, UV-C light can reduce surface bacteria count within a matter of seconds. In certain embodiments, the drugs and light can be delivered concurrently. In embodiments where the light is delivered through the distal tip, the distal tip can be configured to disperse and/or diffuse the light (e.g., using a diffuser, a deflector, and/or the tissue optics properties of the tip itself) such that the appropriate wavelength, intensity, and/or quantity of light can be delivered to activate a specific drug. A control unit can be programmed and/or controlled to vary the wavelength, intensity, pulse width and duty cycle (if pulsed light is used), exposure time, and/or the like of the light.

As another example, sound waves can be delivered through using a sonication device. Such sound waves can advantageously have an inhibiting effect on the sustainability and/or growth of biofilm. Vibrations produced by the sonication device can loosen the tenacious or more adherent biofilm. In some embodiments, one or more sensors or electrodes can be introduced on a probe or catheter to detect one or more physiological conditions or parameters of the patient.

H. Introduction Connector

In some embodiments, an endotracheal tube cleaning system includes an adapter or introduction connector that advantageously enables the patient to remain connected to a mechanical ventilator, thereby maintaining ventilator airflow, during cleaning of the endotracheal tube.

In some embodiments, the distal end of the adapter is configured to removably couple (e.g., directly or indirectly) to the proximal end of the endotracheal tube after removal of the ventilator coupling element. In some embodiments, the distal end of the adapter is sized and configured to be inserted within the lumen of the endotracheal tube. In other embodiments, the distal end of the adapter is sized and configured to fit around the outside surface of the endotracheal tube, thereby reducing the likelihood of the cleaning member of the endotracheal tube cleaning device being snagged on a ridge introduced by the thickness of the inserted adapter during removal from the endotracheal tube.

In some embodiments, the adapter includes a ventilation port and a device insertion port. The ventilator coupling element can be coupled to the ventilation port for connection to the ventilator. The device insertion port can be used to insert the endotracheal tube cleaning device and/or other devices (e.g., catheters, probes, scopes). In one embodiment, the device insertion port includes an elastomeric diaphragm to help prevent loss of ventilator tidal volume. The elastomeric diaphragm can comprise a slit or hole, a one-way valve and/or any other device or feature to substantially seal around the inserted device. This can advantageously help prevent the escape of ventilator tidal volume. The elastomeric diaphragm can comprise one or more elastomeric materials, such as, for example, urethane, latex, silicone, other polymeric or elastomeric materials, and/or the like. The thickness of the diaphragm can range from about 0.002 inches to about 0.030 inches. In some embodiments, the thickness of the diaphragm is about 0.005 inches to about 0.20 inches. However, in other embodiments, the diaphragm thickness is greater than 0.030 inches or smaller than 0.002 inches, as desired or required.

The device insertion port can be sufficiently long such that the entire distal end of the endotracheal tube cleaning device is located proximal to the distal end of the adapter when the adapter is removed. For example, the length of the device insertion port can range from about 30 cm to about 60 cm. The diameter of the device insertion port can range from about 4 mm to about 7 mm. The inner diameter of the ventilation port can be sized to be slightly larger than the outer diameter of the ventilator coupling element. The length of the adapter can range from about 4 cm to about 10 cm. Other dimensions for the adapter can be used as desired and/or required.

The adapter can be Y-shaped, with the ventilation port located at the proximal end of the adapter and the device insertion port extending from the side of the adapter at an acute angle. In one embodiment, the adapter is generally T-shaped, with the device insertion port located at the proximal end of the adapter and the ventilation port extending from the side of the adapter at a right angle. In other embodiments, the adapter can be Y-shaped, with the ventilation port extending from the side of the adapter at an acute angle. The adapter can advantageously provide a straight insertion path for the endotracheal tube cleaning device or other devices. In other embodiments, the adapters can have a different shape or configuration than discussed and illustrated herein.

The adapters can include distance markings from the connection to the proximal end of the endotracheal tube to the opening of the device insertion port to aid in positioning the endotracheal tube cleaning device and the locking of the movable stop. In some embodiments, the distance from the endotracheal tube connection to the opening of the device insertion port can range from about 4 cm to about 8 cm; however, other lengths can be used as desired and/or required.

According to some embodiments, kits of adapters can be provided to accommodate endotracheal tubes having various diameters. The adapters can include markings indicating the tube diameter(s) for which they can be used. In other embodiments, the adapters comprise one-size-fits-all (or one-size-fits-most) adapters that can be used to fit endotracheal tubes of various diameters. For example, the adapter can have three varying cross-sectional diameters so as to enable the adapter to fit endotracheal tubes of three different outer diameters (e.g., 7 mm, 8 mm, or 9 mm).

In some embodiments, adapters can also be used to at least partially contain biofilm that has been removed by the cleaning member. For example, when an adapter is disconnected from the endotracheal tube and ventilator, the distal end of the adapter can be slid over the cleaning member, thereby providing a protective covering over the removed biofilm to prevent contamination and/or facilitate collection and sampling of biofilm.

I. Use

1. General Use

As generally described herein, the endotracheal tube cleaning devices and systems described herein can be used to clean endotracheal tubes while a patient is being supported by a ventilator connected to the endotracheal tube. This cleaning is useful for increasing the available space for airflow in the endotracheal tube and for reducing or preventing the build up of materials that would otherwise constrict airflow through the endotracheal tube and potentially be a nidus for infection. The endotracheal tube cleaning device can advantageously be used to clean the endotracheal tube while the endotracheal tube remains inside the patient.

2. Indications

According to some embodiments, an endotracheal tube cleaning device can be used for a variety of indications. For example, the endotracheal tube cleaning device can be used for preventative indications, for daily use indications, and/or for near total occlusion indications. In some embodiments, the endotracheal tube cleaning device can be used at least once a day to prevent any extensive buildup of biofilm, as biofilm has been shown to start building up as early as within 24 hours of intubation. Daily utilization can coincide with ICU protocols for daily extubation attempts for all patients. In other embodiments, the frequency of endotracheal tube cleaning can vary, depending on patient, the patient's health and other conditions, a desired cleaning protocol and/or the like.

For example, in some embodiments, the endotracheal tube cleaning device can be used multiple times a day for high risk patients. High risk patients can include older patients, smokers, patients with chronic obstructive pulmonary disease (COPD), patients intubated as part of their treatment for respiratory insufficiency related to pneumonia, patients with an indwelling endotracheal tube for longer than 24 to 48 hours and/or others. The frequency of use can be determined by clinical evaluation and observation of the degree of secretions being produced by an individual patient. However, the frequency of cleaning can depend on one or more other features, as desired or required.

In some embodiments, the endotracheal tube cleaning device is used when a nurse or clinician reports that the patient is becoming increasingly difficult to suction, which may be indicative of obstructing secretion buildup within the endotracheal tube. In some embodiments, the endotracheal tube cleaning device is used to clean prior to bronchoscopy for pulmonary toilet in order to be certain that the endotracheal tube is clear of secretions that might otherwise be pushed distally into the tracheobronchial tree by the relatively large and flat-surfaced end of the bronchoscope.

The endotracheal tube cleaning device can advantageously be used on intubated patients with ongoing bloody secretions or frank hemoptysis in order to prevent clots from obstructing the endotracheal tube lumen. In some embodiments, for patients with hemoptysis, blood clots are unable to be suctioned and can solidify and become adherent to the endotracheal tube, causing significant obstruction. The endotracheal tube cleaning device can also be used on patients who fail weaning and extubation trials before tracheostomy is performed. The endotracheal tube cleaning device can advantageously be used on intubated patients who experience an acute, abrupt, and/or unexplained change in their respiratory or ventilatory status in order to rule out mucous plugging or clotting within the endotracheal tube as a cause of the sudden deterioration or increased resistance.

Because of the visualization features of the endotracheal tube cleaning device, the endotracheal tube cleaning device can advantageously be used to verify appropriate position of an indwelling endotracheal tube, which can reduce the requirement for confirmatory chest X-rays. In some embodiments, the endotracheal tube cleaning device is used at the time of bedside percutaneous tracheostomy to help position the tip of the endotracheal tube prior to the tracheostomy procedure and to visualize each step of the procedure to decrease potential complications from a "blind" approach. This use of the endotracheal tube cleaning device can be superior over bronchoscopy as no additional personnel is required, no resterilization is necessary, and the smaller outside diameter of the distal tip of the endotracheal tube cleaning device relative to the bronchoscope allows the patient to be easily ventilated during the tracheostomy procedure.

The amount of biofilm to be removed in the various indications can vary greatly. By way of example, for a prevention indication, the endotracheal tube cleaning device can collect about 1 cc to about 5 ccs (e.g., about 1 cc to about 3 ccs, about 1 cc to about 4 ccs, about 2 ccs to about 5 ccs) of biofilm. By contrast, in daily use indications, the endotracheal tube cleaning device can collect about 2 ccs to about 15 ccs (e.g., about 2 ccs to about 5 ccs, about 3 ccs to about 8 ccs, about 5 ccs to about 10 ccs, about 6 ccs to about 15 ccs) of biofilm. Further, for near total occlusion indications, the endotracheal tube cleaning device can collect more than about 5 to more than about 15 ccs of biofilm. In some embodiments, the endotracheal tube cleaning devices described herein remove a sufficient amount of biofilm such that endotracheal tube resistance is decreased by about 90% or more after cleaning. The decreased resistance can decrease work of breathing and decrease length of ICU stay.

In some embodiments, the endotracheal tube cleaning devices remove about 99% of microbes from the endotracheal tube during cleaning.

In one embodiment, the cleaning member can be radially expanded or otherwise radially deployed in a manner that sufficient contacting force is maintained between a contact surface of the cleaning member and the internal wall of the endotracheal tube and/or the biofilm accumulated thereon. This can advantageously permit the cleaning member to shear, wipe, or otherwise remove the biofilm, while preventing or reducing the risk of hydroplaning, cavitation, and/or invagination.

In several embodiments, the pull-out force used to withdraw the endotracheal tube cleaning devices can be provided by a clinician using a single hand without significant strain. In one embodiment, the cleaning device comprises a mesh scaffold coupled to a silicone O-ring having a softness of 40 Shore A durometer with a pull-out force that is comparable to the mesh scaffold alone. In one embodiment, the removal members do not appreciably increase the pull-out force used to withdraw the endotracheal tube cleaning devices when such devices are being used to remove biofilm deposited on the internal wall of an endotracheal tube in a single pass.

3. Cleaning Processes

An embodiment of a process for cleaning an inside surface of an endotracheal tube (e.g., endotracheal tube) while such an endotracheal tube is inserted within a patient is provided. The cleaning process starts with the head of the bed being positioned at approximately 30° relative to horizontal. In other embodiments, the head of the bed can be positioned at angles larger or smaller than 30° relative to horizontal as desired and/or required. According to some embodiments, information related to the patient's heart rate, heart rhythm, blood pressure, $O_2$ saturation, other vital signs and/or other desired data can be detected and advantageously displayed to the clinician performing the cleaning procedure. In some embodiments, oxygen at 100% $FiO_2$ or nearly 100% $FiO_2$ is delivered to the patient for ten minutes or another desired time period via a ventilator attached to the patient's endotracheal tube. A disposable chux, pad and/or support member can be placed under the endotracheal tube and ventilation connection, and may be spread out over the patient's chest.

Next, in some embodiments, routine endotracheal suction is performed, and the endotracheal tube is checked to confirm that it is properly secured to the patient's face and/or mouth. The exact length from the visible proximal end of the endotracheal tube to its tip within the patient can then be determined from visible markings on the endotracheal tube. According to some embodiments, the endotracheal tube cleaning device is visualized and the movable locking stop that prohibits over-insertion of the endotracheal tube cleaning device is locked to an axial position that deploys the cleaning member no closer than 1.5 cm from the distal tip of the endotracheal tube. In other embodiments, the movable stop on the endotracheal tube cleaning device is set to the position corresponding to the length of the endotracheal tube.

In some embodiments, the ventilator is temporarily disconnected from the endotracheal tube and the endotracheal tube cleaning device is inserted into the endotracheal tube up to the locking stop. In some embodiments, disconnecting the ventilator includes loosening the ventilator coupling element for one hand removal and then removing the ventilator coupling element with one hand while standing at the patient's side at chest level after the ventilator is disconnected. The endotracheal tube cleaning device can be inserted at block in a single-hand operation using the other hand (the hand not used to remove the ventilator coupling element).

The cleaning member can then be deployed (e.g., with a one-hand activation of the actuation assembly) and the endotracheal tube cleaning device can then be withdrawn from the endotracheal tube while applying counter-traction to the endotracheal tube itself. The endotracheal tube cleaning device can be withdrawn over a one to three second time period. In other embodiments, withdrawal of the cleaning device can be faster than one second or longer than three second, as desired, required or permitted for a particular application or use. The removed endotracheal tube cleaning device can be placed on a chux and wrapped up for biohazard disposal or reinserted into the original peel pouch and placed in a biohazard collection unit. In one embodiment, the patient is then reconnected to the ventilator after reconnecting the ventilator coupling element.

The steps of the endotracheal tube cleaning process described above can be repeated multiple times as necessary at a single treatment with the endotracheal tube cleaning device, so long as the patient's heart rate, heart rhythm, blood pressure, and $O_2$ saturation remain stable. The endotracheal tube cleaning process can be performed by a single person or by multiple persons. For example, a first person (e.g., nurse or respiratory therapist) can perform the cleaning with the endotracheal tube cleaning device and a second person (e.g., an ICU technician) can disconnect and reconnect the ventilator, remove the endotracheal tube cleaning device from its packaging, and dispose of the used endotracheal tube cleaning device.

In some embodiments, endotracheal tube cleaning methods can be performed during a daily extubation attempt. A daily extubation process can include the following steps. First, the clinician can perform an initial assessment to ensure that the patient is in a stable condition. The clinician can ensure that no hemodynamic or respiratory system acute clinical changes exist that would make that system a priority. Next, the clinician can discontinue or reverse sedating medications that may interfere with spontaneous ventilation and/or medications that may produce a paralytic effect.

The clinician then can perform a neurological examination to be sure that the patient is alert and able to follow commands. The patient can then be positioned semi-upright (e.g., the head of the bed is elevated to at least approximately 30 degrees relative to horizontal). In some embodiments, the patient is then oxygenated at 100% $FiO_2$ or nearly 100% $FiO_2$ for approximately ten minutes (pre-cleaning ventilation). In other embodiments, the patient is oxygenated for more or less than ten minutes as desired and/or required.

In some embodiments, the ventilator coupling element is removed and an introduction connector (e.g., adapter) is placed between the endotracheal tube and the ventilator. Endotracheal suctioning can be performed to aspirate pooled secretions from the major segments of the tracheobronchial tree. According to some embodiments, the patient is then oxygenated again at 100% $FiO_2$ or nearly 100% $FiO_2$ for ten minutes. In other embodiments, the patient is oxygenated for more or less than ten minutes as desired and/or required.

According to some embodiments, the clinician can insert the endotracheal tube cleaning device through the introduction connector after setting a maximum insertion depth with the movable stop based on the length of the endotracheal tube to be cleaned. The cleaning member can then be expanded by activating the actuation assembly to the appropriate setting corresponding to the predetermined inner diameter of the endotracheal tube.

The endotracheal tube cleaning device, including the introduction connector which may be used to contain the biofilm, can then be withdrawn from the endotracheal tube. Then, the patient can be reconnected to the ventilator after reconnecting the ventilator coupling element. Ventilator weaning can then be performed for approximately ten minutes. In some embodiments, the ventilator weaning period advantageously allows time for improved ventilation/perfusion match to occur following removal of the endotracheal tube cleaning device.

In some embodiments, any or all of the steps in the daily extubation process can be repeated. In other embodiments, one or more steps can be removed, modified, or altered without departing from the spirit and/or scope of the disclosure. The daily extubation process can be performed by a single person and/or multiple persons.

In some embodiments, a process for preventing the buildup of biofilm inside an endotracheal tube is provided. The process begins with an initial assessment of a patient's risk factors for biofilm buildup and VAP is performed. An intervention plan can be created based at least in part on clinical parameters, such as oxygen saturation levels. The patient's airway and/or endotracheal tube can then be viewed using a visualization or imaging element.

In some embodiments, the patient is then prepared for endotracheal tube cleaning by oxygenating the patient at block. For example, the patient can be oxygenated for approximately ten minutes or other desired time period at a 100% or nearly 100% oxygen saturation level. An endotracheal tube cleaning can then be performed by inserting an endotracheal tube cleaning device (e.g., endotracheal tube cleaning device) into the endotracheal tube and then removing it. Biofilm removed by the endotracheal tube cleaning device can then be optionally sampled. The clinician can then identify the drugs that are most appropriate for preventing biofilm buildup and/or treating the bacteria present in the biofilm sample.

According to some embodiments, the identified drugs are delivered to the endotracheal tube and/or to the native airway of the patient. In some embodiments, the drugs are delivered through an internal lumen of the endotracheal tube cleaning device. In other embodiments, the drugs are delivered using a drug delivery catheter without the use of the endotracheal tube cleaning device. The delivery of the identified drugs can be repeated according to a predetermined delivery schedule as desired and/or required.

4. Artificial Biofilm for Training

In some embodiments, an artificial biofilm can be constructed to simulate the build up and distribution of biofilm for the purposes of training ICU personnel "best practices" for identifying, removing, sampling, culturing, suctioning or lavaging of actual biofilm. The artificial biofilm can comprise one or more of the following: slime, gelatin, glycerin, petroleum, egg whites, hair spray or hair gel, and like materials, and combinations thereof. In one embodiment, the artificial biofilm comprises a gelatinous material with a texture and density that mimics natural mucous. The artificial biofilm can be inserted into a standard endotracheal tube positioned within a model of a human airway. The artificial biofilm can be inserted using a syringe and catheter, for example.

In some embodiments, the artificial biofilm can be inserted so as to simulate typical patient conditions after prolonged ventilation (e.g., greater than 24 hours). For example, little to no artificial biofilm can be inserted in the first 2.5 cm from the distal tip of the endotracheal tube, a 0.1 mm thick layer of artificial biofilm can be inserted along the inner surface of the main collection region of the endotracheal tube, and a 0.5 mm thick layer of artificial biofilm can be inserted along the inner surface of the endotracheal tube from the main collection region to the proximal end of the endotracheal tube.

The training of the ICU personnel using the artificial biofilm can be performed with or without a visualization element. If the training is performed without the visualization element, the endotracheal tube cleaning device can be inserted, deployed, and removed as described above. If the training is performed with the visualization element, the images provided by the visualization element can be displayed for viewing by multiple ICU personnel and/or can be recorded for subsequent training.

The use of the artificial biofilm can aid in demonstrating the effect of an occluded endotracheal tube on endotracheal tube resistance and work of breathing oxygen saturation levels. The artificial biofilm can also be used to train ICU personnel on the visualization, sampling, suction, and/or cleaning features of the endotracheal tube cleaning devices, systems and methods described herein. The use of the artificial biofilm to train ICU personnel advantageously allows for simulated role play without compromising patient safety.

J. Other Uses

In some embodiments, the endotracheal tube cleaning device can be inserted into a patient's endotracheal tube at the time of a percutaneous tracheostomy. A percutaneous tracheostomy may be performed, for example, if a patient cannot be weaned after a sufficiently long period of time or if the patient's normal airway is obstructed. If an endotracheal tube is left in the patient for extended time periods, polyps or scarring can develop within the patient's airways. Thus, a clinician or other patient care provider may decide to convert from an endotracheal tube to a tracheostomy tube.

In some embodiments, a percutaneous tracheostomy comprises inserting a hollow needle within the trachea through an incision formed at a position between the patient's larynx, or Adam's Apple, and the patient's sternal notch. Currently, patient care providers determine proper positioning of the hollow needle during a percutaneous tracheostomy by one of two methods. One is by the aspiration of air. However, such an approach is not always accurate, because air can be aspirated from the esophagus. An alternative method is to place a bronchoscope down the endotracheal tube to be able to visualize the needle puncturing the anterior wall of the trachea in the appropriate location. In some embodiments, a guidewire is inserted through the hollow needle to facilitate the introduction of tracheostomy dilators and eventually the tracheostomy tube. Without the assistance of visualization, the hollow needle can be inadvertently inserted through a distal end of an indwelling endotracheal tube, which generally remains within the patient until the tracheostomy is completed. In addition, without visualization, the guidewire can become tied to the endotracheal tube, thereby preventing proper insertion of dilators and/or a tracheostomy tube over the guidewire and preventing removal of the endotracheal tube.

In many instances, bronchoscopes are currently used to provide visualization. However, bronchoscopes have a relatively large diameter that substantially obstructs the patient's airway during use. In addition, the cost of the bronchoscopes prohibitively prevents single-use, disposable visualization devices. Thus, resterilization and cleansing of bronchoscopes is required. The bronchoscope is occasionally damaged by the needle, resulting in an expensive repair. Also, an additional clinician is required to manipulate the bronchoscope while the operating clinician performs the tracheostomy, thereby increasing personnel requirements for the procedure.

In some embodiments, the endotracheal tube cleaning devices described herein can be used to visualize the trachea during the percutaneous tracheostomy in order to verify and confirm proper insertion and positioning of any needles, guidewires, tubes, and/or balloons within the trachea. The use of the visualization features of the endotracheal tube cleaning devices described herein advantageously allows for conversion to a tracheostomy while keeping the patient connected to an external ventilator. In some embodiments, as described above, the visualization element (e.g., a visualization scope) can record one or more images of the trachea to document the proper positioning and/or insertion of the various devices inserted within the trachea during the percutaneous tracheostomy. Recordings, according to some embodiments, are then uploaded or transmitted (e.g., via wired or wireless network communication) to a communication device, database, network, printer or other device for communicating or memorializing that the proper position was confirmed or verified.

The endotracheal tube cleaning device can be inserted within the endotracheal tube through a standard T adapter or connector (for example, as currently used for bronchoscopy) or through a proprietary adapter or connector having an inlet visualization port sized and shaped to conform to the outer diameter of the endotracheal tube cleaning device. In some embodiments, the inlet visualization port can be covered by an elastomeric plug having an opening with a smaller diameter than the opening of the standard T adapter or connector, such as a Portex® Fiberoptic Bronchoscope Swivel Adapter commercially available from Smiths Medical ASD, Inc. The opening of the elastomeric plug can be sized to substantially match or conform to the outer diameter of the endotracheal tube cleaning device. The T adapter or connector can include a side inlet port for connection to an external ventilator, thereby allowing the patient to continue to be supported with supplemental oxygen during the conversion to the percutaneous tracheostomy.

Although the endotracheal tube cleaning devices, methods, and systems described herein have been described in connection with the cleaning of endotracheal tubes or other body-inserted tubes, the embodiments and features described herein can be used for other medical applications, such as, for example, the cleaning of catheters, probes, body lumens, vasculature (e.g., arteries and veins), urinary tracts, grafts (e.g., hemodialysis grafts, vascular grafts), aspiration conduits, ventilation tubes, and the like. Non-medical applications of the devices, methods, and systems described herein include, but are not limited to, the cleaning of pipes, hoses, guns, ventilation ducts and any other hollow or substantially hollow structure and/or the like.

K. Functionality

In one embodiment, the endotracheal tube cleaning device is a fully disposable, single-use device. In other embodiments, one or more components or portions of the endotracheal tube cleaning device are selectively detachable and configured for reuse. For example, the elongate body and the actuation member can be reusable, while the cleaning member can be detachable and disposable. In some embodiments, the spent endotracheal tube cleaning device is deposited in a biohazardous container after removal. In some embodiments, the endotracheal tube cleaning device can perform multiple cleaning passes for a single patient before being disposed.

According to some embodiments, the endotracheal tube cleaning device is configured for single-handed operation by a single practitioner. In alternative embodiments, the endotracheal tube cleaning device can be operated using two hands or by multiple practitioners.

In some embodiments, the endotracheal tube cleaning device is configured to be a single-pass device that clears or removes up to 90% of more of the biofilm. In other embodiments, a single pass device can be designed and otherwise configured to remove more or less than 90% of biofilm, as desired and/or required.

In other embodiments, such as when the endotracheal tube has been in the patient for multiple days without being cleaned and/or more than about 2-5 ccs of biofilm has accumulated within the endotracheal tube, multiple passes may be performed to remove the biofilm. The determination as to whether to perform additional cleaning passes can be made using visualization devices inserted within the endotracheal tube, as described herein, or by visual inspection of the cleaning member upon removal of the endotracheal tube cleaning device. For example, if the capacity of the collection mechanism of the endotracheal tube cleaning device visually appears to have been reached and/or exceeded, another pass may be desirable.

According to some embodiments, the endotracheal tube cleaning device is provided in a pouch or tray and is sterile ready to use. In other embodiments, the endotracheal tube cleaning device can be provided sterilized or clean ready to use. In one embodiment, the endotracheal tube cleaning device is provided in a disposable peel-pack or pouch. At least one sleeve of the peel-pack can be used for disposal of the spent endotracheal tube cleaning device and the removed biofilm.

In some embodiments, the insertion and removal of the endotracheal tube cleaning device can be completed in less than about ten seconds, with 90% of the biofilm being removed. However, as discussed herein, the time period for completing a procedure and/or the exact amount of biofilm removed from a cleaning procedure can vary, as desired or required. For example, in one embodiment, the insertion of the endotracheal tube cleaning device can be performed in less than two seconds and the removal of the endotracheal tube cleaning device can be performed in one to three seconds.

In some embodiments, the endotracheal tube cleaning device can be twisted or rotated manually by a clinician to enhance the wiping action of the removal member (e.g., O-ring). In other embodiments, the removal member (e.g., O-ring) and/or the collection member (e.g., mesh scaffold) have one or more driving mechanisms to effectuate a tangential wiping motion in addition to the pulling wiping motion of the cleaning member. Still other embodiments include a screw mechanism so that the cleaning member twists as the endotracheal tube cleaning device is withdrawn.

EXAMPLES

The following Examples illustrate some embodiments of the endotracheal tube cleaning systems, devices and methods and are not intended in any way to limit the scope of the disclosure. Moreover, the methods and procedures described in the following examples, and in the above disclosure, need not be performed in the sequence presented.

Feasibility testing on the endotracheal tube devices described herein was performed at West Virginia University. In some embodiments, the tests were designed to test the amount of biofilm removal and the amount of bacteria removal after cleaning with the endotracheal tube cleaning devices. In some embodiments, the tests demonstrated the utility of using the endotracheal tube cleaning devices versus blind suctioning for secretions or biofilm (e.g., bound and tenacious biofilm) on the inside of the endotracheal tube. The feasibility testing was performed on endotracheal tubes inserted into models simulating the question mark shape of an endotracheal tube within a patient. The endotracheal tubes were freshly blind suctioned just prior to extubation and tested within two hours of extubation from the patients. In some instances, the performance of the endotracheal tube cleaning devices was compared with bronchoscopes inserted within the endotracheal tubes. The testing found that the endotracheal tube cleaning devices did not dislodge biofilm upon insertion but that the bronchoscopes did dislodge biofilm upon insertion, which dislodged biofilm could be carried into distal lung fields.

Example 1

A feasibility test was performed on an endotracheal tube removed from a patient that was extubated after five days. The endotracheal tube was freshly blind suctioned just prior to extubation. Biofilm was visible from the outside of the endotracheal tube before cleaning. An embodiment of the endotracheal tube cleaning device was inserted within the endotracheal tube and a cleaning procedure was performed as described herein. Two ccs of biofilm was removed. Microbiology testing was performed on the biofilm and the following types of bacteria were found: staph aureus, pseudomonas, streptococcus and candida. After cleaning with the endotracheal tube cleaning device, 99% of the bacteria was removed from the endotracheal tube (as determined by the change in colony counts).

Example 2

A feasibility test was performed on an endotracheal tube removed from a patient that was extubated after four days. The endotracheal tube was freshly blind suctioned just prior to extubation. Biofilm was not visible from the outside of the endotracheal tube before cleaning. An embodiment of the endotracheal tube cleaning device was inserted within the endotracheal tube and a cleaning procedure was performed as described herein. 1.5 ccs of biofilm was removed. Microbiology testing was performed on the biofilm and the following types of bacteria were found: staph aureus, pseudomonas and streptococcus. After cleaning with the endotracheal tube cleaning device, 99% of the bacteria was removed from the endotracheal tube (as determined by the change in colony counts).

Example 3

Endotracheal tube resistance testing was performed on an endotracheal tube removed from a patient. The testing was performed at a ventilation flow rate of 60 liters per minute. Bloody secretions and visible accumulation was present in the distal half of the endotracheal tube. In some embodiments, the secretions and biofilm collect at the "bottom" or distal half of the endotracheal tube. The endotracheal tube was an 8 mm endotracheal tube. The endotracheal tube showed resistance to flow similar to a new 7 mm tube. In one embodiment, an 8 mm to 7 mm reduction in effective internal diameter results in a relative increase in resistance of about 70%. Generally, a 20% increase in resistance is enough to impede flow and be detrimental. An embodiment of the endotracheal tube cleaning device was inserted within the endotracheal tube and a cleaning procedure was performed as described herein. After cleaning, the endotracheal tube resistance was reduced by about 90%. The 8 mm endotracheal tube showed resistance similar to a brand new 8 mm endotracheal tube.

IV. Distal Airway Management Systems

Various combinations of the systems and devices described and/or illustrated herein can be packaged together and provided to patient care facilities as a distal airway management kit. The distal airway management system or kit can include any combination of one or more of the following, depending on the needs or clinical situations handled by the patient care facility: an endotracheal tube with built-in visualization channel (e.g., as described with respect to FIGS. 12A-12I), a visualization member (e.g., a visualization scope as described with respect to FIGS. 2A-2C), a visualization device (e.g., as described with respect to FIGS. 3A-11B), an endotracheal tube cleaning device (e.g., as described with respect to FIGS. 27A-29F), a tongue elevator (e.g., as described with respect to FIG. 13), an airway cleaning device (e.g., as described with respect to FIGS. 14A-21B) and/or any other device or component (e.g., a laryngeal mask, a bronchoscope, an endoscope). In some embodiments, the distal airway management system comprises, or is otherwise compatible with, any currently commercially available endotracheal tubes. In some embodiments, the systems and devices described herein can be used in conjunction with some or all currently commercially available modifications of a standard endotracheal tube.

For example, in one embodiment, a distal airway management system or kit comprises an endotracheal tube cleaning device and a visualization device to confirm and/or treat a condition within or near the endotracheal tube. In other embodiments, a distal airway management system or kit comprises an endotracheal tube cleaning device, a visualization device, a visualization scope and/or an airway cleaning device, which may include a suction line, a visualization line and/or an irrigation line. One or more other devices or features can be included in other embodiments of an airway management system or kit, as desired or required.

In some embodiments, an endotracheal tube having a built-in visualization channel can be inserted within a native airway of a patient during an intubation procedure under direct guidance using a visualization scope inserted within the visualization channel. The visualization scope can be used to facilitate proper insertion of the endotracheal tube with respect to the carina of the patient. The visualization scope can then be removed and the visualization channel can be collapsed through the application of suction to the visualization channel.

In other embodiments, a visualization device comprising a visualization tube and a visualization member can be inserted within an indwelling endotracheal tube after intubation to confirm the proper positioning of the endotracheal tube with respect to the carina of the patient. In some embodiments, the visualization device can be coupled to an endotracheal tube before intubation and a visualization scope can be inserted within the visualization device to facilitate proper intubation (e.g., placement of the endotracheal tube with respect to the carina). The visualization device can also be used to determine the presence of significant build up of biofilm within the lumen of the endotracheal tube that would trigger cleaning of the interior surface of the endotracheal tube. An endotracheal tube cleaning device, such as the endotracheal tube cleaning devices described herein could then be inserted to clean the endotracheal tube as desired and/or required. In some embodiments, the visualization device could be reinserted after removal of the endotracheal tube cleaning device or within the endotracheal tube cleaning device to confirm that the endotracheal tube has been adequately cleaned (e.g., that there are no significant occlusions remaining in the endotracheal tube). In other embodiments, the airway cleaning device can be inserted within the endotracheal tube after being cleaned by an endotracheal tube cleaning device. This can help increase the "working" diameter of the endotracheal tube and can allow for a suction catheter or airway cleaning device having a larger diameter to be inserted within the endotracheal tube. Cleaning an endotracheal tube with an endotracheal tube cleaning device prior to bronchoscopy can advantageously prevent the bronchoscope from carrying endotracheal secretions and biofilm into the distal segments of the lungs, thereby reducing the risk of infection or pneumonia.

In some embodiments, an airway cleaning device, such as the airway cleaning devices described and illustrated herein, can then be inserted into the endotracheal tube and then further inserted through the trachea and into the branches of the tracheobronchial tree to remove pooled secretions or other debris. The cleaning of the tracheobronchial tree (via the suction line) can be facilitated by a visualization member that has been inserted within the visualization channel of the airway cleaning device. An angling or deflection mechanism as described herein can be used to deflect a distal end of the airway cleaning device to facilitate access to all areas of the lungs and bronchus. The visualization member can identify the locations of pooled secretions and can confirm that the pooled secretions or other debris have been removed from all of the branches of the tracheobronchial tree. In some embodiments, the airway cleaning device can be used to determine the presence of significant buildup of biofilm within the endotracheal tube, which can trigger the cleaning of the endotracheal tube using an endotracheal tube cleaning device. In some embodiments, the visualization channels and/or visualization tubes or lumens of each of the devices and systems described herein can be dimensioned such that the same visualization member (e.g., fiber optic visualization scope) can be advantageously used for any of the procedures described above and with any of the devices and systems used to perform the procedures described above.

In some embodiments, the embodiments of the distal airway management systems described herein comprise disposable cleaning devices and reusable suction devices and visualization members that can reduce the device cost per procedure by approximately $500 (current hospital cost is approximately $800), and can enable a bronchoscopy within minutes instead of hours compared to current technology and reduce the staffing required for current bronchoscopy.

The endotracheal tubes described herein can comprise one or more extruded thermoplastic materials. Although the visualization devices, methods, and systems described herein have been described in connection with the cleaning of endotracheal tubes or other body-inserted tubes or with the suctioning of distal airways of a patient, the embodiments and features described herein can be used for other medical applications, such as, for example, the surgical treatment of atrial fibrillation, wherein an ablation device is guided around the heart; urologic applications; endoscopy, laparoscopic applications, orthopedic and spine applications, and for tubes within the body such as dialysis grafts.

Conditional language, for example, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Additionally, the skilled artisan will recognize that any of the above-described methods can be carried out using any appropriate apparatus. Further, the disclosure herein of any particular feature, aspect, method, property, characteristic, quality, attribute, element, or the like in connection with various embodiments can be used in all other embodiments set forth herein. Additionally, process steps may be added, removed, or reordered.

For purposes of this disclosure, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

What is claimed is:

1. A visualization device for confirming proper positioning and placement of an endotracheal tube within a patient without requiring the use of a laryngoscope or bronchoscope, the device comprising:
 a visualization tube adapted to be inserted within an endotracheal tube, the visualization tube having a closed distal end, an open proximal end, and a lumen extending from the proximal end to the distal end;
 wherein the visualization tube is sized to extend at least to the distal end of the endotracheal tube;
 wherein the lumen of the visualization tube is sized and shaped to removably receive a visualization scope;

wherein the closed distal end of the visualization tube comprises a window;

wherein the visualization tube comprises at least one centering assembly mounted on an outer surface of the visualization tube, the at least one centering assembly comprising two or more flexible arms adapted to expand to conform to an inner wall of the endotracheal tube, thereby centering the visualization tube within the endotracheal tube;

a coupling assembly adapted to couple to the endotracheal tube; and a scope retention assembly coupled to a proximal end of the visualization tube;

wherein the scope retention assembly comprises a stretchable elastomeric sleeve having an open proximal end and an open distal end and a scope retention member attached to the open proximal end of the stretchable elastomeric sleeve, the scope retention member being adapted to interface with a locking member coupled to a visualization scope;

wherein the open proximal end of the elastomeric sleeve is adapted to be stretched by pulling the scope retention member proximally to allow the scope retention member of the scope retention assembly to engage the locking member coupled to the visualization scope, thereby exerting a static force on the visualization scope in the direction of the closed distal end of the visualization tube upon release of the elastomeric sleeve, wherein the visualization tube is a separate component from the scope retention assembly.

2. The visualization device of claim 1, wherein the scope retention member comprises a slot, wherein the slot is sized and shaped to receive the visualization scope.

3. The visualization device of claim 1, wherein the locking member is integrally formed on a scope retainer sleeve that is coupled to the visualization scope.

4. The visualization device of claim 1, wherein the visualization tube comprises one or more sensors configured to detect one or more of the following: carbon dioxide levels, the presence of selected bacteria of interest, moisture levels, or respiratory parameters.

5. The visualization device of claim 1, wherein the coupling assembly comprises at least one accessory port.

6. The visualization device of claim 5, wherein the at least one accessory port comprises an oxygen port adapted to connect to an oxygen line or to a ventilator and an access port adapted to receive a stylet or obturator.

7. The visualization device of claim 1, wherein the visualization tube comprises a bend radius that approximates the bend radius of an endotracheal tube.

8. The visualization device of claim 1, wherein the visualization tube has an outer diameter of less than 2 mm.

9. A visualization system for proper positioning or placement of an endotracheal tube within a patient without requiring the use of a laryngoscope or bronchoscope, the system comprising:

the visualization device of claim 1; and an endotracheal tube cleaning device configured to be inserted into an endotracheal tube of a patient either before or after a distal airway cleaning device has been positioned and subsequently removed from one or more distal airways of the patent, said endotracheal tube cleaning device comprising:

an elongated member having a proximal end and a tip along its distal end, said elongated member comprising at least one lumen extending within its interior along at least along a portion of a length of said elongated member;

an expandable structure positioned along the elongated member, said structure being adapted to selectively move between a radially-collapsed position and a radially-expanded position;

an actuation assembly coupled to the proximal end of the elongated member; and a visualization channel within the lumen of the elongated member sized and configured to receive the visualization scope;

wherein the one or more removal members of the cleaning device are configured to engage an interior surface of an endotracheal tube when the expandable structure is in the radially-expanded position; and wherein the one or more removal members are configured to contact and remove debris collected on an interior surface of the endotracheal tube when said cleaning device is moved relative to the endotracheal tube.

10. The system of claim 9, wherein the expandable structure of the endotracheal tube cleaning device is mechanically-expandable.

11. The system of claim 10, wherein the expandable structure comprises a mesh scaffold or expandable struts, wherein the expandable structure comprises an outer sleeve positioned along at least a portion of an exterior surface of the expandable structure, and wherein the at least a portion of the outer sleeve is configured to radially expand together with the expandable structure when the expandable structure moves from the radially-collapsed position to the radially-expanded position.

12. The system of claim 9, further comprising a distal airway cleaning device for removing debris from one or more distal airways of a patient, said distal airway cleaning device comprising:

a suction catheter comprising a main suction lumen and a distal end configured to facilitate steering of the suction catheter within an airway of the patient;

a visualization channel disposed within the main suction lumen of the suction catheter sized and shaped to receive a visualization scope, wherein the visualization channel comprises a window at a closed distal end of the visualization channel; and a control handle configured for one-handed operation of the distal airway cleaning device, wherein the suction catheter comprises a distal angle and a deflection mechanism to facilitate access to all areas of the bronchus and lungs.

13. The system of claim 12, wherein the main suction lumen of the suction catheter further comprises an irrigation channel, said irrigation channel being configured to clean the window at the distal end of the visualization channel and/or to deliver one or more fluids to the distal airways of the patient.

14. The system of claim 12, wherein the distal airway cleaning device is configured to be operated in a closed suction system.

15. The system of claim 12, wherein an elongate shaft of the suction catheter comprises an endotracheal tube cleaning member comprising one or more removal members configured to expand into contact with an interior wall of an endotracheal tube, wherein the endotracheal tube cleaning member comprises an inflatable structure.

16. A system for providing visualized confirmation of proper positioning and cleaning of an endotracheal tube within a patient, the system comprising:

a visualization device adapted to provide visualized confirmation of proper positioning of an endotracheal tube within a patient, the visualization device comprising:
   a visualization tube adapted to be inserted within the endotracheal tube, the visualization tube having a closed distal end, an open proximal end, and a lumen extending from the proximal end to the distal end;
   wherein the lumen of the visualization tube is sized and shaped to removably receive a visualization scope;
   wherein the closed distal end of the visualization tube comprises a window;
   wherein the visualization tube comprises a plurality of centering assemblies spaced apart and mounted on an outer surface of the visualization tube, the plurality of centering assemblies each comprising two or more flexible wings adapted to expand to conform to an inner wall of the endotracheal tube at a location proximal to the closed distal end of the visualization tube, thereby centering the visualization tube within the endotracheal tube and preserving viewing of anatomical features beyond a distal tip of the endotracheal tube; and
an endotracheal tube cleaning device configured to be inserted into an endotracheal tube of a patient, said endotracheal tube cleaning device comprising:
   an elongated member having a proximal end and a tip along its distal end, said elongated member comprising a visualization channel extending within its interior along at least a portion of a length of said elongated member, the visualization channel being sized and configured to receive the visualization scope;
   a non-inflatable, mechanically expandable structure positioned along the elongated member, said structure being adapted to selectively move between a radially-collapsed position and a radially-expanded position; and
   an actuation assembly coupled to the proximal end of the elongated member, the actuation assembly being configured to control the expansion and collapse of the expandable structure;
   wherein the one or more removal members of the endotracheal tube cleaning device are configured to engage an interior surface of an endotracheal tube when the expandable structure is in the radially-expanded position; and
   wherein the one or more removal members are configured to contact and remove debris collected on an interior surface of the endotracheal tube when said endotracheal tube cleaning device is moved relative to the endotracheal tube.

17. The system of claim 16, further comprising a distal airway cleaning device for removing debris from one or more distal airways of a patient, said distal airway cleaning device comprising:
   a suction catheter comprising a main suction lumen and a distal end configured to facilitate steering of the suction catheter within an airway of the patient;
   a visualization channel disposed within the main suction lumen of the suction catheter sized and shaped to receive a visualization scope,
   wherein the visualization channel comprises a window at a closed distal end of the visualization channel; and
   a control handle configured for one-handed operation of the distal airway cleaning device.

18. The system of claim 17, wherein the main suction lumen of the suction catheter further comprises an irrigation channel, said irrigation channel being configured to clean the window at the distal end of the visualization channel and/or to deliver one or more fluids to the distal airways of the patient.

19. The system of claim 17, wherein the distal airway cleaning device is configured to be operated in a closed suction system.

20. The system of claim 16, further comprising an endotracheal tube adapter comprising multiple inlet ports configured to allow the distal airway cleaning device and the endotracheal tube cleaning device to be inserted within the endotracheal tube simultaneously.

21. The system of claim 20, further comprising a ventilation port configured to be coupled to an oxygen supply to provide a continuous supply of oxygen during cleaning procedures performed by the distal airway cleaning device or the endotracheal tube cleaning device.

22. The system of claim 17, wherein an elongate shaft of the suction catheter comprises an endotracheal tube cleaning member configured to expand into contact with an interior wall of an endotracheal tube, wherein the one or more removal members are configured to remove biofilm from the interior wall of the endotracheal tube, and wherein the endotracheal tube cleaning member comprises an inflatable structure.

23. The system of claim 16, wherein the expandable structure of the endotracheal tube cleaning device comprises a mesh scaffold or expandable struts, wherein the expandable structure comprises an outer sleeve positioned along at least a portion of an exterior surface of the expandable structure, and wherein at least a portion of the outer sleeve is configured to radially expand together with the expandable structure when the expandable structure moves from the radially-collapsed position to the radially-expanded position.

* * * * *

UNITED STATES PATENT AND TRADEMARK OFFICE
CERTIFICATE OF CORRECTION

| | | |
|---|---|---|
| PATENT NO. | : 9,579,012 B2 | |
| APPLICATION NO. | : 13/645984 | |
| DATED | : February 28, 2017 | |
| INVENTOR(S) | : Brad E. Vazales | |

It is certified that error appears in the above-identified patent and that said Letters Patent is hereby corrected as shown below:

On the Title Page

In Column 2 (item (56)) at Line 12, Under Other Publications, change "Enotracheal" to --Endotracheal--.

In Column 2 (page 2, item (56)) at Line 45, Under Other Publications, change "SubPageID" to --SubPageID--.

In Column 2 (page 2, item (56)) at Line 49, Under Other Publications, change "SubPageID" to --SubPageID--.

In the Specification

In Column 11 at Line 38, Change "patent" to --patient--.

In Column 13 at Line 53, Change "patent." to --patient.--.

In Column 21 at Line 4, Change "fore" to --for--.

In Column 21 at Line 11, Change "(CDD)" to --(CCD)--.

In Column 25 at Line 11, Change "sterotactically" to --stereotactically--.

In Column 34 at Line 51, After "arm" insert --.--.

In Column 40 at Line 43, Change "12A-121" to --12A-12I--.

In Column 44 at Line 34, Change "steerabilty" to --steerability--.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,579,012 B2

In Column 58 at Line 19, Change "boreoscope." to --borescope.--.

In Column 92 at Line 44, Change "viracidal" to --virucidal--.

In the Claims

In Column 107 at Line 64, In Claim 9, change "patent," to --patient,--.